(12) United States Patent
Seo et al.

(10) Patent No.: US 10,270,039 B2
(45) Date of Patent: Apr. 23, 2019

(54) LIGHT-EMITTING ELEMENT, DISPLAY DEVICE, ELECTRONIC DEVICE, AND LIGHTING DEVICE

(71) Applicant: Semiconductor Energy Laboratory Co., Ltd., Kanagawa-ken (JP)

(72) Inventors: Satoshi Seo, Kanagawa (JP);
Tatsuyoshi Takahashi, Kanagawa (JP);
Kyoko Takeda, Kanagawa (JP); Kanta Abe, Kanagawa (JP); Hiroki Suzuki, Kanagawa (JP)

(73) Assignee: Semiconductor Energy Laboratory Co., Ltd. (JP)

( * ) Notice: Subject to any disclaimer, the term of this patent is extended or adjusted under 35 U.S.C. 154(b) by 0 days.

(21) Appl. No.: 15/812,703

(22) Filed: Nov. 14, 2017

(65) Prior Publication Data
US 2018/0138416 A1 May 17, 2018

(30) Foreign Application Priority Data

Nov. 17, 2016 (JP) .................................. 2016-223771
Nov. 18, 2016 (JP) .................................. 2016-225013

(51) Int. Cl.
*G06F 3/045* (2006.01)
*H01L 51/00* (2006.01)
(Continued)

(52) U.S. Cl.
CPC ...... *H01L 51/0051* (2013.01); *C07F 15/0033* (2013.01); *C09K 11/06* (2013.01); *G06F 3/045* (2013.01); *G06F 3/0412* (2013.01); *H01L 27/3267* (2013.01); *H01L 51/0059* (2013.01); *H01L 51/0061* (2013.01);
(Continued)

(58) Field of Classification Search
CPC ............ H01L 51/0051; H01L 51/0059; H01L 27/3267; H01L 51/0061; H01L 51/0067; H01L 51/0072; H01L 51/0074; H01L 51/5004; H01L 51/5028; H01L 51/5056; H01L 51/5072; H01L 2251/552; H01L 2251/5384; H01L 51/5016; H01L 51/0085;
(Continued)

(56) References Cited

U.S. PATENT DOCUMENTS 9,604,928 B2    3/2017   Shitagaki et al.
2012/0205632 A1*  8/2012   Shitagaki ............ H01L 51/0059
                                                                   257/40
(Continued)

FOREIGN PATENT DOCUMENTS

JP          2010-182699 A         8/2010

*Primary Examiner* — Kyoung Lee
(74) *Attorney, Agent, or Firm* — Husch Blackwell LLP

(57) ABSTRACT

A light-emitting element with a lower voltage and higher emission efficiency is provided. The light-emitting element includes a first organic compound, a second organic compound, and a guest material. The LUMO level of the first organic compound is lower than the LUMO level of the second organic compound, and a difference between them is larger than 0 eV and smaller than or equal to 0.5 eV. Furthermore, the HOMO level of the first organic compound is lower than the HOMO level of the second organic compound. The guest material has a function of converting triplet excitation energy into light emission. The first organic compound and the second organic compound form an exciplex.

15 Claims, 65 Drawing Sheets

(51) Int. Cl.
  *C07F 15/00*  (2006.01)
  *C09K 11/06*  (2006.01)
  *G06F 3/041*  (2006.01)
  *H01L 51/50*  (2006.01)
  *H05B 33/14*  (2006.01)
  *H05B 33/20*  (2006.01)
  *H01L 27/32*  (2006.01)

(52) U.S. Cl.
  CPC ...... *H01L 51/0067* (2013.01); *H01L 51/0072* (2013.01); *H01L 51/0074* (2013.01); *H01L 51/5004* (2013.01); *H01L 51/5028* (2013.01); *H01L 51/5056* (2013.01); *H01L 51/5072* (2013.01); *H05B 33/14* (2013.01); *H05B 33/20* (2013.01); *H01L 51/0085* (2013.01); *H01L 51/5016* (2013.01); *H01L 2251/5384* (2013.01); *H01L 2251/552* (2013.01)

(58) Field of Classification Search
  CPC .... G06F 3/0412; G06F 3/045; C07F 15/0033; H05B 33/20; H05B 33/14; C09K 11/06
  See application file for complete search history.

(56) References Cited

U.S. PATENT DOCUMENTS

2016/0343949 A1  11/2016  Seo et al.
2016/0343954 A1  11/2016  Seo et al.
2017/0025615 A1  1/2017  Seo et al.
2017/0025630 A1  1/2017  Seo et al.

\* cited by examiner

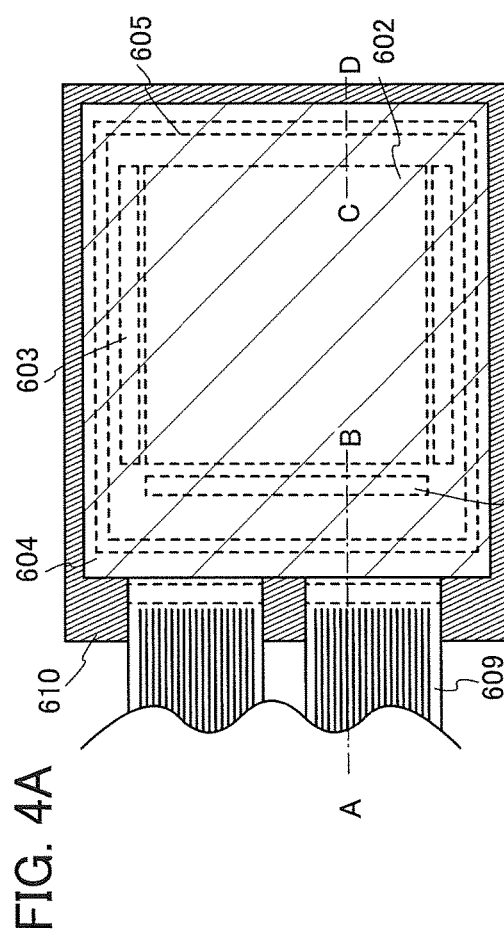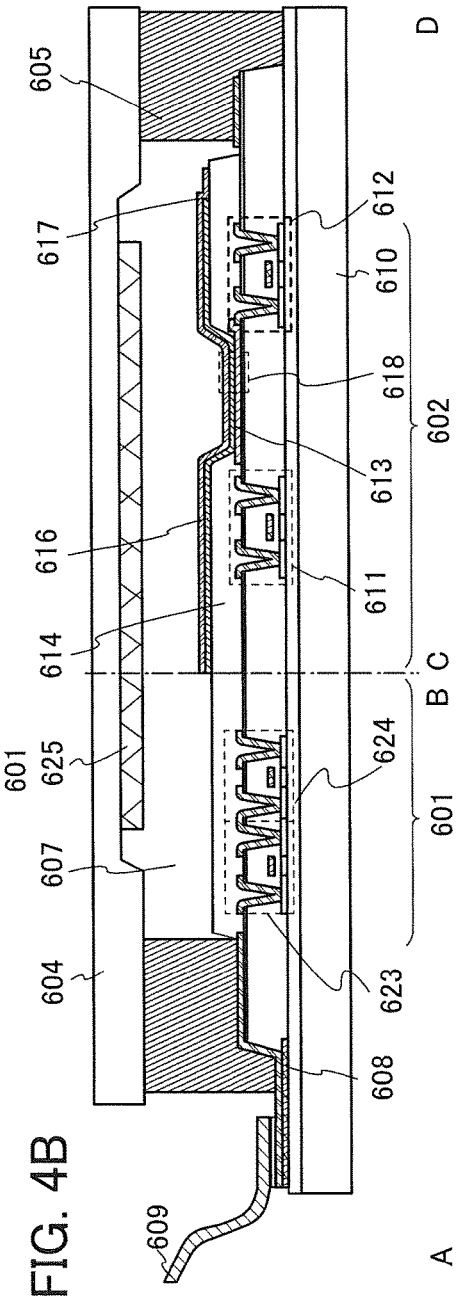

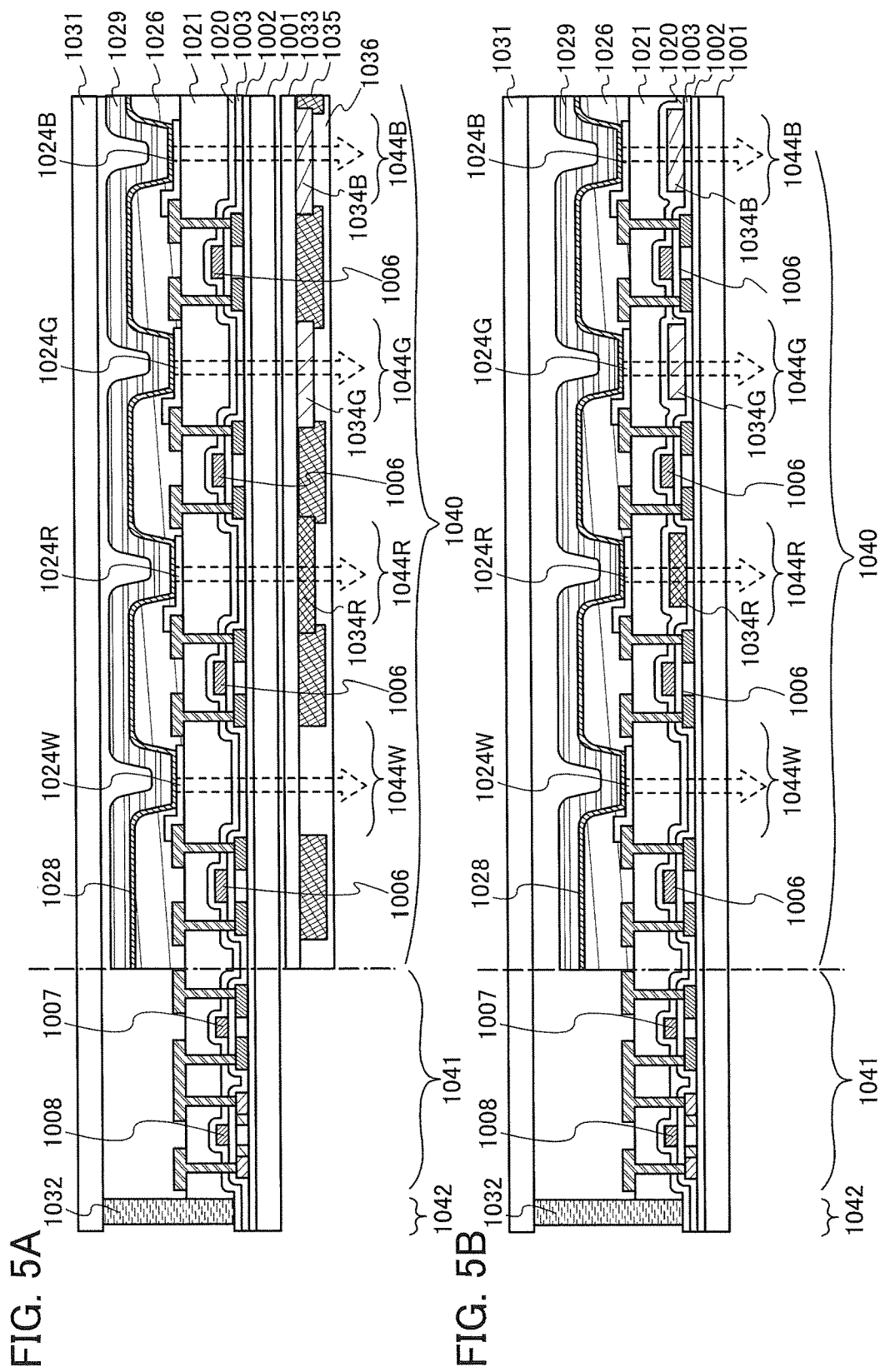

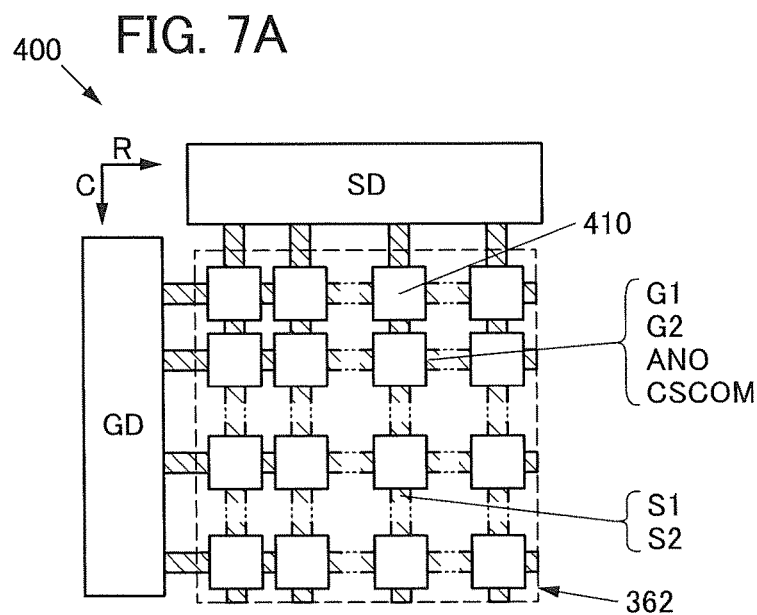
FIG. 7A
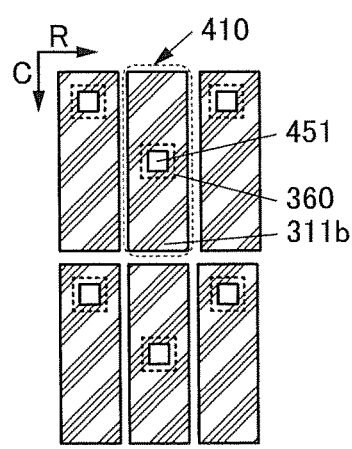
FIG. 7B1
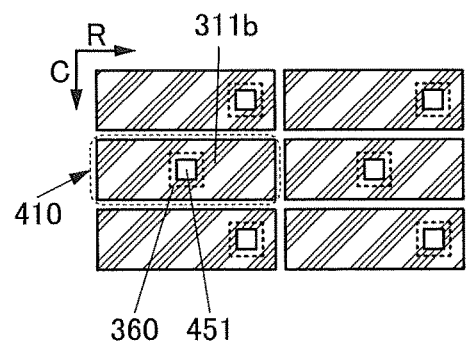
FIG. 7B2

LIGHT-EMITTING ELEMENT, DISPLAY DEVICE, ELECTRONIC DEVICE, AND LIGHTING DEVICE

BACKGROUND OF THE INVENTION

1. Field of the Invention

One embodiment of the present invention relates to a light-emitting element including a combination of organic compounds that form an exciplex, or a display device, an electronic device, and a lighting device each including the light-emitting element.

Note that one embodiment of the present invention is not limited to the above technical field. One embodiment of the present invention relates to an object, a method, or a manufacturing method. The present invention relates to a process, a machine, manufacture, or a composition of matter. In particular, one embodiment of the present invention relates to a semiconductor device, a light-emitting device, a display device, a lighting device, a light-emitting element, or a manufacturing method thereof.

2. Description of the Related Art

In recent years, research and development have been extensively conducted on light-emitting elements utilizing electroluminescence (EL). Such a light-emitting element has a basic structure in which a layer containing a light-emitting material (an EL layer) is interposed between a pair of electrodes. By application of a voltage between the electrodes of this element, light emission from the light-emitting material can be obtained.

Since the above light-emitting element is a self-luminous type, a display device using this light-emitting element has advantages such as high visibility, no necessity of a backlight, and low power consumption. Furthermore, such a light-emitting element also has advantages in that the element can be formed to be thin and lightweight, and has high response speed.

In the case of a light-emitting element in which an EL layer containing an organic material as the light-emitting material is provided between a pair of electrodes (e.g., an organic EL element), application of a voltage between the pair of electrodes causes injection of electrons from the cathode and holes from the anode into the EL layer having a light-emitting property, and thus a current flows. By recombination of the injected electrons and holes, the light-emitting organic material is brought into an excited state to provide light emission.

The excited state formed by an organic material can be a singlet excited state (S*) or a triplet excited state (T*). Light emission from the singlet-excited state is referred to as fluorescence, and light emission from the triplet excited state is referred to as phosphorescence. The statistical generation ratio of the excited states in the light-emitting element is considered to be S*:T*=1:3. In other words, a light-emitting element formed using a material emitting phosphorescence (phosphorescent material) has higher emission efficiency than a light-emitting element formed using a material emitting fluorescence (fluorescent material). Therefore, light-emitting elements formed using a phosphorescent material capable of converting a triplet excited state into light emission has been actively developed in recent years (e.g., see Patent Document 1).

Energy for exciting an organic material depends on an energy difference between the highest occupied molecular orbital (HOMO) level and the lowest unoccupied molecular orbital (LUMO) level of the organic material, and the energy difference approximately corresponds to singlet excitation energy. In a light-emitting element containing a phosphorescent organic material, triplet excitation energy is converted into light emission energy. Thus, when the energy difference between the singlet excited state and the triplet excited state of an organic material is large, the energy for exciting the organic material is higher than the light emission energy by the amount corresponding to the energy difference. The difference between the energy for exciting the organic material and the light emission energy affects characteristics of a light-emitting element: the driving voltage of the light-emitting element increases. Thus, measures to reduce the increase in driving voltage have been demanded.

REFERENCE

Patent Document

[Patent Document 1] Japanese Published Patent Application No. 2010-182699

SUMMARY OF THE INVENTION

In order to reduce driving voltage, an organic material which has a favorable carrier (electron and/or hole)-transport property needs to be used for a light-emitting element. However, in the case of using the organic material, it is difficult to adjust carrier balance and to make the light-emitting element emit light efficiently in some cases; thus, it is not easy to achieve both high emission efficiency and low driving voltage.

In view of the above, an object of one embodiment of the present invention is to provide a novel light-emitting element that contains a phosphorescent material. In particular, an object is to provide a light-emitting element with high emission efficiency. In particular, an object of one embodiment of the present invention is to provide a light-emitting element with a low voltage. Another object of one embodiment of the present invention is to provide a light-emitting element with high reliability.

Another object is to provide a light-emitting element with low power consumption. Another object of one embodiment of the present invention is to provide a novel light-emitting device. Another object of one embodiment of the present invention is to provide a novel display device.

Note that the description of the above object does not disturb the existence of other objects. In one embodiment of the present invention, there is no need to achieve all the objects. Other objects are apparent from and can be derived from the description of the specification and the like.

One embodiment of the present invention is a light-emitting element in which an exciplex capable of efficiently exciting a phosphorescent material can be formed.

Thus, one embodiment of the present invention is a light-emitting element including a light-emitting layer between a pair of electrodes. The light-emitting layer includes a first organic compound, a second organic compound, and a guest material. A LUMO level of the first organic compound is lower than a LUMO level of the second organic compound. A difference between the LUMO level of the first organic compound and the LUMO level of the second organic compound is larger than 0 eV and smaller than or equal to 0.5 eV. A HOMO level of the first organic compound is lower than a HOMO level of the second organic compound. The guest material has a function of converting triplet excitation energy into light emission. The first organic compound and the second organic compound form an exciplex.

In the above structure, the first organic compound preferably includes a first electron-transport skeleton and a first hole-transport skeleton, and the second organic compound preferably includes a second electron-transport skeleton and a second hole-transport skeleton.

In each of the above structures, the difference between the LUMO level of the first organic compound and the LUMO level of the second organic compound is larger than 0 eV and smaller than or equal to 0.3 eV.

In the above structure, the first electron-transport skeleton and the second electron-transport skeleton are preferably any of a π-electron deficient heteroaromatic ring, an arylborane skeleton, and a phosphine oxide skeleton, and the first hole-transport skeleton and the second hole-transport skeleton are preferably any of a π-electron rich heteroaromatic ring and an aromatic amine skeleton.

In the above structure, the first electron-transport skeleton is preferably a nitrogen-containing heteroaromatic ring having 8 to 18 carbon atoms, and the second electron-transport skeleton is preferably a nitrogen-containing heteroaromatic ring having 3 to 8 carbon atoms.

In each of the above structures, the first hole-transport skeleton preferably includes a π-electron rich heteroaromatic ring, and the second hole-transport skeleton preferably includes an aromatic amine skeleton, in particular, a triarylamine skeleton.

In each of the above structures, the second organic compound is preferably any of organic compounds represented by Structural Formulae (100) to (109).

[Chemical Formula 1]

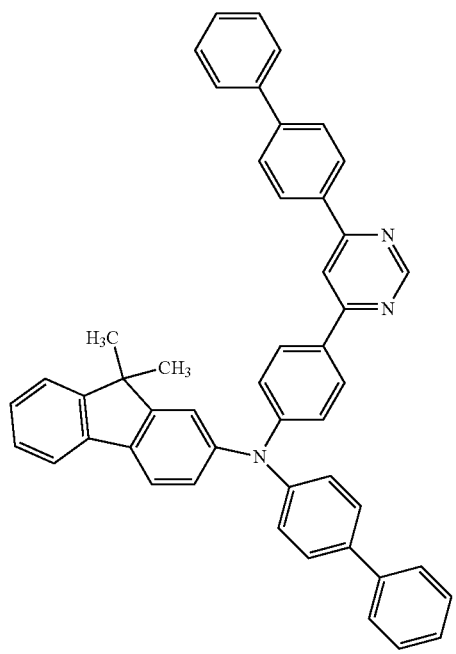

(100)

-continued

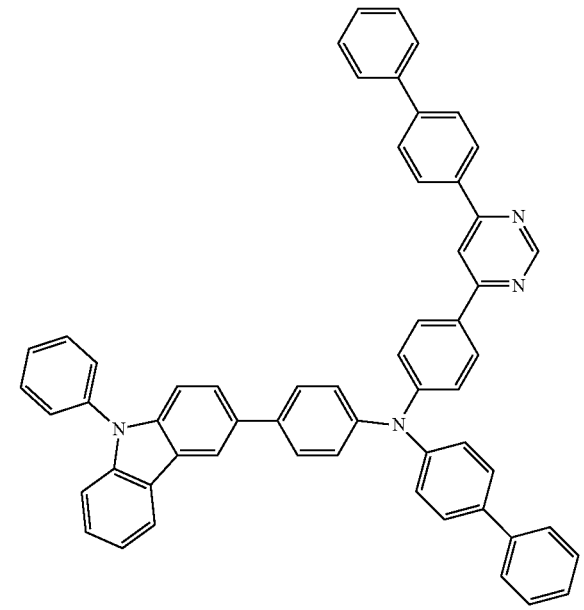

(101)

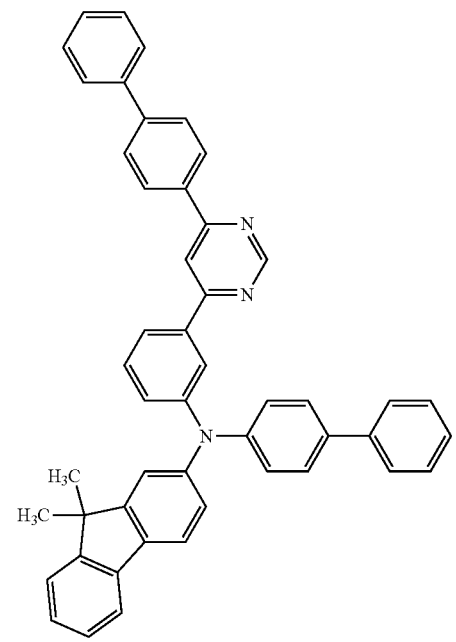

(102)

(103)
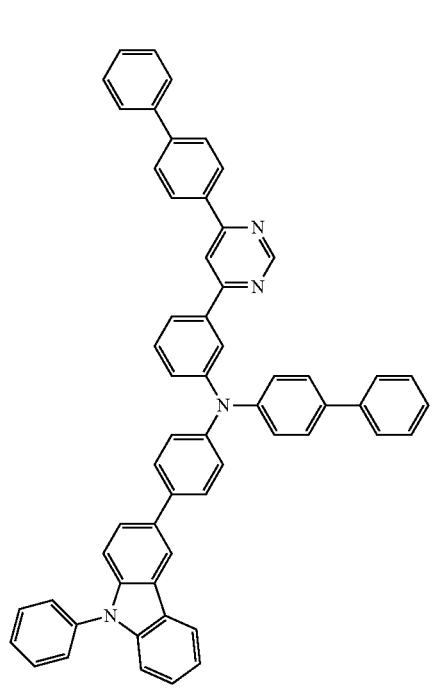
[Chemical Formula 2]
(104)
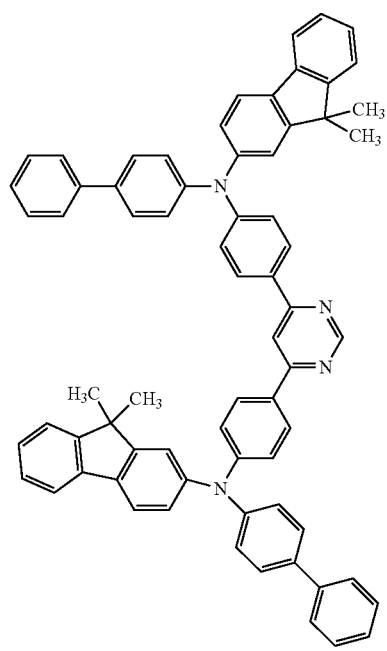
(105)
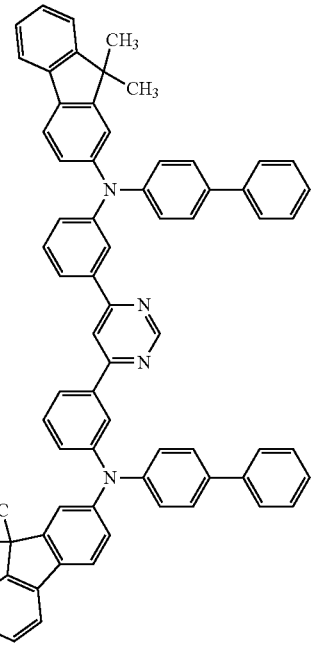
(106)
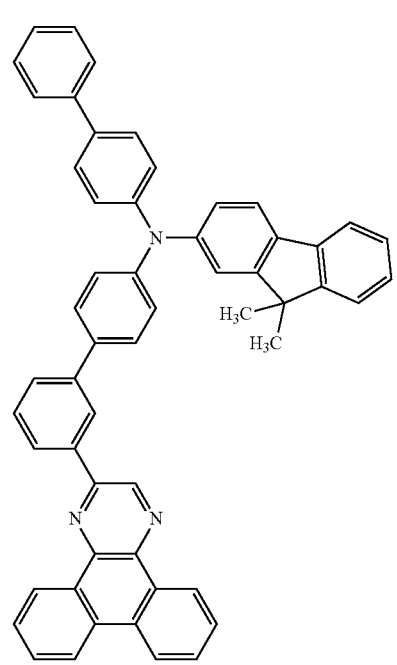

-continued (107)
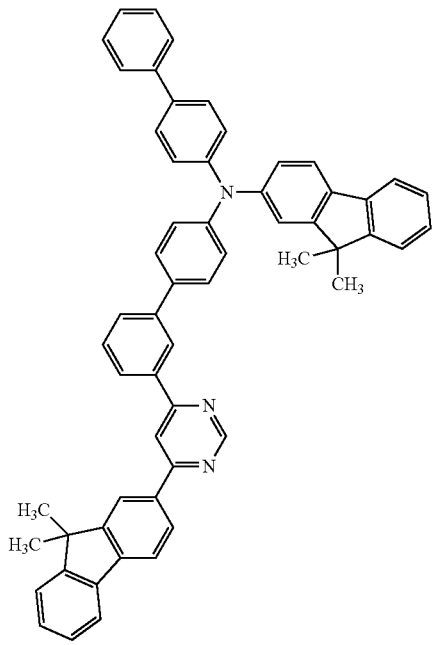

[Chemical Formula 3]

(108)
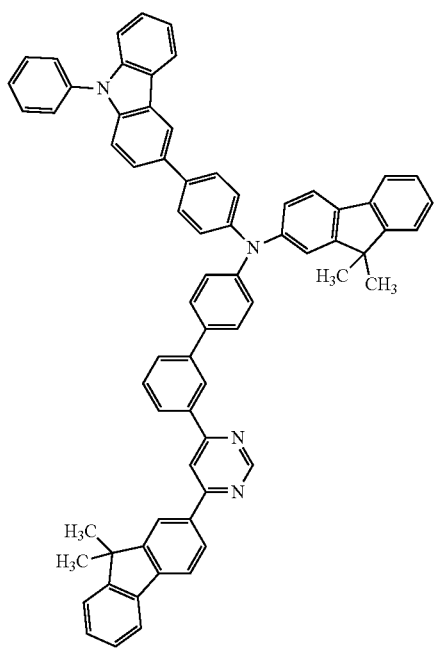

-continued (109)
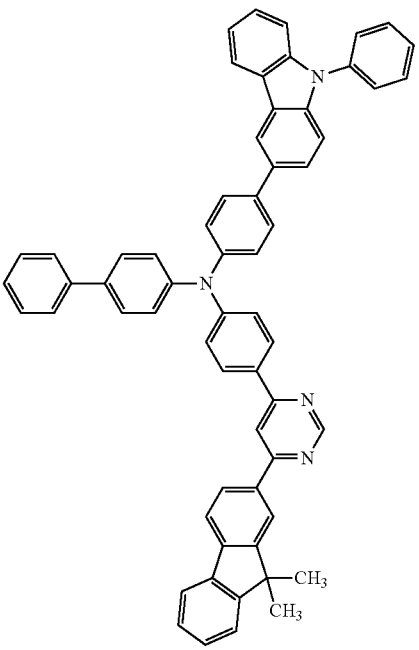

In each of the above structures, it is preferable that the exciplex be configured to transfer excitation energy to the guest material.

In each of the above structures, the guest material preferably contains iridium.

Another embodiment of the present invention is an organic compound represented by Structural Formulae (100) to (109).

Another embodiment of the present invention is a light-emitting element including one or more of organic compounds represented by Structural Formulae (100) to (109).

Another embodiment of the present invention is a display device which includes the light-emitting element and a color filter, a sealant, or a transistor. Another embodiment of the present invention is an electronic device including the display device and a housing or a touch sensor. Another embodiment of the present invention is a lighting device including the light-emitting element having any of the above-described structures and a housing or a touch sensor. The category of one embodiment of the present invention includes not only a light-emitting device including a light-emitting element but also an electronic device including a light-emitting device. Accordingly, a light-emitting device in this specification refers to an image display device or a light source (including a lighting device). The light-emitting device may include, in its category, a module in which a connector such as a flexible printed circuit (FPC) or a tape carrier package (TCP) is connected to a light-emitting element, a module in which a printed wiring board is provided on the tip of a TCP, or a module in which an integrated circuit (IC) is directly mounted on a light-emitting element by a chip on glass (COG) method.

With one embodiment of the present invention, a novel light-emitting element that contains a phosphorescent material is provided. With one embodiment of the present invention, in particular, a light-emitting element with high emission efficiency is provided. With one embodiment of the present invention, in particular, a light-emitting element with a low voltage is provided. With one embodiment of the present invention, a light-emitting element with high reliability is provided.

With one embodiment of the present invention, a light-emitting element with low power consumption is provided. With one embodiment of the present invention, a novel light-emitting device is provided. With one embodiment of the present invention, a novel display device is provided.

Note that the description of these effects does not disturb the existence of other effects. One embodiment of the present invention does not necessarily achieve all the effects listed above. Other effects will be apparent from and can be derived from the description of the specification, the drawings, the claims, and the like.

BRIEF DESCRIPTION OF THE DRAWINGS

In the accompanying drawings:

FIGS. 4A and 4B are conceptual diagrams of an active matrix light-emitting device of one embodiment of the present invention;

FIGS. 5A and 5B are conceptual diagrams of an active matrix light-emitting device of one embodiment of the present invention;

FIGS. 7A, 7B1, and 7B2 are schematic views of a display device of one embodiment of the present invention;

DETAILED DESCRIPTION OF THE INVENTION

Figure 1A:
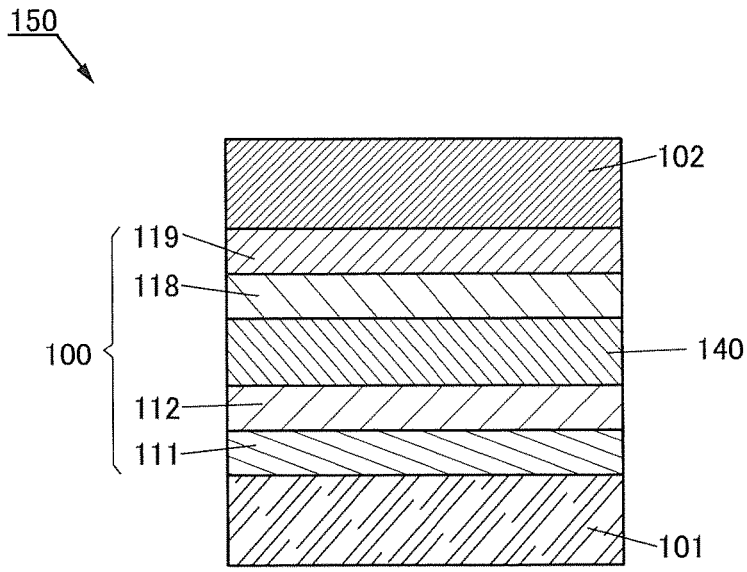
FIGS. 1A and 1B are schematic cross-sectionals views of a light-emitting element of one embodiment of the present invention and FIG. 1C shows the correlation of energy levels.

Embodiments of the present invention will be described in detail below with reference to the drawings. However, the present invention is not limited to description to be given below, and modes and details thereof can be variously modified without departing from the purpose and the scope of the present invention. Accordingly, the present invention should not be interpreted as being limited to the content of the embodiments below.

Note that the position, the size, the range, or the like of each structure illustrated in drawings and the like is not accurately represented in some cases for simplification. Therefore, the disclosed invention is not necessarily limited to the position, the size, the range, or the like disclosed in the drawings and the like.

Note that the ordinal numbers such as "first", "second", and the like in this specification and the like are used for convenience and do not denote the order of steps or the stacking order of layers. Therefore, for example, description can be made even when "first" is replaced with "second" or "third", as appropriate. In addition, the ordinal numbers in this specification and the like are not necessarily the same as those which specify one embodiment of the present invention.

In the description of modes of the present invention in this specification and the like with reference to the drawings, the same components in different diagrams are commonly denoted by the same reference numeral in some cases.

In this specification and the like, the terms "film" and "layer" can be interchanged with each other. For example, the term "conductive layer" can be changed into the term "conductive film" in some cases. Also, the term "insulating film" can be changed into the term "insulating layer" in some cases.

In this specification and the like, a singlet excited state (S*) refers to a singlet state having excitation energy. An S1 level means the lowest level of the singlet excitation energy level, that is, the excitation energy level of the lowest singlet excited state. A triplet excited state (T*) refers to a triplet state having excitation energy. A T1 level means the lowest level of the triplet excitation energy level, that is, the excitation energy level of the lowest triplet excited state. Note that in this specification and the like, a singlet excited state and a singlet excitation energy level mean the lowest singlet excited state and the S1 level, respectively, in some cases. A triplet excited state and a triplet excitation energy level mean the lowest triplet excited state and the T1 level, respectively, in some cases.

In this specification and the like, a fluorescent material refers to a material that emits light in the visible light region when the relaxation from the singlet excited state to the ground state occurs. A phosphorescent material refers to a material that emits light in the visible light region at room temperature when the relaxation from the triplet excited state to the ground state occurs. That is, a phosphorescent material refers to a material that can convert triplet excitation energy into visible light.

Phosphorescence emission energy or a triplet excitation energy can be obtained from a wavelength of an emission peak (including a shoulder) on the shortest wavelength side of phosphorescence emission. Note that the phosphorescence emission can be observed by time-resolved photoluminescence at a low temperature (e.g., 10 K). A thermally activated delayed fluorescence emission energy can be obtained from a wavelength of an emission peak (including a shoulder) on the shortest wavelength side of thermally activated delayed fluorescence.

Note that in this specification and the like, "room temperature" refers to a temperature higher than or equal to 0° C. and lower than or equal to 40° C.

In this specification and the like, a wavelength range of blue refers to a wavelength range of greater than or equal to 400 nm and less than 500 nm, and blue light has at least one peak in that range in an emission spectrum. A wavelength range of green refers to a wavelength range of greater than or equal to 500 nm and less than 580 nm, and green light has at least one peak in that range in an emission spectrum. A wavelength range of red refers to a wavelength range of greater than or equal to 580 nm and less than or equal to 680 nm, and red light has at least one peak in that range in an emission spectrum.

In this specification, a bipolar material is an organic compound having both a hole-transport property and an electron-transport property and including both an electron-transport skeleton and a hole-transport skeleton in one molecule. As an example of the electron-transport skeleton, a π-electron deficient heteroaromatic ring can be given, and as examples of the hole-transport skeleton, an amine skeleton and a π-electron rich heteroaromatic ring can be given.

Embodiment 1

In this embodiment, a light-emitting element of one embodiment of the present invention will be described below with reference to FIGS. 1A to 1C and FIGS. 2A to 2C.

<Structure Example 1 of Light-Emitting Element>

First, a structure of the light-emitting element of one embodiment of the present invention will be described below with reference to FIGS. 1A to 1C.

FIG. 1A is a schematic cross-sectional view of a light-emitting element 150 of one embodiment of the present invention.

The light-emitting element 150 includes a pair of electrodes (an electrode 101 and an electrode 102) and an EL layer 100 between the pair of electrodes. The EL layer 100 includes at least a light-emitting layer 140.

The EL layer 100 illustrated in FIG. 1A includes functional layers such as a hole-injection layer 111, a hole-transport layer 112, an electron-transport layer 118, and an electron-injection layer 119 in addition to the light-emitting layer 140.

In this embodiment, although description is given assuming that the electrode 101 and the electrode 102 of the pair of electrodes serve as an anode and a cathode, respectively, they are not limited thereto for the structure of the light-emitting element 150. That is, the electrode 101 may be a cathode, the electrode 102 may be an anode, and the stacking order of the layers between the electrodes may be reversed. In other words, the hole-injection layer 111, the hole-transport layer 112, the light-emitting layer 140, the electron-transport layer 118, and the electron-injection layer 119 may be stacked in this order from the anode side.

The structure of the EL layer 100 is not limited to the structure illustrated in FIG. 1A, and a structure including at least one layer selected from the hole-injection layer 111, the hole-transport layer 112, the electron-transport layer 118, and the electron-injection layer 119 may be employed. Alternatively, the EL layer 100 may include a functional layer which is capable of lowering a hole- or electron-injection barrier, improving a hole- or electron-transport property, inhibiting a hole- or electron-transport property, or suppressing a quenching phenomenon by an electrode, for example. Note that the functional layers may each be a single layer or stacked layers.

Figure 1B:
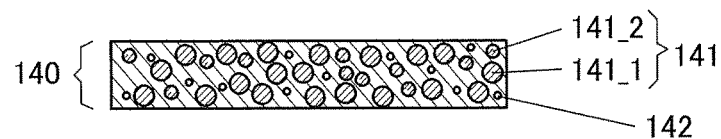

FIG. 1B is a schematic cross-sectional view illustrating an example of the light-emitting layer 140 in FIG. 1A. The light-emitting layer 140 in FIG. 1B includes a host material 141 and a guest material 142. The host material 141 includes an organic compound 141_1 and an organic compound 141_2.

The guest material 142 is a light-emitting organic material, and as examples of the light-emitting organic material, a material capable of emitting fluorescence (hereinafter referred to as a fluorescent material) and a material capable of emitting phosphorescence (hereinafter also referred to as a phosphorescent material) can be given. A structure in which a phosphorescent material is used as the guest material 142 will be described below. The guest material 142 may be rephrased as the phosphorescent material.

In the case where two kinds of host materials such as the organic compound 141_1 and the organic compound 141_2 are used (co-host system) in the light-emitting layer as illustrated in FIG. 1B, one electron-transport material and one hole-transport material are generally used as the two kinds of host materials. Such a structure, with which a hole-injection barrier between the hole-transport layer 112 and the light-emitting layer 140 and an electron-injection barrier between the electron-transport layer 118 and the light-emitting layer 140 are reduced and thus the driving voltage can be reduced, is preferable.

<Light Emission Mechanism of Light-Emitting Element>

Next, the light emission mechanism of the light-emitting layer 140 is described below.

The organic compound 141_1 and the organic compound 141_2 included in the host material 141 in the light-emitting layer 140 form an exciplex.

Figure 1C:
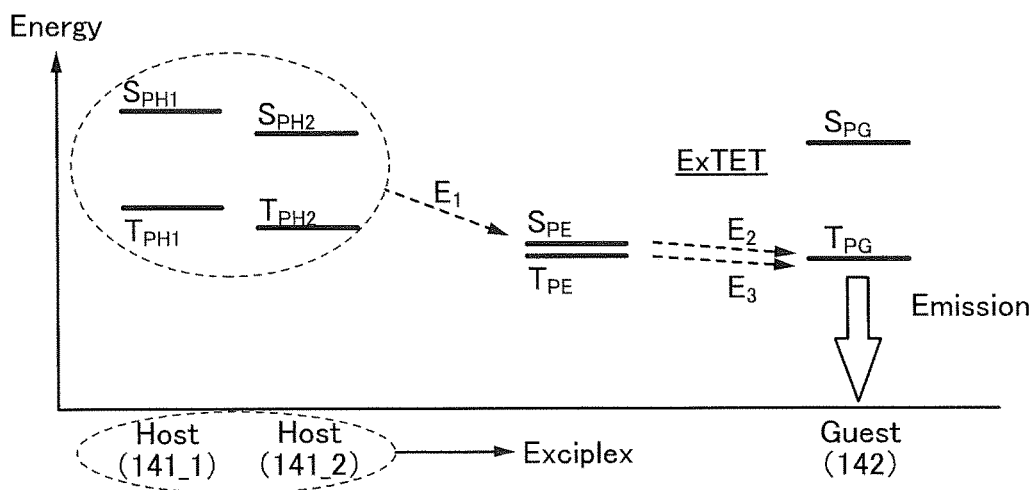

FIG. 1C shows a correlation between the energy levels of the organic compound 141_1, the organic compound 141_2, and the guest material 142 in the light-emitting layer 140. The following explains what terms and numerals in FIG. 1C represent:

Host (141_1): the organic compound 141_1 (host material);
Host (141_2): the organic compound 141_2 (host material);
Guest (142): the guest material 142 (phosphorescent compound);
$S_{PH1}$: the S1 level of the organic compound 141_1 (host material);
$T_{PH1}$: the T1 level of the organic compound 141_1 (host material);
$S_{PH2}$: the S1 level of the organic compound 141_2 (host material);
$T_{PH2}$: the T1 level of the organic compound 141_2 (host material);
$S_{PG}$: the S1 level of the guest material 142 (phosphorescent compound);
$T_{PG}$: the T1 level of the guest material 142 (phosphorescent compound);
$S_{PE}$: the S1 level of the exciplex; and
$T_{PE}$: the T1 level of the exciplex.

The organic compound 141_1 and the organic compound 141_2 form an exciplex, and the S1 level ($S_{PE}$) and the T1 level ($T_{PE}$) of the exciplex are energy levels adjacent to each other (see Route $E_1$ in FIG. 1C).

One of the organic compound 141_1 and the organic compound 141_2 receives a hole and the other receives an electron to readily form an exciplex. Alternatively, when one of the organic compounds is brought into an excited state, the other immediately interacts with the one to form an exciplex. Consequently, most excitons in the light-emitting layer 140 exist as exciplexes. Because the excitation energy levels ($S_{PE}$ and $T_{PE}$) of the exciplex are lower than the S1 levels ($S_{PH1}$ and $S_{PH2}$) of the host materials (the organic compounds 141_1 and 141_2) that form the exciplex, the excited state of the host material 141 can be formed with lower excitation energy. This can reduce the drive voltage of the light emitting element.

Both energies of $S_{PE}$ and $T_{PE}$ of the exciplex are then transferred to the T1 level of the guest material 142 (the phosphorescent compound); thus, light emission is obtained (see Routes $E_2$ and $E_3$ in FIG. 1C).

Furthermore, the T1 level ($T_{PE}$) of the exciplex is preferably higher than the T1 level ($T_{PG}$) of the guest material 142. Thus, the singlet excitation energy and the triplet excitation energy of the formed exciplex can be transferred from the S1 level ($S_{PE}$) and the T1 level ($T_{PE}$) of the exciplex to the T1 level ($T_{PG}$) of the guest material 142.

Note that in order to efficiently transfer excitation energy from the exciplex to the guest material 142, the T1 level ($T_{PE}$) of the exciplex is preferably lower than or equal to the T1 levels ($T_{PH1}$ and $T_{PH2}$) of the organic compounds (the organic compound 141_1 and the organic compound 141_2) which form the exciplex. Thus, quenching of the triplet excitation energy of the exciplex due to the organic compounds (the organic compounds 141_1 and 141_2) is less likely to occur, resulting in efficient energy transfer from the exciplex to the guest material 142.

In the case where the combination of the organic compounds 141_1 and 141_2 is a combination of a compound having a hole-transport property and a compound having an electron-transport property, the carrier balance can be easily controlled by adjusting the mixture ratio. Specifically, the weight ratio of the compound having a hole-transport property to the compound having an electron-transport property is preferably within a range of 1:9 to 9:1. Since the carrier balance can be easily controlled with the structure, a carrier recombination region can also be controlled easily.

Note that the above-described processes through Routes $E_2$ and $E_3$ may be referred to as exciplex-triplet energy transfer (ExTET) in this specification and the like. In other words, in the light-emitting layer 140, excitation energy is transferred from the exciplex to the guest material 142. In this case, the efficiency of reverse intersystem crossing from $T_{PE}$ to $S_{PE}$ and the emission quantum yield from $S_{PE}$ are not necessarily high; thus, materials can be selected from a wide range of options.

Although it is acceptable as long as the combination of the organic compound 141_1 and the organic compound 141_2 can form an exciplex, it is preferable that one have a lower HOMO (highest occupied molecular orbital) level and a lower LUMO (lowest unoccupied molecular orbital) level than the other.

The above-described ExTET is a technique which greatly contributes to improving the efficiency and reliability of a phosphorescent light-emitting element and reducing the driving voltage. Since exciplex formation is essential for ExTET, the selection of the organic compound 141_1 and the organic compound 141_2 is important.

Here, the present inventors have found that the combination of the organic compounds such that the difference between the LUMO level of the organic compound 141_1 and the LUMO level of the organic compound 141_2 is larger than 0 eV and smaller than or equal to 0.5 eV can contribute to further reducing the driving voltage of the light-emitting element. Further preferably, the difference between the LUMO level of the organic compound 141_1 and the LUMO level of the organic compound 141_2 is larger than 0 eV and smaller than or equal to 0.3 eV.

The HOMO level and the LUMO level of an organic material are generally estimated by cyclic voltammetry (CV), photoelectron spectroscopy, optical absorption spectroscopy, inverse photoemission spectroscopy, or the like. When values of materials are compared with each other, it is preferable that values estimated by the same measurement method be used.

As described above, one of the organic compounds 141_1 and 141_2 receives a hole and the other receives an electron to immediately form an exciplex. In the light-emitting element of one embodiment of the present invention, both of the organic compounds 141_1 and 141_2 are preferably bipolar materials. Since a bipolar material includes both a hole-transport skeleton and an electron-transport skeleton in one molecule, the carrier-transport property in the light-emitting layer can be improved to contribute to reducing the driving voltage.

In the case where a bipolar material is used for each of the organic compounds 141_1 and 141_2, one of them needs to receive a hole and the other needs to receive an electron to form an exciplex. Thus, in the light-emitting layer 140, it is preferable that the HOMO level of the bipolar material which receives a hole be higher than that of the bipolar material which receives an electron and the LUMO level of the bipolar material which receives an electron be lower than that of the bipolar material which receives a hole.

Here, for example, in the case where an electron-transport material is used as the organic compound 141_1 and a hole-transport material is used as the organic compound 141_2, in the light-emitting layer, the carrier (electron and/or hole)-transport property is lowered depending on the mixing ratio in some cases. That is, generally, a certain amount of electron-transport material and a certain amount of hole-transport material are required in the layer to form an exciplex; however, the electron-transport material and the hole-transport material impair the hole-transport property and the electron-transport property, respectively, so that the driving voltage is increased in some cases. In contrast, in the case where the bipolar materials are used for the organic compounds 141_1 and 141_2, the driving voltage can be reduced regardless of the mixing ratio because the bipolar material has both the electron-transport property and the hole-transport property.

<Structure Example 2 of Light-Emitting Element>

Figure 2A:
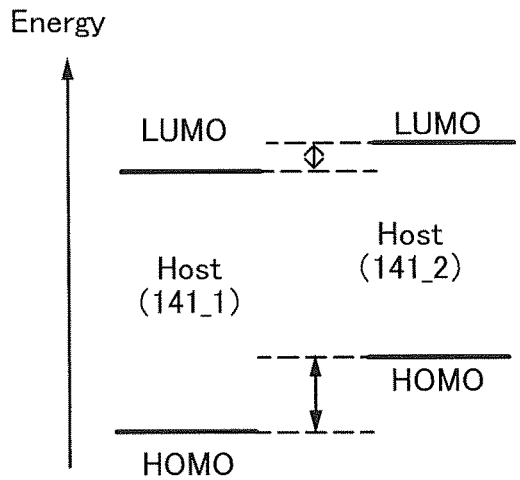
FIGS. 2A to 2C each show the correlation between energy levels in a light-emitting layer of a light-emitting element of one embodiment of the present invention.
Figure 2B:
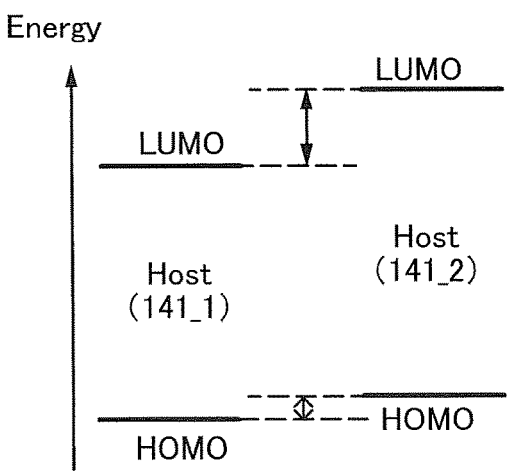
Figure 2C:
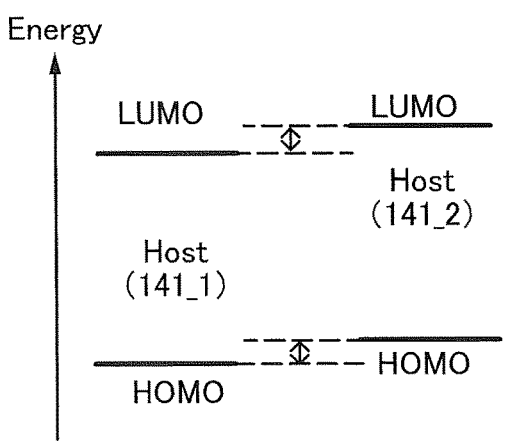

FIGS. 2A to 2C each show an energy relationship between the HOMO levels of the organic compounds 141_1 and 141_2 in the light-emitting layer 140 and an energy relationship between the LUMO levels of the organic compounds 141_1 and 141_2. In FIGS. 2A to 2C, the organic compound 141_1 is a bipolar material which receives an electron and the organic compound 141_2 is a bipolar material which receives a hole.

Since a bipolar material includes both an electron-transport skeleton and a hole-transport skeleton in one molecule, the bipolar material has excellent electron-transport and hole-transport properties. In addition, in many cases, the LUMO level and the HOMO level of the bipolar material relate to the electron-transport skeleton and the hole-transport skeleton, respectively. Thus, when appropriate skeletons are selected, the difference between the LUMO levels of the two kinds of bipolar materials and the difference between the HOMO levels thereof can be adjusted. That is, materials including appropriate skeletons are selected, whereby an electron-injection barrier and a hole-injection barrier between the two kinds of materials can be reduced. There are combinations of bipolar materials forming an exciplex which have energy relationships as shown in FIGS. 2A, 2B, and 2C.

FIG. 2A shows an example in which ExTET is utilized and a difference between the LUMO levels of two kinds of organic materials is small. The difference between the LUMO levels is preferably larger than 0 eV and smaller than or equal to 0.5 eV, further preferably larger than 0 eV and smaller than or equal to 0.3 eV. Since the difference between the LUMO levels is small, the electron-injection barrier is reduced, and the driving voltage can be reduced. In this case, hole-transport skeletons included in the bipolar materials are not particularly limited. Thus, such a structure widens the range of material choices, which is preferable. In addition, with such a structure, a material whose HOMO level is high can be selected; thus, even if a guest material whose HOMO level is high is used for a light-emitting layer, the guest material does not easily serve as a hole-trapping material. Thus, an increase in the driving voltage can be suppressed.

To utilize ExTET, as described above, it is preferable that a bipolar material which receives a hole have a higher HOMO level than a bipolar material which receives an electron and the bipolar material which receives an electron have a lower LUMO level than the bipolar material which receives a hole.

As examples of the electron-transport skeletons included in the first organic compound and the second organic compound, a π-electron deficient heteroaromatic ring, an arylborane skeleton, and a phosphine oxide skeleton are given. In particular, as the π-electron deficient heteroaromatic ring, a six-membered nitrogen-containing heterocycle, specifically, a pyridine ring, a pyridazine ring, a pyrimidine ring, a pyrazine ring, or a triazine ring, is preferable. As examples of the hole-transport skeletons included in the first organic compound and the second organic compound, a π-electron rich heteroaromatic ring and an aromatic amine skeleton are given. As the π-electron rich heteroaromatic ring, a five-membered nitrogen-containing heterocycle, specifically, a pyrrole ring, a furan ring, or a thiophene ring, is particularly preferable. Furthermore, as the aromatic amine skeleton, a triarylamine skeleton is particularly preferable. Note that in each of the first organic compound and the second organic compound, the above-described heteroaromatic ring may further condense with an aromatic ring such as a benzene ring or another heteroaromatic ring.

In one embodiment of the present invention, some of the above skeletons are appropriately selected, and a combination of the first organic compound and the second organic compound which enable ExTET is appropriately selected. The variations of the combination are described below referring to specific skeletons.

In order to achieve such a combination of materials (a combination of materials which enable ExTET) using bipolar materials, the bipolar material which receives an electron preferably includes a nitrogen-containing heteroaromatic ring as the electron-transport skeleton and a π-electron rich heteroaromatic ring as the hole-transport skeleton. A nitrogen-containing heteroaromatic ring having 8 to 18 carbon atoms is preferably included as the electron-transport skeleton so that the LUMO level is easily lowered; however, the electron-transport skeleton is not limited thereto. As examples of the electron-transport skeleton, a quinoline skeleton, a quinazoline skeleton, a quinoxaline skeleton, and a benzofuropyrimidine skeleton are further preferably given, and a dibenzoquinoxaline skeleton is still further preferably given. As examples of the hole-transport skeleton, a carbazole skeleton, a dibenzothiophene skeleton, and a dibenzofuran skeleton are further preferably given. Any of these hole-transport skeletons is preferably included so that the HOMO level is relatively easily reduced. To keep the HOMO level low, it is preferable that the bipolar material which receives an electron not include a triarylamine skeleton.

To enable ExTET, the bipolar material which receives a hole preferably includes a nitrogen-containing heteroaromatic ring as the electron-transport skeleton, and an aromatic amine skeleton, in particular a triarylamine skeleton, as the hole-transport skeleton. Note that the bipolar material which receives a hole may include a π-electron rich heteroaromatic ring. A nitrogen-containing heteroaromatic ring having 3 to 8 carbon atoms is preferably included as the electron-transport skeleton so that the LUMO level is easily increased; however, the electron-transport skeleton is not limited thereto. Specifically, a triazine skeleton or a diazine skeleton is preferable, and as examples of the diazine skeleton, a pyrimidine skeleton, a pyrazine skeleton, a quinoxaline skeleton, a dibenzoquinoxaline skeleton, a quinazoline skeleton, a benzofuropyrimidine skeleton, and the like are given. A pyrimidine skeleton is further preferable as the electron-transport skeleton. The LUMO level of a material including any of these electron-transport skeletons easily becomes higher than that of the bipolar material which receives an electron (the material including a nitrogen-containing heteroaromatic ring having 8 to 18 carbon atoms). The HOMO level of a material including an aromatic amine skeleton easily becomes higher than that of the bipolar material which receives an electron (the material including a π-electron rich heteroaromatic ring). Thus, the bipolar material which receives an electron and the bipolar material which receives a hole can form an exciplex.

To enable ExTET, the bipolar material which receives a hole may be any of compounds represented by Structural Formulae (100) to (109). The bipolar material which receives a hole is not limited to the following compounds.

[Chemical Formula 4]

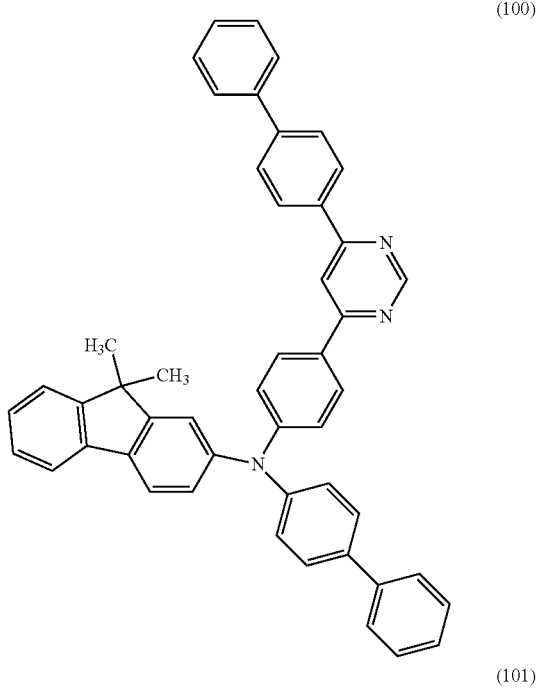

(100)

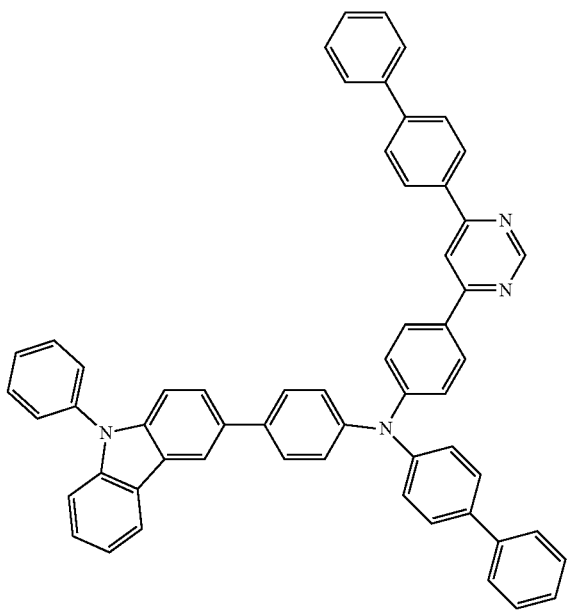

(101)

(102)
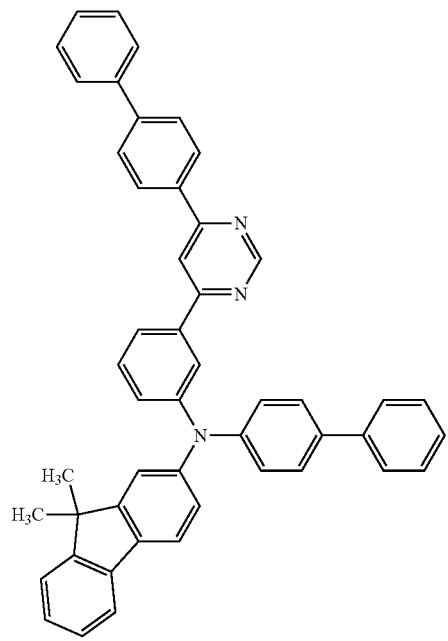
[Chemical Formula 5]
(104)
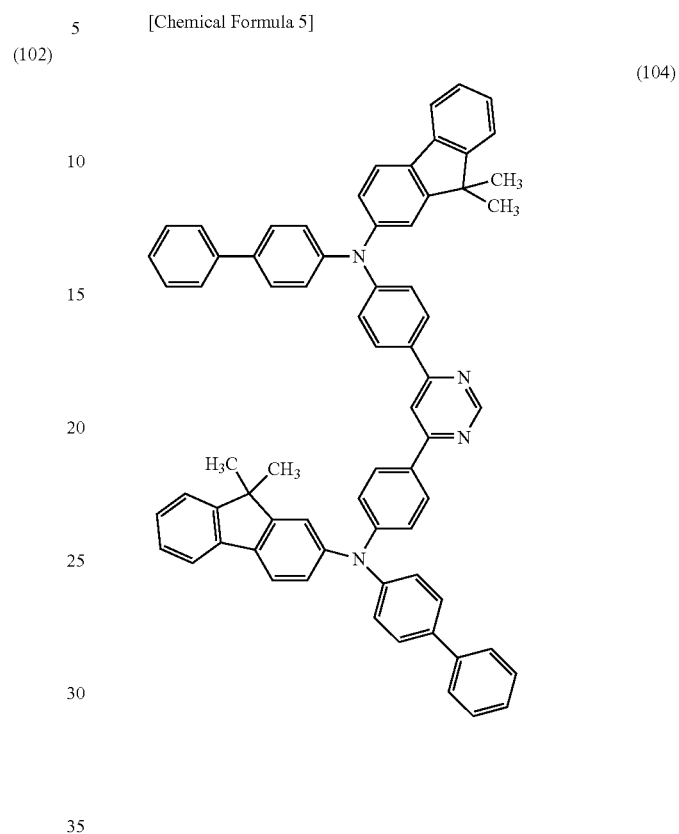
(103)
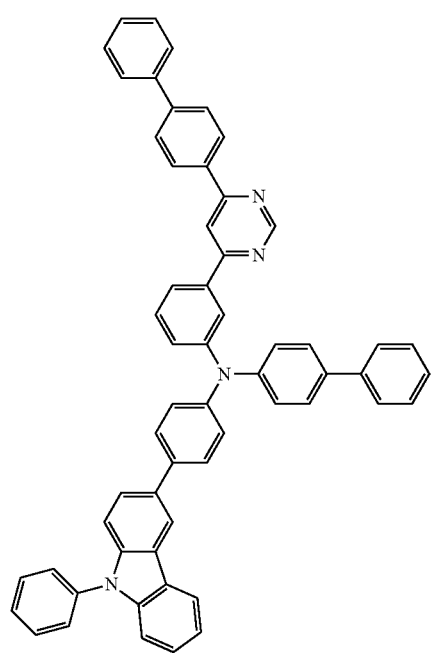
(105)
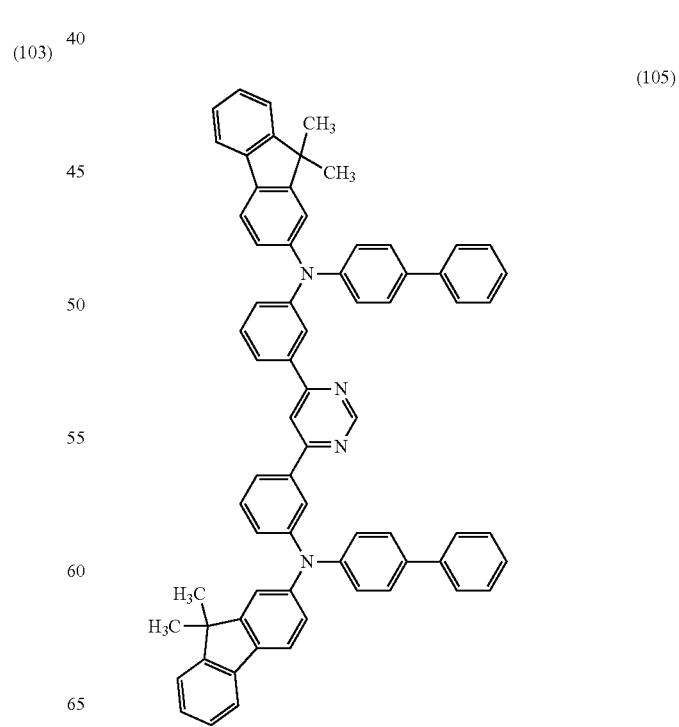

[Chemical Formula 6]

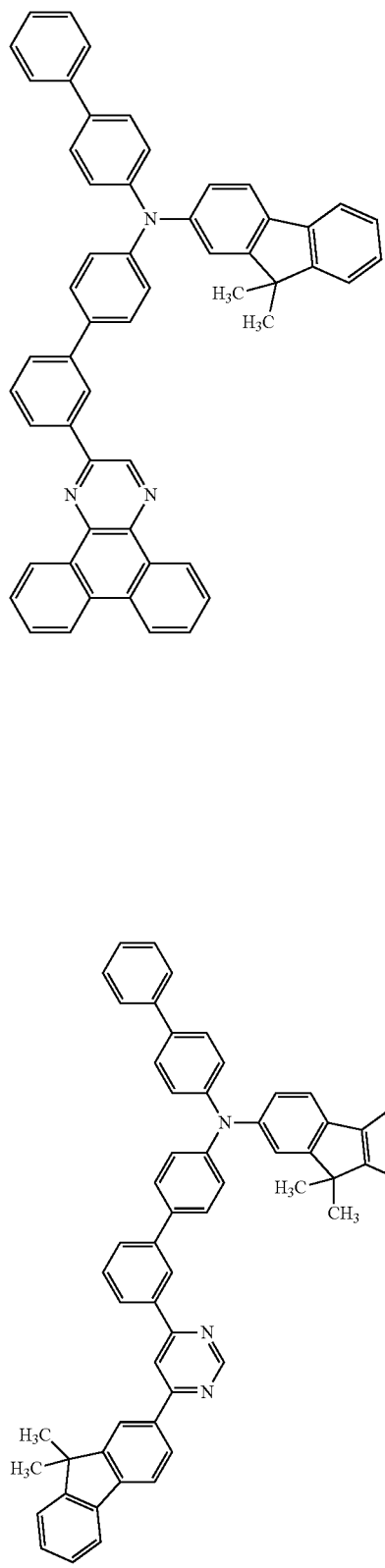

(106)

(107)

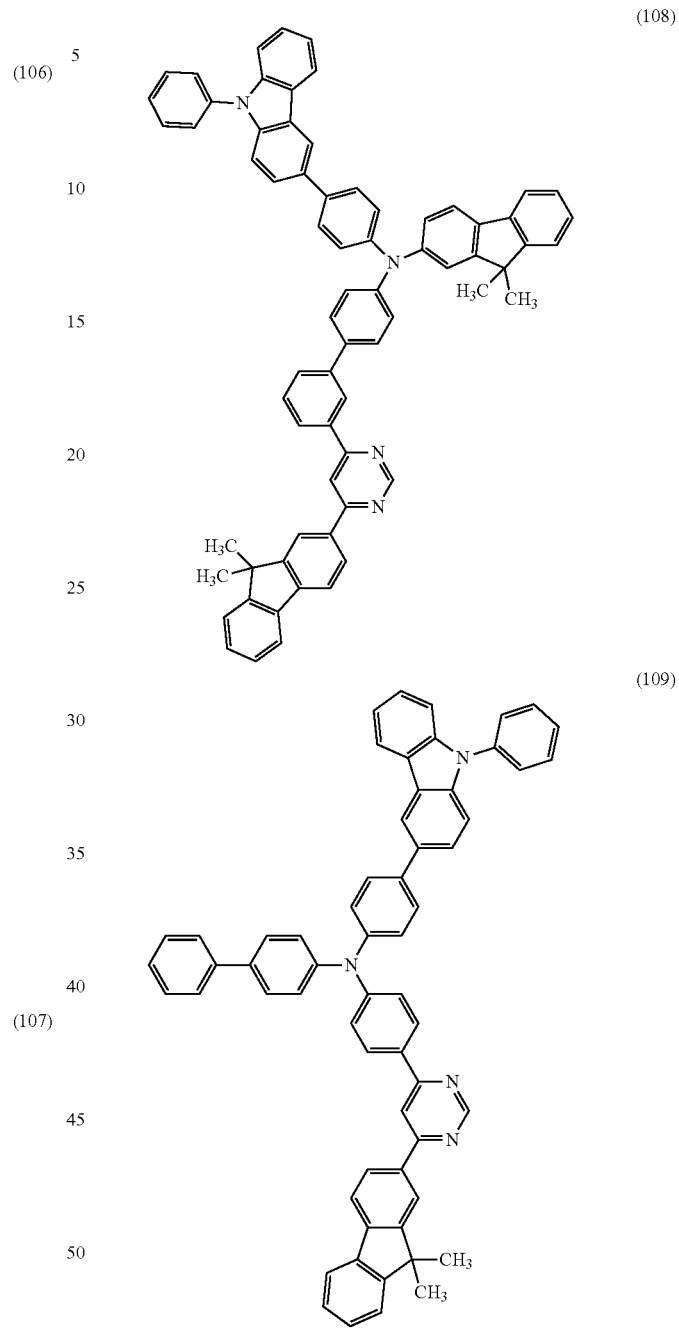

(108)

(109)

FIG. 2B shows an example in which ExTET is utilized and a difference between the HOMO levels of two kinds of organic materials, preferably bipolar materials, is small. The difference between the HOMO levels is preferably larger than 0 eV and smaller than or equal to 0.5 eV, further preferably larger than 0 eV and smaller than or equal to 0.3 eV. Since the difference between the HOMO levels is small, the hole-injection barrier is reduced, and the driving voltage can be reduced. In the case where bipolar materials are used in such a structure, electron-transport skeletons included in the bipolar materials are not particularly limited. Thus, such a structure widens the range of material choices, which is preferable. In addition, with such a structure, a material whose LUMO level is low can be selected; thus, even if a guest material whose LUMO level is low is used for a light-emitting layer, the guest material does not easily serve as an electron-trapping material. Thus, an increase in the driving voltage can be suppressed.

FIG. 2C shows an example in which ExTET is utilized and a difference between the HOMO levels and a difference between the LUMO levels of two kinds of organic materials, preferably bipolar materials, are small. Since the difference between the HOMO levels and the difference between the LUMO levels are small, the electron-injection barrier and the hole-injection barrier are reduced, and the driving voltage can be reduced.
<Material>

Next, components of a light-emitting element of one embodiment of the present invention are described in detail below.
<<Light-Emitting Layer>>

In the light-emitting layer 140, the host material 141 is present in the largest proportion by weight, and the guest material 142 (the phosphorescent material) is dispersed in the host material 141. The T1 level of the host material 141 (the organic compound 141_1 and the organic compound 141_2) in the light-emitting layer 140 is preferably higher than the T1 level of the guest material (the guest material 142) in the light-emitting layer 140.

As the organic compound 141_1, a material having a property of transporting more electrons than holes can be used, and a material having an electron mobility of $1\times10^{-6}$ $cm^2/Vs$ or higher is preferable. A compound including a π-electron deficient heteroaromatic ring skeleton such as a nitrogen-containing heteroaromatic compound, a metal complex, or a zinc- or aluminum-based metal complex can be used, for example, as the material which easily accepts electrons (the material having an electron-transport property). In particular, a nitrogen-containing heterocondensed ring is preferable. Specific examples are a metal complex having a quinoline ligand, a benzoquinoline ligand, an oxazole ligand, or a thiazole ligand, which is described as the electron-transport material that can be used in the light-emitting layer 130, an oxadiazole derivative, a triazole derivative, a benzimidazole derivative, a quinoxaline derivative, a dibenzoquinoxaline derivative, a phenanthroline derivative, a pyridine derivative, a bipyridine derivative, a pyrimidine derivative, and a triazine derivative, which are given as materials having electron-transport properties which can used for the light-emitting layer 130.

Specific examples include metal complexes having a quinoline or benzoquinoline skeleton, such as tris(8-quinolinolato)aluminum(III) (abbreviation: Alq), tris(4-methyl-8-quinolinolato)aluminum(III) (abbreviation: Almq$_3$), bis(10-hydroxybenzo[h]quinolinato)beryllium(II) (abbreviation: BeBq$_2$), bis(2-methyl-8-quinolinolato)(4-phenylphenolato)aluminum(III) (abbreviation: BAlq) and bis(8-quinolinolato)zinc(II) (abbreviation: Znq), and the like. Alternatively, a metal complex having an oxazole-based or thiazole-based ligand, such as bis[2-(2-benzoxazolyl)phenolato]zinc(II) (abbreviation: ZnPBO) or bis[2-(2-benzothiazolyl)phenolato]zinc(II) (abbreviation: ZnBTZ) can be used. Other than such metal complexes, any of the following can be used: heterocyclic compounds such as 2-(4-biphenylyl)-5-(4-tert-butylphenyl)-1,3,4-oxadiazole (abbreviation: PBD), 1,3-bis[5-(p-tert-butylphenyl)-1,3,4-oxadiazol-2-yl]benzene (abbreviation: OXD-7), 9-[4-(5-phenyl-1,3,4-oxadiazol-2-yl)phenyl]-9H-carbazole (abbreviation: CO11), 3-(biphenyl-4-yl)-4-phenyl-5-(4-tert-butylphenyl)-1,2,4-triazole (abbreviation: TAZ), 9-[4-(4,5-diphenyl-4H-1,2,4-triazol-3-yl)phenyl]-9H-carbazole (abbreviation: CzTAZ1), 2,2',2"-(1,3,5-benzenetriyl)tris(1-phenyl-1H-benzimidazole) (abbreviation: TPBI), 2-[3-(dibenzothiophen-4-yl)phenyl]-1-phenyl-1H-benzimidazole (abbreviation: mDBTBIm-II), bathophenanthroline (abbreviation: BPhen), and bathocuproine (abbreviation: BCP); heterocyclic compounds having a diazine skeleton such as 2-[3-(dibenzothiophen-4-yl)phenyl]dibenzo[f,h]quinoxaline (abbreviation: 2mDBTPDBq-II), 2-[3'-(dibenzothiophen-4-yl)biphenyl-3-yl]dibenzo[f,h]quinoxaline (abbreviation: 2mDBTBPDBq-II), 2-[3'-(9H-carbazol-9-yl)biphenyl-3-yl]dibenzo[f,h]quinoxaline (abbreviation: 2mCzBPDBq), 2-[4-(3,6-diphenyl-9H-carbazol-9-yl)phenyl]dibenzo[f,h]quinoxaline (abbreviation: 2CzPDBq-III), 7-[3-(dibenzothiophen-4-yl)phenyl]dibenzo[f,h]quinoxaline (abbreviation: 7mDBTPDBq-II), 6-[3-(dibenzothiophen-4-yl)phenyl]dibenzo[f,h]quinoxaline (abbreviation: 6mDBTPDBq-II), 2-[3-(3,9'-bi-9H-carbazol-9-yl)phenyl]dibenzo[f,h]quinoxaline (abbreviation: 2mCzCzPDBq), 4,6-bis[3-(phenanthren-9-yl)phenyl]pyrimidine (abbreviation: 4,6mPnP2Pm), 4,6-bis[3-(4-dibenzothienyl)phenyl]pyrimidine (abbreviation: 4,6mDBTP2Pm-II), and 4,6-bis[3-(9H-carbazol-9-yl)phenyl]pyrimidine (abbreviation: 4,6mCzP2Pm); heterocyclic compounds having a triazine skeleton such as 2-{4-[3-(N-phenyl-9H-carbazol-3-yl)-9H-carbazol-9-yl]phenyl}-4,6-diphenyl-1,3,5-triazine (abbreviation: PCCzPTzn); heterocyclic compounds having a pyridine skeleton such as 3,5-bis[3-(9H-carbazol-9-yl)phenyl]pyridine (abbreviation: 35DCzPPy) and 1,3,5-tri[3-(3-pyridyl)-phenyl]benzene (abbreviation: TmPyPB); and heteroaromatic compounds such as 4,4'-bis(5-methylbenzoxazol-2-yl)stilbene (abbreviation: BzOs).

Among the heterocyclic compounds, the heterocyclic compounds having a triazine skeleton, a diazine skeleton (pyrimidine, pyrazine, pyridazine), or a pyridine skeleton are highly reliable and stable and are thus preferably used. In addition, the heterocyclic compounds having the skeletons have a high electron-transport property to contribute to a reduction in driving voltage. Further alternatively, a high molecular compound such as poly(2,5-pyridinediyl) (abbreviation: PPy), poly[(9,9-dihexylfluorene-2,7-diyl)-co-(pyridine-3,5-diyl)] (abbreviation: PF-Py), or poly[(9,9-dioctylfluorene-2,7-diyl)-co-(2,2'-bipyridine-6,6'-diyl)] (abbreviation: PF-BPy) can be used. The substances described here are mainly substances having an electron mobility of $1\times10^{-6}$ $cm^2/Vs$ or higher. Note that other substances may also be used as long as their electron-transport properties are high.

As the organic compound 141_2, a substance which can form an exciplex together with the organic compound 141_1 is preferably used. Specifically, the organic compound 141_2 preferably includes a skeleton having a high donor property, such as a π-electron rich heteroaromatic ring skeleton or an aromatic amine skeleton. Examples of the compound having a π-electron rich heteroaromatic ring skeleton include heteroaromatic compounds such as a dibenzothiophene derivative, a dibenzofuran derivative, and a carbazole derivative. In that case, it is preferable that the organic compound 141_1, the organic compound 141_2, and the guest material 142 (the phosphorescent material) be selected such that the emission peak of the exciplex formed by the organic compound 141_1 and the organic compound 1412 overlaps with an absorption, specifically an absorption band on the longest wavelength side, of a triplet metal to ligand charge transfer (MLCT) transition of the guest material 142 (the phosphorescent material). This makes it possible to provide a light-emitting element with drastically improved emission efficiency. Note that in the case where a thermally activated delayed fluorescence material is used instead of the phosphorescent material, it is preferable that the absorption band on the longest wavelength side be a singlet absorption band.

As the organic compound 141_2, materials having a high hole-transport property given below can be used.

As the material having a high hole-transport property, a material having a hole mobility of $1 \times 10^{-6}$ cm$^2$/Vs or higher is preferably used. Specifically, an aromatic amine, a carbazole derivative, an aromatic hydrocarbon, a stilbene derivative, or the like can be used. Furthermore, the hole-transport material may be a high molecular compound.

Examples of the aromatic amine compounds that can be used as the material having a high hole-transport property are N,N'-di(p-tolyl)-N,N'-diphenyl-pphenylenediamine (abbreviation: DTDPPA), 4,4'-bis[N-(4-diphenylaminophenyl)-N-phenylamino]biphenyl (abbreviation: DPAB), N,N'-bis{4-[bis(3-methylphenyl)amino]phenyl}-N,N'-diphenyl-(1,1'-biphenyl)-4,4'-diamine (abbreviation: DNTPD), 1,3,5-tris[N-(4-diphenylaminophenyl)-N-phenylamino]benzene (abbreviation: DPA3B), and the like.

Specific examples of the carbazole derivative are 3-[N-(4-diphenylaminophenyl)-N-phenylamino]-9-phenylcarbazole (abbreviation: PCzDPA1), 3,6-bis[N-(4-diphenylaminophenyl)-N-phenylamino]-9-phenylcarbazole (abbreviation: PCzDPA2), 3,6-bis[N-(4-diphenylaminophenyl)-N-(1-naphthyl)amino]-9-phenylcarbazole (abbreviation: PCzTPN2), 3-[N-(9-phenylcarbazol-3-yl)-N-phenylamino]-9-phenylcarbazole (abbreviation: PCzPCA1), 3,6-bis[N-(9-phenylcarbazol-3-yl)-N-phenylamino]-9-phenylcarbazole (abbreviation: PCzPCA2), 3-[N-(1-naphthyl)-N-(9-phenylcarbazol-3-yl)amino]-9-phenylcarbazole (abbreviation: PCzPCN1), and the like.

Other examples of the carbazole derivative are 4,4'-di(N-carbazolyl)biphenyl (abbreviation: CBP), 1,3,5-tris[4-(N-carbazolyl)phenyl]benzene (abbreviation: TCPB), 9-[4-(10-phenyl-9-anthracenyl)phenyl]-9H-carbazole (abbreviation: CzPA), 1,4-bis[4-(N-carbazolyl)phenyl]-2,3,5,6-tetraphenylbenzene, and the like.

Examples of the aromatic hydrocarbon are 2-tert-butyl-9,10-di(2-naphthyl)anthracene (abbreviation: t-BuDNA), 2-tert-butyl-9,10-di(1-naphthyl)anthracene, 9,10-bis(3,5-diphenylphenyl)anthracene (abbreviation: DPPA), 2-tert-butyl-9,10-bis(4-phenylphenyl)anthracene (abbreviation: t-BuDBA), 9,10-di(2-naphthyl)anthracene (abbreviation: DNA), 9,10-diphenylanthracene (abbreviation: DPAnth), 2-tert-butylanthracene (abbreviation: t-BuAnth), 9,10-bis(4-methyl-1-naphthyl)anthracene (abbreviation: DMNA), 2-tert-butyl-9,10-bis[2-(1-naphthyl)phenyl]anthracene, 9,10-bis[2-(1-naphthyl)phenyl]anthracene, 2,3,6,7-tetramethyl-9,10-di(1-naphthyl)anthracene, 2,3,6,7-tetramethyl-9,10-di(2-naphthyl)anthracene, 9,9'-bianthryl, 10,10'-diphenyl-9,9'-bianthryl, 10,10'-bis(2-phenylphenyl)-9,9'-bianthryl, 10,10'-bis[(2,3,4,5,6-pentaphenyl)phenyl]-9,9'-bianthryl, anthracene, tetracene, rubrene, perylene, 2,5,8,11-tetra(tert-butyl)perylene, and the like. Other examples are pentacene, coronene, and the like. The aromatic hydrocarbon having a hole mobility of $1 \times 10^{-6}$ cm$^2$/Vs or higher and having 14 to 42 carbon atoms is particularly preferable.

The aromatic hydrocarbon may have a vinyl skeleton. Examples of the aromatic hydrocarbon having a vinyl group are 4,4'-bis(2,2-diphenylvinyl)biphenyl (abbreviation: DPVBi), 9,10-bis[4-(2,2-diphenylvinyl)phenyl]anthracene (abbreviation: DPVPA), and the like.

Other examples are high molecular compounds such as poly(N-vinylcarbazole) (abbreviation: PVK), poly(4-vinyltriphenylamine) (abbreviation: PVTPA), poly[N-(4-{N'-[4-(4-diphenylamino)phenyl]phenyl-N'-phenylamino}phenyl)methacrylamide] (abbreviation: PTPDMA), and poly[N,N'-bis(4-butylphenyl)-N,N'-bis(phenyl)benzidine] (abbreviation: poly-TPD).

Examples of the material having a high hole-transport property are aromatic amine compounds such as 4,4'-bis[N-(1-naphthyl)-N-phenylamino]biphenyl (abbreviation: NPB or α-NPD), N,N'-bis(3-methylphenyl)-N,N'-diphenyl-[1,1'-biphenyl]-4,4'-diamine (abbreviation: TPD), 4,4',4"-tris(carbazol-9-yl)triphenylamine (abbreviation: TCTA), 4,4',4"-tris[N-(1-naphthyl)-N-phenylamino]triphenylamine (abbreviation: 1'-TNATA), 4,4',4"-tris(N,N-diphenylamino)triphenylamine (abbreviation: TDATA), 4,4',4"-tris[N-(3-methylphenyl)-N-phenylamino]triphenylamine (abbreviation: MTDATA), 4,4'-bis[N-(spiro-9,9'-bifluoren-2-yl)-N-phenylamino]biphenyl (abbreviation: BSPB), 4-phenyl-4'-(9-phenylfluoren-9-yl)triphenylamine (abbreviation: BPAFLP), 4-phenyl-3'-(9-phenylfluoren-9-yl)triphenylamine (abbreviation: mBPAFLP), N-(9,9-dimethyl-9H-fluoren-2-yl)-N-{9,9-dimethyl-2-[N'-phenyl-N'-(9,9-dimethyl-9H-fluoren-2-yl)amino]-9H-fluoren-7-yl}phenylamine (abbreviation: DFLADFL), N-(9,9-dimethyl-2-diphenylamino-9H-fluoren-7-yl)diphenylamine (abbreviation: DPNF), 2-[N-(4-diphenylaminophenyl)-N-phenylamino]spiro-9,9'-bifluorene (abbreviation: DPASF), 4-phenyl-4'-(9-phenyl-9H-carbazol-3-yl)triphenylamine (abbreviation: PCBA1BP), 4,4'-diphenyl-4"-(9-phenyl-9H-carbazol-3-yl)triphenylamine (abbreviation: PCBBi1BP), 4-(1-naphthyl)-4'-(9-phenyl-9H-carbazol-3-yl)triphenylamine (abbreviation: PCBANB), 4,4'-di(1-naphthyl)-4"-(9-phenyl-9H-carbazol-3-yl)triphenylamine (abbreviation: PCBNBB), 4-phenyldiphenyl-(9-phenyl-9H-carbazol-3-yl)amine (abbreviation: PCA1BP), N,N'-bis(9-phenylcarbazol-3-yl)-N,N'-diphenylbenzene-1,3-diamine (abbreviation: PCA2B), N,N',N"-triphenyl-N,N',N"-tris(9-phenylcarbazol-3-yl)benzene-1,3,5-triamine (abbreviation: PCA3B), N-(4-biphenyl)-N-(9,9-dimethyl-9H-fluor-2-yl)-9-phenyl-9H-carbazol-3-amine (abbreviation: PCBiF), N-(1,1'-biphenyl-4-yl)-N-[4-(9-phenyl-9H-carbazol-3-yl)phenyl]-9,9-dimethyl-9H-fluor en-2-amine (abbreviation: PCBBiF), 9,9-dimethyl-N-phenyl-N-[4-(9-phenyl-9H-carbazol-3-yl)phenyl]fluoren-2-amine (abbreviation: PCBAF), N-phenyl-N-[4-(9-phenyl-9H-carbazol-3-yl)phenyl]spiro-9,9'-bifluoren-2-amine (abbreviation: PCBASF), 2-[N-(9-phenylcarbazol-3-yl)-N-phenylamino]spiro-9,9'-bifluorene (abbreviation: PCASF), 2,7-bis[N-(4-diphenylaminophenyl)-N-phenylamino]-spiro-9,9'-bifluorene (abbreviation: DPA2SF), N-[4-(9H-carbazol-9-yl)phenyl]-N-(4-phenyl)phenylaniline (abbreviation: YGA1BP), and N,N'-bis[4-(carbazol-9-yl)phenyl]-N,N'-diphenyl-9,9-dimethylfluorene-2,7-diamine (abbreviation: YGA2F). Other examples are amine compounds, carbazole compounds, thiophene compounds, furan compounds, fluorene compounds; triphenylene compounds; phenanthrene compounds, and the like such as 3-[4-(1-naphthyl)-phenyl]-9-phenyl-9H-carbazole (abbreviation: PCPN), 3-[4-(9-phenanthryl)-phenyl]-9-phenyl-9H-carbazole (abbreviation: PCPPn), 3,3'-bis(9-phenyl-9H-carbazole) (abbreviation: PCCP), 1,3-bis(N-carbazolyl)benzene (abbreviation: mCP), 3,6-bis(3,5-diphenylphenyl)-9-phenylcarbazole (abbreviation: CzTP), 3,6-di(9H-carbazol-9-yl)-9-phenyl-9H-carbazole (abbreviation: PhCzGI), 2,8-di(9H-carbazol-9-yl)-dibenzothiophene (abbreviation: Cz2DBT), 4-{3-[3-(9-phenyl-9H-fluoren-9-yl)phenyl]phenyl}dibenzofuran (abbreviation: mmDBFFLBi-II), 4,4',4"-(benzene-1,3,5-triyl)tri(dibenzofuran) (abbreviation: DBF3P-II), 1,3,5-tri(dibenzothiophen-4-yl)-benzene (abbreviated as DBT3P-II), 2,8-diphenyl-4-[4-(9-phenyl-9H-fluoren-9-yl)phenyl]dibenzothiophene (abbreviation: DBTFLP-III), 4-[4-(9-phenyl-9H-fluoren-9-yl)phenyl]-6-phenyldibenzothiophene (abbreviation: DBTFLP-IV), and 4-[3-(triphenylen-2-yl)phenyl]dibenzothiophene (abbreviation: mDBTPTp-II). Among the above compounds, compounds including a pyrrole skeleton, a furan skeleton, a thiophene skeleton, or an aromatic amine skeleton are preferred because of their high stability and reliability. In addition, the compounds having such skeletons have a high hole-transport property to contribute to a reduction in driving voltage.

As the guest material 142 (phosphorescent material), an iridium-, rhodium-, or platinum-based organometallic complex or metal complex can be used; in particular, an organoiridium complex such as an iridium-based ortho-metalated complex is preferable. As an ortho-metalated ligand, a 4H-triazole ligand, a 1H-triazole ligand, an imidazole ligand, a pyridine ligand, a pyrimidine ligand, a pyrazine ligand, an isoquinoline ligand, and the like can be given. As the metal complex, a platinum complex having a porphyrin ligand and the like can be given.

The organic compound 141_1, the organic compound 141_2, and the guest material 142 (phosphorescent material) are preferably selected such that the LUMO level of the guest material 142 (the phosphorescent material) is lower than that of the organic compound 141_1 and the HOMO level of the guest material 142 is lower than that of the organic compound 141_2. With this structure, a light-emitting element with high emission efficiency and low driving voltage can be obtained.

Examples of the substance that has an emission peak in the blue or green wavelength range include organometallic iridium complexes having a 4H-triazole skeleton, such as tris{2-[5-(2-methylphenyl)-4-(2,6-dimethylphenyl)-4H-1,2,4-triazol-3-yl-κN2]phenyl-κC}iridium(III) (abbreviation: Ir(mpptz-dmp)$_3$), tris(5-methyl-3,4-diphenyl-4H-1,2,4-triazolato)iridium(III) (abbreviation: Ir(Mptz)$_3$), tris[4-(3-biphenyl)-5-isopropyl-3-phenyl-4H-1,2,4-triazolato]iridium(III) (abbreviation: Ir(iPrptz-3b)$_3$), and tris[3-(5-biphenyl)-5-isopropyl-4-phenyl-4H-1,2,4-triazolato]iridium(III) (abbreviation: Ir(iPr5btz)$_3$); organometallic iridium complexes having a 1H-triazole skeleton, such as tris[3-methyl-1-(2-methylphenyl)-5-phenyl-1H-1,2,4-triazolato]iridium(III) (abbreviation: Ir(Mptz1-mp)$_3$) and tris(1-methyl-5-phenyl-3-propyl-1H-1,2,4-triazolato)iridium(III) (abbreviation: Ir(Prptz1-Me)$_3$); organometallic iridium complexes having an imidazole skeleton, such as fac-tris[1-(2,6-diisopropylphenyl)-2-phenyl-1H-imidazole]iridium(III) (abbreviation: Ir(iPrpmi)$_3$) and tris[3-(2,6-dimethylphenyl)-7-methylimidazo[1,2-f]phenanthridinato]iridium(III) (abbreviation: Ir(dmpimpt-Me)$_3$); and organometallic iridium complexes in which a phenylpyridine derivative having an electron-withdrawing group is a ligand, such as bis[2-(4',6'-difluorophenyl)pyridinato-N,C$^{2'}$]iridium(III) tetrakis(1-pyrazolyl)borate (abbreviation: Fr6), bis[2-(4',6'-difluorophenyl)pyridinato-N,C$^{2'}$]iridium(III) picolinate (abbreviation: FIrpic), bis{2-[3',5'-bis(trifluoromethyl)phenyl]pyridinato-N,C$^{2'}$}iridium(III) picolinate (abbreviation: Ir(CF$_3$ppy)$_2$(pic)), and bis[2-(4',6'-difluorophenyl)pyridinato-N,C$^{2'}$]iridium(III) acetylacetonate (abbreviation: FIr(acac)). Among the materials given above, the organic metal iridium complexes including a nitrogen-containing five-membered heterocyclic skeleton, such as a 4H-triazole skeleton, a 1H-triazole skeleton, or an imidazole skeleton have high triplet excitation energy, reliability, and emission efficiency and are thus especially preferable.

Examples of the substance that has an emission peak in the green or yellow wavelength range include organometallic iridium complexes having a pyrimidine skeleton, such as tris(4-methyl-6-phenylpyrimidinato)iridium(III) (abbreviation: Ir(mppm)$_3$), tris(4-t-butyl-6-phenylpyrimidinato)iridium(III) (abbreviation: Ir(tBuppm)$_3$), (acetylacetonato)bis(6-methyl-4-phenylpyrimidinato)iridium(III) (abbreviation: Ir(mppm)$_2$(acac)), (acetylacetonato)bis(6-tert-butyl-4-phenylpyrimidinato)iridium(III) (abbreviation: Ir(tBuppm)$_2$(acac)), (acetylacetonato)bis[4-(2-norbornyl)-6-phenylpyrimidinato]iridium(III) (abbreviation: Ir(nbppm)2(acac)), (acetylacetonato)bis[5-methyl-6-(2-methylphenyl)-4-phenylpyrimidinato]iridium(III) (abbreviation: Ir(mpmppm)$_2$(acac)), (acetylacetonato)bis{4,6-dimethyl-2-[6-(2,6-dimethylphenyl)-4-pyrimidinyl-κN3]phenyl-κ1-κC}iridium(III) (abbreviation: Ir(dmppm-dmp)$_2$(acac)), (acetylacetonato)bis(4,6-diphenylpyrimidinato)iridium(III) (abbreviation: Ir(dppm)$_2$(acac)); organometallic iridium complexes having a pyrazine skeleton, such as (acetylacetonato)bis(3,5-dimethyl-2-phenylpyrazinato)iridium(III) (abbreviation: Ir(mppr-Me)$_2$(acac)) and (acetylacetonato)bis(5-isopropyl-3-methyl-2-phenylpyrazinato)iridium(III) (abbreviation: Ir(mppr-iPr)$_2$(acac)); organometallic iridium complexes having a pyridine skeleton, such as tris(2-phenylpyridinato-N,C$^{2'}$)iridium(III) (abbreviation: Ir(ppy)$_3$), bis(2-phenylpyridinato-N,C$^{2'}$)iridium(III) acetylacetonate (abbreviation: Ir(ppy)$_2$(acac)), bis(benzo[h]quinolinato)iridium(III) acetylacetonate (abbreviation: Ir(bzq)$_2$(acac)), tris(benzo[h]quinolinato)iridium(III) (abbreviation: Ir(bzq)$_3$), tris(2-phenylquinolinato-N,C$^{2'}$)iridium(III) (abbreviation: Ir(pq)$_3$), and bis(2-phenylquinolinato-N,C$^{2'}$)iridium(III) acetylacetonate (abbreviation: Ir(pq)$_2$(acac)); organometallic iridium complexes such as bis(2,4-diphenyl-1,3-oxazolato-N,C$^{2'}$)iridium(III) acetylacetonate (abbreviation: Ir(dpo)$_2$(acac)), bis {2-[4'-(perfluorophenyl)phenyl]pyridinato-N,C$^{2'}$}iridium(III) acetylacetonate (abbreviation: Ir(p-PF-ph)$_2$(acac)), and bis(2-phenylbenzothiazolato-N,C$^{2'}$)iridium(III) acetylacetonate (abbreviation: Ir(bt)$_2$(acac)); and a rare earth metal complex such as tris(acetylacetonato)(monophenanthroline)terbium(II) (abbreviation: Tb(acac)$_3$(Phen)). Among the materials given above, the organometallic iridium complexes having a pyrimidine skeleton have distinctively high reliability and light emission efficiency and are thus particularly preferable.

Examples of the substance that has an emission peak in the yellow or red wavelength range include organometallic iridium complexes having a pyrimidine skeleton, such as (diisobutyrylmethanato)bis[4,6-bis(3-methylphenyl)pyrimidinato]iridium(III) (abbreviation: Ir(5mdppm)$_2$(dibm)), bis[4,6-bis(3-methylphenyl)pyrimidinato](dipivaloylmethanato)iridium(III) (abbreviation: Ir(5mdppm)$_2$(dpm)), and bis[4,6-di(naphthalen-1-yl)pyrimidinato](dipivaloylmethanato)iridium(III) (abbreviation: Ir(d1npm)$_2$(dpm)); organometallic iridium complexes having a pyrazine skeleton, such as (acetylacetonato)bis(2,3,5-triphenylpyrazinato)iridium(III) (abbreviation: Ir(tppr)2(acac)), bis(2,3,5-triphenylpyrazinato) (dipivaloylmethanato)iridium(III) (abbreviation: Ir(tppr)$_2$(dpm)), and (acetylacetonato)bis[2,3-bis(4-fluorophenyl)quinoxalinato]iridium(III) (abbreviation: Ir(Fdpq)$_2$(acac)); organometallic iridium complexes having a pyridine skeleton, such as tris(1-phenylisoquinolinato-N,C$^{2'}$)iridium(III) (abbreviation: Ir(piq)$_3$) and bis(1-phenylisoquinolinato-N,C$^{2'}$)iridium(III) acetylacetonate (abbreviation: Ir(piq)$_2$(acac)); a platinum complex such as 2,3,7,8,12,13,17,18-octaethyl-21H,23H-porphyrin platinum(II) (abbreviation: PtOEP); and rare earth metal complexes such as tris(1,3-diphenyl-1,3-propanedionato)(monophenanthroline)europium(III) (abbreviation: Eu(DBM)$_3$(Phen)) and tris[1-(2-thenoyl)-3,3,3-trifluoroacetonato](monophenanthroline)europium(III) (abbreviation: Eu(TTA)$_3$(Phen)). Among the materials given above, the organometallic iridium complexes having a pyrimidine skeleton have distinctively high reliability and light emission efficiency and are thus particularly preferable. Further, the organometallic iridium complexes having a pyrazine skeleton can provide red light emission with favorable chromaticity.

The above-described organometallic iridium complexes having a pyrimidine skeleton or a pyrazine skeleton have ligands with a high electron-accepting property and easily have a low LUMO level and thus are suitable for one embodiment of the present invention. Similarly, compounds (e.g., iridium complexes) with an electron-withdrawing group, such as a halogen group (e.g., a fluoro group) or a cyano group, easily have a low LUMO level and thus are suitable.

As the light-emitting material included in the light-emitting layer 140, any material can be used as long as the material can convert the triplet excitation energy into light emission. As an example of the material that can convert the triplet excitation energy into light emission, a thermally activated delayed fluorescent (TADF) material can be given in addition to a phosphorescent material. Therefore, it is acceptable that the "phosphorescent material" in the description is replaced with the "thermally activated delayed fluorescence material". Note that the thermally activated delayed fluorescence material is a material having a small difference between the triplet excitation energy level and the singlet excitation energy level and a function of converting triplet excitation energy into singlet excitation energy by reverse intersystem crossing. Thus, the TADF material can up-convert a triplet excited state into a singlet excited state (i.e., reverse intersystem crossing is possible) using a little thermal energy and efficiently exhibit light emission (fluorescence) from the singlet excited state. The TADF is efficiently obtained under the condition where the difference in energy between the triplet excitation energy level and the singlet excitation energy level is preferably larger than 0 eV and smaller than or equal to 0.2 eV, further preferably larger than 0 eV and smaller than or equal to 0.1 eV.

In the case where the thermally activated delayed fluorescence material is composed of one kind of material, any of the following materials can be used, for example.

First, a fullerene, a derivative thereof, an acridine derivative such as proflavine, eosin, and the like can be given. Furthermore, a metal-containing porphyrin, such as a porphyrin containing magnesium (Mg), zinc (Zn), cadmium (Cd), tin (Sn), platinum (Pt), indium (In), or palladium (Pd), can be given. Examples of the metal-containing porphyrin include a protoporphyrin-tin fluoride complex (SnF$_2$(Proto IX)), a mesoporphyrin-tin fluoride complex (SnF$_2$(Meso IX)), a hematoporphyrin-tin fluoride complex (SnF$_2$(Hemato IX)), a coproporphyrin tetramethyl ester-tin fluoride complex (SnF$_2$(Copro III-4Me)), an octaethylporphyrin-tin fluoride complex (SnF$_2$(OEP)), an etioporphyrin-tin fluoride complex (SnF$_2$(Etio I)), and an octaethylporphyrin-platinum chloride complex (PtCl$_2$(OEP)).

As the thermally activated delayed fluorescence material composed of one kind of material, a heterocyclic compound including a π-electron rich heteroaromatic ring and a π-electron deficient heteroaromatic ring can also be used. Specifically, 2-(biphenyl-4-yl)-4,6-bis(12-phenylindolo[2,3-a]carbazol-11-yl)-1,3,5-triazine (abbreviation: PIC-TRZ), 2-{4-[3-(N-phenyl-9H-carbazol-3-yl)-9H-carbazol-9-yl]phenyl}-4,6-diphenyl-1,3,5-triazine (abbreviation: PCCzPTzn), 2-[4-(10H-phenoxazin-10-yl)phenyl]-4,6-diphenyl-1,3,5-triazine (abbreviation: PXZ-TRZ), 3-[4-(5-phenyl-5,10-dihydrophenazin-10-yl)phenyl]-4,5-diphenyl-1,2,4-triazole (abbreviation: PPZ-3TPT), 3-(9,9-dimethyl-9H-acridin-10-yl)-9H-xanthen-9-one (abbreviation: ACRXTN), bis[4-(9,9-dimethyl-9,10-dihydroacridine)phenyl]sulfone (abbreviation: DMAC-DPS), or 10-phenyl-10H,10'H-spiro[acridin-9,9'-anthracen]-10'-one (abbreviation: ACRSA) can be used. The heterocyclic compound is preferable because of having the π-electron rich heteroaromatic ring and the π-electron deficient heteroaromatic ring, for which the electron-transport property and the hole-transport property are high. Among skeletons having the π-electron deficient heteroaromatic ring, a diazine skeleton (a pyrimidine skeleton, a pyrazine skeleton, or a pyridazine skeleton) and a triazine skeleton have high stability and reliability and are particularly preferable. Among skeletons having the π-electron rich heteroaromatic ring, an acridine skeleton, a phenoxazine skeleton, a thiophene skeleton, a furan skeleton, and a pyrrole skeleton have high stability and reliability; therefore, one or more of these skeletons are preferably included. As the pyrrole skeleton, an indole skeleton, a carbazole skeleton, or a 3-(9-phenyl-9H-carbazol-3-yl)-9H-carbazole skeleton is particularly preferred. Note that a substance in which the π-electron rich heteroaromatic ring is directly bonded to the π-electron deficient heteroaromatic ring is particularly preferable because the donor property of the π-electron rich heteroaromatic ring and the acceptor property of the π-electron deficient heteroaromatic ring are both increased and the difference between the singlet excitation energy level and the triplet excitation energy level becomes small.

The light-emitting layer 140 can have a structure in which two or more layers are stacked. For example, in the case where the light-emitting layer 140 is formed by stacking a first light-emitting layer and a second light-emitting layer in this order from the hole-transport layer side, the first light-emitting layer is formed using a substance having a hole-transport property as the host material and the second light-emitting layer is formed using a substance having an electron-transport property as the host material. A light-emitting material included in the first light-emitting layer may be the same as or different from a light-emitting material included in the second light-emitting layer. In addition, the materials may have functions of emitting light of the same color or light of different colors. Two kinds of light-emitting materials having functions of emitting light of different colors are used for the two light-emitting layers, so that light of a plurality of emission colors can be obtained at the same time. It is particularly preferable to select light-emitting materials of the light-emitting layers so that white light can be obtained by combining light emission from the two light-emitting layers.

The light-emitting layer 140 may include a material other than the host material 141 and the guest material 142.

Note that the light-emitting layer 140 can be formed by an evaporation method (including a vacuum evaporation method), an inkjet method, a coating method, gravure printing, or the like. Besides the above-mentioned materials, an inorganic compound such as a quantum dot or a high molecular compound (e.g., an oligomer, a dendrimer, and a polymer) may be used.

<<Hole-Injection Layer>>

The hole-injection layer 111 has a function of reducing a barrier for hole injection from one of the pair of electrodes (the electrode 101 or the electrode 102) to promote hole injection and is formed using a transition metal oxide, a phthalocyanine derivative, or an aromatic amine, for example. As the transition metal oxide, molybdenum oxide, vanadium oxide, ruthenium oxide, tungsten oxide, manganese oxide, or the like can be given. As the phthalocyanine derivative, phthalocyanine, metal phthalocyanine, or the like can be given. As the aromatic amine, a benzidine derivative, a phenylenediamine derivative, or the like can be given. It is also possible to use a high molecular compound such as polythiophene or polyaniline; a typical example thereof is poly(ethylenedioxythiophene)/poly(styrenesulfonic acid), which is self-doped polythiophene.

As the hole-injection layer 111, a layer containing a composite material of a hole-transport material and a material having a property of accepting electrons from the hole-transport material can also be used. Alternatively, a stack of a layer containing a material having an electron accepting property and a layer containing a hole-transport material may also be used. In a steady state or in the presence of an electric field, electric charge can be transferred between these materials. As examples of the material having an electron-accepting property, organic acceptors such as a quinodimethane derivative, a chloranil derivative, and a hexaazatriphenylene derivative can be given. A specific example is a compound having an electron-withdrawing group (a halogen group or a cyano group), such as 7,7,8,8-tetracyano-2,3,5,6-tetrafluoroquinodimethane (abbreviation: $F_4$-TCNQ), chloranil, or 2,3,6,7,10,11-hexacyano-1,4,5,8,9,12-hexaazatriphenylene (abbreviation: HAT-CN). Alternatively, a transition metal oxide such as an oxide of a metal from Group 4 to Group 8 can also be used. Specifically, vanadium oxide, niobium oxide, tantalum oxide, chromium oxide, molybdenum oxide, tungsten oxide, manganese oxide, rhenium oxide, or the like can be used. In particular, molybdenum oxide is preferable because it is stable in the air, has a low hygroscopic property, and is easily handled.

A material having a property of transporting more holes than electrons can be used as the hole-transport material, and a material having a hole mobility of $1 \times 10^{-6}$ cm$^2$/Vs or higher is preferable. Specifically, any of the aromatic amine, carbazole derivative, aromatic hydrocarbon, stilbene derivative, and the like described as examples of the hole-transport material that can be used in the light-emitting layer 140 can be used. Furthermore, the hole-transport material may be a high molecular compound.

<<Hole-Transport Layer>>

The hole-transport layer 112 is a layer containing a hole-transport material and can be formed using any of the hole-transport materials given as examples of the material of the hole-injection layer 111. In order that the hole-transport layer 112 has a function of transporting holes injected into the hole-injection layer 111 to the light-emitting layer 140, the HOMO level of the hole-transport layer 112 is preferably equal or close to the HOMO level of the hole-injection layer 111.

As the hole-transport material, a substance having a hole mobility of $1 \times 10^{-6}$ cm$^2$/Vs or higher is preferably used. Note that any substance other than the above substances may be used as long as the hole-transport property is higher than the electron-transport property. The layer including a substance having a high hole-transport property is not limited to a single layer, and two or more layers containing the aforementioned substances may be stacked.

<<Electron-Transport Layer>>

The electron-transport layer 118 has a function of transporting, to the light-emitting layer 140, electrons injected from the other of the pair of electrodes (the electrode 101 or the electrode 102) through the electron-injection layer 119. A material having a property of transporting more electrons than holes can be used as the electron-transport material, and a material having an electron mobility of $1 \times 10^{-6}$ cm$^2$/Vs or higher is preferable. As the compound which easily accepts electrons (the material having an electron-transport property), a π-electron deficient heteroaromatic compound such as a nitrogen-containing heteroaromatic compound, a metal complex, or the like can be used, for example. Specifically, a metal complex having a quinoline ligand, a benzoquinoline ligand, an oxazole ligand, or a thiazole ligand can be given. In addition, an oxadiazole derivative, a triazole derivative, a benzimidazole derivative, a quinoxaline derivative, a dibenzoquinoxaline derivative, a phenanthroline derivative, a pyridine derivative, a bipyridine derivative, a pyrimidine derivative, and a triazine derivative can be given. A substance having an electron mobility of $1 \times 10^{-6}$ cm$^2$/Vs or higher is preferable. Note that other than these substances, any substance that has a property of transporting more electrons than holes may be used for the electron-transport layer. The electron-transport layer 118 is not limited to a single layer, and may include stacked two or more layers containing the aforementioned substances.

Between the electron-transport layer 118 and the light-emitting layer 140, a layer that controls transfer of electron carriers may be provided. This is a layer formed by addition of a small amount of a substance having a high electron-trapping property to a material having a high electron-transport property described above, and the layer is capable of adjusting carrier balance by suppressing transfer of electron carriers. Such a structure is very effective in preventing a problem (such as a reduction in element lifetime) caused when electrons pass through the light-emitting layer.

<<Electron-Injection Layer>>

The electron-injection layer 119 has a function of reducing a barrier for electron injection from the electrode 102 to promote electron injection and can be formed using a Group 1 metal or a Group 2 metal, or an oxide, a halide, or a carbonate of any of the metals, for example. Alternatively, a composite material containing an electron-transport material (described above) and a material having a property of donating electrons to the electron-transport material can also be used. As the material having an electron-donating property, a Group 1 metal, a Group 2 metal, an oxide of any of the metals, or the like can be given. Specifically, an alkali metal, an alkaline earth metal, or a compound thereof, such as lithium fluoride (LiF), sodium fluoride (NaF), cesium fluoride (CsF), calcium fluoride (CaF$_2$), or lithium oxide (LiO$_x$), can be used. Alternatively, a rare earth metal compound like erbium fluoride (ErF$_3$) can be used. Electride may also be used for the electron-injection layer 119. Examples of the electride include a substance in which electrons are added at high concentration to calcium oxide-aluminum oxide. The electron-injection layer 119 can be formed using the substance that can be used for the electron-transport layer 118.

A composite material in which an organic compound and an electron donor (donor) are mixed may also be used for the electron-injection layer 119. Such a composite material is excellent in an electron-injection property and an electron-transport property because electrons are generated in the organic compound by the electron donor. In this case, the organic compound is preferably a material that is excellent in transporting the generated electrons. Specifically, the above-listed substances for forming the electron-transport layer 118 (e.g., the metal complexes and heteroaromatic compounds) can be used, for example. As the electron donor, a substance showing an electron-donating property with respect to the organic compound may be used. Specifically, an alkali metal, an alkaline earth metal, and a rare earth metal are preferable, and lithium, sodium, cesium, magnesium, calcium, erbium, and ytterbium are given. In addition, an alkali metal oxide or an alkaline earth metal oxide is preferable, and lithium oxide, calcium oxide, barium oxide, and the like are given. A Lewis base such as magnesium oxide can also be used. An organic compound such as tetrathiafulvalene (abbreviation: TTF) can also be used.

Note that the light-emitting layer, the hole-injection layer, the hole-transport layer, the electron-transport layer, and the electron-injection layer described above can each be formed by an evaporation method (including a vacuum evaporation method), an inkjet method, a coating method, a gravure printing method, or the like. Besides the above-mentioned materials, an inorganic compound such as a quantum dot or a high molecular compound (e.g., an oligomer, a dendrimer, and a polymer) may be used in the light-emitting layer, the hole-injection layer, the hole-transport layer, the electron-transport layer, and the electron-injection layer.

The quantum dot may be a colloidal quantum dot, an alloyed quantum dot, a core-shell quantum dot, or a core quantum dot, for example. The quantum dot containing elements belonging to Groups 2 and 16, elements belonging to Groups 13 and 15, elements belonging to Groups 13 and 17, elements belonging to Groups 11 and 17, or elements belonging to Groups 14 and 15 may be used. Alternatively, the quantum dot containing an element such as cadmium (Cd), selenium (Se), zinc (Zn), sulfur (S), phosphorus (P), indium (In), tellurium (Te), lead (Pb), gallium (Ga), arsenic (As), or aluminum (Al) may be used.

<<Pair of Electrodes>>

The electrodes 101 and 102 function as an anode and a cathode of each light-emitting element. The electrodes 101 and 102 can be formed using a metal, an alloy, or a conductive compound, a mixture or a stack thereof, or the like.

One of the electrode 101 and the electrode 102 is preferably formed using a conductive material having a function of reflecting light. Examples of the conductive material include aluminum (Al), an alloy containing Al, and the like. Examples of the alloy containing Al include an alloy containing Al and L (L represents one or more of titanium (Ti), neodymium (Nd), nickel (Ni), and lanthanum (La)), such as an alloy containing Al and Ti and an alloy containing Al, Ni, and La. Aluminum has low resistance and high light reflectivity. Aluminum is included in earth's crust in large amount and is inexpensive; therefore, it is possible to reduce costs for manufacturing a light-emitting element with aluminum. Alternatively, Ag, an alloy of silver (Ag) and N (N represents one or more of yttrium (Y), Nd, magnesium (Mg), ytterbium (Yb), Al, Ti, gallium (Ga), zinc (Zn), indium (In), tungsten (W), manganese (Mn), tin (Sn), iron (Fe), Ni, copper (Cu), palladium (Pd), iridium (Ir), or gold (Au)), or the like can be used. Examples of the alloy containing silver include an alloy containing silver, palladium, and copper, an alloy containing silver and copper, an alloy containing silver and magnesium, an alloy containing silver and nickel, an alloy containing silver and gold, an alloy containing silver and ytterbium, and the like. Besides, a transition metal such as tungsten, chromium (Cr), molybdenum (Mo), copper, or titanium can be used.

Light emitted from the light-emitting layer is extracted through the electrode 101 and/or the electrode 102. Thus, at least one of the electrode 101 and the electrode 102 is preferably formed using a conductive material having a function of transmitting light. As the conductive material, a conductive material having a visible light transmittance higher than or equal to 40% and lower than or equal to 100%, preferably higher than or equal to 60% and lower than or equal to 100%, and a resistivity lower than or equal to $1 \times 10^{-2}$ Ω·cm can be used.

The electrodes 101 and 102 may each be formed using a conductive material having functions of transmitting light and reflecting light. As the conductive material, a conductive material having a visible light reflectivity higher than or equal to 20% and lower than or equal to 80%, preferably higher than or equal to 40% and lower than or equal to 70%, and a resistivity lower than or equal to $1 \times 10^{-2}$ Ω·cm can be used. For example, one or more kinds of conductive metals and alloys, conductive compounds, and the like can be used. Specifically, a metal oxide such as indium tin oxide (hereinafter, referred to as ITO), indium tin oxide containing silicon or silicon oxide (ITSO), indium oxide-zinc oxide (indium zinc oxide), indium oxide-tin oxide containing titanium, indium titanium oxide, or indium oxide containing tungsten oxide and zinc oxide can be used. A metal thin film having a thickness that allows transmission of light (preferably, a thickness greater than or equal to 1 nm and less than or equal to 30 nm) can also be used. As the metal, Ag, an alloy of Ag and Al, an alloy of Ag and Mg, an alloy of Ag and Au, an alloy of Ag and ytterbium (Yb), or the like can be used.

In this specification and the like, as the material transmitting light, a material that transmits visible light and has conductivity is used. Examples of the material include, in addition to the above-described oxide conductor typified by an ITO, an oxide semiconductor and an organic conductor containing an organic substance. Examples of the organic conductive containing an organic substance include a composite material in which an organic compound and an electron donor (donor material) are mixed and a composite material in which an organic compound and an electron acceptor (acceptor material) are mixed. Alternatively, an inorganic carbon-based material such as graphene may be used. The resistivity of the material is preferably lower than or equal to $1 \times 10^5$ Ω·cm, further preferably lower than or equal to $1 \times 10^4$ Ω·cm.

Alternatively, the electrode 101 and/or the electrode 102 may be formed by stacking two or more of these materials.

In order to improve the light extraction efficiency, a material whose refractive index is higher than that of an electrode having a function of transmitting light may be formed in contact with the electrode. The material may be electrically conductive or non-conductive as long as it has a function of transmitting visible light. In addition to the oxide conductors described above, an oxide semiconductor and an organic substance are given as the examples of the material. Examples of the organic substance include the materials for the light-emitting layer, the hole-injection layer, the hole-transport layer, the electron-transport layer, and the electron-injection layer. Alternatively, an inorganic carbon-based material or a metal film thin enough to transmit light can be used. Further alternatively, stacked layers with a thickness of several nanometers to several tens of nanometers may be used.

In the case where the electrode 101 or the electrode 102 functions as the cathode, the electrode preferably contains a material having a low work function (lower than or equal to 3.8 eV). The examples include an element belonging to Group 1 or 2 of the periodic table (e.g., an alkali metal such as lithium, sodium, or cesium, an alkaline earth metal such as calcium or strontium, or magnesium), an alloy containing any of these elements (e.g., Ag—Mg or Al—Li), a rare earth metal such as europium (Eu) or Yb, an alloy containing any of these rare earth metals, an alloy containing aluminum and silver, and the like.

When the electrode 101 or the electrode 102 is used as an anode, a material with a high work function (4.0 eV or higher) is preferably used.

The electrode 101 and the electrode 102 may be a stacked layer of a conductive material having a function of reflecting light and a conductive material having a function of transmitting light. In that case, the electrode 101 and the electrode 102 can have a function of adjusting the optical path length so that light with a desired wavelength emitted from each light-emitting layer resonates and is intensified, which is preferable.

As the method for forming the electrode 101 and the electrode 102, a sputtering method, an evaporation method, a printing method, a coating method, a molecular beam epitaxy (MBE) method, a CVD method, a pulsed laser deposition method, an atomic layer deposition (ALD) method, or the like can be used as appropriate.

<<Substrate>>

A light-emitting element in one embodiment of the present invention may be formed over a substrate of glass, plastic, or the like. As the way of stacking layers over the substrate, layers may be sequentially stacked from the electrode 101 side or sequentially stacked from the electrode 102 side.

For the substrate over which the light-emitting element of one embodiment of the present invention can be formed, glass, quartz, plastic, or the like can be used, for example. Alternatively, a flexible substrate can be used. The flexible substrate means a substrate that can be bent, such as a plastic substrate made of polycarbonate or polyarylate, for example. Alternatively, a film, an inorganic vapor deposition film, or the like can be used. Another material may be used as long as the substrate functions as a support in a manufacturing process of the light-emitting element or an optical element or as long as it has a function of protecting the light-emitting element or an optical element.

The structure described above in this embodiment can be combined with any of the other embodiments as appropriate.

Embodiment 2

In this embodiment, one embodiment of a light-emitting element having a structure in which a plurality of light-emitting units are stacked (hereinafter, also referred to as stacked-type element) is described with reference to FIG. 3. This light-emitting element includes a plurality of light-emitting units between a first electrode and a second electrode. Each light-emitting unit can have the same structure as the EL layer 103 which is described in Embodiment 1. In other words, the light-emitting element described in Embodiment 1 includes one light-emitting unit while the light-emitting element described in this embodiment includes a plurality of light-emitting units.

<Structure Example 3 of Light-Emitting Element>

Figure 3:
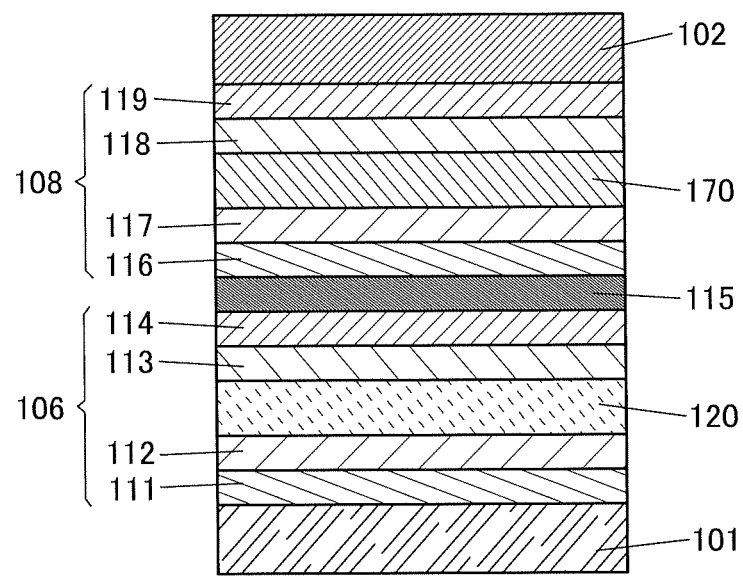
FIG. 3 is a schematic cross-sectional view of a light-emitting element of one embodiment of the present invention.

FIG. 3 is a schematic cross-sectional view of a light-emitting element 250.

The light-emitting element 250 illustrated in FIG. 3 includes a plurality of light-emitting units (a light-emitting unit 106 and a light-emitting unit 108 in FIG. 3) between a pair of electrodes (the electrode 101 and the electrode 102). One of light-emitting units preferably has the same structure as the EL layer 100 illustrated in FIGS. 1A and 1B. That is, it is preferable that the light-emitting element 150 in FIGS. 1A and 1B include one light-emitting unit, while the light-emitting element 250 include a plurality of light-emitting units. Note that the electrode 101 functions as an anode and the electrode 102 functions as a cathode in the following description of the light-emitting element 250; however, the functions may be interchanged in the light-emitting element 250.

In the light-emitting element 250 illustrated in FIG. 3, the light-emitting unit 106 and the light-emitting unit 108 are stacked, and a charge-generation layer 115 is provided between the light-emitting unit 106 and the light-emitting unit 108. Note that the light-emitting unit 106 and the light-emitting unit 108 may have the same structure or different structures. For example, it is preferable that the EL layer 100 illustrated in FIGS. 1A and 1B be used in the light-emitting unit 108.

The light-emitting element 250 includes a light-emitting layer 120 and a light-emitting layer 170. The light-emitting unit 106 includes the hole-injection layer 111, the hole-transport layer 112, an electron-transport layer 113, and an electron-injection layer 114 in addition to the light-emitting layer 120. The light-emitting unit 108 includes a hole-injection layer 116, a hole-transport layer 117, an electron-transport layer 118, and an electron-injection layer 119 in addition to the light-emitting layer 170.

The charge-generation layer 115 may have either a structure in which an acceptor substance that is an electron acceptor is added to a hole-transport material or a structure in which a donor substance that is an electron donor is added to an electron-transport material. Alternatively, both of these structures may be stacked.

In the case where the charge-generation layer 115 contains a composite material of an organic compound and an acceptor substance, the composite material that can be used for the hole-injection layer 111 described in Embodiment 1 may be used for the composite material. As the organic compound, a variety of compounds such as an aromatic amine compound, a carbazole compound, an aromatic hydrocarbon, and a high molecular compound (such as an oligomer, a dendrimer, or a polymer) can be used. A substance having a hole mobility of $1 \times 10^{-6}$ cm$^2$/Vs or higher is preferably used as the organic compound. Note that any other material may be used as long as it has a property of transporting more holes than electrons. Since the composite material of an organic compound and an acceptor substance has excellent carrier-injection and carrier-transport properties, low-voltage driving or low-current driving can be realized. Note that when a surface of a light-emitting unit on the anode side is in contact with the charge-generation layer 115, the charge-generation layer 115 can also serve as a hole-injection layer or a hole-transport layer of the light-emitting unit; thus, a hole-injection layer or a hole-transport layer is not necessarily included in the light-emitting unit. Alternatively, when a surface of the light-emitting unit on the cathode side is in contact with the charge-generation layer 115, the charge-generation layer 115 can also serve as an electron-injection layer or an electron-transport layer of the light-emitting unit; thus, an electron-injection layer or an electron-transport layer is not necessarily included in the light-emitting unit.

The charge-generation layer 115 may have a stacked structure of a layer containing the composite material of an organic compound and an acceptor substance and a layer containing another material. For example, the charge-generation layer 115 may be formed using a combination of a layer containing the composite material of an organic compound and an acceptor substance with a layer containing one compound selected from among electron-donating materials and a compound having a high electron-transport property. Furthermore, the charge-generation layer 115 may be formed using a combination of a layer containing the composite material of an organic compound and an acceptor substance with a layer containing a transparent conductive material.

Note that the charge-generation layer 115 provided between the light-emitting unit 106 and the light-emitting unit 108 may have any structure as long as electrons can be injected to the light-emitting unit on one side and holes can be injected into the light-emitting unit on the other side when a voltage is applied between the electrode 101 and the electrode 102. For example, in FIG. 3, the charge-generation layer 115 injects electrons into the light-emitting unit 106 and holes into the light-emitting unit 108 when a voltage is applied such that the potential of the electrode 101 is higher than that of the electrode 102.

Note that in terms of light extraction efficiency, the charge-generation layer 115 preferably has a visible light transmittance (specifically, a visible light transmittance of higher than or equal to 40%). The charge-generation layer 115 functions even if it has lower conductivity than the pair of electrodes (the electrodes 101 and 102).

Forming the charge-generation layer 115 by using any of the above materials can suppress an increase in drive voltage caused by the stack of the light-emitting layers.

Furthermore, as described in Embodiment 1, in the light-emitting layer 140 or the light-emitting layer 170, bipolar materials are used as the two kinds of host materials in the light-emitting layer and the LUMO levels or the HOMO levels of the bipolar materials are adjusted, whereby the driving voltage can be further reduced.

The charge-generation layer 115 may have a stacked-layer structure of a layer containing a composite material of an organic compound and a metal oxide and a layer containing another material. For example, a layer containing the composite material of an organic compound and a metal oxide may be combined with a layer containing a compound of a substance selected from electron-donating substances and a compound having a high electron-transport property. Moreover, the charge-generation layer 115 may be formed using a combination of a layer containing the composite material of an organic compound and a metal oxide with a transparent conductive film.

The charge-generation layer 115 provided between the light-emitting unit 106 and the light-emitting unit 108 may have any structure as long as electrons can be injected into the light-emitting unit on one side and holes can be injected into the light-emitting unit on the other side when a voltage is applied between the first electrode 101 and the second electrode 102. For example, in FIG. 3, the charge-generation layer 115 injects electrons into the light-emitting unit 106 and holes into the light-emitting unit 108 when a voltage is applied such that the potential of the first electrode 101 is higher than that of the second electrode 102.

Although the light-emitting element having two light-emitting units is described in this embodiment, the present invention can be similarly applied to a light-emitting element in which three or more light-emitting units are stacked. With a plurality of light-emitting units partitioned by the charge-generation layer between a pair of electrodes, as in the light-emitting element of this embodiment, light with high luminance can be obtained while current density is kept low; thus, a light-emitting element having a long lifetime can be obtained. Moreover, a light-emitting device that can be driven at a low voltage and has low power consumption can be achieved.

Note that in each of the above-described structures, the emission colors of the guest materials used in the light-emitting unit 106 and the light-emitting unit 108 may be the same or different. In the case where the same guest materials emitting light of the same color are used for the light-emitting unit 106 and the light-emitting unit 108, the light-emitting element 250 can exhibit high emission luminance at a small current value, which is preferable. In the case where guest materials emitting light of different colors are used for the light-emitting unit 106 and the light-emitting unit 108, the light-emitting element 250 can exhibit multi-color light emission, which is preferable. In that case, when a plurality of light-emitting materials with different emission wavelengths are used in one or both of the light-emitting layers 120 and 170, lights with different emission peaks synthesize light emission from the light-emitting element 250. That is, the emission spectrum of the light-emitting element 250 has at least two maximum values.

The above structure is also suitable for obtaining white light emission. When the light-emitting layer 120 and the light-emitting layer 170 emit light of complementary colors, white light emission can be obtained. It is particularly favorable to select the guest materials so that white light emission with high color rendering properties or light emission of at least red, green, and blue can be obtained.

At least one of the light-emitting layers 120 and 170 may be divided into layers and each of the divided layers may contain a different light-emitting material. That is, at least one of the light-emitting layers 120 and 170 may consist of two or more layers. For example, in the case where the light-emitting layer is formed by stacking a first light-emitting layer and a second light-emitting layer in this order from the hole-transport layer side, the first light-emitting layer is formed using a material having a hole-transport property as the host material and the second light-emitting layer is formed using a material having an electron-transport property as the host material. In that case, a light-emitting material included in the first light-emitting layer may be the same as or different from a light-emitting material included in the second light-emitting layer. In addition, the materials may have functions of emitting light of the same color or light of different colors. White light emission with a high color rendering property that is formed of three primary colors or four or more colors can be obtained by using a plurality of light-emitting materials emitting light of different colors.

This embodiment can be combined with any of the other embodiments as appropriate.

Embodiment 3

In this embodiment, a light-emitting device including the light-emitting element described in Embodiment 1 and Embodiment 2 is described with reference to FIGS. 4A and 4B.

FIG. 4A is a top view of the light-emitting device and FIG. 4B is a cross-sectional view taken along the lines A-B and C-D in FIG. 4A. The light-emitting device includes a driver circuit portion (source side driver circuit) 601, a pixel portion 602, and a driver circuit portion (gate side driver circuit) 603, which control light emission of a light-emitting element and are illustrated with dotted lines. Moreover, a reference numeral 604 denotes a sealing substrate, a reference numeral 625 denotes a desiccant, and a reference numeral 605 denotes a sealant. A portion surrounded by the sealant 605 is a space 607.

Note that a lead wiring 608 is a wiring for transmitting signals to be input to the source side driver circuit 601 and the gate side driver circuit 603 and for receiving a video signal, a clock signal, a start signal, a reset signal, and the like from a flexible printed circuit (FPC) 609 functioning as an external input terminal. Although only the FPC is illustrated here, a printed wiring board (PWB) may be attached to the FPC. The light-emitting device in this specification includes, in its category, not only the light-emitting device itself but also the light-emitting device provided with the FPC or the PWB.

Next, a cross-sectional structure of the light-emitting device is described with reference to FIG. 4B. The driver circuit portion and the pixel portion are formed over an element substrate 610. Here, the source side driver circuit 601, which is the driver circuit portion, and one pixel of the pixel portion 602 are illustrated.

In the source side driver circuit 601, a CMOS circuit is formed in which an n-channel TFT 623 and a p-channel TFT 624 are combined. The driver circuit may be formed using various circuits such as a CMOS circuit, a PMOS circuit, or an NMOS circuit. Although a driver-integrated type in which the driver circuit is formed over the substrate is described in this embodiment, the driver circuit is not necessarily formed over the substrate, and may be formed outside the substrate.

The pixel portion 602 includes a plurality of pixels including a switching TFT 611, a current controlling TFT 612, and a first electrode 613 electrically connected to a drain of the current controlling TFT 612. Note that an insulator 614 is formed to cover an end portion of the first electrode 613. The insulator 614 can be formed using a positive photosensitive resin film.

In order to improve coverage with a film that is formed over the insulator 614, the insulator 614 is formed to have a curved surface with curvature at its upper or lower end portion. For example, in the case where photosensitive acrylic is used as a material of the insulator 614, only the upper end portion of the insulator 614 preferably has a curved surface. The radius of curvature of the curved surface is preferably greater than or equal to 0.2 μm and less than or equal to 0.3 μm. As the insulator 614, either a negative photosensitive material or a positive photosensitive material can be used.

An EL layer 616 and a second electrode 617 are formed over the first electrode 613. As a material used for the first electrode 613 which functions as an anode, a material having a high work function is preferably used. For example, a single-layer film of an ITO film, an indium tin oxide film containing silicon, an indium oxide film containing zinc oxide at 2 wt % to 20 wt %, a titanium nitride film, a chromium film, a tungsten film, a Zn film, a Pt film, or the like, a stack including a titanium nitride film and a film containing aluminum as its main component, a stack including three layers of a titanium nitride film, a film containing aluminum as its main component, and a titanium nitride film, or the like can be used. The stacked structure achieves low wiring resistance, a favorable ohmic contact, and a function as an anode.

The EL layer 616 is formed by any of a variety of methods such as an evaporation method using an evaporation mask, an inkjet method, and a spin coating method. As another material included in the EL layer 616, a low molecular compound or a high molecular compound (including an oligomer or a dendrimer) may be used.

As a material used for the second electrode 617, which is formed over the EL layer 616 and functions as a cathode, a material having a low work function (e.g., Al, Mg, Li, Ca, or an alloy or a compound thereof, such as MgAg, MgIn, or AlLi) is preferably used. In the case where light generated in the EL layer 616 passes through the second electrode 617, a stack including a thin metal film and a transparent conductive film (e.g., ITO, indium oxide containing zinc oxide at 2 wt % or higher and 20 wt % or lower, indium tin oxide containing silicon, or zinc oxide (ZnO)) is preferably used for the second electrode 617.

Note that a light-emitting element 618 is formed with the first electrode 613, the EL layer 616, and the second electrode 617. The light-emitting element 618 preferably has the structure described in Embodiment 1 and Embodiment 2. In the light-emitting device of this embodiment, the pixel portion, which includes a plurality of light-emitting elements, may include both the light-emitting element with the structure described in Embodiment 1 and Embodiment 2 and a light-emitting element with a different structure.

The sealing substrate 604 is attached to the element substrate 610 with the sealant 605, so that the light-emitting element 618 is provided in the space 607 surrounded by the element substrate 610, the sealing substrate 604, and the sealant 605. The space 607 is filled with a filler. The filler may be an inert gas (such as nitrogen or argon), or a resin and/or a desiccant.

An epoxy-based resin or glass frit is preferably used for the sealant 605. It is preferable that such a material do not transmit moisture or oxygen as much as possible. As the sealing substrate 604, a glass substrate, a quartz substrate, or a plastic substrate formed of fiber reinforced plastic (FRP), polyvinyl fluoride (PVF), polyester, acrylic, or the like can be used.

As described above, the light-emitting device including the light-emitting element described in Embodiment 1 and Embodiment 2 can be obtained.

<Structure Example 1 of Light-Emitting Device>

As an example of a display device, FIGS. 5A and 5B each illustrate a light-emitting device including a light-emitting element exhibiting white light emission and a coloring layer (a color filter).

FIG. 5A illustrates a substrate 1001, a base insulating film 1002, a gate insulating film 1003, gate electrodes 1006, 1007, and 1008, a first interlayer insulating film 1020, a second interlayer insulating film 1021, a peripheral portion 1042, a pixel portion 1040, a driver circuit portion 1041, first electrodes 1024W, 1024R, 1024G, and 1024B of light-emitting elements, a partition 1026, an EL layer 1028, a second electrode 1029 of the light-emitting elements, a sealing substrate 1031, a sealant 1032, and the like.

In FIGS. 5A and 5B, coloring layers (a red coloring layer 1034R, a green coloring layer 1034G, and a blue coloring layer 1034B) are provided on a transparent base material 1033. A black layer (a black matrix) 1035 may be additionally provided. The transparent base material 1033 provided with the coloring layers and the black layer is positioned and fixed to the substrate 1001. Note that the coloring layers and the black layer are covered with an overcoat layer 1036. In FIG. 5A, light emitted from some of the light-emitting layers does not pass through the coloring layers, while light emitted from the others of the light-emitting layers passes through the coloring layers. Since light that does not pass through the coloring layers is white and light that passes through any one of the coloring layers is red, blue, or green, an image can be displayed using pixels of the four colors.

FIG. 5B illustrates an example in which the red coloring layer 1034R, the green coloring layer 1034G, and the blue coloring layer 1034B are formed between the gate insulating film 1003 and the first interlayer insulating film 1020. As illustrated in FIG. 5B, the coloring layers may be provided between the substrate 1001 and the sealing substrate 1031.

The above-described light-emitting device has a structure in which light is extracted from the substrate 1001 side where the TFTs are formed (a bottom emission structure), but may have a structure in which light is extracted from the sealing substrate 1031 side (a top emission structure).

<Structure Example 2 of Light-Emitting Device>

Figure 6:
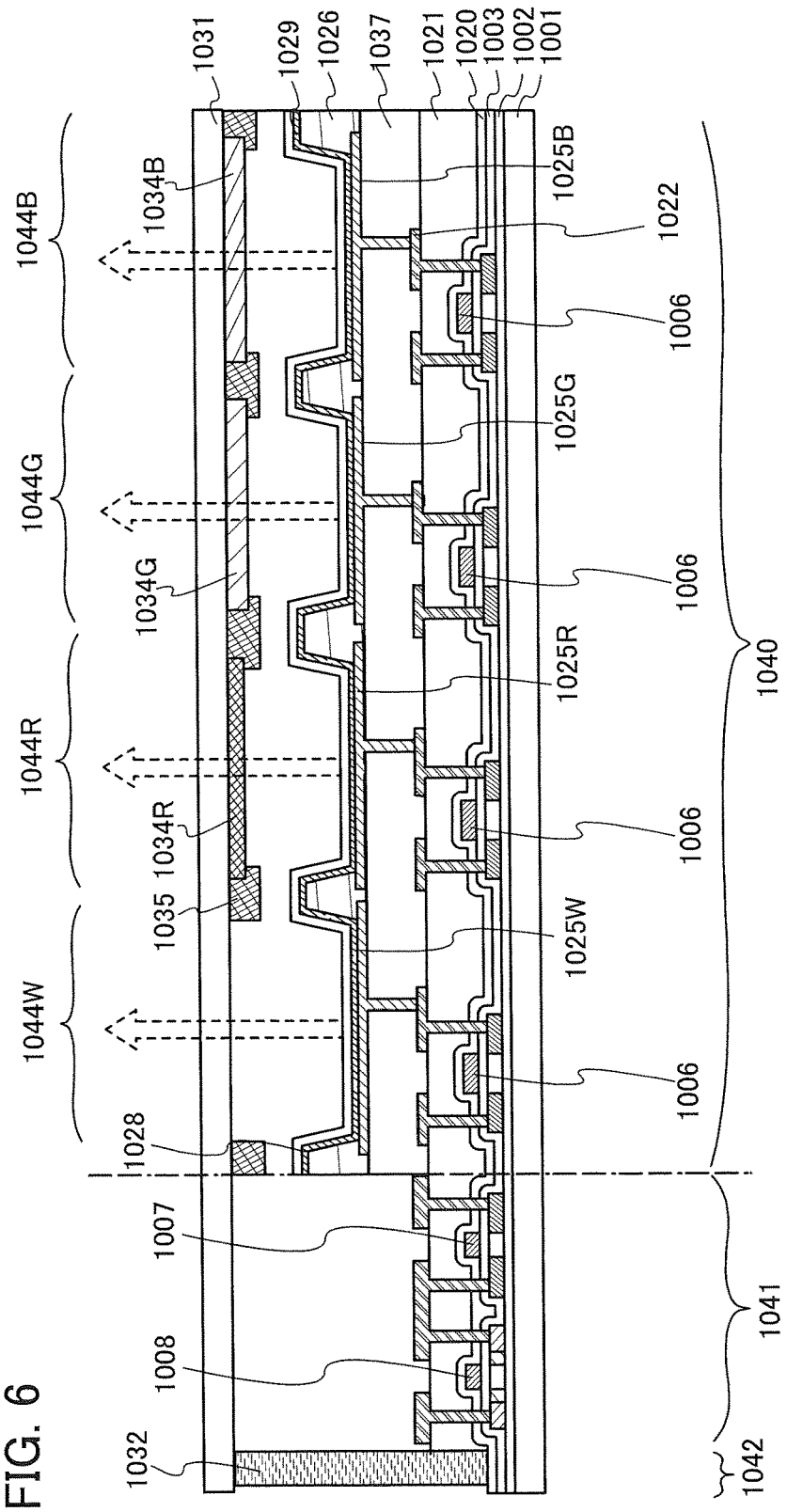
FIG. 6 is a conceptual diagram of an active matrix light-emitting device of one embodiment of the present invention.

FIG. 6 is a cross-sectional view of a light-emitting device having a top emission structure. In this case, a substrate that does not transmit light can be used as the substrate 1001. The process up to the step of forming of a connection electrode which connects the TFT and the anode of the light-emitting element is performed in a manner similar to that of the light-emitting device having a bottom emission structure. Then, a third interlayer insulating film 1037 is formed to cover an electrode 1022. This insulating film may have a planarization function. The third interlayer insulating film 1037 can be formed using a material similar to that of the second interlayer insulating film 1021, or can be formed using any other various materials.

Lower electrodes 1025W, 1025R, 1025G, and 1025B of the light-emitting elements each function as an anode here, but may function as a cathode. Furthermore, in the case of the light-emitting device having a top emission structure as illustrated in FIG. 6, the lower electrodes 1025W, 1025R, 1025G, and 1025B are preferably reflective electrodes. Note that the second electrode 1029 preferably has a function of reflecting light and a function of transmitting light. It is preferable that a microcavity structure be used between the second electrode 1029 and the lower electrodes 1025W, 1025R, 1025G, and 1025B, in which case light having a specific wavelength is amplified. The EL layer 1028 is formed to have a structure similar to the structure described in Embodiment 2, with which white light emission can be obtained.

In FIGS. 5A and 5B and FIG. 6, the structure of the EL layer for providing white light emission can be achieved by, for example, using a plurality of light-emitting layers or using a plurality of light-emitting units. Note that the structure to provide white light emission is not limited to the above.

In the case of a top emission structure as illustrated in FIG. 6, sealing can be performed with the sealing substrate 1031 on which the coloring layers (the red coloring layer 1034R, the green coloring layer 1034G, and the blue coloring layer 1034B) are provided. The sealing substrate 1031 may be provided with the black layer (the black matrix) 1035 which is positioned between pixels. The coloring layers (the red coloring layer 1034R, the green coloring layer 1034G, and the blue coloring layer 1034B) and the black layer (the black matrix) may be covered with the overcoat layer. Note that a light-transmitting substrate is used as the sealing substrate 1031.

Although an example in which full color display is performed using four colors of red, green, blue, and white is shown here, there is no particular limitation and full color display using three colors of red, green, and blue or four colors of red, green, blue, and yellow may be performed.

As described above, the light-emitting device including the light-emitting element described in Embodiment 1 and Embodiment 2 can be obtained.

This embodiment can be combined with any of the other embodiments as appropriate.

Embodiment 4

In this embodiment, a specific example of a display device including the light-emitting element described in Embodiment 1 and Embodiment 2 is described. A display device described below includes both a reflective liquid crystal element and a light-emitting element. The display device can perform display in a transmissive mode and in a reflective mode. The light-emitting element described in Embodiment 1 and Embodiment 2 is preferably used.

<Structure Example 1 of Display Device>

FIG. 7A is a block diagram illustrating an example of the structure of a display device 400. The display device 400 includes a plurality of pixels 410 that are arranged in a matrix in a display portion 362. The display device 400 also includes a circuit GD and a circuit SD. In addition, the display device 400 includes a plurality of wirings G1, a plurality of wirings G2, a plurality of wirings ANO, and a plurality of wirings CSCOM, which are electrically connected to the circuit GD and the plurality of pixels 410 arranged in a direction R. Moreover, the display device 400 includes a plurality of wirings S1 and a plurality of wirings S2 which are electrically connected to the circuit SD and the plurality of pixels 410 arranged in a direction C.

The pixel 410 includes a reflective liquid crystal element and a light-emitting element. In the pixel 410, the liquid crystal element and the light-emitting element partly overlap with each other.

FIG. 7B1 illustrates a structure example of an electrode 311b included in the pixel 410. The electrode 311b serves as a reflective electrode of the liquid crystal element in the pixel 410. The electrode 311b has an opening 451.

In FIG. 7B1, a light-emitting element 360 in a region overlapping with the electrode 311b is denoted by a dashed line. The light-emitting element 360 overlaps with the opening 451 included in the electrode 311b. Thus, light from the light-emitting element 360 is emitted to the display surface side through the opening 451.

In FIG. 7B1, the pixels 410 adjacent in the direction R correspond to different emission colors. As illustrated in FIG. 7B1, the openings 451 are preferably provided in different positions in the electrodes 311b so as not to be aligned in the two pixels adjacent to each other in the direction R. This allows the two light-emitting elements 360 to be apart from each other, thereby preventing light emitted from the light-emitting element 360 from entering a coloring layer in the adjacent pixel 410 (such a phenomenon is also referred to as crosstalk). Furthermore, since the two adjacent light-emitting elements 360 can be arranged apart from each other, a high-resolution display device is achieved even when EL layers of the light-emitting elements 360 are separately formed with a shadow mask or the like.

Alternatively, arrangement illustrated in FIG. 7B2 may be employed.

If the ratio of the total area of the opening 451 to the total area except for the opening is too large, display performed using the liquid crystal element is dark. If the ratio of the total area of the opening 451 to the total area except for the opening is too small, display performed using the light-emitting element 360 is dark.

If the area of the opening 451 in the electrode 311b serving as a reflective electrode is too small, light emitted from the light-emitting element 360 is not efficiently extracted.

The opening 451 may have a polygonal shape, a quadrangular shape, an elliptical shape, a circular shape, a cross-like shape, a stripe shape, a slit-like shape, or a checkered pattern, for example. The opening 451 may be close to the adjacent pixel. Preferably, the opening 451 is provided close to another pixel emitting light of the same color, in which case crosstalk can be suppressed.

[Circuit Configuration Example]

Figure 8:
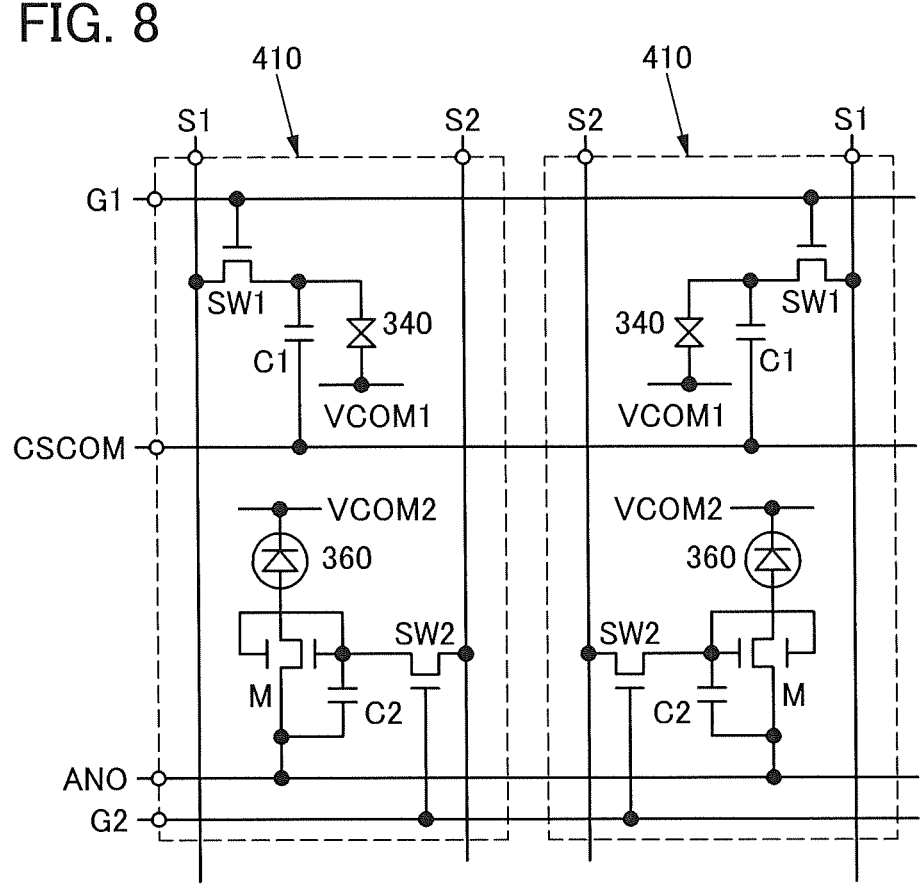
FIG. 8 is a circuit diagram of a display device of one embodiment of the present invention.

FIG. 8 is a circuit diagram illustrating a configuration example of the pixel 410. FIG. 8 illustrates two adjacent pixels 410.

The pixel 410 includes a switch SW1, a capacitor C1, a liquid crystal element 340, a switch SW2, a transistor M, a capacitor C2, the light-emitting element 360, and the like. The pixel 410 is electrically connected to the wiring G1, the wiring G2, the wiring ANO, the wiring CSCOM, the wiring S1, and the wiring S2. FIG. 8 also illustrates a wiring VCOM1 electrically connected to the liquid crystal element 340 and a wiring VCOM2 electrically connected to the light-emitting element 360.

FIG. 8 illustrates an example in which a transistor is used as each of the switches SW1 and SW2.

A gate of the switch SW1 is connected to the wiring G1. One of a source and a drain of the switch SW1 is connected to the wiring S1, and the other of the source and the drain is connected to one electrode of the capacitor C1 and one electrode of the liquid crystal element 340. The other electrode of the capacitor C1 is connected to the wiring CSCOM. The other electrode of the liquid crystal element 340 is connected to the wiring VCOM1.

A gate of the switch SW2 is connected to the wiring G2. One of a source and a drain of the switch SW2 is connected to the wiring S2, and the other of the source and the drain is connected to one electrode of the capacitor C2 and a gate of the transistor M. The other electrode of the capacitor C2 is connected to one of a source and a drain of the transistor M and the wiring ANO. The other of the source and the drain of the transistor M is connected to one electrode of the light-emitting element 360. The other electrode of the light-emitting element 360 is connected to the wiring VCOM2.

FIG. 8 illustrates an example in which the transistor M includes two gates between which a semiconductor is provided and which are connected to each other. This structure can increase the amount of current flowing through the transistor M.

The wiring G1 can be supplied with a signal for changing the on/off state of the switch SW1. A predetermined potential can be supplied to the wiring VCOM1. The wiring S1 can be supplied with a signal for changing the orientation of liquid crystals of the liquid crystal element 340. A predetermined potential can be supplied to the wiring CSCOM.

The wiring G2 can be supplied with a signal for changing the on/off state of the switch SW2. The wiring VCOM2 and the wiring ANO can be supplied with potentials having a difference large enough to make the light-emitting element 360 emit light. The wiring S2 can be supplied with a signal for changing the conduction state of the transistor M.

In the pixel 410 of FIG. 8, for example, an image can be displayed in the reflective mode by driving the pixel with the signals supplied to the wiring G1 and the wiring S1 and utilizing the optical modulation of the liquid crystal element 340. In the case where an image is displayed in the transmissive mode, the pixel is driven with the signals supplied to the wiring G2 and the wiring S2 and the light-emitting element 360 emits light. In the case where both modes are performed at the same time, the pixel can be driven with the signals supplied to the wiring G1, the wiring G2, the wiring S1, and the wiring S2.

Figure 9A:
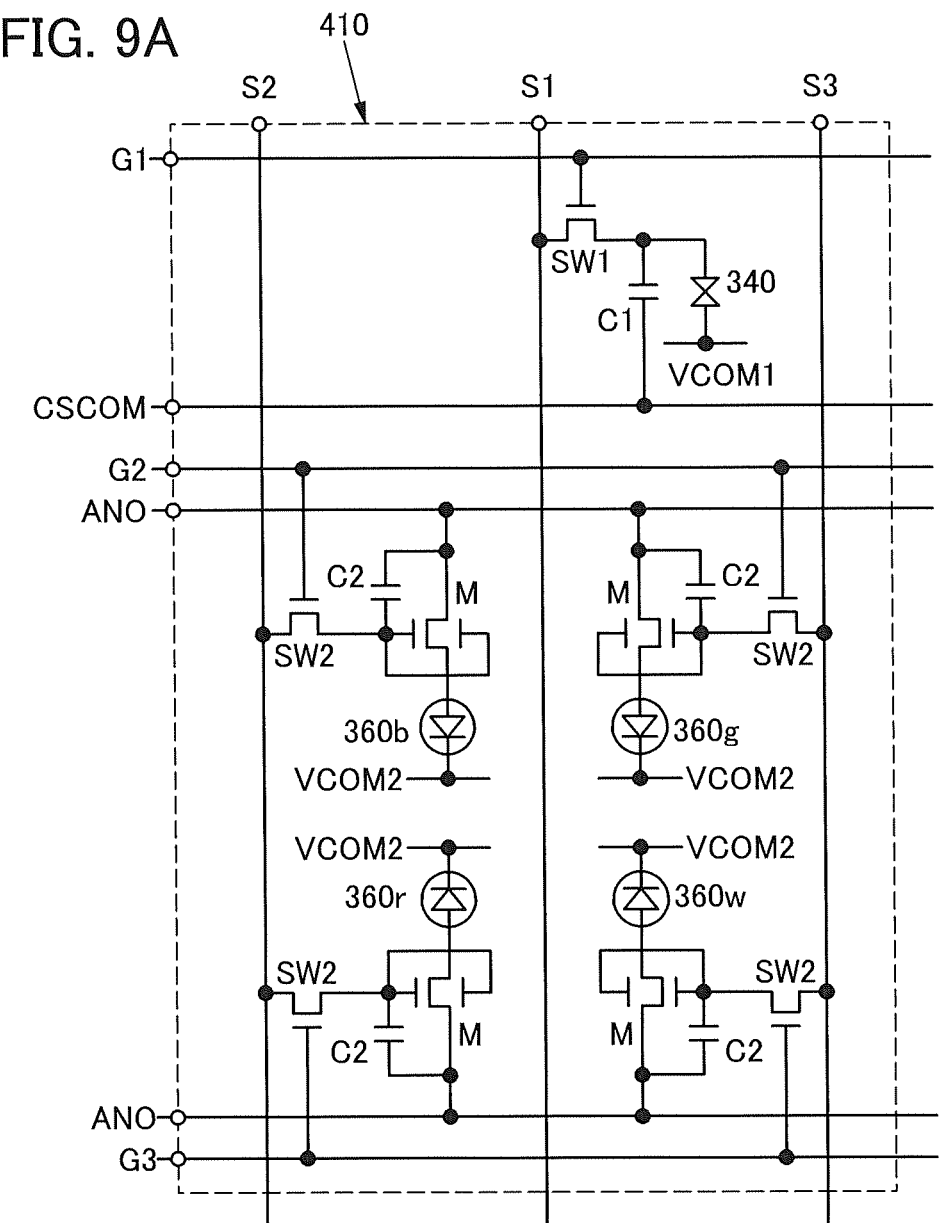
FIGS. 9A and 9B are circuit diagrams of a display device of one embodiment of the present invention.

Although FIG. 8 illustrates an example in which one liquid crystal element 340 and one light-emitting element 360 are provided in one pixel 410, one embodiment of the present invention is not limited to this example. FIG. 9A illustrates an example in which one liquid crystal element 340 and four light-emitting elements 360 (light-emitting elements 360r, 360g, 360b, and 360w) are provided in one pixel 410. The pixel 410 illustrated in FIG. 9A differs from that in FIG. 8 in being capable of performing full-color display by one pixel.

In addition to the example in FIG. 8, the pixel 410 in FIG. 9A is connected to a wiring G3 and a wiring S3.

In the example illustrated in FIG. 9A, for example, light-emitting elements which exhibit red (R), green (G), blue (B), and white (W) can be used as the four light-emitting elements 360. Furthermore, as the liquid crystal element 340, a reflective liquid crystal element emitting white light can be used. Thus, in the case of performing display in the reflective mode, white display with high reflectivity can be performed. In the case of performing display in the transmissive mode, an image can be displayed with a higher color rendering property at low power consumption.

Figure 9B:
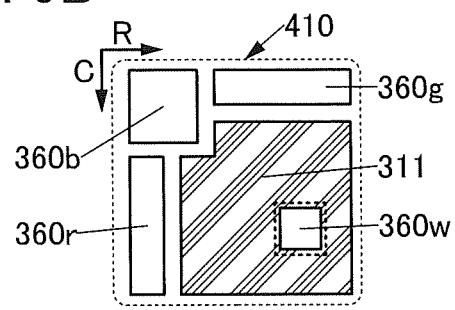

FIG. 9B illustrates a configuration example of the pixel 410. The pixel 410 includes the light-emitting element 360w which overlaps with the opening in the electrode 311 and the light-emitting elements 360r, 360g, and 360b which are located near the electrode 311. It is preferable that the light-emitting elements 360r, 360g, and 360b have substantially the same light-emitting area.

<Structure Example 2 of Display Device>

Figure 10:
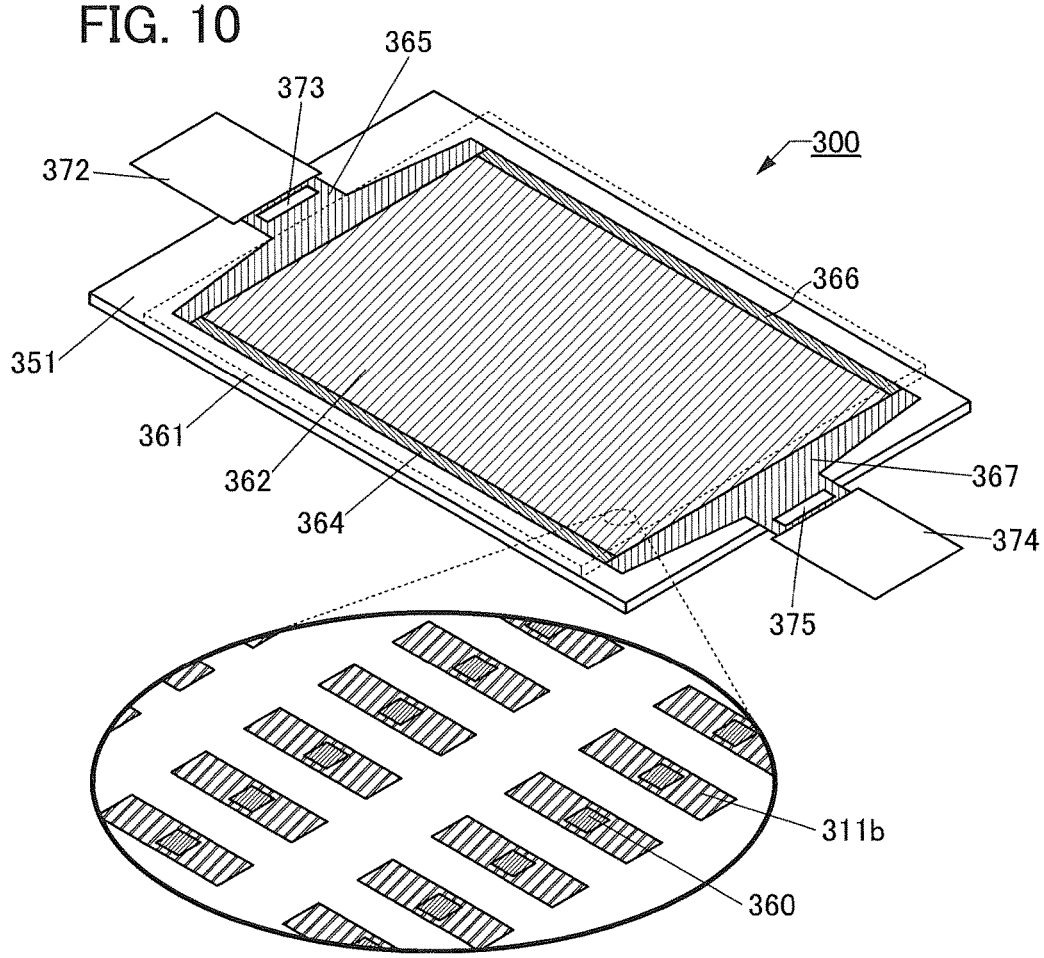
FIG. 10 is a schematic view of a display device of one embodiment of the present invention.

FIG. 10 is a schematic perspective view of a display device 300 of one embodiment of the present invention. In the display device 300, a substrate 351 and a substrate 361 are bonded to each other. In FIG. 10, the substrate 361 is denoted by a dashed line.

The display device 300 includes the display portion 362, a circuit portion 364, a wiring 365, a circuit portion 366, a wiring 367, and the like. The substrate 351 is provided with the circuit portion 364, the wiring 365, the circuit portion 366, the wiring 367, the electrode 311b functioning as a pixel electrode, and the like. In FIG. 10, an IC 373, an FPC 372, an IC 375, and an FPC 374 are mounted on the substrate 351. Thus, the structure illustrated in FIG. 10 can be referred to as a display module including the display device 300, the IC 373, the FPC 372, the IC 375, and the FPC 374.

For the circuit portion 364, a circuit functioning as a scan line driver circuit can be used, for example.

The wiring 365 has a function of supplying a signal and electric power to the display portion and the circuit portion 364. The signal and electric power are input to the wiring 365 from the outside through the FPC 372 or from the IC 373.

FIG. 10 illustrates an example in which the IC 373 is provided on the substrate 351 by a chip on glass (COG) method or the like. As the IC 373, an IC functioning as a scan line driver circuit, a signal line driver circuit, or the like can be used. Note that it is possible that the IC 373 is not provided, for example, when the display device 300 includes circuits functioning as a scan line driver circuit and a signal line driver circuit and when the circuits functioning as a scan line driver circuit and a signal line driver circuit are provided outside and signals for driving the display device 300 are input through the FPC 372. Alternatively, the IC 373 may be mounted on the FPC 372 by a chip on film (COF) method or the like.

FIG. 10 illustrates an enlarged view of a part of the display portion 362. Electrodes 311b included in a plurality of display elements are arranged in a matrix in the display portion 362. The electrode 311b has a function of reflecting visible light and serves as a reflective electrode of the liquid crystal element 340 described later.

As illustrated in FIG. 10, the electrode 311b has an opening. The light-emitting element 360 is positioned closer to the substrate 351 than the electrode 311b is. Light is emitted from the light-emitting element 360 to the substrate 361 side through the opening in the electrode 311b.

Figure 11:
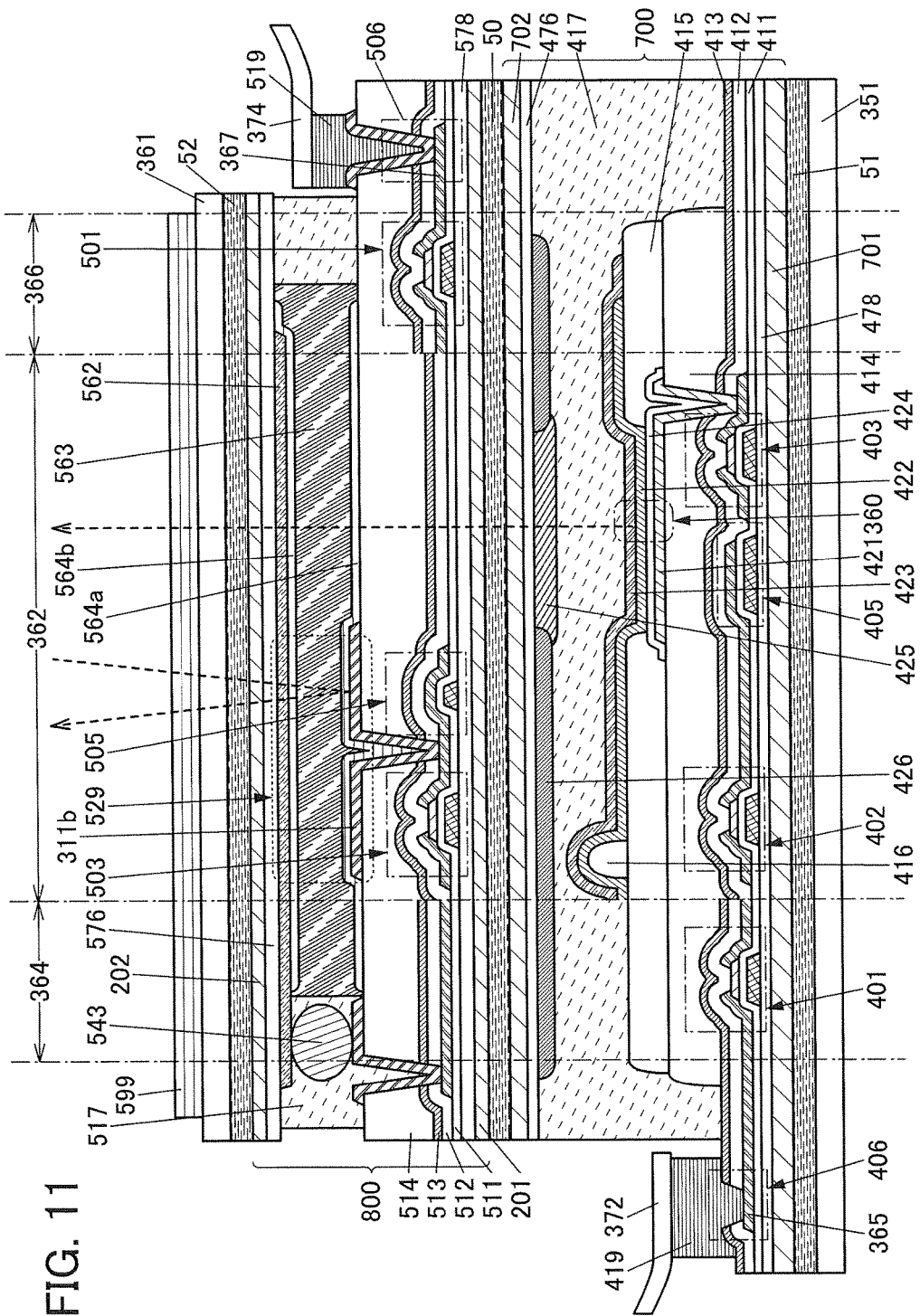
FIG. 11 is a schematic view of a display device of one embodiment of the present invention.

FIG. 11 illustrates an example of cross sections of part of a region including the FPC 372, part of a region including the circuit portion 364, part of a region including the display portion 362, part of a region including the circuit portion 366, and part of a region including the FPC 374 of the display device illustrated in FIG. 10.

The display device illustrated in FIG. 11 has a structure in which a display panel 700 and a display panel 800 are stacked. The display panel 700 includes a resin layer 701 and a resin layer 702. The display panel 800 includes a resin layer 201 and a resin layer 202. The resin layers 702 and 201 are bonded to each other with an adhesive layer 50. The resin layer 701 is bonded to the substrate 351 with an adhesive layer 51. The resin layer 202 is bonded to the substrate 361 with an adhesive layer 52.

[Display Panel 700]

The display panel 700 includes the resin layer 701, an insulating layer 478, a plurality of transistors, a capacitor 405, an insulating layer 411, an insulating layer 412, an insulating layer 413, an insulating layer 414, an insulating layer 415, the light-emitting element 360, a spacer 416, an adhesive layer 417, a coloring layer 425, a light-blocking layer 426, an insulating layer 476, and the resin layer 702.

The circuit portion 364 includes a transistor 401. The display portion 362 includes a transistor 402 and a transistor 403.

Each of the transistors includes a gate, the insulating layer 411, a semiconductor layer, a source, and a drain. The gate and the semiconductor layer overlap with each other with the insulating layer 411 provided therebetween. Part of the insulating layer 411 functions as a gate insulating layer, and another part of the insulating layer 411 functions as a dielectric of the capacitor 405. A conductive layer that functions as the source or the drain of the transistor 402 also functions as one electrode of the capacitor 405.

The transistors illustrated in FIG. 11 have bottom-gate structures. The transistor structures may be different between the circuit portion 364 and the display portion 362. The circuit portion 364 and the display portion 362 may each include a plurality of kinds of transistors.

Figure 12:
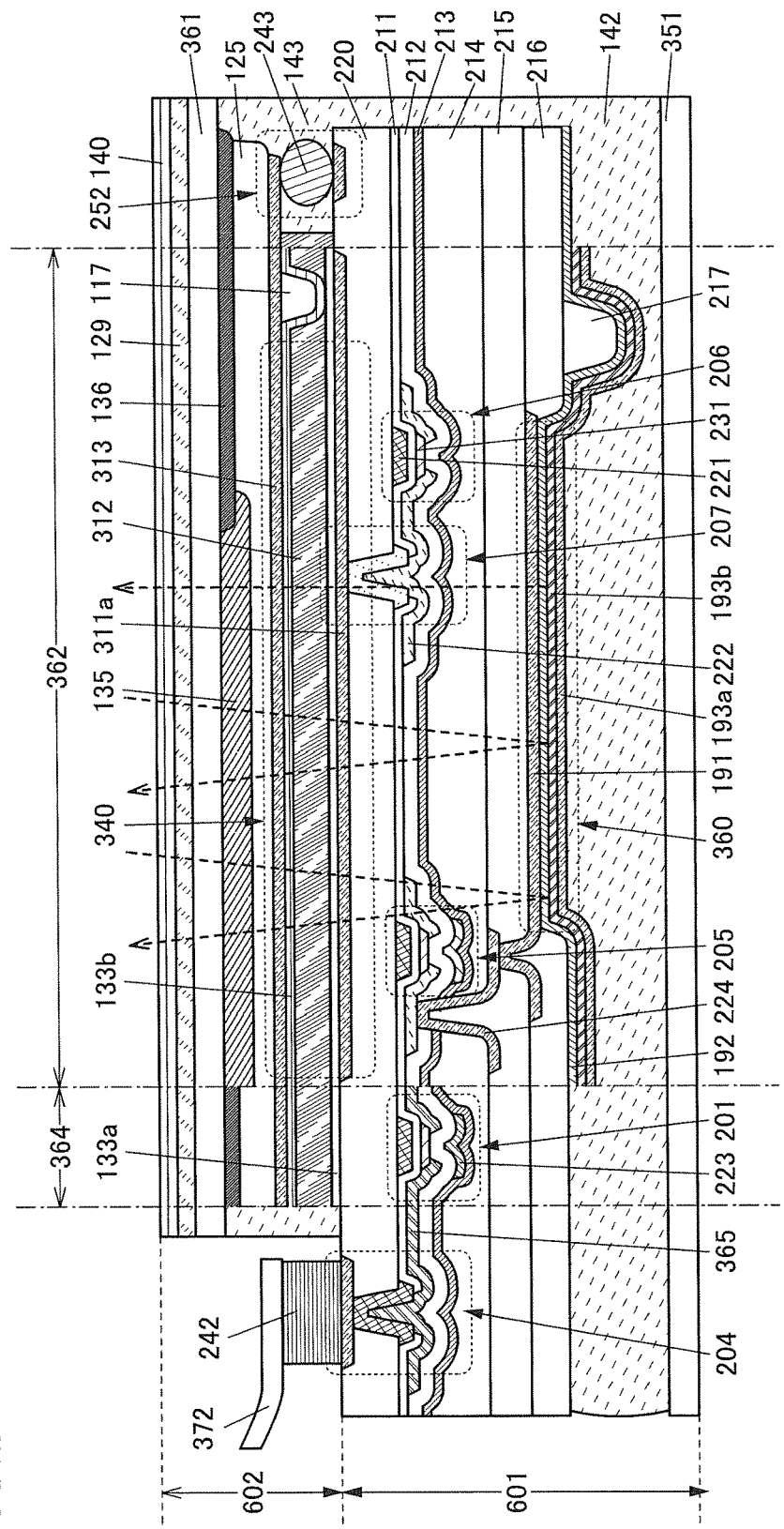
FIG. 12 is a schematic view of a display device of one embodiment of the present invention.

For example, as illustrated in FIG. 12, where the structure of the display device in FIG. 11 is modified, components included in transistors 205 and 206 and a connection portion 207 can be formed using light-transmitting conductors. Light emitted from the light-emitting element 360 can pass through part or the whole of the transistors 205 and 206 and the connection portion 207. Furthermore, light entering from the substrate 361 side and passing through liquid crystal 312 can be reflected by a conductive layer 193b. To improve the reliability of the transistors 205 and 206, one of or both the conductive layer serving as a gate electrode and the conductive layer serving as a backgate electrode may be formed using a material which does not have a light-transmitting property, such as metal.

In FIG. 11, the capacitor 405 includes a pair of electrodes and the dielectric therebetween. The capacitor 405 includes a conductive layer that is formed using the same material and the same process as the gates of the transistors, and a conductive layer that is formed using the same material and the same process as the sources and the drains of the transistors.

The insulating layer 412, the insulating layer 413, and the insulating layer 414 are each provided to cover the transistors and the like. The number of the insulating layers covering the transistors and the like is not particularly limited. The insulating layer 414 functions as a planarization layer. It is preferable that at least one of the insulating layer 412, the insulating layer 413, and the insulating layer 414 be formed using a material inhibiting diffusion of impurities such as water and hydrogen. Diffusion of impurities from the outside into the transistors can be effectively inhibited, leading to improved reliability of the display device.

In the case of using an organic material for the insulating layer 414, impurities such as moisture might enter the light-emitting element 360 or the like from the outside of the display device through the insulating layer 414 exposed at an end portion of the display device. Deterioration of the light-emitting element 360 due to the entry of impurities can lead to deterioration of the display device. For this reason, the insulating layer 414 is preferably not positioned at the end portion of the display device, as illustrated in FIG. 11. Since an insulating layer formed using an organic material is not positioned at the end portion of the display device in the structure of FIG. 11, entry of impurities into the light-emitting element 360 can be inhibited.

The light-emitting element 360 includes an electrode 421, an EL layer 422, and an electrode 423. The light-emitting element 360 may include an optical adjustment layer 424. The light-emitting element 360 has a top emission structure with which light is emitted to the coloring layer 425 side.

The transistors, the capacitor, the wiring, and the like are positioned so as to overlap with a light-emitting region of the light-emitting element 360; accordingly, the aperture ratio of the display portion 362 can be increased.

One of the electrode 421 and the electrode 423 functions as an anode and the other functions as a cathode. When a voltage higher than the threshold voltage of the light-emitting element 360 is applied between the electrode 421 and the electrode 423, holes are injected to the EL layer 422 from the anode side and electrons are injected to the EL layer 422 from the cathode side. The injected electrons and holes are recombined in the EL layer 422 and a light-emitting substance contained in the EL layer 422 emits light.

The electrode 421 is electrically connected to the source or the drain of the transistor 403 directly or through a conductive layer. The electrode 421 functioning as a pixel electrode is provided for each light-emitting element 360. Two adjacent electrodes 421 are electrically insulated from each other by the insulating layer 415.

The electrode 423 functioning as a common electrode is shared by a plurality of light-emitting elements 360. A fixed potential is supplied to the electrode 423.

The light-emitting element 360 overlaps with the coloring layer 425 with the adhesive layer 417 provided therebetween. The spacer 416 overlaps with the light-blocking layer 426 with the adhesive layer 417 provided therebetween. Although FIG. 11 illustrates the case where a space is provided between the electrode 423 and the light-blocking layer 426, the electrode 423 and the light-blocking layer 426 may be in contact with each other. Although the spacer 416 is provided on the substrate 351 side in the structure illustrated in FIG. 11, the spacer 416 may be provided on the substrate 361 side (e.g., in a position closer to the substrate 361 than that of the light-blocking layer 426).

Owing to the combination of a color filter (the coloring layer 425) and a microcavity structure (the optical adjustment layer 424), light with high color purity can be extracted from the display device. The thickness of the optical adjustment layer 424 is varied depending on the color of the pixel.

The coloring layer 425 is a coloring layer that transmits light in a specific wavelength range. For example, a color filter for transmitting light in a red, green, blue, or yellow wavelength range can be used.

Note that one embodiment of the present invention is not limited to a color filter method, and a separate coloring method, a color conversion method, a quantum dot method, and the like may be employed.

The light-blocking layer 426 is provided between the adjacent coloring layers 425. The light-blocking layer 426 blocks light emitted from the adjacent light-emitting element 360 to inhibit color mixture between the adjacent light-emitting elements 360. Here, the coloring layer 425 is provided such that its end portion overlaps with the light-blocking layer 426, whereby light leakage can be reduced. For the light-blocking layer 426, a material that blocks light emitted from the light-emitting element 360 can be used. Note that it is preferable to provide the light-blocking layer 426 in a region other than the display portion 362, such as the circuit portion 364, in which case undesired leakage of guided light or the like can be inhibited.

The insulating layer 478 is formed on a surface of the resin layer 701. The insulating layer 476 is formed on a surface of the resin layer 702. The insulating layer 476 and the insulating layer 478 are preferably highly resistant to moisture. The light-emitting element 360, the transistors, and the like are preferably provided between a pair of insulating layers with high resistance to moisture, in which case impurities such as water can be prevented from entering these elements, leading to an increase in the reliability of the display device.

Examples of the insulating film highly resistant to moisture include a film containing nitrogen and silicon (e.g., a silicon nitride film and a silicon nitride oxide film) and a film containing nitrogen and aluminum (e.g., an aluminum nitride film). Alternatively, a silicon oxide film, a silicon oxynitride film, an aluminum oxide film, or the like may be used.

For example, the moisture vapor transmittance of the insulating film with high resistance to moisture is lower than or equal to $1 \times 10^{-5}$ [g/(m$^2$·day)], preferably lower than or equal to $1 \times 10^{-6}$ [g/(m$^2$·day)], further preferably lower than or equal to $1 \times 10^{-7}$ [g/(m$^2$·day)], and still further preferably lower than or equal to $1 \times 10^{-7}$ [g/(m$^2$·day)].

A connection portion 406 includes the wiring 365. The wiring 365 can be formed using the same material and the same process as those of the sources and the drains of the transistors. The connection portion 406 is electrically connected to an external input terminal through which a signal and a potential from the outside are transmitted to the circuit portion 364. Here, an example in which the FPC 372 is provided as the external input terminal is described. The FPC 372 is electrically connected to the connection portion 406 through a connection layer 419.

The connection layer 419 can be formed using any of various kinds of anisotropic conductive films (ACF), anisotropic conductive pastes (ACP), and the like.

The above is the description of the display panel 700.

[Display Panel 800]

The display panel 800 is a reflective liquid crystal display device employing a vertical electric field mode.

The display panel 800 includes the resin layer 201, an insulating layer 578, a plurality of transistors, a capacitor 505, the wiring 367, an insulating layer 511, an insulating layer 512, an insulating layer 513, an insulating layer 514, a liquid crystal element 529, an alignment film 564a, an alignment film 564b, an adhesive layer 517, an insulating layer 576, and the resin layer 202.

The resin layers 201 and 202 are bonded to each other with the adhesive layer 517. Liquid crystal 563 is sealed in a region surrounded by the resin layer 201, the resin layer 202, and the adhesive layer 517. A polarizing plate 599 is positioned on an outer surface of the substrate 361.

The liquid crystal element 529 includes the electrode 311b, an electrode 562, and the liquid crystal 563. The electrode 311b functions as a pixel electrode. The electrode 562 functions as a common electrode. Alignment of the liquid crystal 563 can be controlled with an electric field generated between the electrode 311b and the electrode 562. The alignment film 564a is provided between the liquid crystal 563 and the electrode 311b. The alignment film 564b is provided between the liquid crystal 563 and the electrode 562.

The resin layer 202 is provided with the insulating layer 576, the electrode 562, the alignment film 564b, and the like.

The resin layer 201 is provided with the electrode 311b, the alignment film 564a, a transistor 501, a transistor 503, the capacitor 505, a connection portion 506, the wiring 367, and the like.

Insulating layers such as the insulating layer 511, the insulating layer 512, the insulating layer 513, and the insulating layer 514 are provided over the resin layer 201.

Note that a portion of the conductive layer functioning as the source or the drain of the transistor 503 which is not electrically connected to the electrode 311b may function as part of a signal line. The conductive layer functioning as a gate of the transistor 503 may function as part of a scan line.

FIG. 11 illustrates an example of the circuit portion 366 in which the transistor 501 is provided.

A material inhibiting diffusion of impurities such as water and hydrogen is preferably used for at least one of the insulating layers 512 and 513 which cover the transistors.

The electrode 311b is provided over the insulating layer 514. The electrode 311b is electrically connected to one of the source and the drain of the transistor 503 through an opening formed in the insulating layer 514, the insulating layer 513, the insulating layer 512, and the like. The electrode 311b is electrically connected to one electrode of the capacitor 505.

Since the display panel 800 is a reflective liquid crystal display device, a conductive material that reflects visible light is used for the electrode 311b and a conductive material that transmits visible light is used for the electrode 562.

For example, a material containing one of indium (In), zinc (Zn), and tin (Sn) is preferably used for the conductive material that transmits visible light. Specific examples include indium oxide, indium tin oxide (ITO), indium zinc oxide, indium oxide containing tungsten oxide, indium zinc oxide containing tungsten oxide, indium oxide containing titanium oxide, indium tin oxide containing titanium oxide, indium tin oxide containing silicon oxide (ITSO), zinc oxide, and zinc oxide containing gallium.

Note that a film containing graphene can be used as well. The film containing graphene can be formed, for example, by reducing a film containing graphene oxide.

Examples of the conductive material that reflects visible light include aluminum, silver, and an alloy containing any of these metal materials. A metal material such as gold, platinum, nickel, tungsten, chromium, molybdenum, iron, cobalt, copper, or palladium, or an alloy containing any of these metal materials can also be used. Furthermore, lanthanum, neodymium, germanium, or the like may be added to the metal material or the alloy. Furthermore, an alloy containing aluminum (an aluminum alloy) such as an alloy of aluminum and titanium, an alloy of aluminum and nickel, an alloy of aluminum and neodymium, or an alloy of aluminum, nickel, and lanthanum (Al—Ni—La); or an alloy containing silver such as an alloy of silver and copper, an alloy of silver, palladium, and copper (also referred to as Ag—Pd—Cu or APC), or an alloy of silver and magnesium may be used.

As the polarizing plate 599, a linear polarizing plate or a circularly polarizing plate can be used. An example of a circularly polarizing plate is a stack including a linear polarizing plate and a quarter-wave retardation plate. Such a structure can reduce reflection of external light. The cell gap, alignment, driving voltage, and the like of the liquid crystal element used as the liquid crystal element 529 are controlled depending on the kind of the polarizing plate 599 so that desirable contrast is obtained.

The electrode 562 is electrically connected to a conductive layer on the resin layer 201 side through a connector 543 in a portion close to an end portion of the resin layer 202. Thus, a potential or a signal can be supplied from the FPC 374, an IC, or the like placed on the resin layer 201 side to the electrode 562.

As the connector 543, a conductive particle can be used, for example. As the conductive particle, a particle of an organic resin, silica, or the like coated with a metal material can be used. It is preferable to use nickel or gold as the metal material because contact resistance can be decreased. It is also preferable to use a particle coated with layers of two or more kinds of metal materials, such as a particle coated with nickel and further with gold. As the connector 543, a material capable of elastic deformation or plastic deformation is preferably used. As illustrated in FIG. 11, the connector 543, which is the conductive particle, has a shape that is vertically crushed in some cases. With the crushed shape, the contact area between the connector 543 and a conductive layer electrically connected to the connector 543 can be increased, thereby reducing contact resistance and suppressing the generation of problems such as disconnection.

The connector 543 is preferably provided so as to be covered with the adhesive layer 517. For example, the connectors 543 are dispersed in the adhesive layer 517 before curing of the adhesive layer 517.

The connection portion 506 is provided in a region near an end portion of the resin layer 201. The connection portion 506 is electrically connected to the FPC 374 through a connection layer 519.

The above is the description of the display panel 800.

[Display Element]

As a display element included in a first pixel located on the display surface side, an element which performs display by reflecting external light can be used. Such an element does not include a light source and thus power consumption in display can be significantly reduced. As the display element included in the first pixel, a reflective liquid crystal element can be typically used. Alternatively, as the display element included in the first pixel, an element using a microcapsule method, an electrophoretic method, an electrowetting method, an Electronic Liquid Powder (registered trademark) method, or the like can be used, other than a micro electro mechanical systems (MEMS) shutter element or an optical interference type MEMS element.

As a display element included in a second pixel located on the side opposite to the display surface side, an element which includes a light source and performs display using light from the light source can be used. Since the luminance and the chromaticity of light emitted from such a pixel are not affected by external light, an image with high color reproducibility (a wide color gamut) and a high contrast, i.e., a clear image can be displayed. As the display element included in the second pixel, a self-luminous light-emitting element such as an organic light-emitting diode (OLED), a light-emitting diode (LED), or a quantum-dot light-emitting diode (QLED) can be used. Alternatively, a combination of a backlight that is a light source and a transmissive liquid crystal element that controls the amount of transmitted light emitted from a backlight may be used as the display element included in the second pixel.

[Liquid Crystal Element]

The liquid crystal element can employ, for example, a vertical alignment (VA) mode. Examples of the vertical alignment mode include a multi-domain vertical alignment (MVA) mode, a patterned vertical alignment (PVA) mode, and an advanced super view (ASV) mode.

The liquid crystal element can employ a variety of modes. For example, a liquid crystal element using, instead of a VA mode, a twisted nematic (TN) mode, an in-plane switching (IPS) mode, a fringe field switching (FFS) mode, an axially symmetric aligned micro-cell (ASM) mode, an optically compensated birefringence (OCB) mode, a ferroelectric liquid crystal (FLC) mode, an antiferroelectric liquid crystal (AFLC) mode, or the like can be used.

The liquid crystal element controls transmission or non-transmission of light utilizing an optical modulation action of a liquid crystal. The optical modulation action of the liquid crystal is controlled by an electric field applied to the liquid crystal (including a horizontal electric field, a vertical electric field, and an oblique electric field). As the liquid crystal used for the liquid crystal element, thermotropic liquid crystal, low-molecular liquid crystal, high-molecular liquid crystal, polymer dispersed liquid crystal (PDLC), ferroelectric liquid crystal, anti-ferroelectric liquid crystal, guest-host liquid crystal, or the like can be used. These liquid crystal materials exhibit a cholesteric phase, a smectic phase, a cubic phase, a chiral nematic phase, an isotropic phase, or the like depending on conditions.

As the liquid crystal material, either a positive liquid crystal or a negative liquid crystal may be used, and an appropriate liquid crystal material can be used depending on the mode or design to be used.

An alignment film can be provided to adjust the alignment of a liquid crystal. In the case where a horizontal electric field mode is employed, a liquid crystal exhibiting a blue phase for which an alignment film is unnecessary may be used. The blue phase is one of liquid crystal phases, which is generated just before a cholesteric phase changes into an isotropic phase while temperature of a cholesteric liquid crystal is increased. Since the blue phase appears only in a narrow temperature range, a liquid crystal composition in which a chiral material is mixed to account for several weight percent or more is used for the liquid crystal layer in order to improve the temperature range. The liquid crystal composition that includes a liquid crystal exhibiting a blue phase and a chiral material has a short response time and has optical isotropy. In addition, the liquid crystal composition that includes a liquid crystal exhibiting a blue phase and a chiral material does not need alignment treatment and has small viewing angle dependence. An alignment film does not need to be provided and rubbing treatment is thus not necessary; accordingly, electrostatic discharge damage caused by the rubbing treatment can be prevented and defects and damage of the liquid crystal display device in the manufacturing process can be reduced.

In the case where a reflective liquid crystal element is used, a polarizing plate is provided on the display surface side. In addition, a light diffusion plate is preferably provided on the display surface side to improve visibility.

[Light-Emitting Element]

As the light-emitting element, a self-luminous element can be used, and an element whose luminance is controlled by current or voltage is included in the category of the light-emitting element. For example, an LED, a QLED, an organic EL element, or an inorganic EL element can be used; however, any of the light-emitting elements described in Embodiment 1 and Embodiment 2 is preferably used.

In this embodiment, in particular, the light-emitting element preferably has a top emission structure. A conductive film that transmits visible light is used as the electrode through which light is extracted. A conductive film that reflects visible light is preferably used as the electrode through which light is not extracted. The light-emitting element may be a single element including one EL layer or a tandem element in which a plurality of EL layers are stacked with a charge-generation layer positioned therebetween.

The EL layer includes at least a light-emitting layer. In addition to the light-emitting layer, the EL layer may further include one or more layers containing any of a substance with a high hole-injection property, a substance with a high hole-transport property, a hole-blocking material, a substance with a high electron-transport property, a substance with a high electron-injection property, a substance with a bipolar property (a substance with a high electron- and hole-transport property), and the like.

For the EL layer, the low-molecular compound, the high-molecular compound, or the inorganic compound described in Embodiment 1 can be used. Each of the layers included in the EL layer can be formed by any of the following methods: an evaporation method (including a vacuum evaporation method), a transfer method, a printing method, an inkjet method, a coating method, and the like.

[Adhesive Layer]

As the adhesive layer, a variety of curable adhesives such as a reactive curable adhesive, a thermosetting adhesive, an anaerobic adhesive, and a photocurable adhesive such as an ultraviolet curable adhesive can be used. Examples of these adhesives include an epoxy resin, an acrylic resin, a silicone resin, a phenol resin, a polyimide resin, an imide resin, a polyvinyl chloride (PVC) resin, a polyvinyl butyral (PVB) resin, and an ethylene vinyl acetate (EVA) resin. In particular, a material with low moisture permeability, such as an epoxy resin, is preferred. Alternatively, a two-component type resin may be used. Further alternatively, an adhesive sheet or the like may be used.

Furthermore, the resin may include a drying agent. For example, a substance that adsorbs moisture by chemical adsorption, such as oxide of an alkaline earth metal (e.g., calcium oxide or barium oxide), can be used. Alternatively, a substance that adsorbs moisture by physical adsorption, such as zeolite or silica gel, may be used. The drying agent is preferably included because it can prevent impurities such as moisture from entering the element, thereby improving the reliability of the display panel.

In addition, it is preferable to mix a filler with a high refractive index or light-scattering member into the resin, in which case light extraction efficiency can be enhanced. For example, titanium oxide, barium oxide, zeolite, or zirconium can be used.

[Connection Layer]

As the connection layer, an anisotropic conductive film (ACF), an anisotropic conductive paste (ACP), or the like can be used.

[Coloring Layer]

Examples of a material that can be used for the coloring layer include a metal material, a resin material, and a resin material containing a pigment or dye.

[Light-Blocking Layer]

Examples of a material that can be used for the light-blocking layer include carbon black, titanium black, a metal, a metal oxide, and a composite oxide containing a solid solution of a plurality of metal oxides. The light-blocking layer may be a film containing a resin material or a thin film of an inorganic material such as a metal. Stacked films containing the material of the coloring layer can also be used for the light-blocking layer. For example, a stacked-layer structure of a film containing a material for a coloring layer that transmits light of a certain color and a film containing a material for a coloring layer that transmits light of another color can be employed. It is preferable that the coloring layer and the light-blocking layer be formed using the same material because the same manufacturing apparatus can be used and the process can be simplified.

The structure described in this embodiment can be combined as appropriate with any of the structures described in the other embodiments.

Embodiment 5

In this embodiment, electronic devices each including the light-emitting element described in Embodiment 1 and Embodiment 2 are described. The light-emitting element described in Embodiment 1 and Embodiment 2 includes the light-emitting element of one embodiment of the present invention and thus has low driving voltage, high emission efficiency, and high reliability; as a result, the electronic O80 devices described in this embodiment can each include a display portion having reduced power consumption and high reliability.

<Electronic Device>

FIGS. 13A to 13G illustrate electronic devices. These electronic devices can include a housing 9000, a display portion 9001, a speaker 9003, operation keys 9005 (including a power switch or an operation switch), a connection terminal 9006, a sensor 9007 (a sensor having a function of measuring or sensing force, displacement, position, speed, acceleration, angular velocity, rotational frequency, distance, light, liquid, magnetism, temperature, chemical substance, sound, time, hardness, electric field, current, voltage, power, radiation, flow rate, humidity, gradient, oscillation, odor, or infrared ray), a microphone 9008, and the like. In addition, the sensor 9007 may have a function of measuring biological information like a pulse sensor and a finger print sensor.

The electronic devices illustrated in FIGS. 13A to 13G can have a variety of functions, for example, a function of displaying a variety of data (a still image, a moving image, a text image, and the like) on the display portion, a touch sensor function, a function of displaying a calendar, date, time, and the like, a function of controlling a process with a variety of software (programs), a wireless communication function, a function of being connected to a variety of computer networks with a wireless communication function, a function of transmitting and receiving a variety of data with a wireless communication function, a function of reading a program or data stored in a memory medium and displaying the program or data on the display portion, and the like. Note that functions that can be provided for the electronic devices illustrated in FIGS. 13A to 13G are not limited to those described above, and the electronic devices can have a variety of functions. Although not illustrated in FIGS. 13A to 13G, the electronic devices may include a plurality of display portions. The electronic devices may have a camera or the like and a function of taking a still image, a function of taking a moving image, a function of storing the taken image in a memory medium (an external memory medium or a memory medium incorporated in the camera), a function of displaying the taken image on the display portion, or the like.

The electronic devices illustrated in FIGS. 13A to 13G will be described in detail below.

Figure 13A:
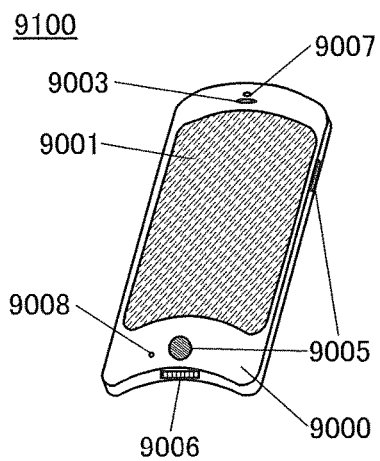
FIGS. 13A to 13G are schematic views of electronic devices of one embodiment of the present invention.

FIG. 13A is a perspective view of a portable information terminal 9100. The display portion 9001 of the portable information terminal 9100 is flexible. Therefore, the display portion 9001 can be incorporated along a bent surface of a bent housing 9000. In addition, the display portion 9001 includes a touch sensor, and operation can be performed by touching the screen with a finger, a stylus, or the like. For example, when an icon displayed on the display portion 9001 is touched, an application can be started.

Figure 13D:
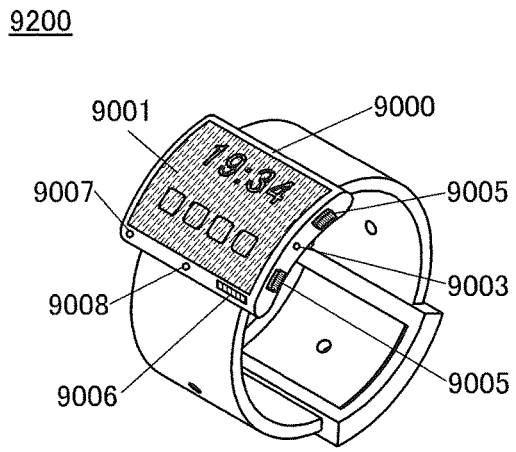
Figure 13B:
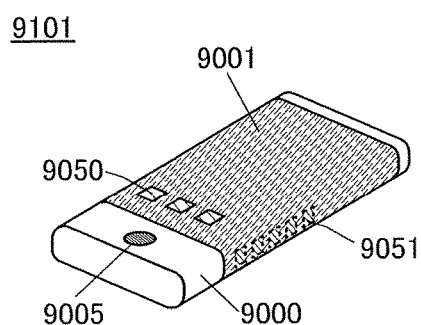

FIG. 13B is a perspective view of a portable information terminal 9101. The portable information terminal 9101 functions as, for example, one or more of a telephone set, a notebook, and an information browsing system. Specifically, the portable information terminal can be used as a smartphone. Note that the speaker 9003, the connection terminal 9006, the sensor 9007, and the like, which are not illustrated in the drawing, can be positioned in the portable information terminal 9101 as in the portable information terminal 9100 illustrated in FIG. 13A. The portable information terminal 9101 can display characters and image information on its plurality of surfaces. For example, three operation buttons 9050 (also referred to as operation icons, or simply, icons) can be displayed on one surface of the display portion 9001. Furthermore, information 9051 indicated by dashed rectangles can be displayed on another surface of the display portion 9001. Examples of the information 9051 include display indicating reception of an incoming email, social networking service (SNS) message, call, and the like; the title and sender of an email and SNS message; the date; the time; remaining battery; and display indicating the strength of a received signal such as a radio wave. Instead of the information 9051, the operation buttons 9050 or the like may be displayed on the position where the information 9051 is displayed.

As a material of the housing 9000, for example, an alloy, a plastic, or a ceramic can be used. As a plastic, a reinforced plastic can also be used. A carbon fiber reinforced plastic (CFRP), which is a kind of reinforced plastic, has advantages of lightweight and corrosion-free. Other examples of reinforced plastics include one including glass fiber and one including aramid fiber. As the alloy, an aluminum alloy and a magnesium alloy can be given. The alloy includes an aluminum alloy and a magnesium alloy. In particular, an amorphous alloy (also referred to as metal glass) containing zirconium, copper, nickel, and titanium is superior in terms of high elastic strength. This amorphous alloy includes a glass transition region at room temperature, which is also referred to as a bulk-solidifying amorphous alloy and substantially has an amorphous atomic structure. By a solidification casting method, an alloy material is molded in a mold of at least part of the housing and coagulated so that the part of the housing is formed using a bulk-solidifying amorphous alloy. The amorphous alloy may include beryllium, silicon, niobium, boron, gallium, molybdenum, tungsten, manganese, iron, cobalt, yttrium, vanadium, phosphorus, carbon, or the like in addition to zirconium, copper, nickel, and titanium. The amorphous alloy may be formed by a vacuum evaporation method, a sputtering method, an electroplating method, an electroless plating method, or the like instead of the solidification casting method. The amorphous alloy may include a microcrystal or a nanocrystal as long as a state without a long-range order (a periodic structure) is maintained as a whole. Note that the term alloy refers to both a complete solid solution alloy which has a single solid phase structure and a partial solution that has two or more phases. The housing 9000 using the amorphous alloy can have high elastic strength. Even if the portable information terminal 9101 is dropped and the impact causes temporary deformation, the use of the amorphous alloy in the housing 9000 allows a return to the original shape; thus, the impact resistance of the portable information terminal 9101 can be improved.

Figure 13E:
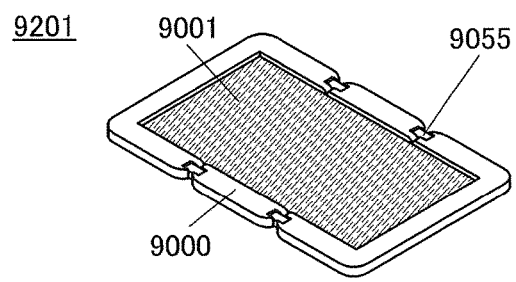
Figure 13C:
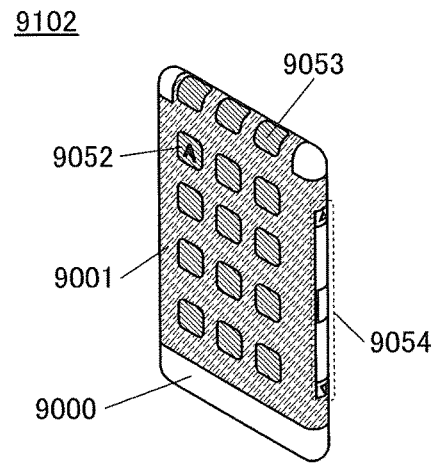

FIG. 13C is a perspective view of a portable information terminal 9102. The portable information terminal 9102 has a function of displaying information on three or more surfaces of the display portion 9001. Here, information 9052, information 9053, and information 9054 are displayed on different surfaces. For example, a user of the portable information terminal 9102 can see the display (here, the information 9053) with the portable information terminal 9102 put in a breast pocket of his/her clothes. Specifically, a caller's phone number, name, or the like of an incoming call is displayed in a position that can be seen from above the portable information terminal 9102. Thus, the user can see the display without taking out the portable information terminal 9102 from the pocket and decide whether to answer the call.

FIG. 13D is a perspective view of a watch-type portable information terminal 9200. The portable information terminal 9200 is capable of executing a variety of applications such as mobile phone calls, e-mailing, viewing and editing texts, music reproduction, Internet communication, and computer games. The display surface of the display portion 9001 is bent, and images can be displayed on the bent display surface. The portable information terminal 9200 can employ near field communication that is a communication method based on an existing communication standard. In that case, for example, mutual communication between the portable information terminal and a headset capable of wireless communication can be performed, and thus hands-free calling is possible. The portable information terminal 9200 includes the connection terminal 9006, and data can be directly transmitted to and received from another information terminal via a connector. Power charging through the connection terminal 9006 is possible. Note that the charging operation may be performed by wireless power feeding without using the connection terminal 9006.

Figure 13F:
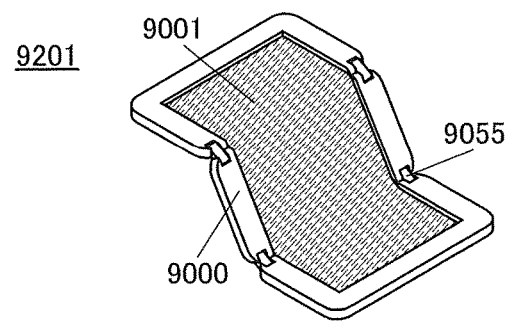
Figure 13G:
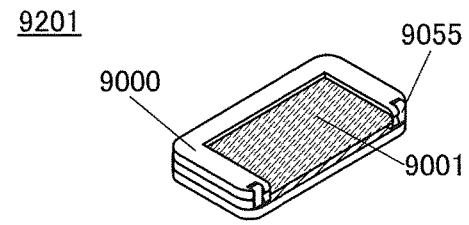

FIGS. 13E, 13F, and 13G are perspective views of a foldable portable information terminal 9201. FIG. 13E is a perspective view illustrating the portable information terminal 9201 which is opened. FIG. 13F is a perspective view illustrating the portable information terminal 9201 which is being opened or being folded. FIG. 13G is a perspective view illustrating the portable information terminal 9201 which is folded. The portable information terminal 9201 is highly portable when folded. When the portable information terminal 9201 is opened, a seamless large display region is highly browsable. The display portion 9001 of the portable information terminal 9201 is supported by three housings 9000 joined together by hinges 9055. By folding the portable information terminal 9201 at a connection portion between two housings 9000 with the hinges 9055, the portable information terminal 9201 can be reversibly changed in shape from an opened state to a folded state. For example, the portable information terminal 9201 can be bent with a radius of curvature greater than or equal to 1 mm and less than or equal to 150 mm.

Examples of electronic devices are a television set (also referred to as a television or a television receiver), a monitor of a computer or the like, a camera such as a digital camera or a digital video camera, a digital photo frame, a mobile phone handset (also referred to as a mobile phone or a mobile phone device), a goggle-type display (head-mounted display), a portable game machine, a portable information terminal, an audio reproducing device, and a large-sized game machine such as a pachinko machine.

Furthermore, the electronic device of one embodiment of the present invention may include a secondary battery. It is preferable that the secondary battery be capable of being charged by non-contact power transmission.

Examples of the secondary battery include a lithium-ion secondary battery such as a lithium polymer battery using a gel electrolyte (lithium-ion polymer battery), a lithium-ion battery, a nickel-hydride battery, a nickel-cadmium battery, an organic radical battery, a lead-acid battery, an air secondary battery, a nickel-zinc battery, and a silver-zinc battery.

The electronic device of one embodiment of the present invention may include an antenna. When a signal is received by the antenna, the electronic device can display an image, data, or the like on a display portion. When the electronic device includes a secondary battery, the antenna may be used for non-contact power transmission.

Figure 14A:
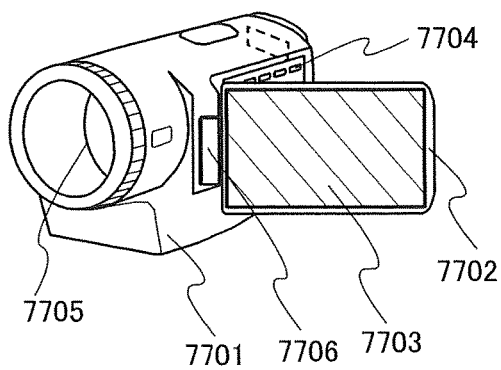
FIGS. 14A to 14E are schematic views of electronic devices of one embodiment of the present invention.

FIG. 14A illustrates a video camera including a housing 7701, a housing 7702, a display portion 7703, operation keys 7704, a lens 7705, a joint 7706, and the like. The operation keys 7704 and the lens 7705 are provided for the housing 7701, and the display portion 7703 is provided for the housing 7702. The housing 7701 and the housing 7702 are connected to each other with the joint 7706, and the angle between the housing 7701 and the housing 7702 can be changed with the joint 7706. Images displayed on the display portion 7703 may be switched in accordance with the angle at the joint 7706 between the housing 7701 and the housing 7702.

Figure 14B:
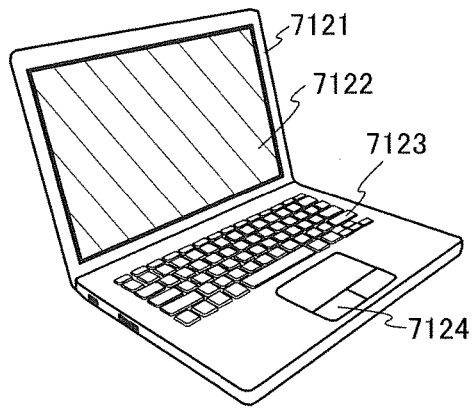

FIG. 14B illustrates a notebook personal computer including a housing 7121, a display portion 7122, a keyboard 7123, a pointing device 7124, and the like. Note that the display portion 7122 is small- or medium-sized but can perform 8 k display because it has greatly high pixel density and high resolution; therefore, a significantly clear image can be obtained.

Figure 14C:
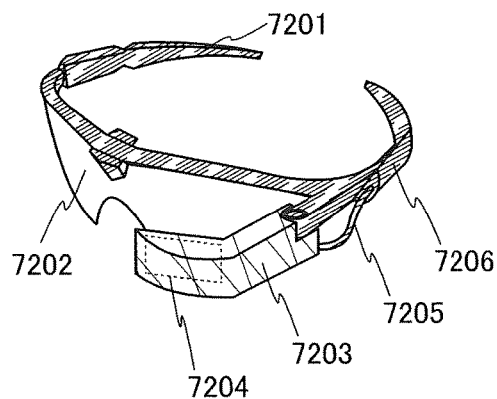

FIG. 14C is an external view of a head-mounted display 7200.

The head-mounted display 7200 includes a mounting portion 7201, a lens 7202, a main body 7203, a display portion 7204, a cable 7205, and the like. The mounting portion 7201 includes a battery 7206.

Power is supplied from the battery 7206 to the main body 7203 through the cable 7205. The main body 7203 includes a wireless receiver or the like to receive video data, such as image data, and display it on the display portion 7204. The movement of the eyeball and the eyelid of a user is captured by a camera in the main body 7203 and then coordinates of the points the user looks at are calculated using the captured data to utilize the eye point of the user as an input means.

The mounting portion 7201 may include a plurality of electrodes so as to be in contact with the user. The main body 7203 may have a function of sensing current flowing through the electrodes with the movement of the user's eyeball to recognize the direction of his or her eyes. The main body 7203 may have a function of sensing current flowing through the electrodes to monitor the user's pulse. The mounting portion 7201 may include sensors, such as a temperature sensor, a pressure sensor, or an acceleration sensor, so that the user's biological information can be displayed on the display portion 7204. The main body 7203 may sense the movement of the user's head or the like to move an image displayed on the display portion 7204 in synchronization with the movement of the user's head or the like.

Figure 14D:
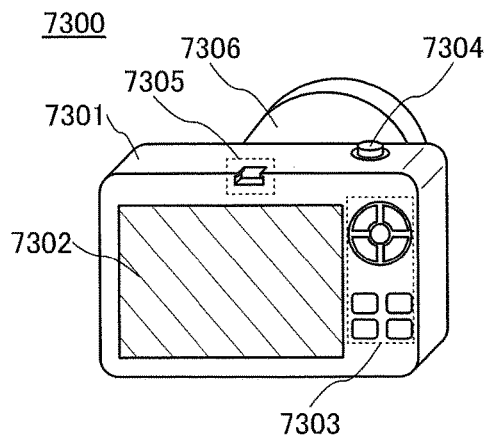

FIG. 14D is an external view of a camera 7300. The camera 7300 includes a housing 7301, a display portion 7302, an operation button 7303, a shutter button 7304, a connection portion 7305, and the like. A lens 7306 can be put on the camera 7300.

The connection portion 7305 includes an electrode to connect with a finder 7400, which is described below, a stroboscope, or the like.

Although the lens 7306 of the camera 7300 here is detachable from the housing 7301 for replacement, the lens 7306 may be included in the housing 7301.

Images can be taken at the touch of the shutter button 7304. In addition, images can be taken by operation of the display portion 7302 including a touch sensor.

In the display portion 7302, the display device of one embodiment of the present invention or a touch sensor can be used.

Figure 14E:
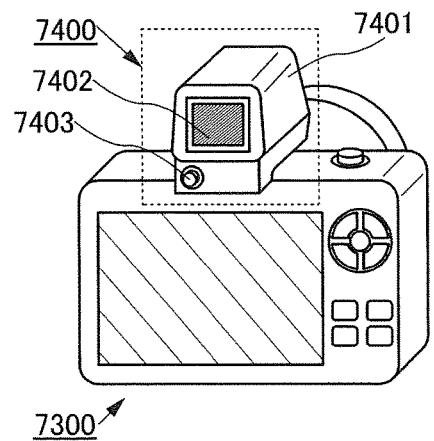

FIG. 14E illustrates the camera 7300 with the finder 7400 connected.

The finder 7400 includes a housing 7401, a display portion 7402, a button 7403, and the like.

The housing 7401 includes a connection portion for engagement with the connection portion 7305 of the camera 7300 so that the finder 7400 can be connected to the camera 7300. The connection portion includes an electrode, and an image or the like received from the camera 7300 through the electrode can be displayed on the display portion 7402.

The button 7403 functions as a power supply button. With the button 7403, on/off of display on the display portion 7402 can be switched.

Although the camera 7300 and the finder 7400 are separate and detachable electronic devices in FIGS. 14D and 14E, the housing 7301 of the camera 7300 may include a finder having a display device of one embodiment of the present invention or a touch sensor.

FIGS. 15A to 15E are external views of a head-mounted display 7500 and a head-mounted display 7510.

The head-mounted display 7500 includes a housing 7501, two display portions 7502, an operation button 7503, and a fixing band 7504.

The head-mounted display 7500 has the functions of the above-described head-mounted display 7200 and further includes two display portions.

With the two display portions 7502, the user can see one display portion with one eye and the other display portion with the other eye. Thus, a high-resolution image can be displayed even when three-dimensional display using parallax or the like is performed. The display portion 7502 is curved around an arc with the user's eye as an approximate center. Thus, distances between the user's eye and the display surface of the display portion are uniform; thus, the user can see a more natural image. Even when the luminance or chromaticity of light from the display portion is changed depending on the angle at which the user see it, since the user's eye is positioned in the normal direction of the display surface of the display portion, the influence of the change can be substantially ignorable and thus a more realistic image can be displayed.

The operation button 7503 serves as a power button or the like. A button other than the operation button 7503 may be included.

The head-mounted display 7510 includes the housing 7501, the display portion 7502, the fixing bands 7504, and the pair of lenses 7505.

The user can view display on the display portion 7502 through the lenses 7505. It is favorable that the display portion 7502 be curved. The curved display portion 7502 gives the user a high realistic sensation.

Figure 15A:
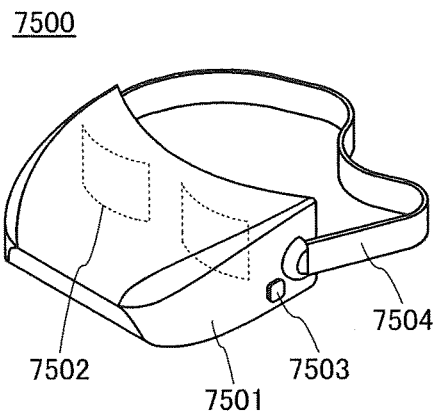
FIGS. 15A to 15E are schematic views of electronic devices of one embodiment of the present invention.
Figure 15B:
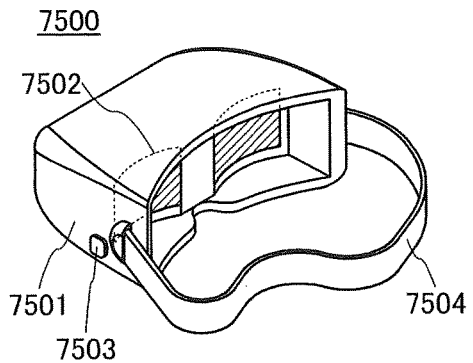
Figure 15C:
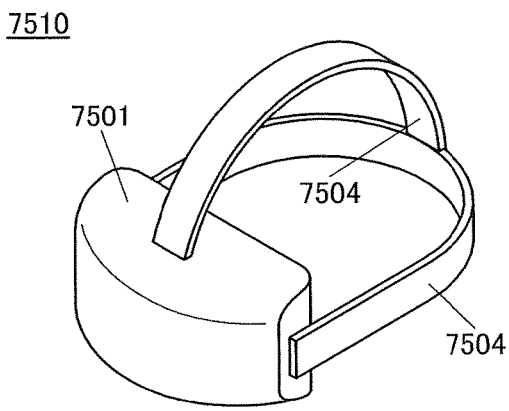
Figure 15D:
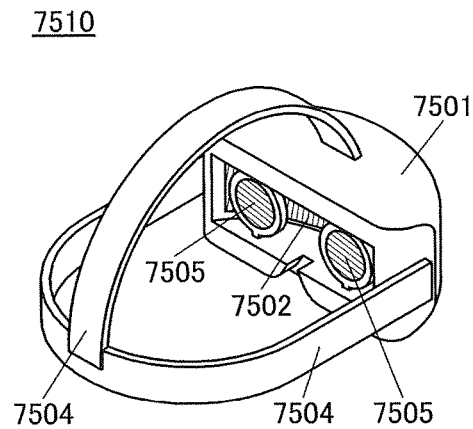
Figure 15E:
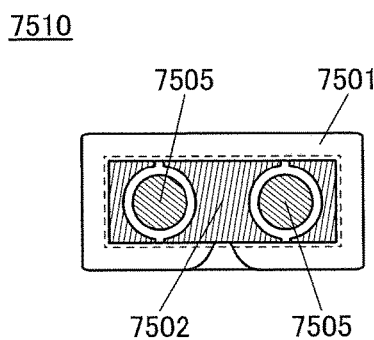

The display device of one embodiment of the present invention can be used in the display portion 7502. The display device of one embodiment of the present invention can have a high resolution; thus, even when an image is magnified using the lenses 7505 as illustrated in FIG. 15E, the user does not perceive pixels, and thus a more realistic image can be displayed.

Figure 16A:
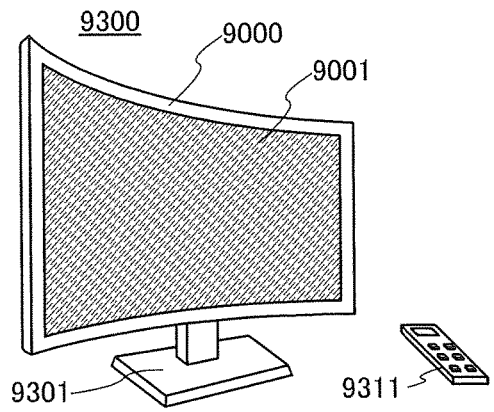
FIGS. 16A to 16D are schematic views of electronic devices of one embodiment of the present invention.

FIG. 16A illustrates an example of a television set. In a television set 9300, the display portion 9001 is incorporated into the housing 9000. Here, the housing 9000 is supported by a stand 9301.

The television set 9300 illustrated in FIG. 16A can be operated with an operation switch of the housing 9000 or a separate remote controller 9311. The display portion 9001 may include a touch sensor. The television set 9300 can be operated by touching the display portion 9001 with a finger or the like. The remote controller 9311 may be provided with a display portion for displaying data output from the remote controller 9311. With operation keys or a touch panel of the remote controller 9311, channels or volume can be controlled and images displayed on the display portion 9001 can be controlled.

The television set 9300 is provided with a receiver, a modem, or the like. With the use of the receiver, general television broadcasting can be received. Moreover, when the television device is connected to a communication network with or without wires via the modem, one-way (from a sender to a receiver) or two-way (between a sender and a receiver or between receivers) information communication can be performed.

The electronic device or the lighting device of one embodiment of the present invention has flexibility and therefore can be incorporated along a curved inside/outside wall surface of a house or a building or a curved interior/exterior surface of a car.

Figure 16B:
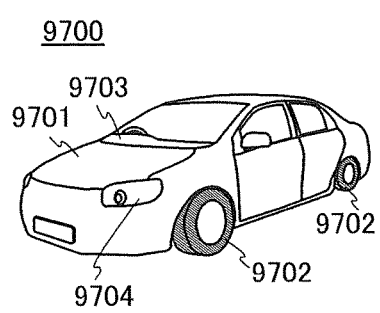
Figure 16C:
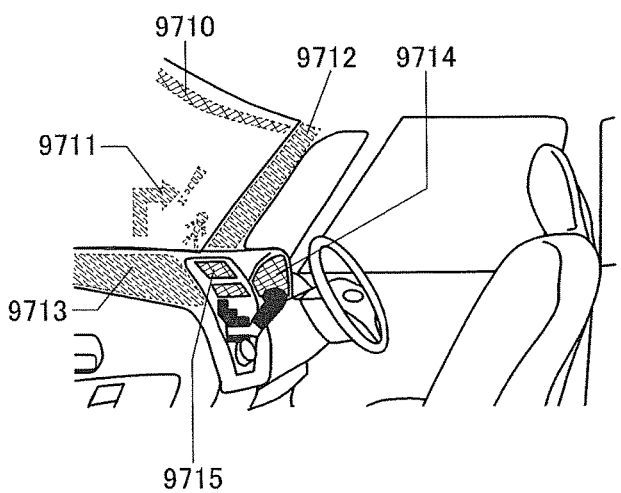

FIG. 16B is an external view of an automobile 9700. FIG. 16C illustrates a driver's seat of the automobile 9700. The automobile 9700 includes a car body 9701, wheels 9702, a dashboard 9703, lights 9704, and the like. The display device, the light-emitting device, or the like of one embodiment of the present invention can be used in a display portion or the like of the automobile 9700. For example, the display device, the light-emitting device, or the like of one embodiment of the present invention can be used in display portions 9710 to 9715 illustrated in FIG. 16C.

The display portion 9710 and the display portion 9711 are display devices provided in an automobile windshield. The display device, the light-emitting device, or the like of one embodiment of the present invention can be a see-through display device, through which the opposite side can be seen, using a light-transmitting conductive material for its electrodes and wirings. Such a see-through display portion 9710 or 9711 does not hinder driver's vision during driving the automobile 9700. Thus, the display device, the light-emitting device, or the like of one embodiment of the present invention can be provided in the windshield of the automobile 9700. Note that in the case where a transistor or the like for driving the display device, the light-emitting device, or the like is provided, a transistor having a light-transmitting property, such as an organic transistor using an organic semiconductor material or a transistor using an oxide semiconductor, is preferably used.

The display portion 9712 is a display device provided on a pillar portion. For example, the display portion 9712 can compensate for the view hindered by the pillar portion by showing an image taken by an imaging unit provided on the car body. The display portion 9713 is a display device provided on the dashboard portion. For example, the display portion 9713 can compensate for the view hindered by the dashboard portion by showing an image taken by an imaging unit provided on the car body. That is, showing an image taken by an imaging unit provided on the outside of the car body leads to elimination of blind areas and enhancement of safety. In addition, showing an image so as to compensate for the area which a driver cannot see makes it possible for the driver to confirm safety easily and comfortably.

Figure 16D:
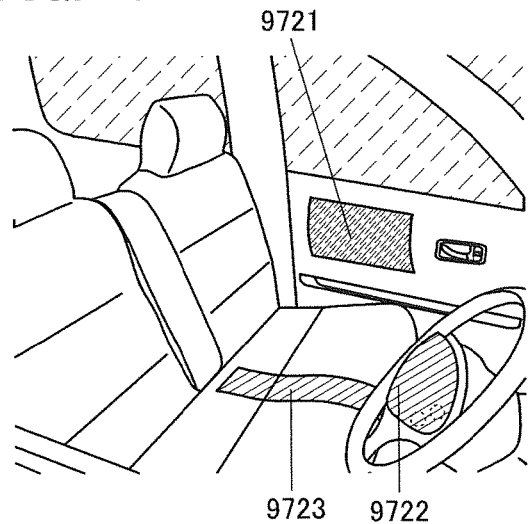

FIG. 16D illustrates the inside of a car in which a bench seat is used as a driver seat and a front passenger seat. A display portion 9721 is a display device provided in a door portion. For example, the display portion 9721 can compensate for the view hindered by the door portion by showing an image taken by an imaging unit provided on the car body. A display portion 9722 is a display device provided in a steering wheel. A display portion 9723 is a display device provided in the middle of a seating face of the bench seat. Note that the display device can be used as a seat heater by providing the display device on the seating face or backrest and by using heat generation of the display device as a heat source.

The display portion 9714, the display portion 9715, and the display portion 9722 can display a variety of kinds of information such as navigation data, a speedometer, a tachometer, a mileage, a fuel meter, a gearshift indicator, and air-condition setting. The content, layout, or the like of the display on the display portions can be changed freely by a user as appropriate. The information listed above can also be displayed on the display portions 9710 to 9713, 9721, and 9723. The display portions 9710 to 9715 and 9721 to 9723 can also be used as lighting devices. The display portions 9710 to 9715 and 9721 to 9723 can also be used as heating devices.

The electronic devices described in this embodiment each include the display portion for displaying some sort of data. Note that the light-emitting element of one embodiment of the present invention can also be used for an electronic device which does not have a display portion. The structure in which the display portion of the electronic device described in this embodiment is flexible and display can be performed on the bent display surface or the structure in which the display portion of the electronic device is foldable is described as an example; however, the structure is not limited thereto and a structure in which the display portion of the electronic device is not flexible and display is performed on a plane portion may be employed.

The structure described in this embodiment can be used in appropriate combination with the structure described in any of the other embodiments and the example.

Embodiment 6

In this embodiment, examples in which the light-emitting element of one embodiment of the present invention is used for various electronic devices and lighting devices will be described with reference to FIGS. 17A to 17C and FIG. 18.

An electronic device or a lighting device that has a light-emitting region with a curved surface can be obtained with use of the light-emitting element of one embodiment of the present invention which is fabricated over a substrate having flexibility.

Furthermore, a light-emitting device in which the light-emitting element of one embodiment of the present invention is used can also be used for lighting for motor vehicles, examples of which are lighting for a windshield, a ceiling, and the like.

Figure 17A:
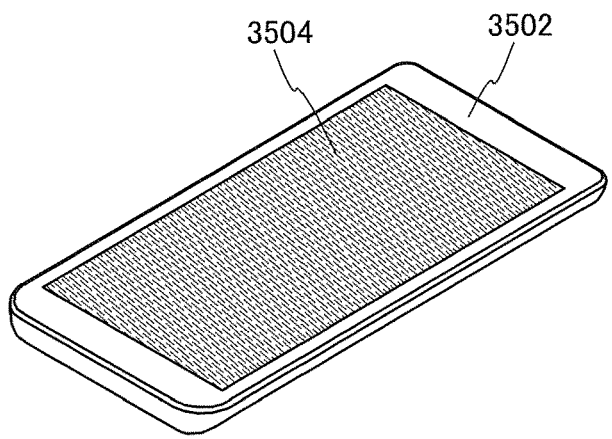
FIGS. 17A to 17C illustrate lighting devices of one embodiment of the present invention.
Figure 17B:
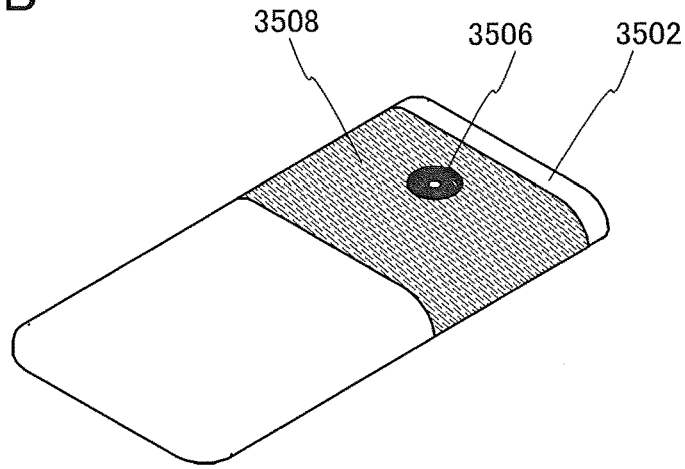

FIG. 17A is a perspective view illustrating one surface of a multifunction terminal 3500, and FIG. 17B is a perspective view illustrating the other surface of the multifunction terminal 3500. In a housing 3502 of the multifunction terminal 3500, a display portion 3504, a camera 3506, lighting 3508, and the like are incorporated. The light-emitting element of one embodiment of the present invention can be used for the lighting 3508.

The lighting 3508 that includes the light-emitting element of one embodiment of the present invention functions as a planar light source. Thus, unlike a point light source typified by an LED, the lighting 3508 can provide light emission with low directivity. When the lighting 3508 and the camera 3506 are used in combination, for example, imaging can be performed by the camera 3506 with the lighting 3508 lighting or flashing. Because the lighting 3508 functions as a planar light source, a photograph as if taken under natural light can be taken.

Note that the multifunction terminal 3500 illustrated in FIGS. 17A and 17B can have a variety of functions as in the electronic devices illustrated in FIGS. 13A to 13G.

The housing 3502 can include a speaker, a sensor (a sensor having a function of measuring or sensing force, displacement, position, speed, acceleration, angular velocity, rotational frequency, distance, light, liquid, magnetism, temperature, chemical substance, sound, time, hardness, electric field, current, voltage, power, radiation, flow rate, humidity, gradient, oscillation, odor, or infrared rays), a microphone, and the like. When a detection device including a sensor for detecting inclination, such as a gyroscope sensor or an acceleration sensor, is provided inside the multifunction terminal 3500, display on the screen of the display portion 3504 can be automatically switched by determining the orientation of the multifunction terminal 3500 (whether the multifunction terminal is placed horizontally or vertically for a landscape mode or a portrait mode).

The display portion 3504 may function as an image sensor. For example, an image of a palm print, a fingerprint, or the like is taken when the display portion 3504 is touched with the palm or the finger, whereby personal authentication can be performed. Furthermore, by providing a backlight or a sensing light source which emits near-infrared light in the display portion 3504, an image of a finger vein, a palm vein, or the like can be taken. Note that the light-emitting element of one embodiment of the present invention may be used for the display portion 3504.

Figure 17C:
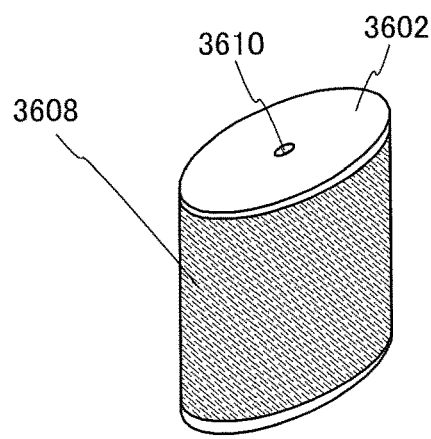

FIG. 17C is a perspective view of a security light 3600. The light 3600 includes lighting 3608 on the outside of the housing 3602, and a speaker 3610 and the like are incorporated in the housing 3602. The light-emitting element of one embodiment of the present invention can be used for the lighting 3608.

The light 3600 emits light when the lighting 3608 is gripped or held, for example. An electronic circuit that can control the manner of light emission from the light 3600 may be provided in the housing 3602. The electronic circuit may be a circuit that enables light emission once or intermittently a plurality of times or may be a circuit that can adjust the amount of emitted light by controlling the current value for light emission. A circuit with which a loud audible alarm is output from the speaker 3610 at the same time as light emission from the lighting 3608 may be incorporated.

The light 3600 can emit light in various directions; therefore, it is possible to intimidate a thug or the like with light, or light and sound. Moreover, the light 3600 may include a camera such as a digital still camera to have a photography function.

Figure 18:
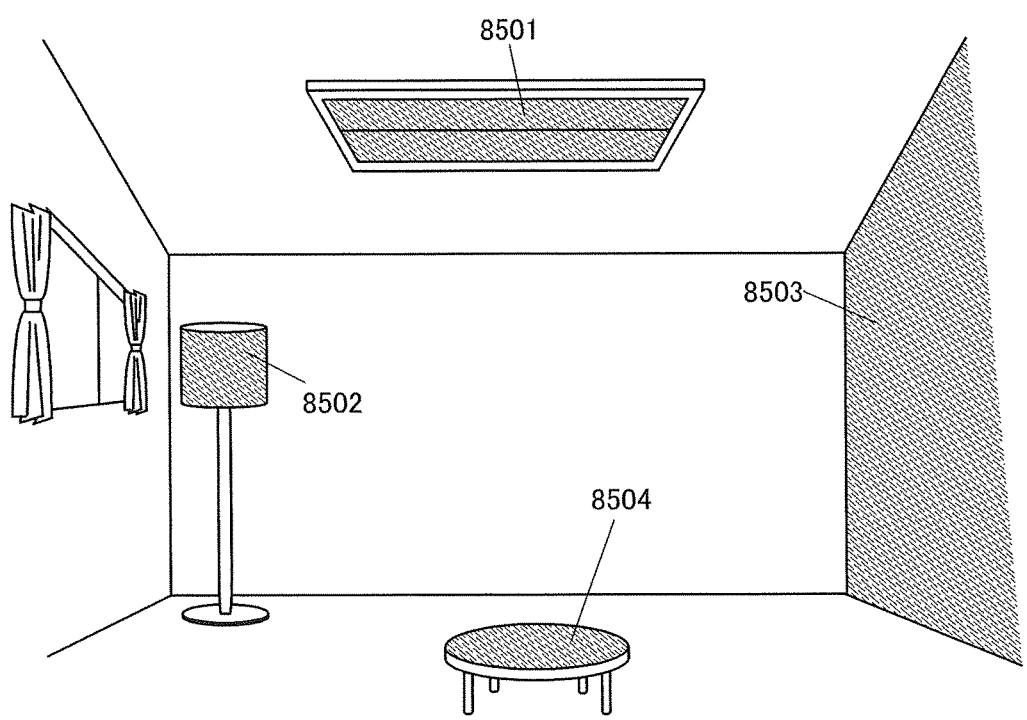
FIG. 18 illustrates lighting devices of one embodiment of the present invention.

FIG. 18 illustrates an example in which the light-emitting element is used for an indoor lighting device 8501. Since the light-emitting element can have a larger area, a lighting device having a large area can also be formed. In addition, a lighting device 8502 in which a light-emitting region has a curved surface can also be formed with use of a housing with a curved surface. A light-emitting element described in this embodiment is in the form of a thin film, which allows the housing to be designed more freely. Therefore, the lighting device can be elaborately designed in a variety of ways. Furthermore, a wall of the room may be provided with a large-sized lighting device 8503. Touch sensors may be provided in the lighting devices 8501, 8502, and 8503 to control the power on/off of the lighting devices.

Moreover, when the light-emitting element is used on the surface side of a table, a lighting device 8504 which has a function as a table can be obtained. When the light-emitting element is used as part of other furniture, a lighting device which has a function as the furniture can be obtained.

As described above, lighting devices and electronic devices can be obtained by application of the light-emitting element of one embodiment of the present invention. Note that the light-emitting device can be used for electronic devices in a variety of fields without being limited to the lighting devices and the electronic devices described in this embodiment.

The structure described in this embodiment can be combined with any of the structures described in the other embodiments and the example as appropriate.

Example 1

In this example, a method for synthesizing N-(biphenyl-4-yl)-N-{4-[6-(biphenyl-4-yl)pyrimidin-4-yl]phenyl}-9,9-dimethyl-9H-fluoren-2-amine (abbreviation: 6BP-4FBiPPm), which is the organic compound of one embodiment of the present invention represented by Structural Formula (100), and the physical properties of the compound are described.

Synthesis Example 1

Step 1: Synthesis of N-(biphenyl-4-yl)-N-{4-[6-(biphenyl-4-yl)pyrimidin-4-yl]phenyl}-9,9-dimethyl-9H-fluoren-2-amine (abbreviation: 6BP-4FBiPPm) (Structural Formula (100))

Into a 200 mL three-neck flask were put 1.2 g (4.5 mmol) of 4-(4-biphenyl)-6-chloropyrimidine, 2.2 g (4.5 mmol) of 4-[N-(biphenyl-4-yl)-N-(9,9-dimethyl-9H-fluoren-2-yl) amino]phenylboronic acid, 1.9 g (13.5 mmol) of potassium carbonate, and 55 mg (0.18 mmol) of tris(2-methylphenyl) phosphine. To this mixture, 25 mL of toluene, 10 mL of ethanol, and 7 mL of water were added. The resulting mixture was degassed by being stirred while the pressure was reduced. Then, 20 mg (0.090 mmol) of palladium(II) acetate was added to this mixture, and the mixture was stirred under a nitrogen stream at 90° C. for 6 hours. After the stirring, the aqueous layer of this mixture was subjected to extraction with toluene, and the solution of the extract and the organic layer were combined and washed with water and saturated brine. The organic layer was dried with magnesium sulfate. This mixture was separated by gravity filtration, and the filtrate was concentrated to give a solid. This solid was purified by silica gel column chromatography (developing solvent: toluene and then toluene and ethyl acetate in a 4:1 ratio) to give a solid. Note that for the purification, silica gel produced by KANTO CHEMICAL CO., INC., catalog No. 37560-84, was used. The obtained solid was recrystallized with toluene/ethanol to give 2.7 g of a yellow solid in a yield of 89%. The synthesis scheme of Step 1 is shown in (A-1) below.

[Chemical Formula 7]

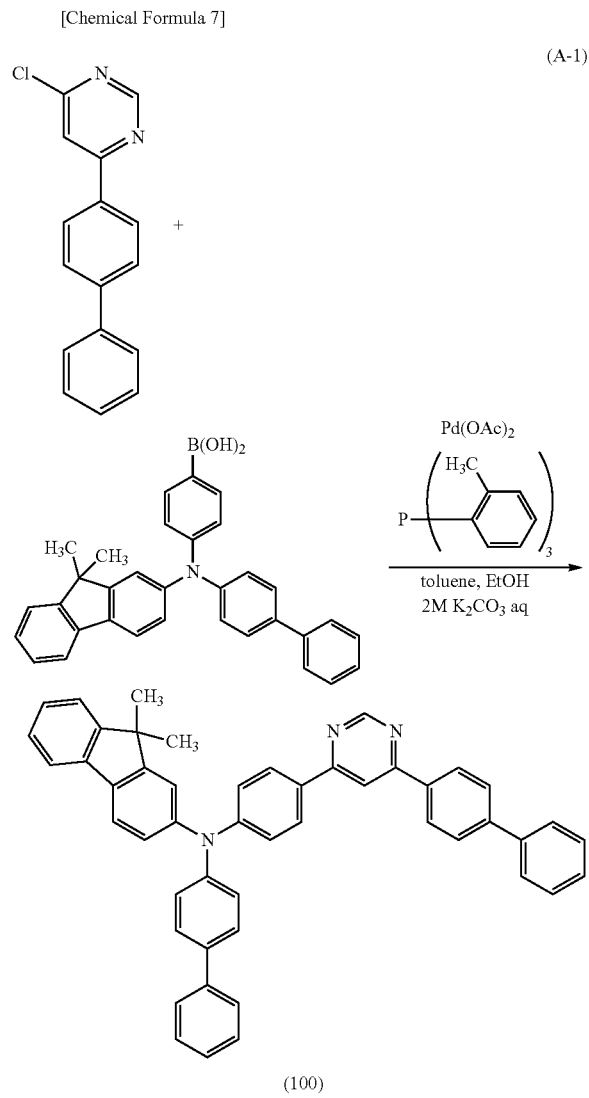

Then, 2.7 g of the obtained solid was purified by a train sublimation method. The purification by sublimation was performed by heating at 305° C. under a pressure of 2.8 Pa with an argon flow rate of 15 mL/min to give 2.3 g of a yellow solid was obtained at a collection rate of 88%.

The obtained solid was subjected to analysis by nuclear magnetic resonance spectrometry ($^1$H NMR), and the results are shown below.

$^1$H NMR (DMSO-$d_6$, 300 MHz):δ=1.43 (s, 6H), 7.12-7.18 (m, 3H), 7.26 (d, $J_1$=8.7 Hz, 2H), 7.30-7.38 (m, 3H), 7.40-7.56 (m, 7H), 7.68-7.73 (m, 4H), 7.80 (dd, $J_1$=7.2 Hz, $J_2$=1.5 Hz, 3H), 7.85 (d, $J_1$=8.1 Hz, 1H), 8.89 (d, $J_1$=8.4 Hz, 2H), 8.34 (d, $J_1$=8.7 Hz, 2H), 8.46 (d, $J_1$=8.1 Hz, 2H), 8.58 (d, $J_1$=1.5 Hz, 1H), 9.24 (d, $J_1$=1.5 Hz, 1H).

Figure 19A:
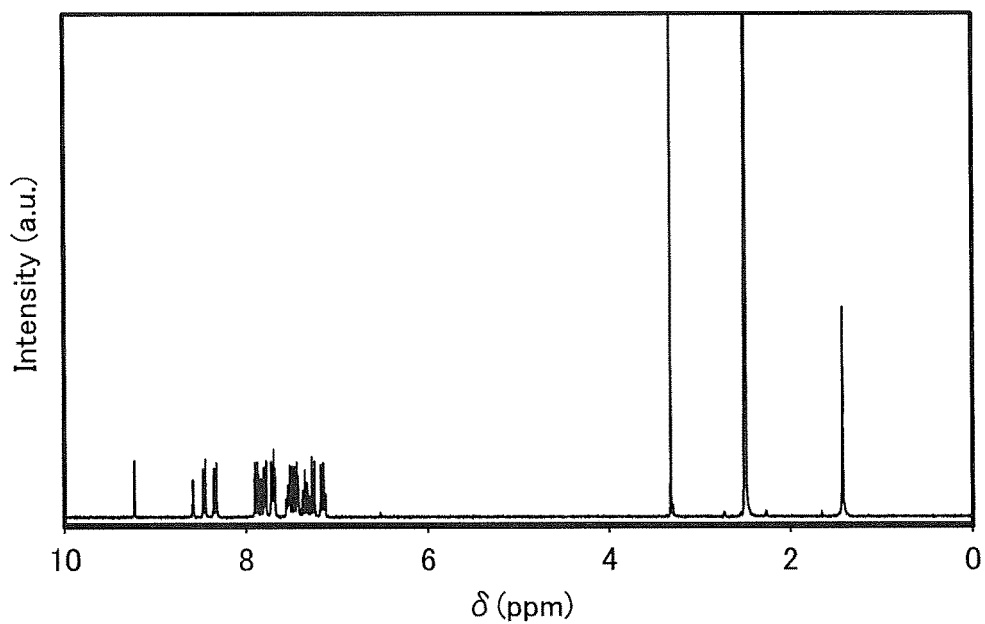
FIGS. 19A and 19B are NMR charts of Example.
Figure 19B:
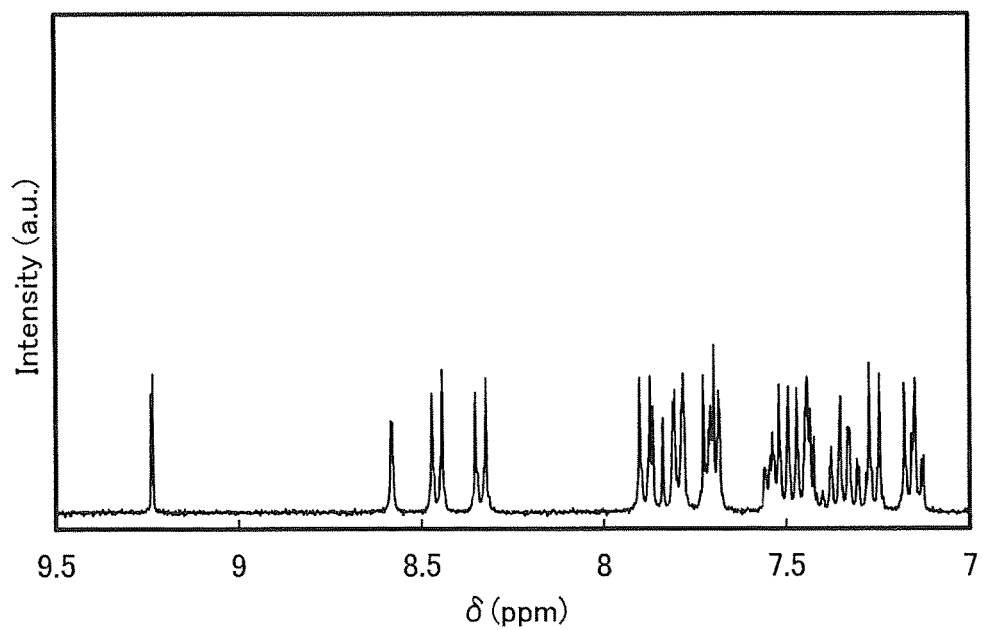

FIGS. 19A and 19B are $^1$H NMR charts of the obtained solid. Note that FIG. 19B is a chart showing an enlarged part in the range of 7.0 ppm to 9.5 ppm of FIG. 19A. The measurement results reveal that 6BP-4FBiPPm, which is the target substance, was obtained.

<Properties of 6BP-4FBiPPm>

Figure 20:
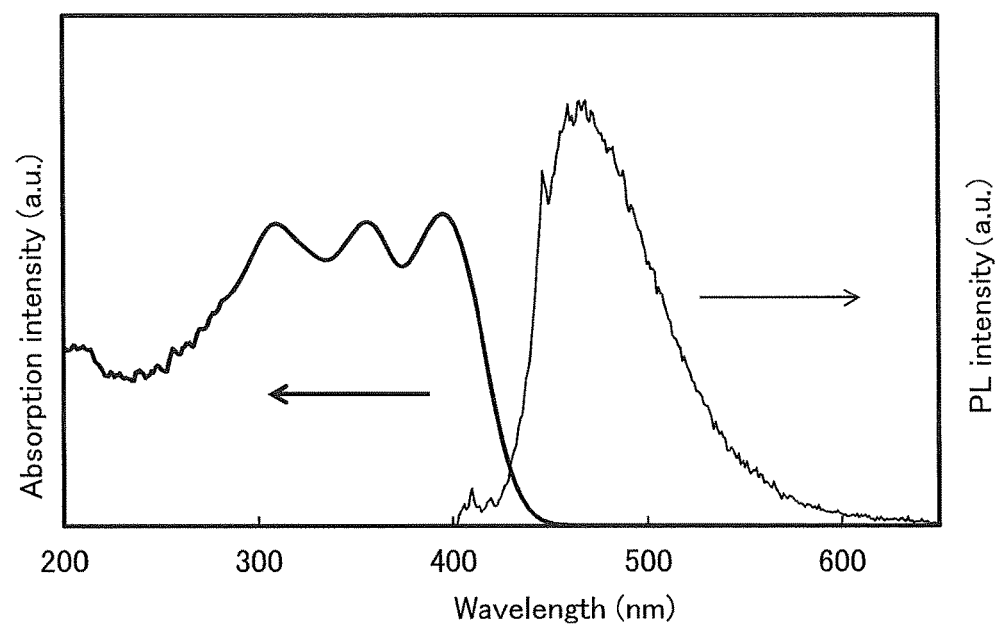
FIG. 20 shows absorption and emission spectra of a compound in Example.
Figure 21:
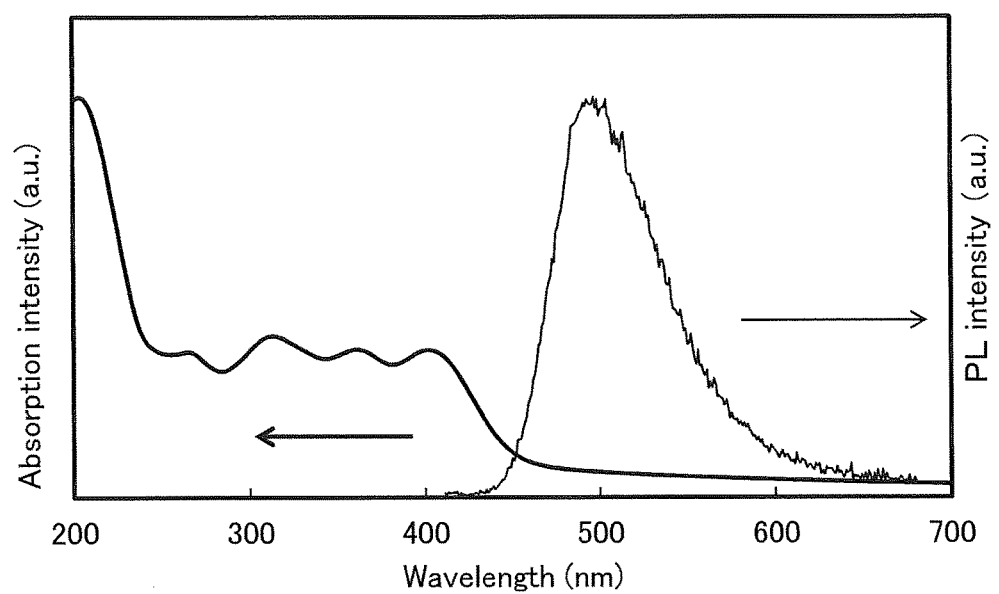
FIG. 21 shows absorption and emission spectra of a compound in Example.

FIG. 20 shows an absorption spectrum and an emission spectrum of 6BP-4FBiPPm in a toluene solution. FIG. 21 shows an absorption spectrum and an emission spectrum of a thin film of 6BP-4FBiPPm. The solid thin film was formed over a quartz substrate by a vacuum evaporation method. The absorption spectrum of the toluene solution was measured using an ultraviolet-visible light spectrophotometer (V550 type manufactured by JASCO Corporation). The absorption spectrum of 6BP-4FBiPPm in the toluene solution shown in FIG. 20 was obtained by subtracting an absorption spectrum of toluene only put in a quartz cell from the absorption spectrum of 6BP-4FBiPPm in the toluene solution in a quartz cell. The absorption spectrum of the thin film was measured with a spectrophotometer (U-4100 Spectrophotometer, manufactured by Hitachi High-Technologies Corporation). The emission spectra were measured using a fluorescence spectrophotometer (FS920 manufactured by Hamamatsu Photonics K.K.).

As shown in FIG. 20, 6BP-4FBiPPm in the toluene solution has absorption peaks at around 395 nm, 356 nm, and 310 nm, and an emission wavelength peak at 468 nm (excitation wavelength: 393 nm). As shown in FIG. 21, the thin film of 6BP-4FBiPPm has absorption peaks at around 402 nm, 362 nm, 313 nm, 265 nm, and 204 nm, and an emission wavelength peak at around 497 nm (excitation wavelength: 402 nm). It was found that 6BP-4FBiPPm emits blue light. The compound of one embodiment of the present invention can be used as a host material for a light-emitting substance or a host material for a substance emitting fluorescence in the visible region.

It was found that aggregation of the thin film of 6BP-4FBiPPm is not easily caused even under the air and the thin film suffers only a small change in shape and has high film quality.

The HOMO level and the LUMO level of 6BP-4FBiPPm were obtained through a cyclic voltammetry (CV) measurement. A calculation method is shown below.

An electrochemical analyzer (ALS model 600A or 600C, manufactured by BAS Inc.) was used as a measurement apparatus. As for a solution used for the CV measurement, dehydrated dimethylformamide (DMF, manufactured by Sigma-Aldrich Co. LLC., 99.8%, catalog No. 22705-6) was used as a solvent, and tetra-n-butylammonium perchlorate (n-Bu$_4$NClO$_4$, manufactured by Tokyo Chemical Industry Co., Ltd., catalog No. T0836), which was a supporting electrolyte, was dissolved in the solvent such that the concentration of tetra-n-butylammonium perchlorate was 100 mmol/L. Furthermore, the object to be measured was also dissolved in the solvent such that the concentration thereof was 2 mmol/L. A platinum electrode (PTE platinum electrode, manufactured by BAS Inc.) was used as a working electrode, another platinum electrode (Pt counter electrode for VC-3, (5 cm), manufactured by BAS Inc.) was used as an auxiliary electrode, and an Ag/Ag$^+$ electrode (RE7 reference electrode for nonaqueous solvent, manufactured by BAS Inc.) was used as a reference electrode. Note that the measurement was performed at a room temperature (20° C. to 25° C.). In addition, the scan speed at the CV measurement was set to 0.1 V/sec, and an oxidation potential Ea [V] and a reduction potential Ec [V] with respect to the reference electrode were measured. Note that Ea represents an intermediate potential of an oxidation-reduction wave, and Ec represents an intermediate potential of a reduction-oxidation wave. Here, the potential energy of the reference electrode used in this example with respect to the vacuum level is found to be −4.94 [eV], and thus, the HOMO level and the LUMO level can be obtained from the following formulae: HOMO level [eV]=−4.94−Ea and LUMO level [eV]=−4.94−Ec.

Furthermore, the CV measurement was repeated 100 times, and the oxidation-reduction wave at the hundredth cycle and the oxidation-reduction wave at the first cycle were compared with each other to examine the electric stability of the compound.

As a result, in the measurement of an oxidation potential Ea [V] of 6BP-4FBiPPm, the HOMO level was −5.48 eV. In contrast, the LUMO level was found to be −2.79 eV. When the oxidation-reduction wave was repeatedly measured, in the Ea measurement, the peak intensity of the oxidation-reduction wave after the hundredth cycle was maintained to be 92% of that of the oxidation-reduction wave at the first cycle, and in the Ec measurement, the peak intensity of the oxidation-reduction wave after the hundredth cycle was maintained to be 87% of that of the oxidation-reduction wave at the first cycle; thus, resistance to oxidation and reduction of 6BP-4FBiPPm was found to be extremely high.

Example 2

In this example, a method for synthesizing 4-[6-(biphenyl-4-yl)pyrimidin-4-yl]-4'-phenyl-4"-(9-phenyl-9H-carbazol-3-yl)triphenylamine (abbreviation: 6BP-4PCBBiPPm), which is the organic compound of one embodiment of the present invention represented by Structural Formula (101), and the physical properties of the compound are described.

Synthesis Example 2

Step 1: Synthesis of 4-[6-(biphenyl-4-yl)pyrimidin-4-yl]-4'-phenyl-4"-(9-phenyl-9H-carbazol-3-yl)triphenylamine (abbreviation: 6BP-4PCBBiPPm)

Into a 200 mL three-neck flask were put 1.7 g (5.0 mmol) of 4-(4-biphenyl)-6-(4-chlorophenyl)pyrimidine, 2.7 g (5.5 mmol) of N-biphenyl-[4-(9-phenyl-9H-carbazol-3-yl)phenyl]amine, 1.5 g (15 mmol) of sodium tert-butoxide, and 90 mg (0.25 mmol) of di(1-adamantyl)-n-butylphosphine. To this mixture, 25 mL of toluene was added, and the resulting mixture was degassed by being stirred while the pressure was reduced. To this mixture was added 29 mg (0.050 mmol) of bis(dibenzylideneacetone)palladium(0), and the mixture was heated and stirred under a nitrogen stream at 110° C. for 23.5 hours. After the stirring, toluene was added to the mixture, and the resulting suspension was suction filtered through Florisil (manufactured by Wako Pure Chemical Industries, Ltd., Catalog No. 540-00135), Celite (manufactured by Wako Pure Chemical Industries, Ltd., Catalog No. 531-16855), and alumina to give a filtrate. This filtrate was concentrated to give a solid. The obtained solid was recrystallized by toluene, so that 3.3 g of a pale yellow solid was obtained in a yield of 82%. The synthesis scheme of Step 1 is shown in (A-2) below.

[Chemical Formula 8]

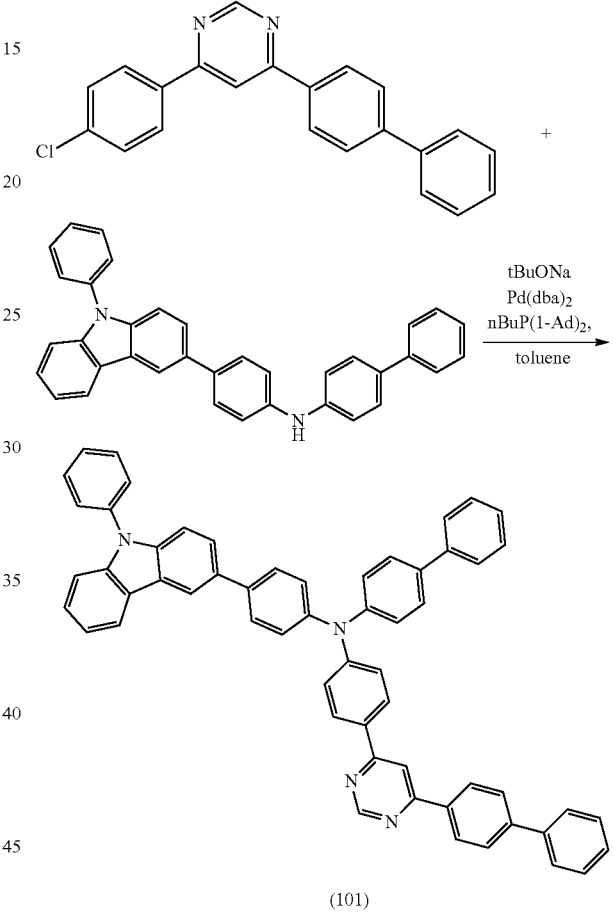

Then, 3.2 g of the obtained pale yellow solid was purified by a train sublimation method. The purification by sublimation was performed by heating at 380° C. under a pressure of 2.9 Pa with an argon flow rate of 15 mL/min to give 2.8 g of a yellow solid was obtained at a collection rate of 88%.

The obtained solid was subjected to analysis by nuclear magnetic resonance spectrometry ($^1$H NMR), and the results are shown below.

$^1$H NMR (1,1,2,2-Tetrachloroethane-d$_2$, 300 MHz): δ=7.31-7.41 (m, 8H), 7.43-7.54 (m, 9H), 7.61-7.75 (m, 13H), 7.81 (d, J$_1$=8.4 Hz, 1H), 8.11-8.14 (m, 3H), 8.21-8.28 (m, 3H), 8.39 (d, J$_1$=0.9 Hz, 2H), 9.30 (s, 1H).

Figure 22A:
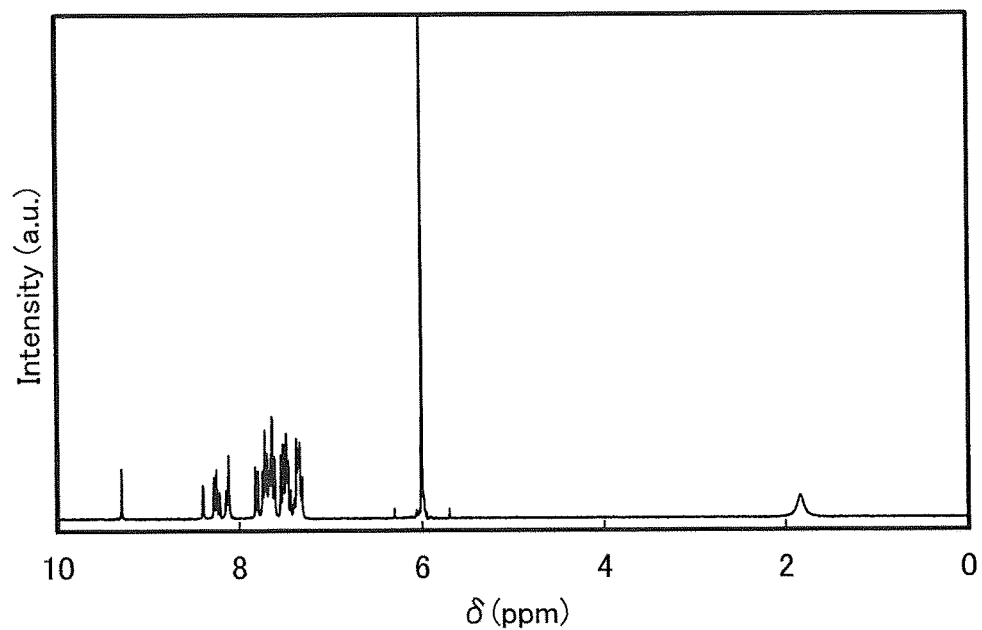
FIGS. 22A and 22B are NMR charts of Example.
Figure 22B:
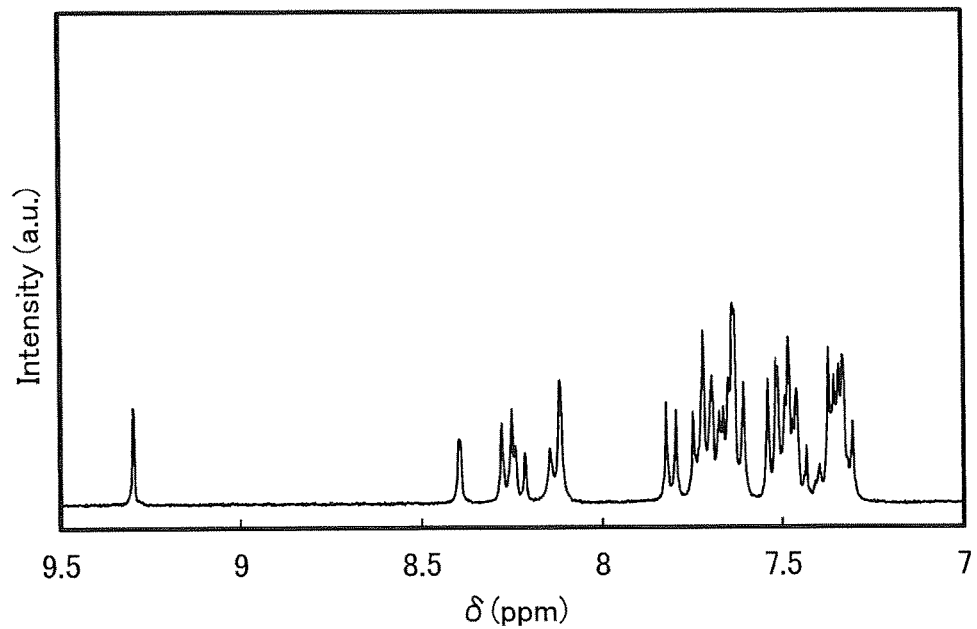

FIGS. 22A and 22B are $^1$H NMR charts of the obtained solid. Note that FIG. 22B is a chart showing an enlarged part in the range of 7.0 ppm to 9.5 ppm of FIG. 22A. The measurement results reveal that 6BP-4PCBBiPPm, which is the target substance, was obtained.

<Properties of 6BP-4PCBBiPPm>

Figure 23:
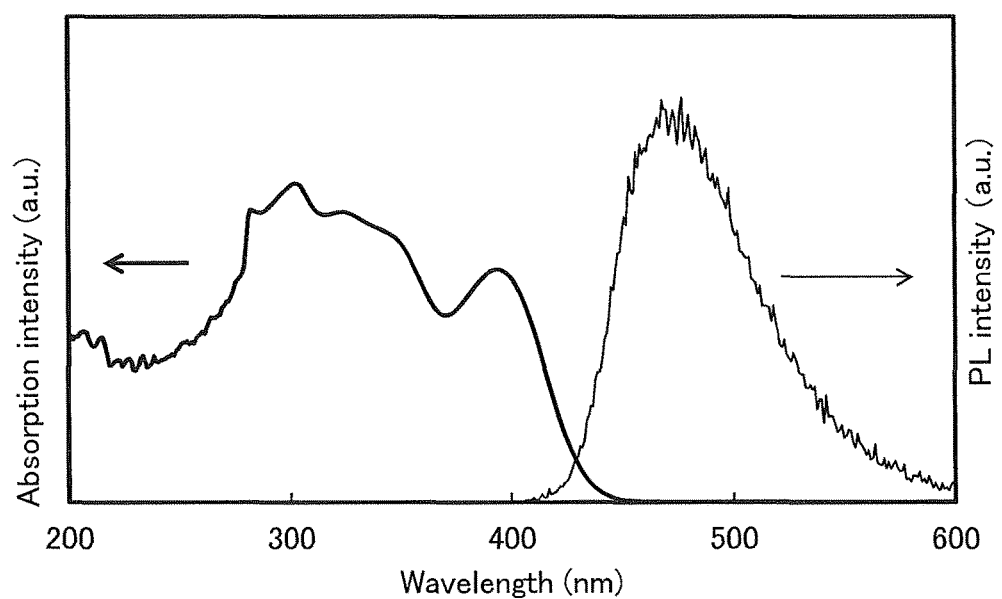
FIG. 23 shows absorption and emission spectra of a compound in Example.
Figure 24:
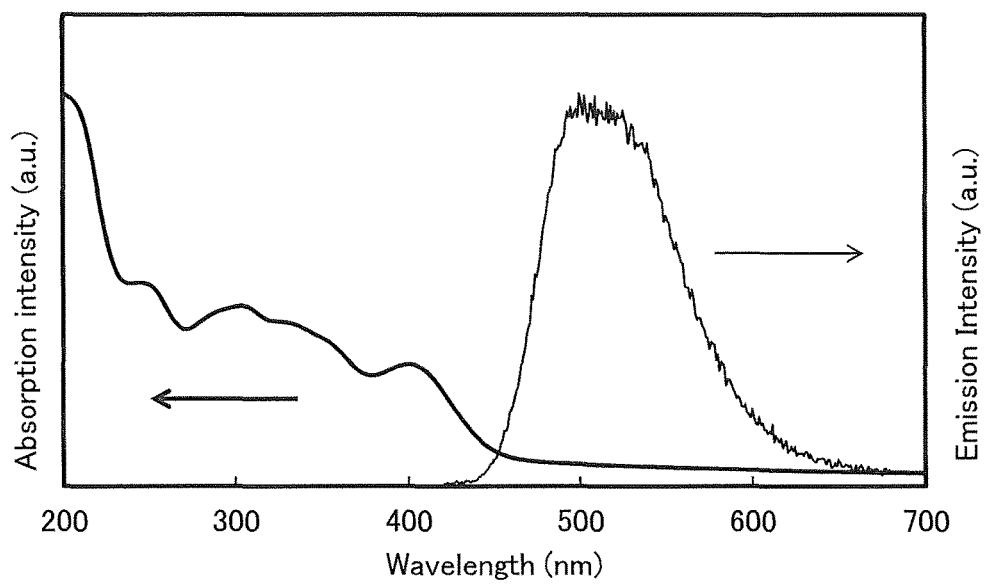
FIG. 24 shows absorption and emission spectra of a compound in Example.

FIG. 23 shows an absorption spectrum and an emission spectrum of 6BP-4PCBBiPPm in a toluene solution. FIG. 24 shows an absorption spectrum and an emission spectrum of a thin film of 6BP-4PCBBiPPm. The measurement was performed in a manner similar to that described in Example 1.

As shown in FIG. 23, 6BP-4PCBBiPPm in the toluene solution has absorption peaks at around 394 nm, 347 nm, 324 nm, 302 nm, and 282 nm, and an emission wavelength peak at 468 nm (excitation wavelength: 396 nm). As shown in FIG. 24, the thin film of 6BP-4PCBBiPPm has absorption peaks at around 400 nm, 355 nm, 332 nm, 304 nm, 282 nm, and 244 nm, and an emission wavelength peak at around 512 nm (excitation wavelength: 413 nm). The compound of one embodiment of the present invention can be used as a host material for a light-emitting substance or a host material for a substance emitting fluorescence in the visible region.

It was found that aggregation of the thin film of 6BP-4PCBBiPPm is not easily caused even under the air and the thin film suffers only a small change in shape and has high film quality.

Next, the HOMO level and the LUMO level of 6BP-4PCBBiPPm were obtained through a cyclic voltammetry (CV) measurement. A calculation method is similar to that described in Example 1.

As a result, in the measurement of an oxidation potential Ea [V] of 6BP-4PCBBiPPm, the HOMO level was −5.48 eV. In contrast, the LUMO level was found to be −2.82 eV. When the oxidation-reduction wave was repeatedly measured, in the Ea measurement, the peak intensity of the oxidation-reduction wave after the hundredth cycle was maintained to be 79% of that of the oxidation-reduction wave at the first cycle, and in the Ec measurement, the peak intensity of the oxidation-reduction wave after the hundredth cycle was maintained to be 94% of that of the oxidation-reduction wave at the first cycle; thus, resistance to oxidation and reduction of 6BP-4PCBBiPPm was found to be extremely high.

Example 3

In this example, a method for synthesizing N-(biphenyl-4-yl)-N-{3-[6-(biphenyl-4-yl)pyrimidin-4-yl]phenyl}-9,9-dimethyl-9H-fluoren-2-amine (abbreviation: 6BP-4mFBiPPm), which is the organic compound of one embodiment of the present invention represented by Structural Formula (102), and the physical properties of the compound are described.

Synthesis Example 3

Step 1: Synthesis of N-(biphenyl-4-yl)-N-{3-[6-(biphenyl-4-yl)pyrimidin-4-yl]phenyl}-9,9-dimethyl-9H-fluoren-2-amine (abbreviation: 6BP-4mFBiPPm)

Into a 200 mL three-neck flask were put 2.1 g (6.0 mmol) of 4-(4-biphenyl)-6-(3-chlorophenyl)pyrimidine, 2.4 g (6.6 mmol) of N-(biphenyl-4-yl)-9,9-dimethyl-9H-fluoren-2-amine, 1.73 g (18.0 mmol) of sodium tert-butoxide, and 107 mg (0.30 mmol) of di(1-adamantyl)-n-butylphosphine. To this mixture, 30 mL of toluene was added, and the resulting mixture was degassed by being stirred while the pressure was reduced. To this mixture was added 34 mg (0.060 mmol) of bis(dibenzylideneacetone)palladium(0), and the mixture was heated and stirred under a nitrogen stream at 110° C. for 35 hours. After the stirring, toluene was added to the mixture, and the resulting suspension was suction filtered through Florisil, Celite, and alumina to give a filtrate. The obtained filtrate was concentrated to give a solid. This solid was purified by silica gel column chromatography (developing solvent: toluene and then toluene and ethyl acetate in a 100:3 ratio) to give a solid. The obtained solid was recrystallized with toluene/ethanol to give 3.9 g of a pale yellow solid in a yield of 97%. The synthesis scheme of Step 1 is shown in (A-3) below.

[Chemical Formula 9]

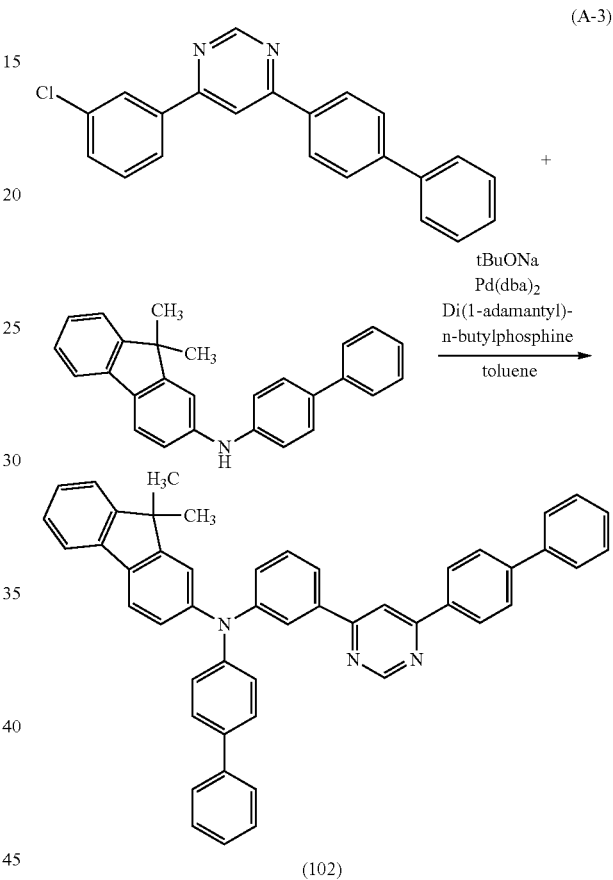

(A-3)

(102)

Then, 3.8 g of the obtained pale yellow solid was purified by a train sublimation method. The purification by sublimation was performed by heating at 300° C. under a pressure of 2.7 Pa with an argon flow rate of 15 mL/min to give 3.2 g of a pale yellow solid was obtained at a collection rate of 84%.

The obtained solid was subjected to analysis by nuclear magnetic resonance spectrometry ($^1$H NMR), and the results are shown below.

$^1$H NMR (DMSO-$d_6$, 300 MHz):δ=1.40 (s, 6H), 7.09 (dd, $J_1$=7.8 Hz, $J_2$=2.1 Hz, 1H), 7.19 (d, $J_1$=8.7 Hz, 2H), 7.26-7.58 (m, 12H), 7.66-7.70 (m, 4H), 7.76-7.82 (m, 4H), 7.87 (d, $J_1$=8.7 Hz, 2H), 8.12 (d, $J_1$=7.8 Hz, 1H), 8.18 (t, $J_1$=2.1 Hz, 1H), 8.45 (d, $J_1$=8.4 Hz, 2H), 8.64 (d, $J_1$=0.9 Hz, 1H), 9.22 (d, $J_1$=0.9 Hz, 1H).

Figure 25A:
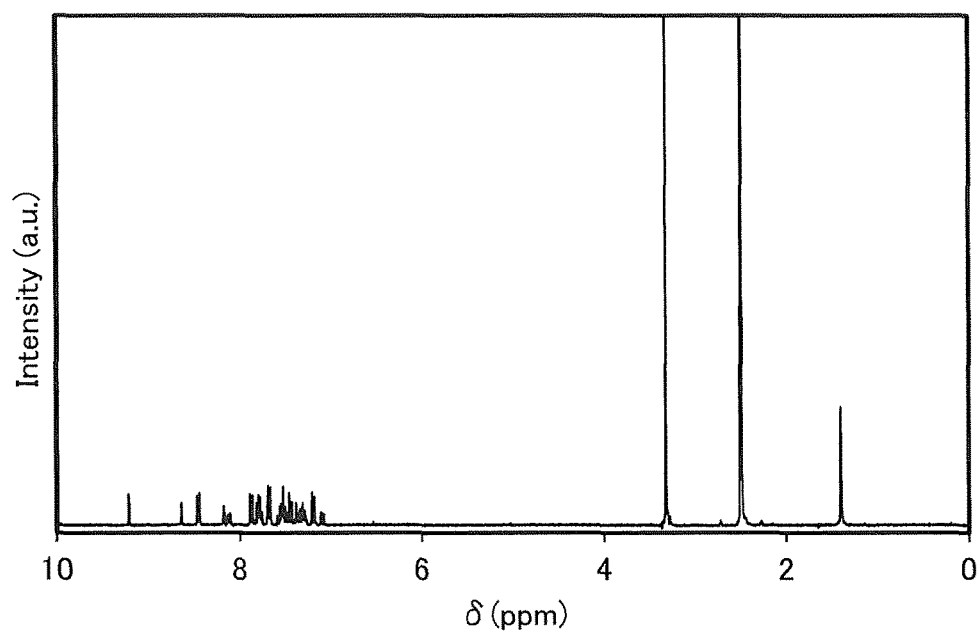
FIGS. 25A and 25B are NMR charts of Example.
Figure 25B:
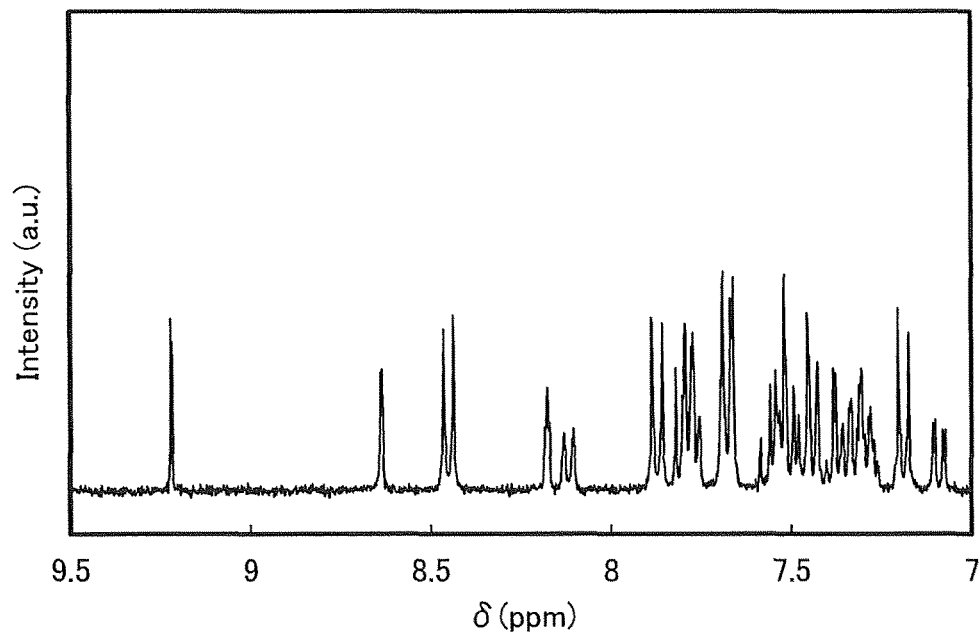

FIGS. 25A and 25B are $^1$H NMR charts of the obtained solid. Note that FIG. 25B is a chart showing an enlarged part in the range of 7.0 ppm to 9.5 ppm of FIG. 25A. The measurement results reveal that 6BP-4mFBiPPm, which is the target substance, was obtained.

<Properties of 6BP-4mFBiPPm>

Figure 26:
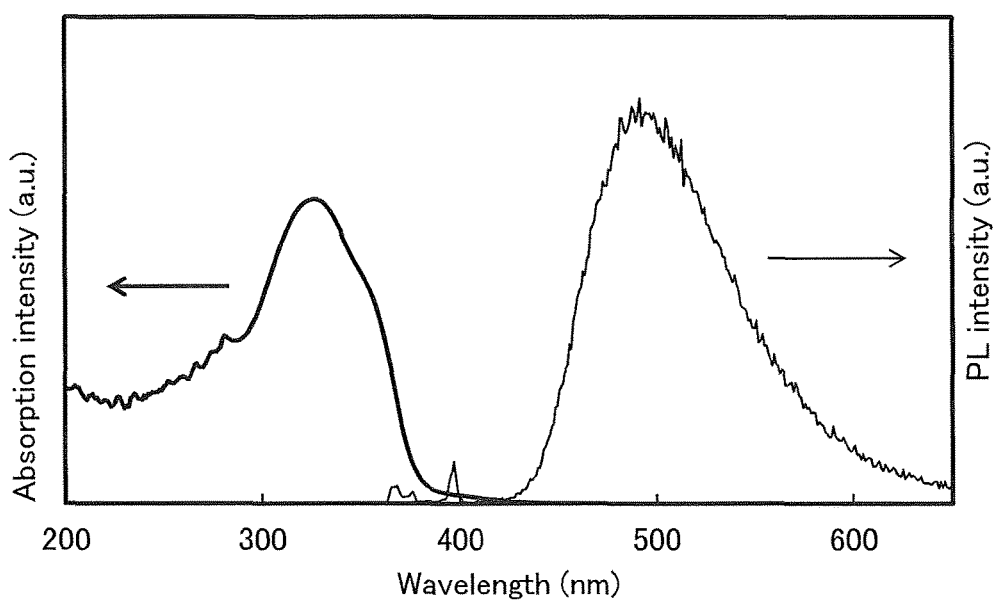
FIG. 26 shows absorption and emission spectra of a compound in Example.
Figure 27:
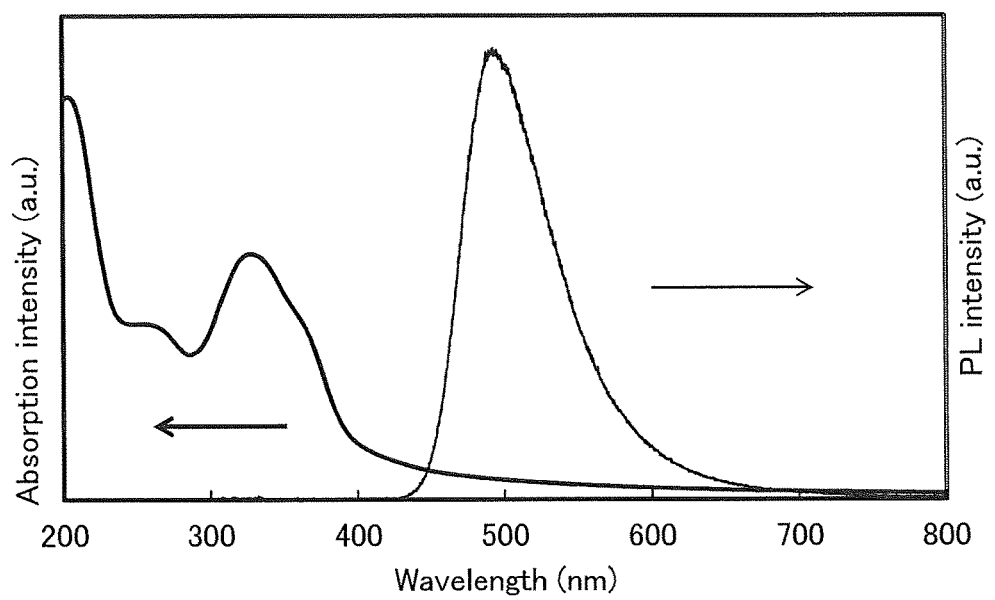
FIG. 27 shows absorption and emission spectra of a compound in Example.

FIG. 26 shows an absorption spectrum and an emission spectrum of 6BP-4mFBiPPm in a toluene solution. FIG. 27 shows an absorption spectrum and an emission spectrum of a thin film of 6BP-4mFBiPPm. The measurement of an absorption spectrum and an emission spectrum of the solution and an absorption spectrum of the thin film was performed in a manner similar to that described in Example 1. The measurement of the emission spectrum of the thin film was performed with a PL microscope (LabRAM HR-PL, produced by HORIBA, Ltd.).

As shown in FIG. 26, 6BP-4mFBiPPm in the toluene solution has absorption peaks at around 352 nm and 327 nm, and an emission wavelength peak at 496 nm (excitation wavelength: 354 nm). As shown in FIG. 27, the thin film of 6BP-4mFBiPPm has absorption peaks at around 365 nm, 327 nm, 264 nm, and 204 nm, and an emission wavelength peak at around 496 nm (excitation wavelength: 410 nm). The compound of one embodiment of the present invention can be used as a host material for a light-emitting substance or a host material for a substance emitting fluorescence in the visible region.

It was found that aggregation of the thin film of 6BP-4mFBiPPm is not easily caused even under the air and the thin film suffers only a small change in shape and has high film quality.

Next, the HOMO level and the LUMO level of 6BP-4mFBiPPm were obtained through a cyclic voltammetry (CV) measurement. A calculation method is similar to that described in Example 1.

As a result, in the measurement of an oxidation potential Ea [V] of 6BP-4mFBiPPm, the HOMO level was −5.46 eV. In contrast, the LUMO level was found to be −2.83 eV. When the oxidation-reduction wave was repeatedly measured, in the Ea measurement, the peak intensity of the oxidation-reduction wave after the hundredth cycle was maintained to be 91% of that of the oxidation-reduction wave at the first cycle, and in the Ec measurement, the peak intensity of the oxidation-reduction wave after the hundredth cycle was maintained to be 90% of that of the oxidation-reduction wave at the first cycle; thus, resistance to oxidation and reduction of 6BP-4mFBiPPm was found to be extremely high.

Example 4

In this example, a method for synthesizing 3-[6-(biphenyl-4-yl)pyrimidin-4-yl]-4'-phenyl-4"-(9-phenyl-9H-carbazol-3-yl)triphenylamine (abbreviation: 6BP-4mPCBBiPPm), which is the organic compound of one embodiment of the present invention represented by Structural Formula (103), and the physical properties of the compound are described.

Synthesis Example 4

Step 1: Synthesis of 3-[6-(biphenyl-4-yl)pyrimidin-4-yl]-4'-phenyl-4"-(9-phenyl-9H-carbazol-3-yl)triphenylamine (abbreviation: 6BP-4mPCBBiPPm)

Into a 200 mL three-neck flask were put 1.7 g (5.0 mmol) of 4-(4-biphenyl)-6-(3-chlorophenyl)pyrimidine, 2.7 g (5.5 mmol) of N-biphenyl-[4-(9-phenyl-9H-carbazol-3-yl)phenyl]amine, 1.45 g (15.1 mmol) of sodium tert-butoxide, and 90 mg (0.25 mmol) of di(1-adamantyl)-n-butylphosphine. To this mixture, 25 mL of toluene was added, and the resulting mixture was degassed by being stirred while the pressure was reduced. To this mixture was added 29 mg (0.050 mmol) of bis(dibenzylideneacetone)palladium(0), and the mixture was heated and stirred under a nitrogen stream at 110° C. for 35 hours. After the stirring, toluene was added to the mixture, and the resulting suspension was suction filtered through Florisil, Celite, and alumina to give a filtrate. The obtained filtrate was concentrated to give a solid. This solid was purified by silica gel column chromatography (developing solvent: toluene and then toluene and ethyl acetate in a 100:1 ratio) to give a solid. The obtained solid was reprecipitated with ethyl acetate/ethanol to give 3.3 g of a yellow solid in a yield of 83%. The synthesis scheme of Step 1 is shown in (A-4) below.

[Chemical Formula 10]

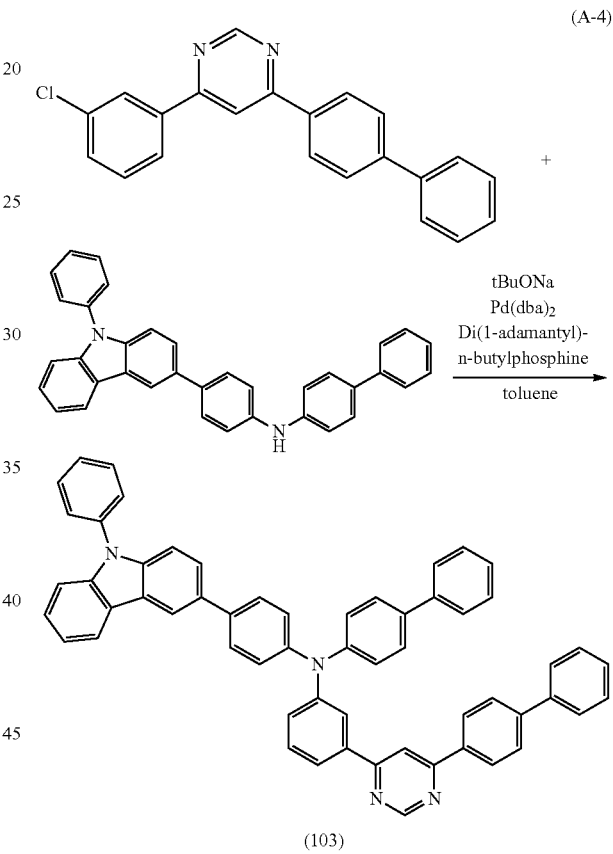

Then, 3.3 g of the obtained yellow solid was purified by a train sublimation method. The purification by sublimation was performed by heating at 370° C. under a pressure of 3.0 Pa with an argon flow rate of 15 mL/min to give 2.7 g of a yellow solid was obtained at a collection rate of 83%.

The obtained solid was subjected to analysis by nuclear magnetic resonance spectrometry ($^1$H NMR), and the results are shown below.

$^1$H NMR (DMSO-d$_6$, 300 MHz):δ=7.24 (dd, J$_1$=8.7 Hz, J$_2$=14.7 Hz, 4H), 7.29-7.62 (m, 13H), 7.65-7.82 (m, 13H), 7.88 (d, J$_1$=8.4 Hz, 2H), 8.15 (d, J$_1$=7.8 Hz, 1H), 8.19 (s, 1H), 8.35 (d, J$_1$=7.2 Hz, 1H), 8.47 (d, J$_1$=8.4 Hz, 2H), 8.60 (d, J$_1$=1.5 Hz, 1H), 8.66 (s, 1H), 9.25 (s, 1H).

Figure 28A:
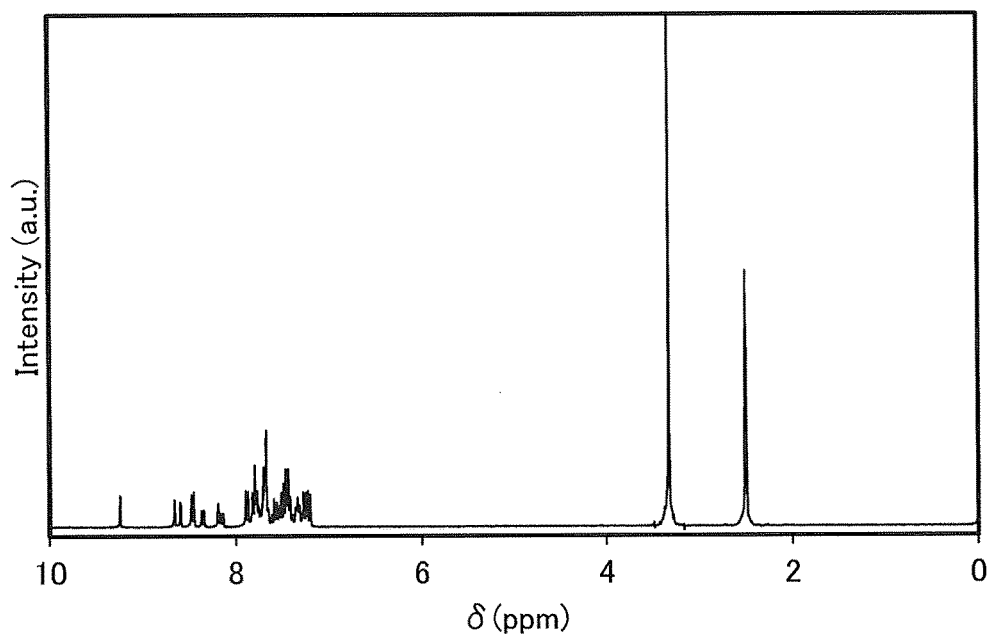
FIGS. 28A and 28B are NMR charts of Example.
Figure 28B:
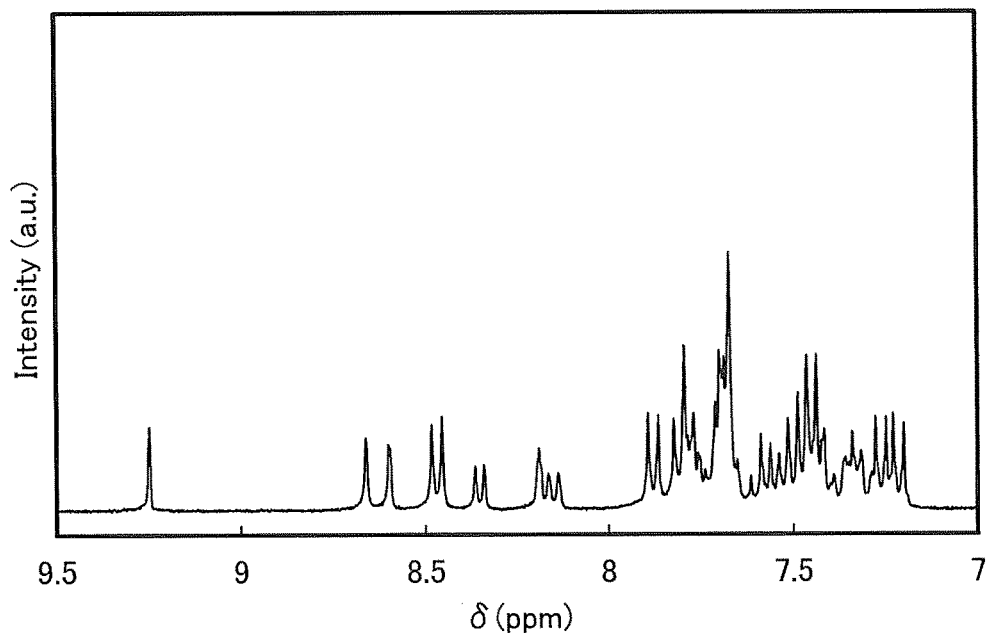

FIGS. 28A and 28B are $^1$H NMR charts of the obtained solid. Note that FIG. 28B is a chart showing an enlarged part in the range of 7.0 ppm to 9.5 ppm of FIG. 28A. The measurement results reveal that 6BP-4mPCBBiPPm, which is the target substance, was obtained.

<Properties of 6BP-4mPCBBiPPm>

Figure 29:
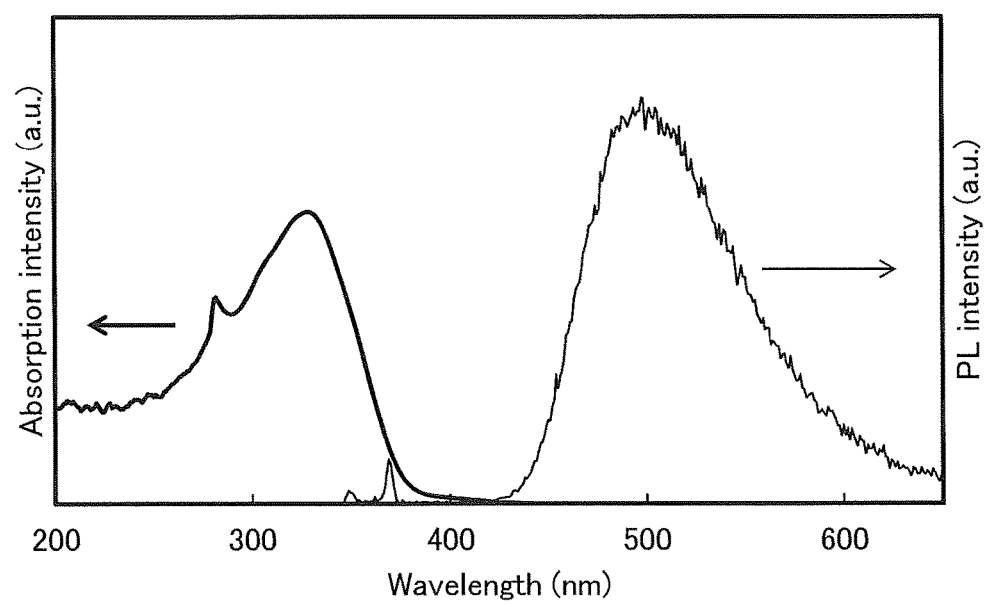
FIG. 29 shows absorption and emission spectra of a compound in Example.
Figure 30:
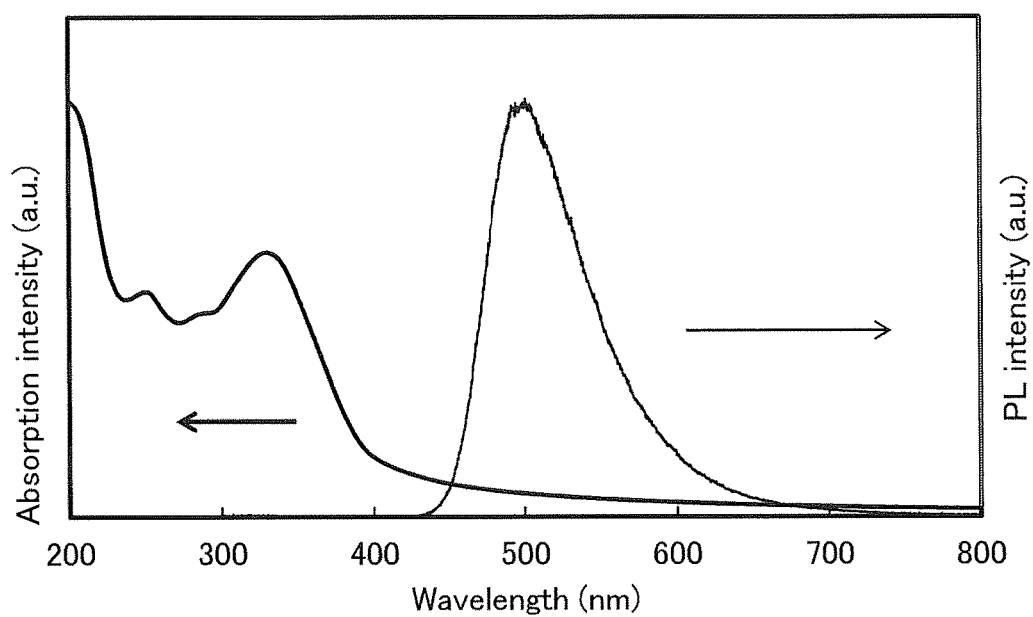
FIG. 30 shows absorption and emission spectra of a compound in Example.

FIG. 29 shows an absorption spectrum and an emission spectrum of 6BP-4mFBiPPm in a toluene solution. FIG. 30 shows an absorption spectrum and an emission spectrum of a thin film of 6BP-4mPCBBiPPm. The measurement of an absorption spectrum and an emission spectrum of the solution and an absorption spectrum of the thin film was performed in a manner similar to that described in Example 1. The measurement of the emission spectrum of the thin film was performed with a PL microscope (LabRAM HR-PL, produced by HORIBA, Ltd.).

As shown in FIG. 29, 6BP-4mPCBBiPPm in the toluene solution has absorption peaks at around 392 nm and 282 nm, and an emission wavelength peak at 498 nm (excitation wavelength: 332 nm). As shown in FIG. 30, the thin film of 6BP-4mPCBBiPPm has absorption peaks at around 363 nm, 330 nm, 285 nm, and 251 nm, and an emission wavelength peak at around 494 nm (excitation wavelength: 410 nm). The compound of one embodiment of the present invention can be used as a host material for a light-emitting substance or a host material for a substance emitting fluorescence in the visible region.

It was found that aggregation of the thin film of 6BP-4mPCBBiPPm is not easily caused even under the air and the thin film suffers only a small change in shape and has high film quality.

Next, the HOMO level and the LUMO level of 6BP-4mPCBBiPPm were obtained through a cyclic voltammetry (CV) measurement. A calculation method is similar to that described in Example 1.

As a result, in the measurement of an oxidation potential Ea [V] of 6BP-4mPCBBiPPm, the HOMO level was −5.45 eV. In contrast, the LUMO level was found to be −2.84 eV. When the oxidation-reduction wave was repeatedly measured, in the Ea measurement, the peak intensity of the oxidation-reduction wave after the hundredth cycle was maintained to be 89% of that of the oxidation-reduction wave at the first cycle, and in the Ec measurement, the peak intensity of the oxidation-reduction wave after the hundredth cycle was maintained to be 90% of that of the oxidation-reduction wave at the first cycle; thus, resistance to oxidation and reduction of 6BP-4mPCBBiPPm was found to be extremely high.

Example 5

In this example, a method for synthesizing 4,6-bis{4-[N-(biphenyl-4-yl)-N-(9,9-dimethyl-9H-fluoren-2-yl)]aminophenyl}pyrimidine (abbreviation: 4,6FBiP2Pm), which is the organic compound of one embodiment of the present invention represented by Structural Formula (104), and the physical properties of the compound are described.

Synthesis Example 5

Step 1: Synthesis of 4,6-bis{4-[N-(biphenyl-4-yl)-N-(9,9-dimethyl-9H-fluoren-2-yl)]aminophenyl}pyrimidine (abbreviation: 4,6FBiP2Pm)

Into a 200 mL three-neck flask were put 1.3 g (4.2 mmol) of 4,6-bis(4-chlorophenyl)pyrimidine, 3.8 g (11 mmol) of N-(biphenyl-4-yl)-9,9-dimethyl-9H-fluoren-2-amine, 0.15 g (0.42 mmol) of di(1-adamantyl)-n-butylphosphine, and 2.43 g (25 mmol) of sodium tert-butoxide. To this mixture, 40 mL of toluene was added, and the resulting mixture was degassed by being stirred while the pressure was reduced. To this mixture was added 48 mg (0.084 mmol) of bis(dibenzylideneacetone)palladium(0), and the mixture was stirred under a nitrogen stream at 110° C. for 14.5 hours. After the stirring, toluene was added to the mixture, and the resulting suspension was suction filtered through Florisil, Celite, and alumina to give a filtrate. The obtained filtrate was concentrated to give a solid. This solid was purified by silica gel column chromatography (developing solvent: toluene and then toluene and ethyl acetate in a 50:1 ratio) to give a solid. This solid was purified by alumina column chromatography (developing solvent: toluene and then toluene and ethyl acetate in a 500:1 ratio) to give a solid. The obtained solid was recrystallized with toluene/ethanol to give a yellow solid. The obtained solid was recrystallized twice more with toluene/ethanol to give 2.9 g of a yellow solid in a yield of 71%. The synthesis scheme of Step 1 is shown in (A-5) below.

[Chemical Formula 11]

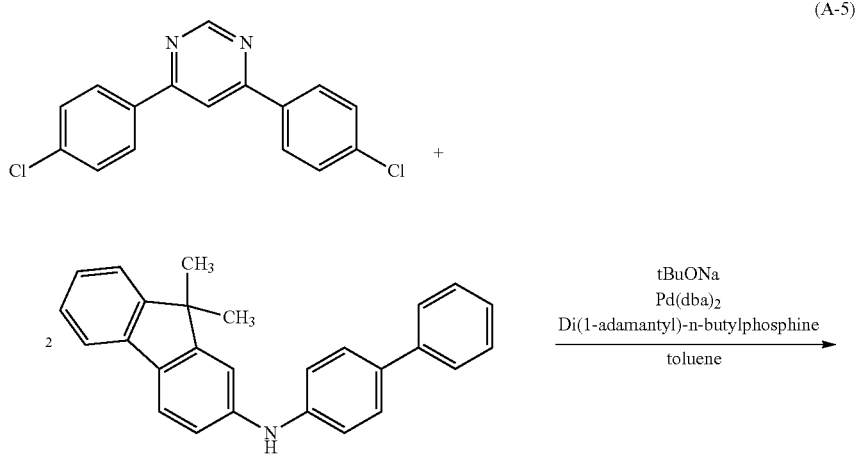

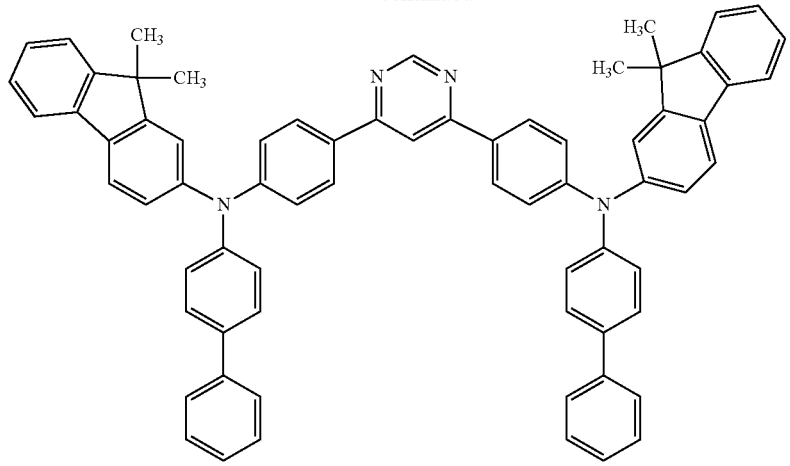

(104)

The obtained solid was subjected to analysis by nuclear magnetic resonance spectrometry ($^1$H NMR), and the results are shown below.

$^1$H NMR (DMSO-$d_6$, 300 MHz):δ=1.42 (s, 12H), 7.10-7.16 (m, 6H), 7.23 (d, $J_1$=8.7 Hz, 4H), 7.27-7.37 (m, 8H), 7.41-7.50 (m, 6H), 7.64-7.67 (m, 8H), 7.74 (d, $J_1$=7.8 Hz, 2H), 7.79 (d, $J_1$=8.4 Hz, 2H), 8.22 (d, $J_1$=8.1 Hz, 4H), 8.31 (s, 1H), 9.12 (s, 1H).

Figure 31A:
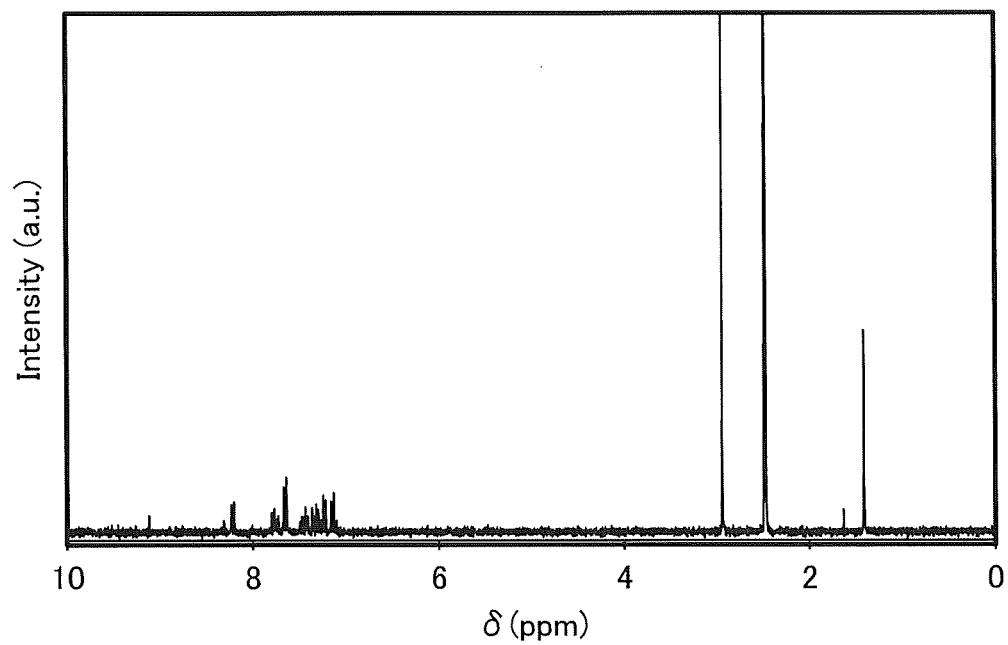
FIGS. 31A and 31B are NMR charts of Example.
Figure 31B:
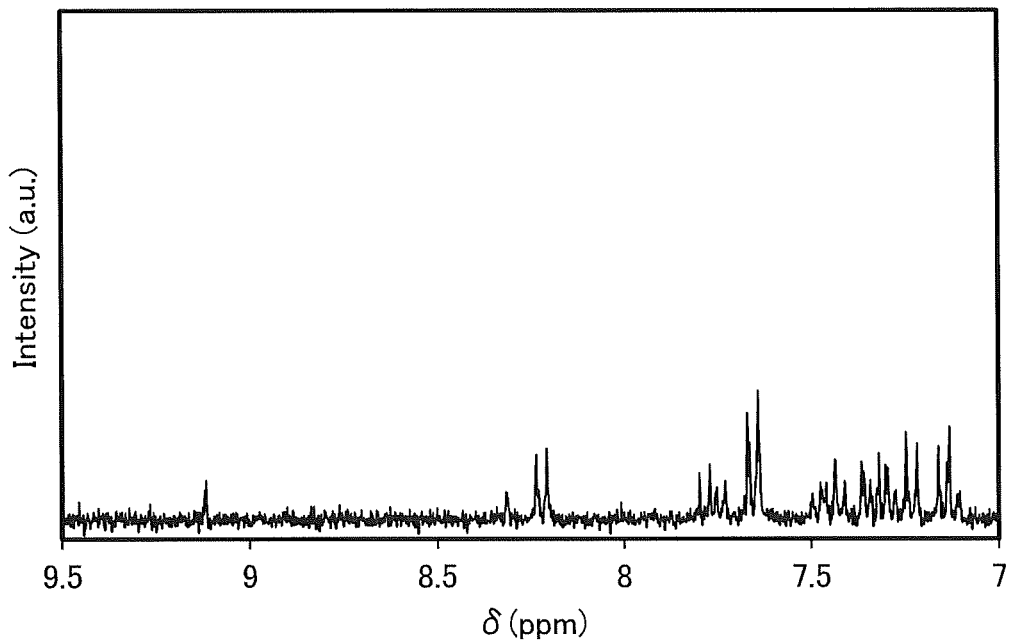

FIGS. 31A and 31B are $^1$H NMR charts of the obtained solid. Note that FIG. 31B is a chart showing an enlarged part in the range of 7.0 ppm to 9.5 ppm of FIG. 31A. The measurement results reveal that 4,6FBiP2Pm, which is the target substance, was obtained.

<Properties of 4,6FBiP2Pm>

Figure 32:
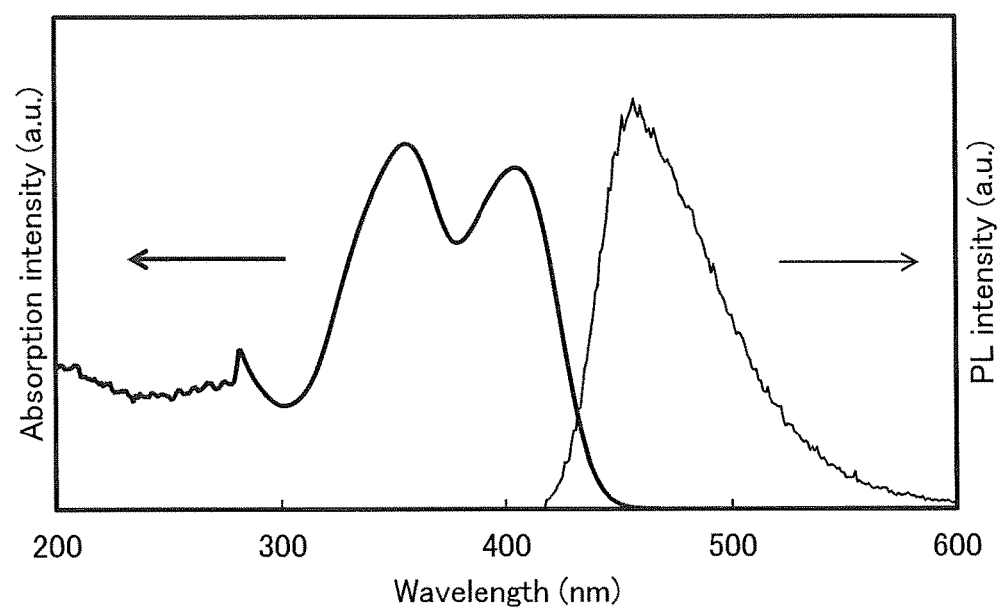
FIG. 32 shows absorption and emission spectra of a compound in Example.
Figure 33:
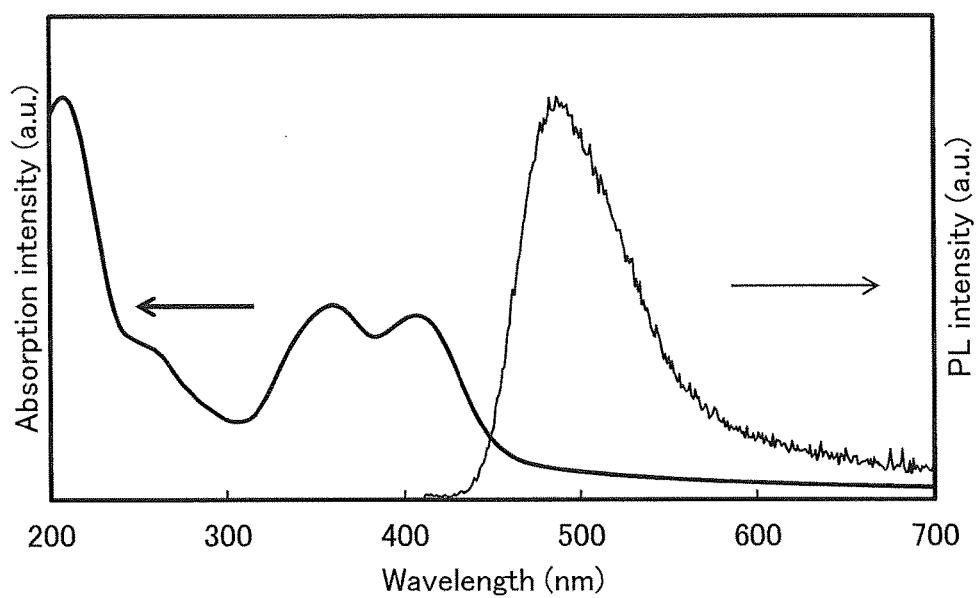
FIG. 33 shows absorption and emission spectra of a compound in Example.

FIG. 32 shows an absorption spectrum and an emission spectrum of 4,6FBiP2Pm in a toluene solution. FIG. 33 shows an absorption spectrum and an emission spectrum of a thin film of 4,6FBiP2Pm. The measurement was performed in a manner similar to that described in Example 1.

As shown in FIG. 32, 4,6FBiP2Pm in the toluene solution has absorption peaks at around 403 nm, 356 nm, and 282 nm, and an emission wavelength peak at 457 nm (excitation wavelength: 408 nm). As shown in FIG. 33, the thin film of 4,6FBiP2Pm has absorption peaks at around 407 nm, 360 nm, 335 nm, 290 nm, 261 nm, and 208 nm, and an emission wavelength peak at around 488 nm (excitation wavelength: 400 nm). The compound of one embodiment of the present invention can be used as a host material for a light-emitting substance or a host material for a substance emitting fluorescence in the visible region.

It was found that aggregation of the thin film of 4,6FBiP2Pm is not easily caused even under the air and the thin film suffers only a small change in shape and has high film quality.

Next, the HOMO level and the LUMO level of 4,6FBiP2Pm were obtained through a cyclic voltammetry (CV) measurement. A calculation method is similar to that described in Example 1.

As a result, in the measurement of an oxidation potential Ea [V] of 4,6FBiP2Pm, the HOMO level was −5.49 eV. In contrast, the LUMO level was found to be −2.72 eV. When the oxidation-reduction wave was repeatedly measured, in the Ea measurement, the peak intensity of the oxidation-reduction wave after the hundredth cycle was maintained to be 93% of that of the oxidation-reduction wave at the first cycle, and in the Ec measurement, the peak intensity of the oxidation-reduction wave after the hundredth cycle was maintained to be 70% of that of the oxidation-reduction wave at the first cycle; thus, resistance to oxidation and reduction of 4,6FBiP2Pm was found to be extremely high.

Example 6

In this example, a method for synthesizing 4,6-bis{3-[N-(biphenyl-4-yl)-N-(9,9-dimethyl-9H-fluoren-2-yl)]aminophenyl}pyrimidine (abbreviation: 4,6mFBiP2Pm), which is the organic compound of one embodiment of the present invention represented by Structural Formula (105), and the physical properties of the compound are described.

Synthesis Example 6

Step 1: Synthesis of 4,6-bis{3-[N-(biphenyl-4-yl)-N-(9,9-dimethyl-9H-fluoren-2-yl)]aminophenyl}pyrimidine (Abbreviation: 4,6mFBiP2Pm)

Figure 36:
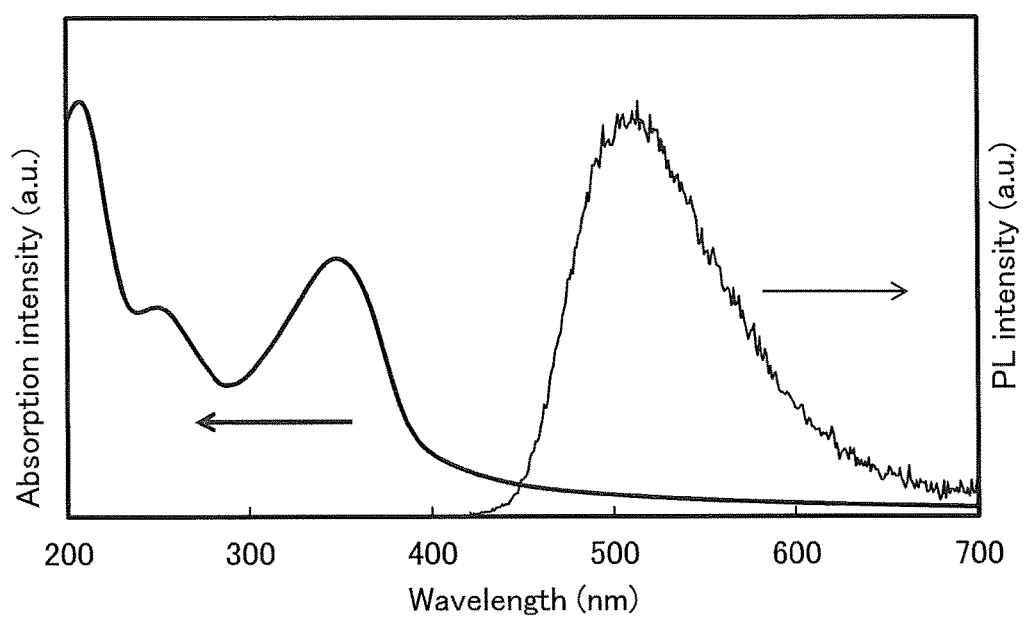
FIG. 36 shows absorption and emission spectra of a compound in Example.

Into a 200 mL three-neck flask were put 1.3 g (4.2 mmol) of 4,6-bis(3-chlorophenyl)pyrimidine, 3.8 g (11 mmol) of N-(biphenyl-4-yl)-9,9-dimethyl-9H-fluoren-2-amine, 151 mg (0.42 mmol) of di(1-adamantyl)-n-butylphosphine, and 2.4 g (25 mmol) of sodium tert-butoxide. To this mixture, 40 mL of toluene was added, and the resulting mixture was degassed by being stirred while the pressure was reduced. To this mixture was added 48 mg (0.084 mmol) of bis(dibenzylideneacetone)palladium(0), and the mixture was stirred under a nitrogen stream at 110° C. for 34.5 hours. After the stirring, toluene was added to the mixture, and the resulting suspension was suction filtered through Florisil, Celite, and alumina to give a filtrate. The obtained filtrate was concentrated to give a solid. This solid was purified by silica gel column chromatography (developing solvent: hexane and toluene in a 2:1 ratio and then toluene) to give a solid. This solid was purified by high performance liquid column chromatography. The high performance liquid column chromatography was performed using chloroform as a developing solvent. The obtained fraction was concentrated to give a solid. Hexane was added to the obtained solid, and the mixture was irradiated with ultrasonic waves and then subjected to filtration to give 1.6 g of a yellow solid in a yield of 41%. The synthesis scheme of Step 1 is shown in (A-6) below.

length: 348 nm). As shown in FIG. 36, the thin film of 4,6mFBiP2Pm has absorption peaks at around 450 nm, 348 nm, 305 nm, 275 nm, 249 nm, and 207 nm, and an emission wavelength peak at around 512 nm (excitation wavelength: 400 nm). The compound of one embodiment of the present invention can be used as a host material for a light-emitting substance or a host material for a substance emitting fluorescence in the visible region.

[Chemical Formula 12]

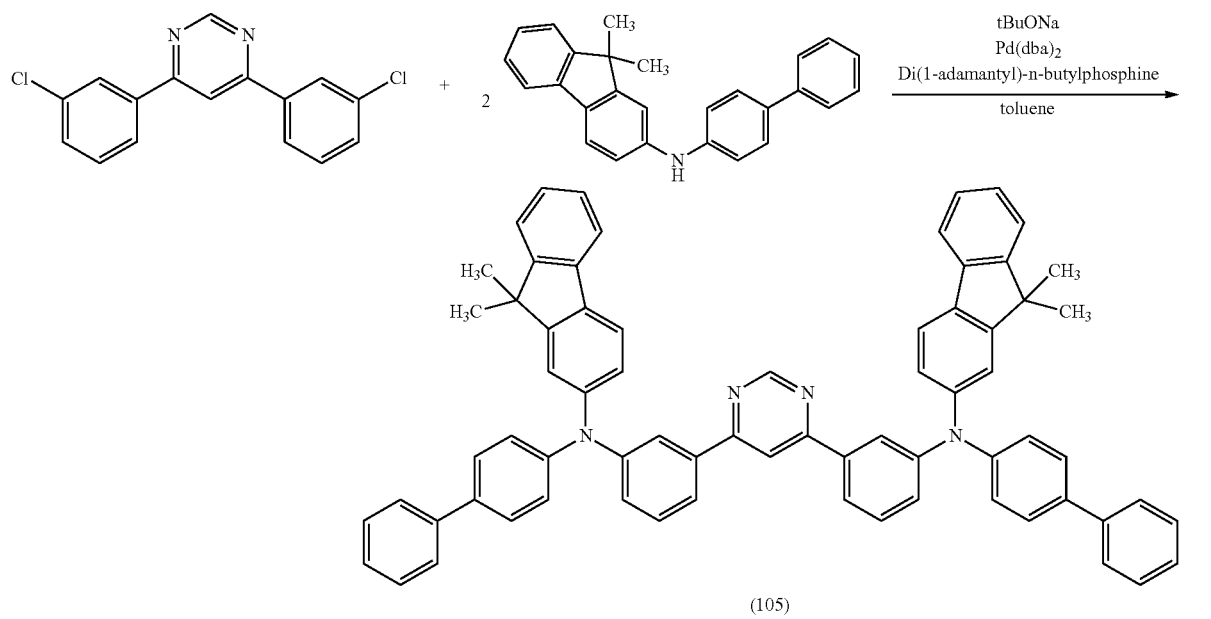

(A-6)

(105)

Then, 1.4 g of the obtained solid was purified by a train sublimation method. The purification by sublimation was performed by heating at 355° C. under a pressure of 2.9 Pa with an argon flow rate of 15 mL/min to give 1.3 g of a yellow solid was obtained at a collection rate of 91%.

The obtained solid was subjected to analysis by nuclear magnetic resonance spectrometry ($^1$H NMR), and the results are shown below.

$^1$H NMR (DMSO-d, 300 MHz):δ=1.38 (s, 12H), 7.05 (dd, $J_1$=8.1 Hz, $J_2$=1.8 Hz, 2H), 7.16 (d, $J_1$=8.7 Hz, 4H), 7.24-7.36 (m, 10H), 7.42-7.54 (m, 8H), 7.64-7.68 (m, 8H), 7.77 (t, $J_1$=8.1 Hz, 4H), 8.03 (d, $J_1$=7.8 Hz, 2H), 8.10 (s, 2H), 8.51 (s, 1H), 9.11 (s, 1H).

Figure 34A:
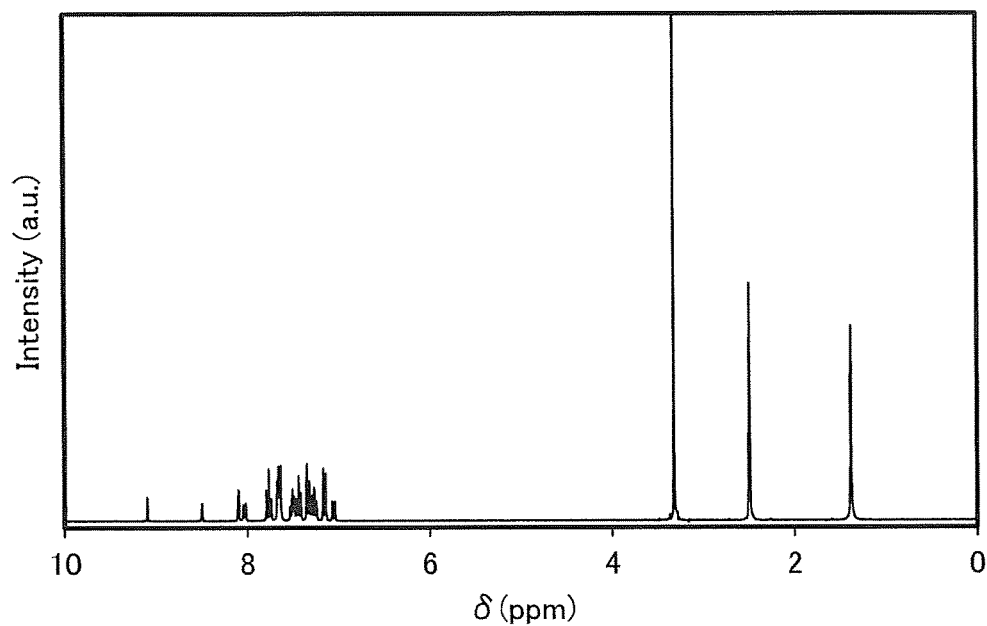
FIGS. 34A and 34B are NMR charts of Example.
Figure 34B:
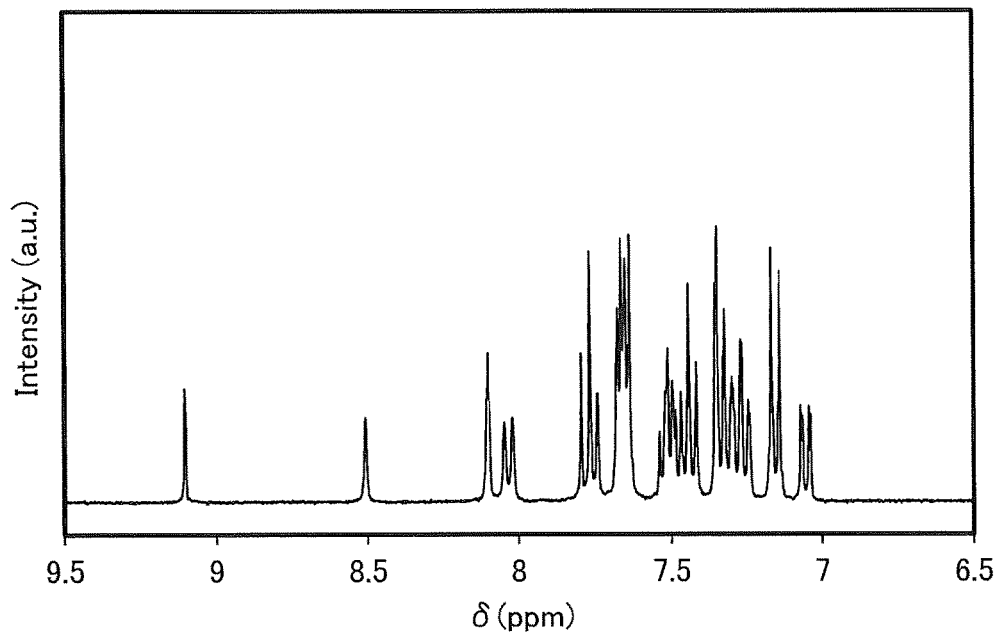

FIGS. 34A and 34B are $^1$H NMR charts of the obtained solid. Note that FIG. 34B is a chart showing an enlarged part in the range of 7.0 ppm to 9.5 ppm of FIG. 34A. The measurement results reveal that 4,6mFBiP2Pm, which is the target substance, was obtained.

<Properties of 4,6mFBiP2Pm>

Figure 35:
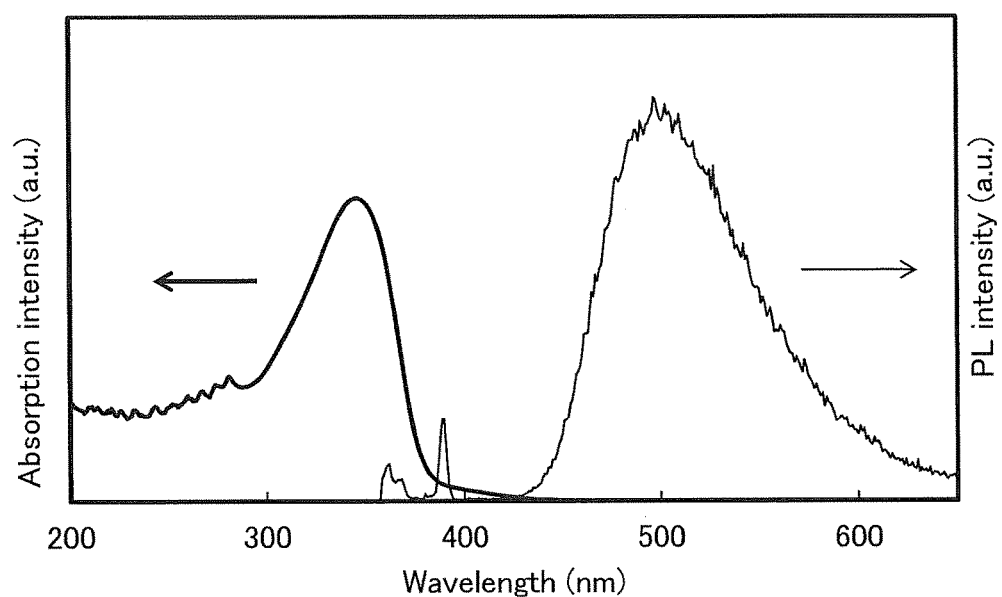
FIG. 35 shows absorption and emission spectra of a compound in Example.

FIG. 35 shows an absorption spectrum and an emission spectrum of 4,6mFBiP2Pm in a toluene solution. FIG. 36 shows an absorption spectrum and an emission spectrum of a thin film of 4,6mFBiP2Pm. The measurement was performed in a manner similar to that described in Example 1.

As shown in FIG. 35, 4,6mFBiP2Pm in the toluene solution has absorption peaks at around 364 nm, and an emission wavelength peak at 498 nm (excitation wave- It was found that aggregation of the thin film of 4,6mFBiP2Pm is not easily caused even under the air and the thin film suffers only a small change in shape and has high film quality.

Next, the HOMO level and the LUMO level of 4,6mFBiP2Pm were obtained through a cyclic voltammetry (CV) measurement. A calculation method is similar to that described in Example 1.

As a result, in the measurement of an oxidation potential Ea [V] of 4,6mFBiP2Pm, the HOMO level was −5.46 eV. In contrast, the LUMO level was found to be −2.80 eV. When the oxidation-reduction wave was repeatedly measured, in the Ea measurement, the peak intensity of the oxidation-reduction wave after the hundredth cycle was maintained to be 97% of that of the oxidation-reduction wave at the first cycle, and in the Ec measurement, the peak intensity of the oxidation-reduction wave after the hundredth cycle was maintained to be 70% of that of the oxidation-reduction wave at the first cycle; thus, resistance to oxidation and reduction of 4,6mFBiP2Pm was found to be extremely high.

Example 7

In this example, a method for synthesizing N-(4-biphenyl)-N-(9,9-dimethyl-9H-fluoren-2-yl)-4-[3-(dibenzo[f,h]quinoxalin-2-yl)phe nyl]phenylamine (abbreviation: 2mpFBiBPDBq), which is the organic compound of one embodiment of the present invention represented by Structural Formula (106), and the physical properties of the compound are described.

Synthesis Example 7

Step 1: Synthesis of N-(4-biphenyl)-N-(9,9-dimethyl-9H-fluoren-2-yl)-4-[3-(dibenzo[fh]quinoxalin-2-yl)phenyl]phenylamine (abbreviation: 2mpFBiBP-DBq)

Into a 200 mL three-neck flask were put 2.0 g (3.9 mmol) of N-(4-bromophenyl)-N-(4-biphenylyl)-9,9-dimethyl-9H-fluoren-2-amine, 1.7 g (3.9 mmol) of 4,4,5,5-tetramethyl-2-[3-(dibenzo[f,h]quinoxalin-2-yl)phenyl]-1,3,2-dioxaborolane, 24 mg (0.078 mmol) of tris(o-tolyl)phosphine, and 1.1 g (7.8 mmol) of potassium carbonate, and the air in the flask was replaced with nitrogen. To the mixture were added 15 mL of toluene, 4.5 mL of ethanol, and 4.0 mL of water, and the resulting mixture was degassed by being stirred while the pressure was reduced. After the degasification, 8.8 mg (0.078 mmol) of palladium(II) acetate was added to the mixture, and the resulting mixture was stirred at approximately 80° C. for 7 hours. After the stirring, this mixture was suction filtered to give a solid. The obtained solid was dissolved in approximately 30 mL of hot toluene, and the obtained solution was purified by silica gel column chromatography (developing solvent: hexane and toluene in a 9:1 ratio) to give a solid. The obtained solid was purified by high performance liquid chromatography (HPLC) to give a solid. The obtained solid was recrystallized with toluene/hexane to give 1.7 g of a pale yellow solid, which was the target substance of the synthesis, in a yield of 59%. The synthesis scheme of Step 1 is shown in (A-7) below.

[Chemical Formula 13]

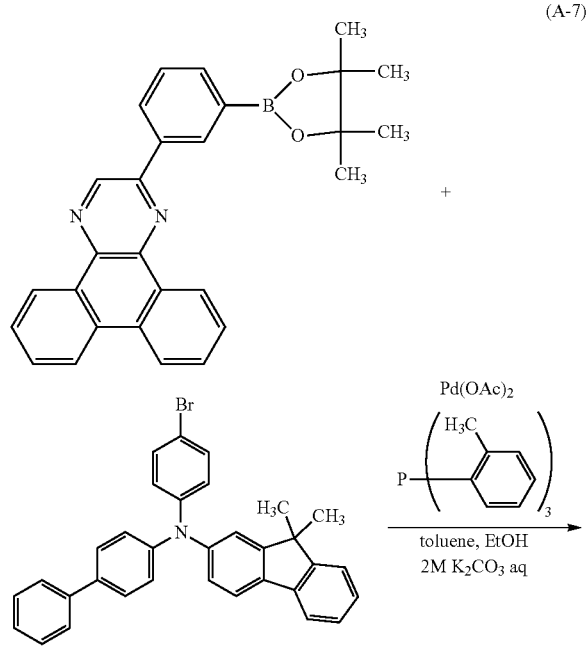

(A-7)

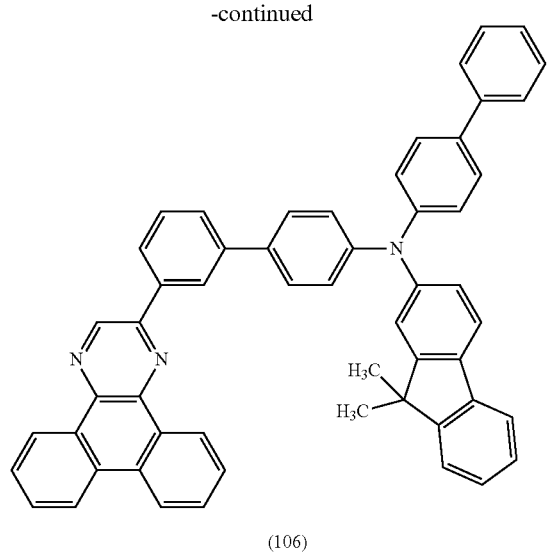

(106)

The obtained solid was subjected to analysis by nuclear magnetic resonance spectrometry ($^1$H NMR), and the results are shown below.

$^1$H NMR (CDCl$_3$, 500 MHz):δ=1.47, (s, 6H), 7.17 (dd, J$_1$=8.5 Hz, J$_2$=2.0 Hz, 1H), 7.27-7.35 (m, 8H), 7.41-7.46 (m, 3H), 7.56 (d, J=9.0 Hz, 2H), 7.61-7.69 (m, 7H), 7.76-7.84, (m, 5H), 8.28 (d, J=8.0 Hz, 1H), 8.60 (s, 1H), 8.66 (d, J=8.0 Hz, 2H), 9.25 (dd, J$_1$=8.0 Hz, J$_2$=2.0 Hz, 1H), 9.44 (dd, J$_1$=8.0 Hz, J$_2$=2.0 Hz, 1H), 9.46 (s, 1H).

Figure 37A:
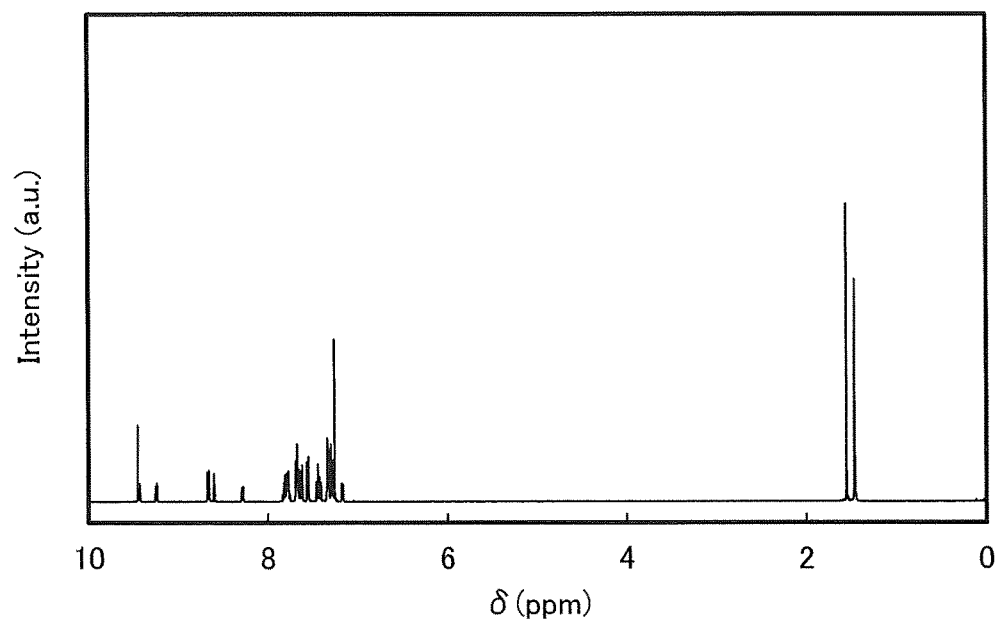
FIGS. 37A and 37B are NMR charts of Example.
Figure 37B:
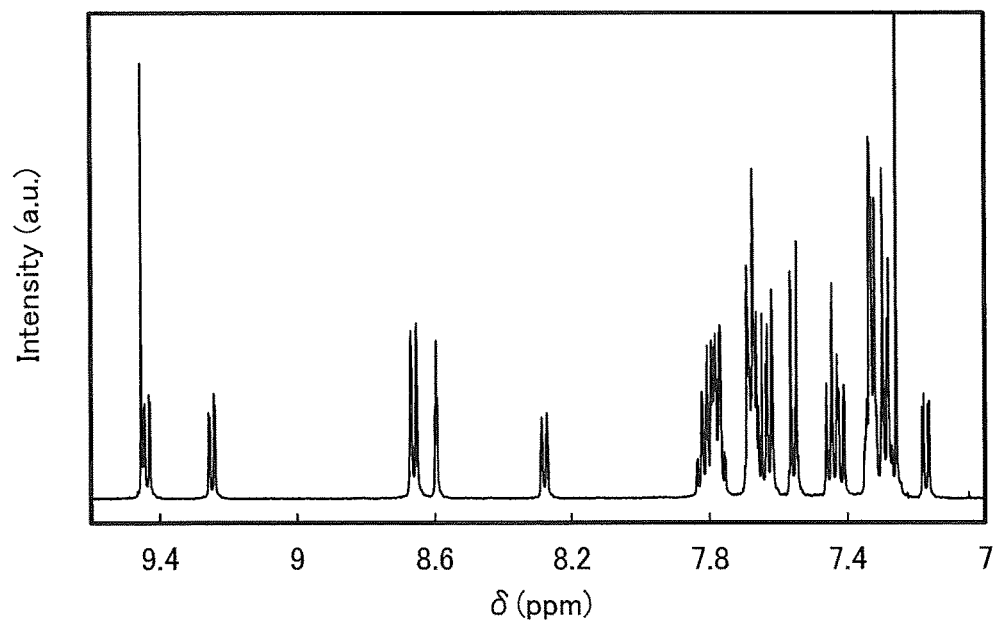

FIGS. 37A and 37B are $^1$H NMR charts of the obtained solid. Note that FIG. 37B is a chart showing an enlarged part in the range of 7.0 ppm to 9.5 ppm of FIG. 37A. The measurement results reveal that 2mpFBiBPDBq, which is the target substance, was obtained.

<Properties of 2mpFBiBPDBq>

Figure 38:
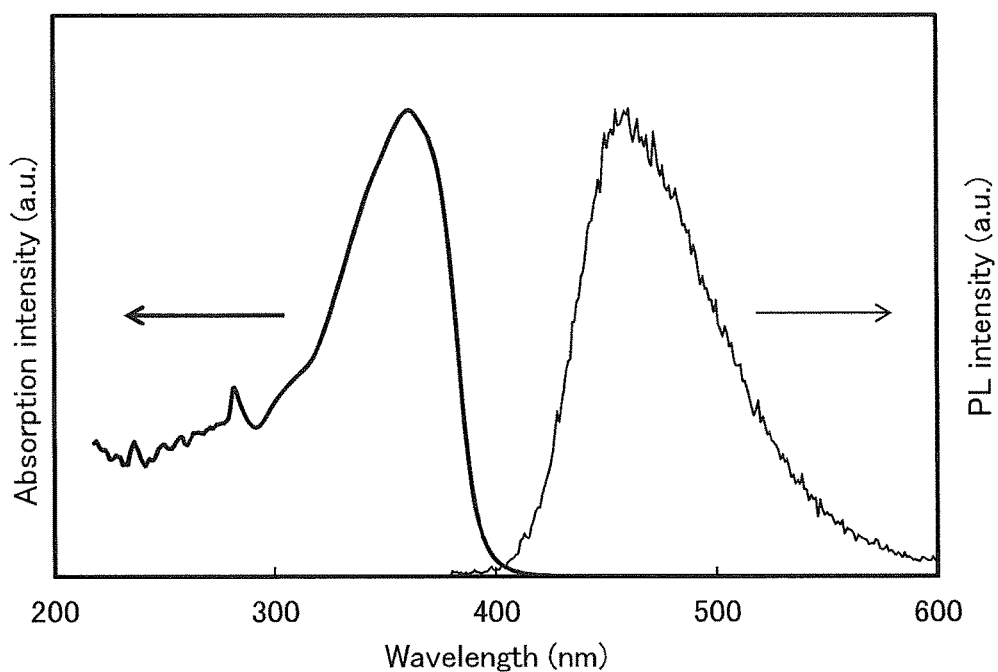
FIG. 38 shows absorption and emission spectra of a compound in Example.
Figure 39:
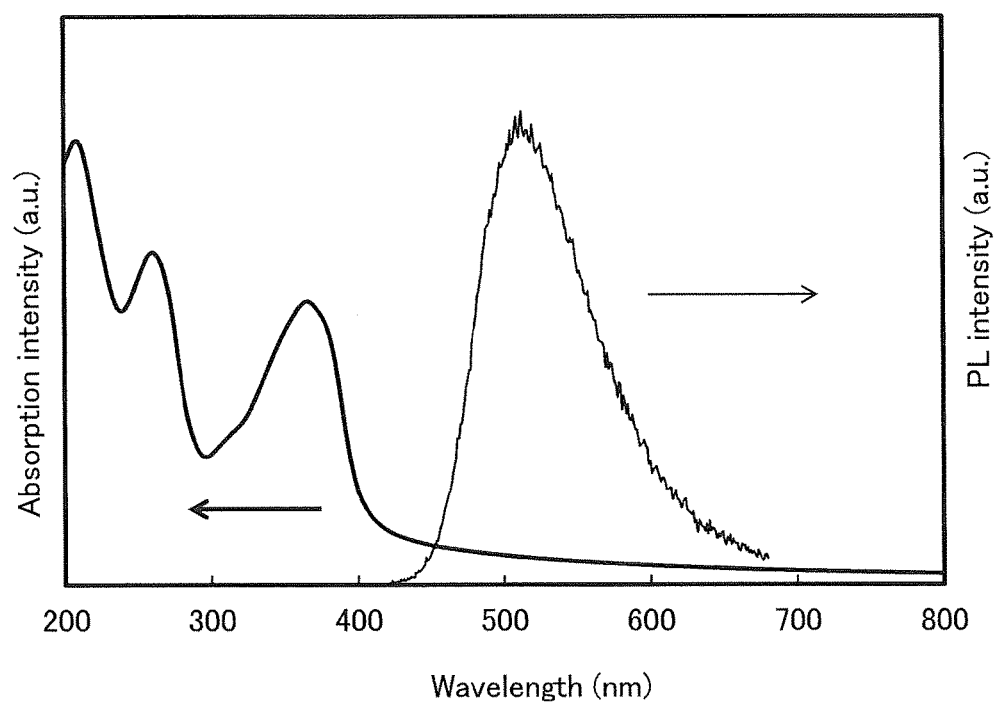
FIG. 39 shows absorption and emission spectra of a compound in Example.

FIG. 38 shows an absorption spectrum and an emission spectrum of 2mpFBiBPDBq in a toluene solution. FIG. 39 shows an absorption spectrum and an emission spectrum of a thin film of 2mpFBiBPDBq. The measurement was performed in a manner similar to that described in Example 1.

As shown in FIG. 38, 2mpFBiBPDBq in the toluene solution has absorption peaks at around 361 nm, and an emission wavelength peak at 466 nm (excitation wavelength: 366 nm). As shown in FIG. 39, the thin film of 2mpFBiBPDBq has absorption peaks at around 366 nm, 311 nm, 260 nm, and 211 nm, and an emission wavelength peak at around 513 nm (excitation wavelength: 384 nm). The compound of one embodiment of the present invention can be used as a host material for a light-emitting substance or a host material for a substance emitting fluorescence in the visible region.

It was found that aggregation of the thin film of 2mpFBiBPDBq is not easily caused even under the air and the thin film suffers only a small change in shape and has high film quality.

Next, the HOMO level and the LUMO level of 2mpFBiB-PDBq were obtained through a cyclic voltammetry (CV) measurement. A calculation method is similar to that described in Example 1.

As a result, in the measurement of an oxidation potential Ea [V] of 2mpFBiBPDBq, the HOMO level was −5.42 eV. In contrast, the LUMO level was found to be −2.93 eV. When the oxidation-reduction wave was repeatedly measured, in the Ea measurement, the peak intensity of the oxidation-reduction wave after the hundredth cycle was maintained to be 91% of that of the oxidation-reduction wave at the first cycle, and in the Ec measurement, the peak intensity of the oxidation-reduction wave after the hundredth cycle was maintained to be 86% of that of the oxidation-reduction wave at the first cycle; thus, resistance to oxidation and reduction of 2mpFBiBPDBq was found to be extremely high.

Thermogravimetry-differential thermal analysis (TG-DTA) was performed on 2mpFBiBPDBq. The measurement was conducted by using a high vacuum differential type differential thermal balance (TG-DTA 2410SA, manufactured by Bruker AXS K.K.). The measurement was performed using a high vacuum differential type differential thermal balance (TG-DTA2410SA, manufactured by Bruker AXS K.K.). It was found from the relationship between weight and temperature (thermogravimetry) that the 5% weight loss temperature of 2mpFBiBPDBq was higher than or equal to 500° C. This indicates that 2mpFBiBPDBq has high heat resistance.

Example 8

In this example, a method for synthesizing N-(4-biphenylyl)-N-(9,9-dimethyl-9H-fluoren-2-yl)-(4-{3-[6-(9,9-dimethyl-9H-fluoren-2-yl)pyrimidin-4-yl]phenyl}phenyl)amine (abbreviation: 6FL-4mpFBiBPPm), which is the organic compound of one embodiment of the present invention represented by Structural Formula (107), and the physical properties of the compound are described.

Synthesis Example 8

Step 1: Synthesis of 4-chloro-6-(9,9-dimethyl-9H-fluoren-2-yl)pyrimidine

Into a 200 mL three-neck flask were put 13.0 g (87 mmol) of 4,6-dichloropyrimidine, 13 g (40 mmol) of 4,4,5,5-tetramethyl-2-(9,9-dimethyl-9H-fluoren-2-yl)-1,3,2-dioxaborolane, and 13.0 g (120 mmol) of sodium carbonate, and the air in the flask was replaced with nitrogen. In the flask were put 200 mL of 1,4-dioxane and 60 mL of water, and the resulting mixture was degassed by being stirred while the pressure was reduced. After the degasification, 0.3 g (0.40 mmol) of bis(triphenylphosphine)palladium(II) dichloride was added to the mixture, and the resulting mixture was irradiated with microwaves at 400 W for 8 hours. After the irradiation for a predetermined period of time, the mixture was suction filtered, and the aqueous layer of the obtained filtrate was subjected to extraction with toluene. The obtained solution of the extract and the organic layer were combined and washed with saturated brine. The solution was dried over magnesium sulfate, and this mixture was gravity-filtered to give a filtrate. To an oily substance obtained by concentration of the obtained filtrate was added 20 mL of toluene, and the solution was suction filtered through Celite, alumina, and Florisil. An oily substance obtained by concentration of the obtained filtrate was purified by high performance liquid chromatography (HPLC), and the obtained fraction was concentrated to give an oily substance. The obtained oily substance was dried under reduced pressure to give 7.3 g of a pale brown oily substance, which was the target substance, in a yield of 60%. By repeating the above procedure twice, 15 g of a pale brown oily substance of 4-chloro-6-(9,9-dimethyl-9H-fluoren-2-yl)pyrimidine, which was the target substance, was obtained. The synthesis scheme of Step 1 is shown in (A-8) below.

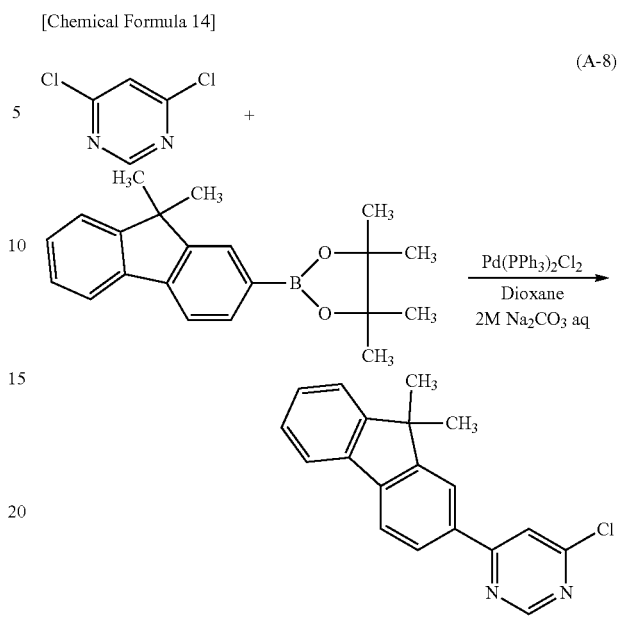

Step 2: Synthesis of 4-(3-chlorophenyl)-6-(9,9-dimethyl-9H-fluoren-2-yl)pyrimidine Into a 200 mL three-neck flask were put 10 g (32 mmol) of 4-chloro-6-(9,9-dimethyl-9H-fluoren-2-yl)pyrimidine, 5.0 g (32 mmol) of 3-chlorophenylboronic acid, 0.19 g (0.64 mmol) of tri(o-tolyl)phosphine, and 8.8 g (64 mmol) of potassium carbonate, and the air in the flask was replaced with nitrogen. To this mixture, 140 mL of toluene, 20 mL of ethanol, and 32 mL of water were added, and the resulting mixture was degassed by being stirred while the pressure was reduced. After the degasification, 72 mg (0.32 mmol) of palladium(II) acetate was added to the mixture, and the resulting mixture was stirred at approximately 80° C. for 27 hours. After the stirring, the aqueous layer of the mixture was subjected to extraction with toluene, and the solution of the extract and the organic layer were combined and washed with saturated brine. The solution was dried over magnesium sulfate, and this mixture was gravity-filtered to give filtrate. To an oily substance obtained by concentration of the obtained filtrate was added 20 mL of toluene, and the solution was suction filtered through Florisil, Celite, and alumina. An oily substance obtained by concentration of the obtained filtrate was purified by high performance liquid chromatography (HPLC), and the obtained fraction was concentrated to give an oily substance. The obtained oily substance was dried under reduced pressure to give 6.0 g of a pale brown oily substance of 4-(3-chlorophenyl)-6-(9,9-dimethyl-9H-fluoren-2-yl)pyrimidine, which was the target substance, in a yield of 50%. The synthesis scheme of Step 2 is shown in (A-9) below.

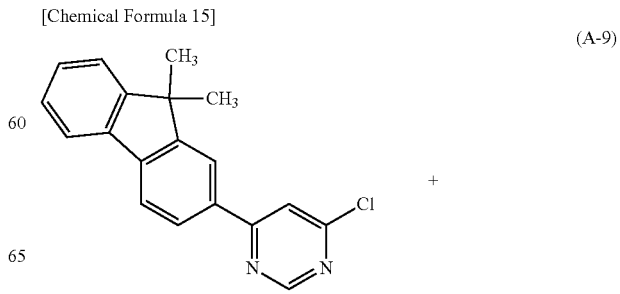

-continued

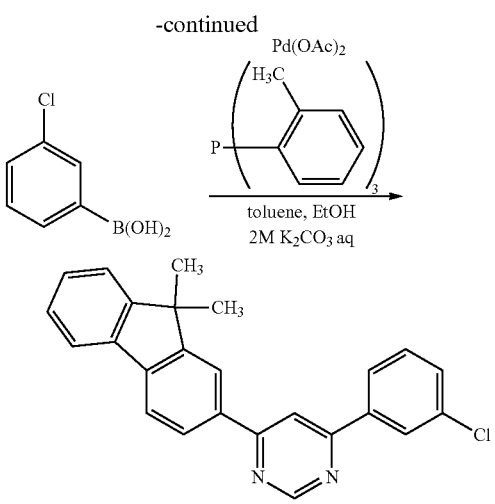

Step 3: Synthesis of 4,4,5,5-tetramethyl-2-{3-[6-(9,9-dimethyl-9H-fluoren-2-yl)pyrimidin-4-yl]phenyl}-1,3,2-dioxaborolane Into a 200 mL three-neck flask were put 6.0 g (15 mmol) of 4-(3-chlorophenyl)-6-(9,9-dimethyl-9H-fluoren-2-yl)pyrimidine, 5.0 g (20 mmol) of bis(pinacolato)diboron, 0.14 g (0.40 mmol) of di(1-adamantyl)-n-butylphosphine, and 3.9 g (40 mmol) of potassium acetate, and the air in the flask was replaced with nitrogen. To this mixture was added 80 mL of xylene, and the resulting mixture was degassed by being stirred while the pressure was reduced. To this mixture heated to 40° C. was added 0.16 g (0.20 mmol) of [1,1'-bis(diphenylphosphino)ferrocene]palladium(II) dichloride dichloromethane adduct, and the resulting mixture was stirred under a nitrogen stream at 140° C. for 17 hours. After the stirring, this mixture was suction-filtered, and the obtained filtrate was concentrated to give an oily substance. The obtained oily substance was purified by silica gel column chromatography (developing solvent: hexane and toluene in a 2:1 ratio) to give an oily substance. The obtained oily substance was dried under reduced pressure to give 2.9 g of a pale yellow oily substance of 4,4,5,5-tetramethyl-2-{3-[6-(9,9-dimethyl-9H-fluoren-2-yl)pyrimidin-4-yl]phenyl}-1,3,2-dioxaborolane, which was the target substance, in a yield of 41%. The synthesis scheme of Step 3 is shown in (A-10) below.

[Chemical Formula 16]

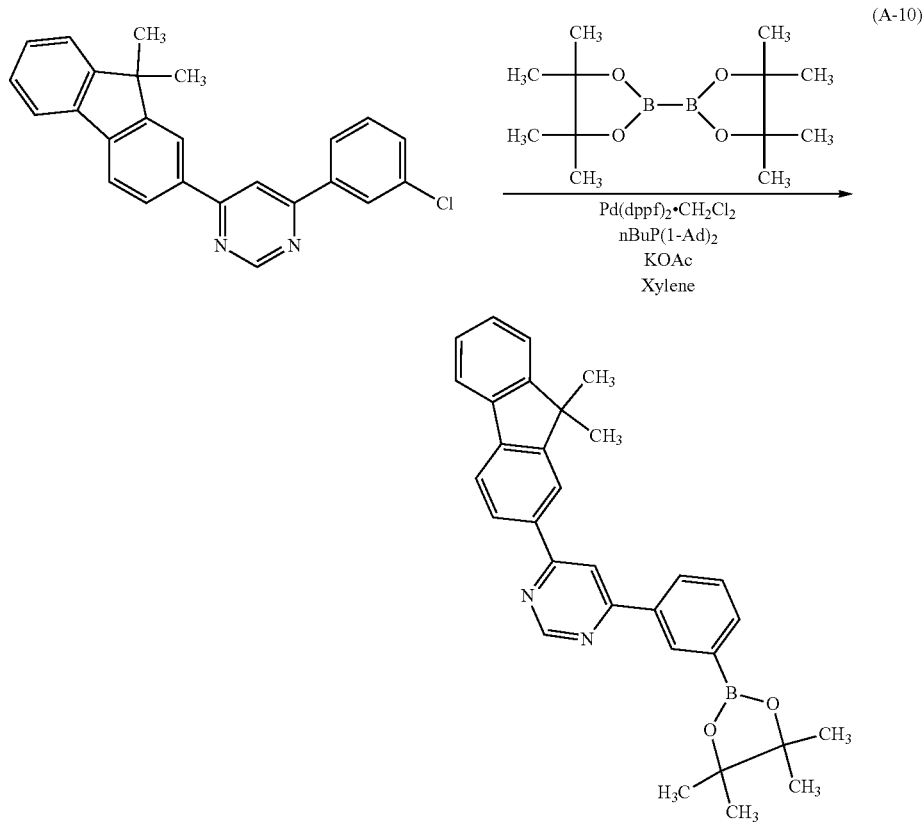

Step 4: Synthesis of N-(4-biphenylyl)-N-(9,9-dimethyl-9H-fluoren-2-yl)-(4-{3-[6-(9,9-dimethyl-9H-fluoren-2-yl)pyrimidin-4-yl]phenyl}phenyl)amine (abbreviation: 6FL-4mpFBiBPPm)

Into a 100 mL three-neck flask were put 1.5 g (3.0 mmol) of N-(4-bromophenyl)-N-(4-biphenyl)-9,9-dimethyl-9H-fluoren-2-amine, 1.4 g (3.0 mmol) of 4,4,5,5-tetramethyl-2-{3-[6-(9,9-dimethyl-9H-fluoren-2-yl)pyrimidin-4-yl]phenyl}-1,3,2-dioxaborolane, 18 mg (0.060 mmol) of tri(o-tolyl)phosphine, and 0.83 g (6.0 mmol) of potassium carbonate, and the air in the flask was replaced with nitrogen. To the mixture were added 12 mL of toluene, 3.0 mL of ethanol, and 3.0 mL of water, and the resulting mixture was degassed by being stirred while the pressure was reduced. After the degasification, 6.7 mg (0.039 mmol) of palladium(II) acetate was added to the mixture, and the resulting mixture was stirred at approximately 80° C. for 8 hours. After the stirring, the aqueous layer of the mixture was subjected to extraction with toluene, and the solution of the extract and the organic layer were combined and washed with saturated brine. The solution was dried over magnesium sulfate, and this mixture was gravity-filtered to give filtrate. The oily substance obtained by concentration of the obtained filtrate was purified by silica gel column chromatography (developing solvent: toluene) to give an oily substance. The obtained oily substance was purified by high performance liquid chromatography (HPLC) to give a solid. The obtained solid was washed with hexane to give 0.89 g of a pale yellow solid, which was the target substance, in a yield of 37%. The synthesis scheme of Step 4 is shown in (A-11) below.

[Chemical Formula 17]

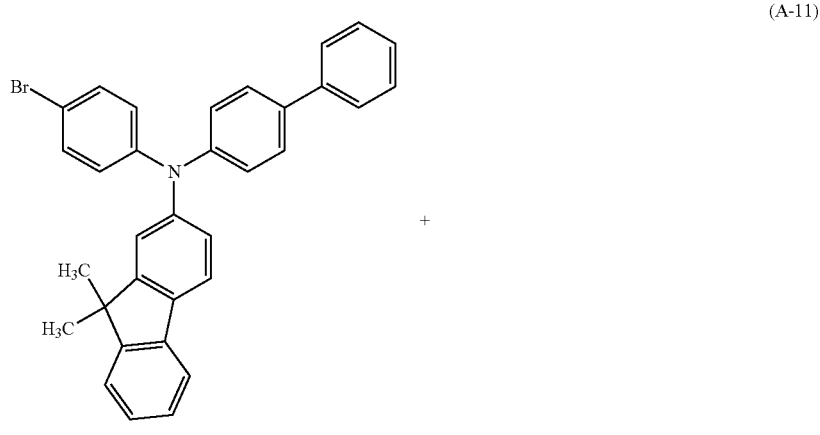

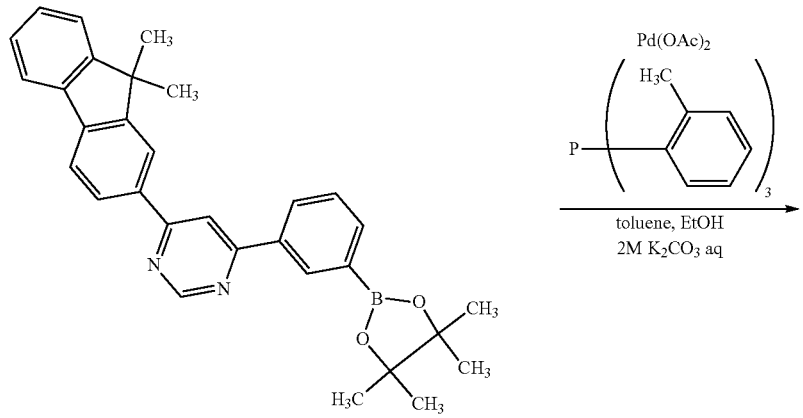

-continued

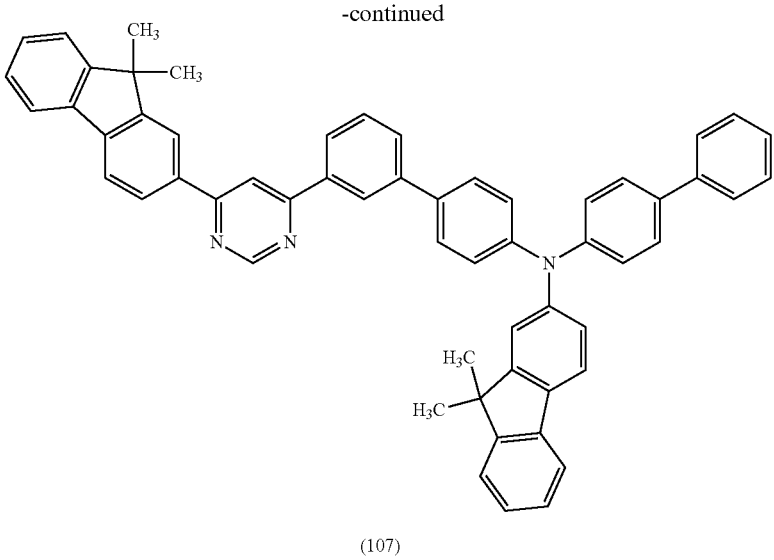

(107)

By a train sublimation method, 0.82 g of the pale yellow solid was purified. In the purification by sublimation, the pale yellow solid was heated at 320° C. under a pressure of 10 Pa with a flow rate of an argon gas of 5.0 mL/min. After the purification by sublimation, 0.65 g of a yellow solid of 6FL-4mpFBiBPPm was obtained in at a collection rate of 79%.

The obtained solid was subjected to analysis by nuclear magnetic resonance spectrometry ($^1$H NMR), and the results are shown below.

$^1$H NMR (CDCl$_3$, 500 MHz): δ=1.46 (s, 6H), 1.59 (s, 6H), 7.14 (dd, $J_1$=8.5 Hz, $J_2$=2.0 Hz, 1H), 7.25-7.53 (m, 14H), 7.54 (d, J=9.0 Hz, 2H), 7.61-7.68 (m, 7H), 7.77-7.81 (m, 2H), 7.87 (d, J=8.0 Hz, 1H), 8.10 (d, J=8.0 Hz, 1H), 8.14 (dd, $J_1$=8.0 Hz, $J_2$=2.0 Hz, 1H), 8.22 (d, J=1.5 Hz, 1H), 8.29 (d, J=1.5 Hz, 1H), 8.41 (t, J=1.5 15 Hz, 1H), 9.36 (d, J=1.5 Hz, 1H).

Figure 40A:
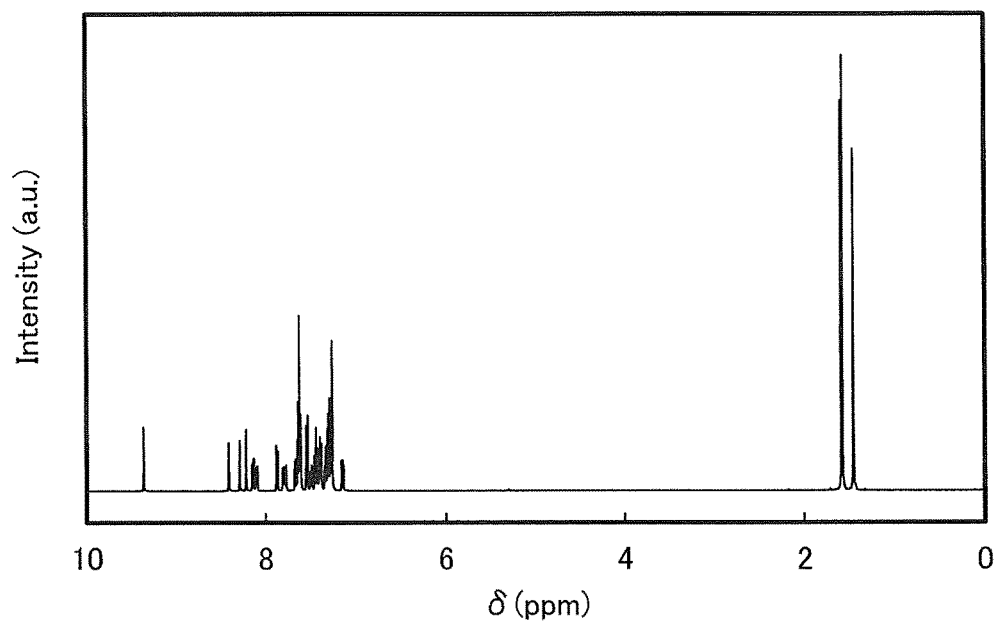
FIGS. 40A and 40B are NMR charts of Example.
Figure 40B:
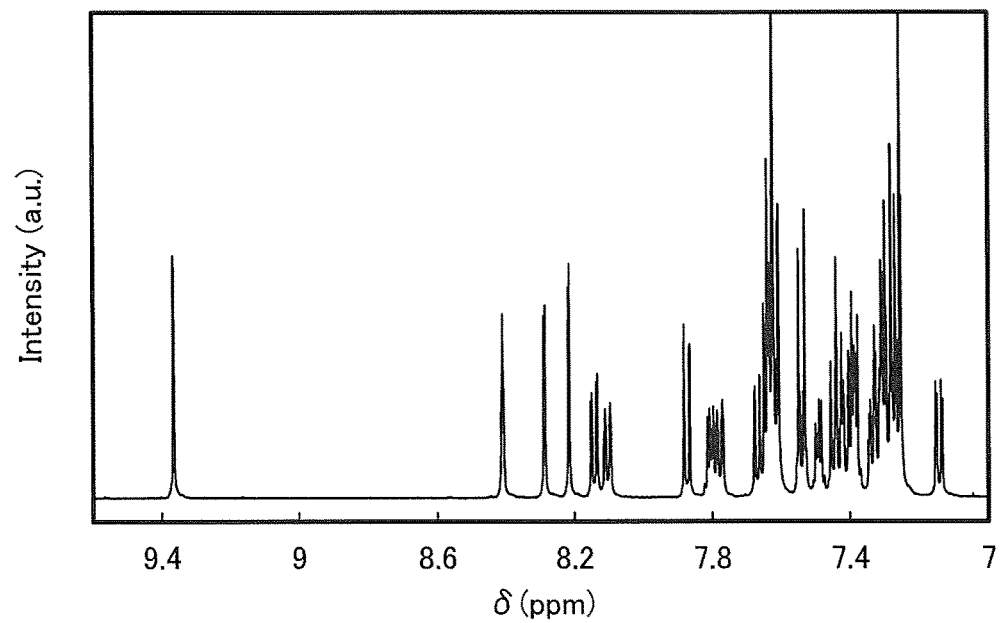

FIGS. 40A and 40B are $^1$H NMR charts of the obtained solid. Note that FIG. 40B is a chart showing an enlarged part in the range of 7.0 ppm to 9.5 ppm of FIG. 40A. The measurement results reveal that 6FL-4mpFBiBPPm, which is the target substance, was obtained.

<Properties of 6FL-4mpFBiBPPm>

Figure 41:
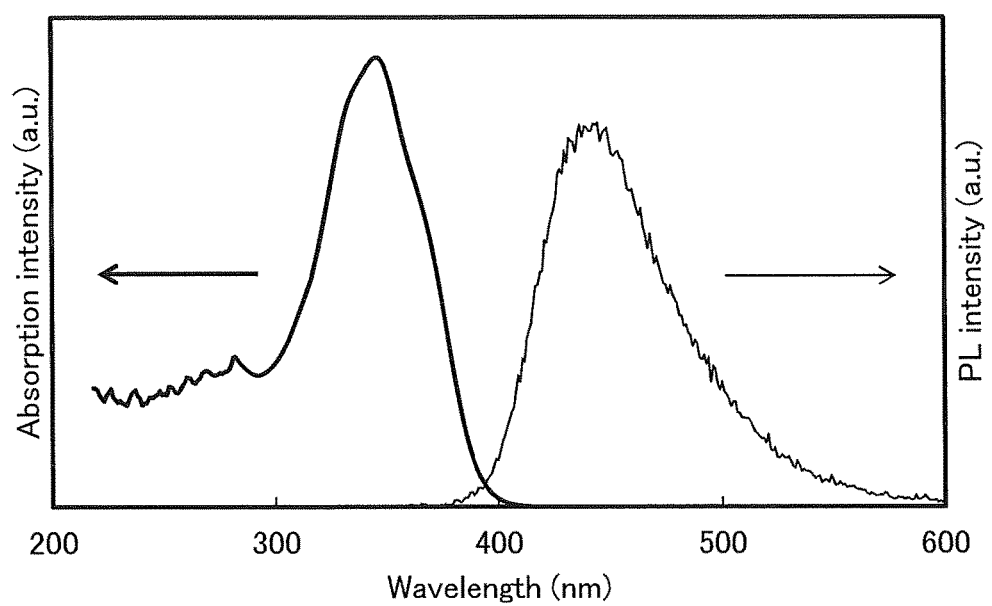
FIG. 41 shows absorption and emission spectra of a compound in Example.
Figure 42:
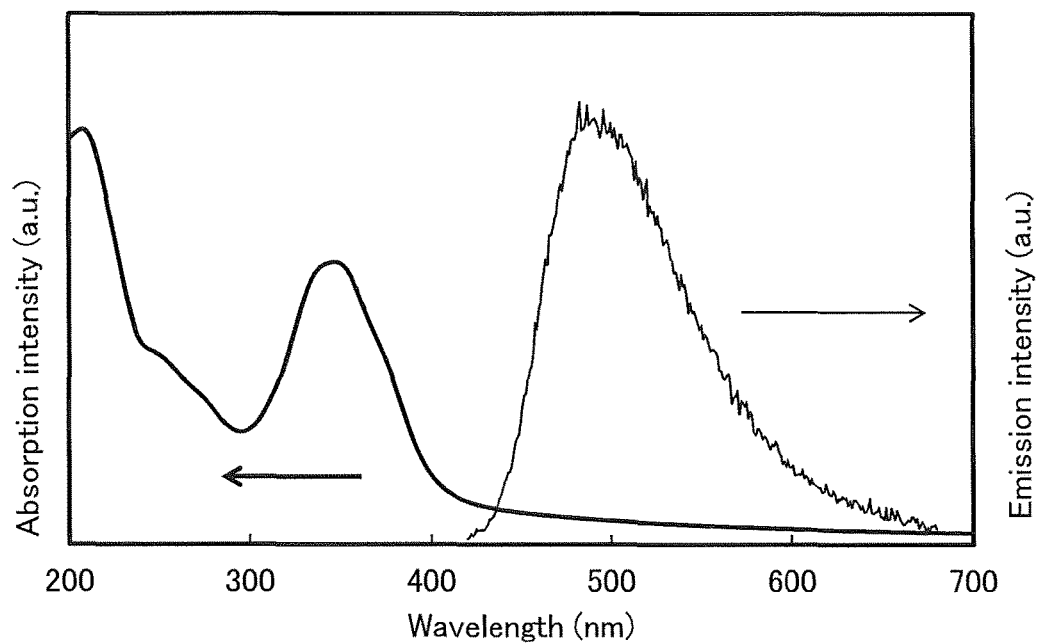
FIG. 42 shows absorption and emission spectra of a compound in Example.

FIG. 41 shows an absorption spectrum and an emission spectrum of 6FL-4mpFBiBPPm in a toluene solution. FIG. 42 shows an absorption spectrum and an emission spectrum of a thin film of 6FL-4mpFBiBPPm. The measurement was performed in a manner similar to that described in Example 1.

As shown in FIG. 41, 6FL-4mpFBiBPPm in the toluene solution has absorption peaks at around 346 nm, and an emission wavelength peak at 445 nm (excitation wavelength: 346 nm). As shown in FIG. 42, the thin film of 6FL-4mpFBiBPPm has absorption peaks at around 380 nm, 348 nm, 277 nm, 215 nm, and 207 nm, and an emission wavelength peak at around 490 nm (excitation wavelength: 376 nm). The compound of one embodiment of the present invention can be used as a host material for a light-emitting substance or a host material for a substance emitting fluorescence in the visible region.

It was found that aggregation of the thin film of 6FL-4mpFBiBPPm is not easily caused even under the air and the thin film suffers only a small change in shape and has high film quality.

Next, the HOMO level and the LUMO level of 6Fl-4mpFBiBPPm were obtained through a cyclic voltammetry (CV) measurement. A calculation method is similar to that described in Example 1.

As a result, in the measurement of an oxidation potential Ea [V] of 6FL-4mpFBiBPPm, the HOMO level was −5.42 eV. In contrast, the LUMO level was found to be −2.80 eV. When the oxidation-reduction wave was repeatedly measured, in the Ea measurement, the peak intensity of the oxidation-reduction wave after the hundredth cycle was maintained to be 93% of that of the oxidation-reduction wave at the first cycle, and in the Ec measurement, the peak intensity of the oxidation-reduction wave after the hundredth cycle was maintained to be 83% of that of the oxidation-reduction wave at the first cycle; thus, resistance to oxidation and reduction of 6FL-4mpFBiBPPm was found to be extremely high.

Example 9

In this example, a method for synthesizing N-[4-(9-phenyl-9H-carbazol-3-yl)phenyl]-N-(9,9-dimethyl-9H-fluoren-2-yl)-(4-{3-[6-(9,9-dimethyl-9H-fluoren-2-yl)pyrimidin-4-yl]phenyl}phenyl)amine (abbreviation: 6FL-4mpPCBFBPPm), which is the organic compound of one embodiment of the present invention represented by Structural Formula (108), and the physical properties of the compound are described.

Synthesis Example 9

Synthesis of N-[4-(9-phenyl-9H-carbazol-3-yl)phenyl]-N-(9,9-dimethyl-9H-fluoren-2-yl)-(4-{3-[6-(9, 9-dimethyl-9H-fluoren-2-yl)pyrimidin-4-yl] phenyl}phenyl)amine (abbreviation: 6FL-4mpPCBFBPPm)

Into a 100 mL three-neck flask were put 1.7 g (2.7 mmol) of N-(4-chlorophenyl)-N-[4-(9-phenyl-9H-carbazol-3-yl) phenyl]-9,9-dimethyl-9H-fluoren-2-amine, 1.3 g (2.7 mmol) of 4,4,5,5-tetramethyl-2-{3-[6-(9,9-dimethyl-9H-fluoren-2-yl)pyrimidin-4-yl]phenyl}-1,3,2-dioxaborolane, 1.9 g (9.0 mmol) of tripotassium phosphate, and 22 mg (0.060 mmol)

of di(1-adamantyl)-n-butylphosphine, and the air in the flask was replaced with nitrogen. To this mixture were added 15 mL of 1,4-dioxane and 0.67 g (9.0 mmol) of tert-butyl alcohol, and the resulting mixture was degassed by being stirred while the pressure was reduced. After the degasification, 6.7 mg (0.030 mmol) of palladium(II) acetate was added to the mixture, and the resulting mixture was stirred at approximately 80° C. for 14 hours. After the stirring, the mixture was suction filtered, and the oily substance obtained by concentration of the obtained filtrate was purified by silica gel column chromatography (developing solvent: toluene) to give an oily substance. The obtained oily substance was washed with hexane to give 1.4 g of a yellow solid, which was the target substance, in a yield of 54%. The synthesis scheme of Step 1 is shown in (A-12) below.

[Chemical Formula 18]

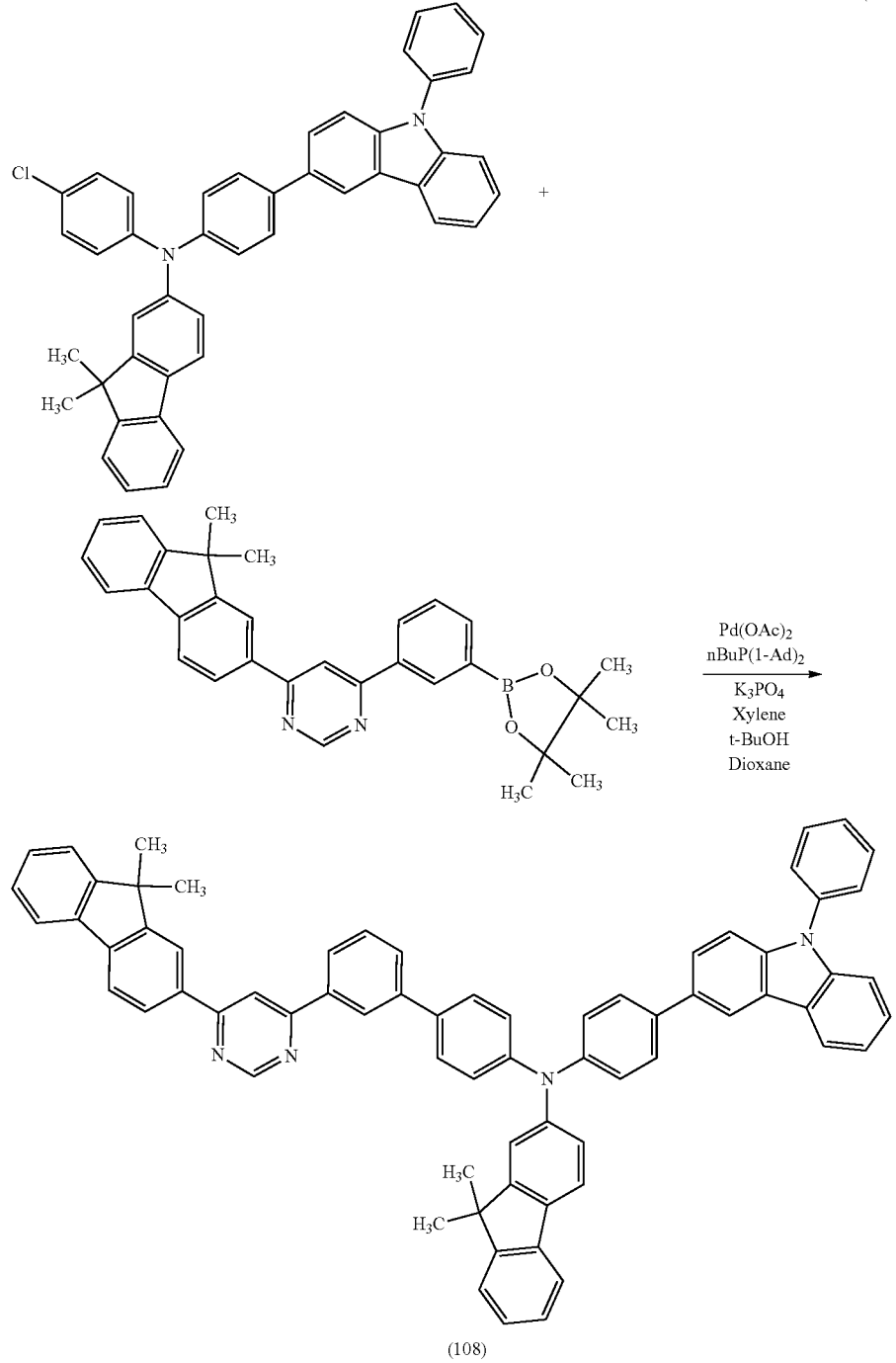

The obtained solid was subjected to analysis by nuclear magnetic resonance spectrometry ($^1$H NMR), and the results are shown below.

$^1$H NMR (CDCl$_3$, 300 MHz):δ=1.47 (s, 6H), 1.59 (s, 6H), 7.17 (dd, J$_1$=8.4 Hz, J$_2$=1.8 Hz, 1H), 7.28-7.51 (m, 15H), 7.60-7.69 (m, 13H), 7.77-7.82 (m, 2H), 7.87 (d, J=8.4 Hz, 1H), 8.11 (d, J=7.8 Hz, 1H), 8.15 (dd, J$_1$=7.8 Hz, J$_2$=1.5 Hz, 1H), 8.20 (d, J=7.5 Hz, 1H), 8.22 (d, J=1.5 Hz, 1H), 8.29 (d, J=1.5 Hz, 1H), 8.37 (d, J=1.5 Hz, 1H), 8.42 (t, J=1.5 Hz, 1H), 9.37 (d, J=0.9 Hz, 1H).

Figure 43A:
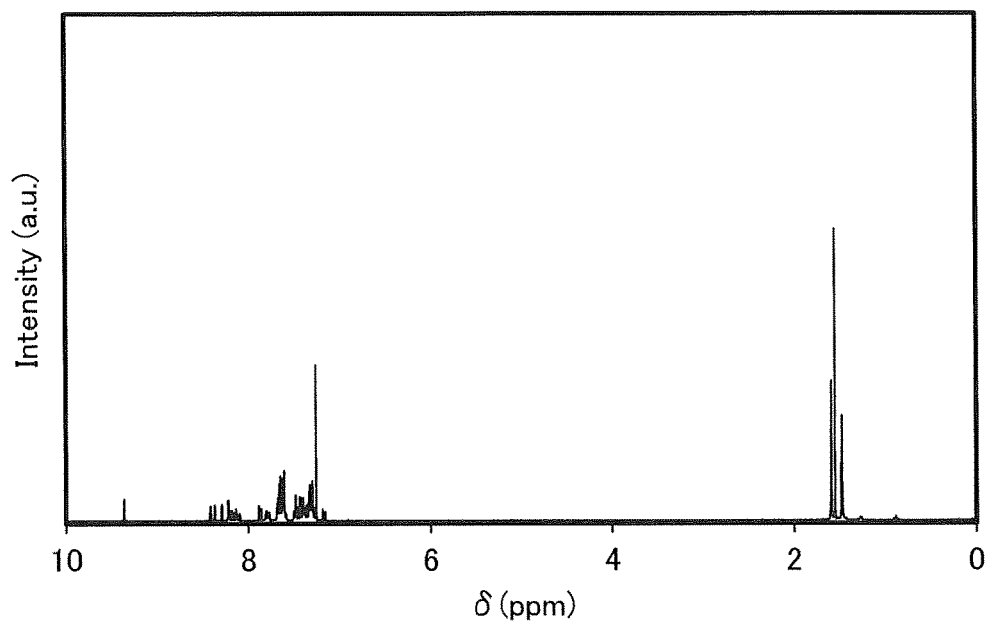
FIGS. 43A and 43B are NMR charts of Example.
Figure 43B:
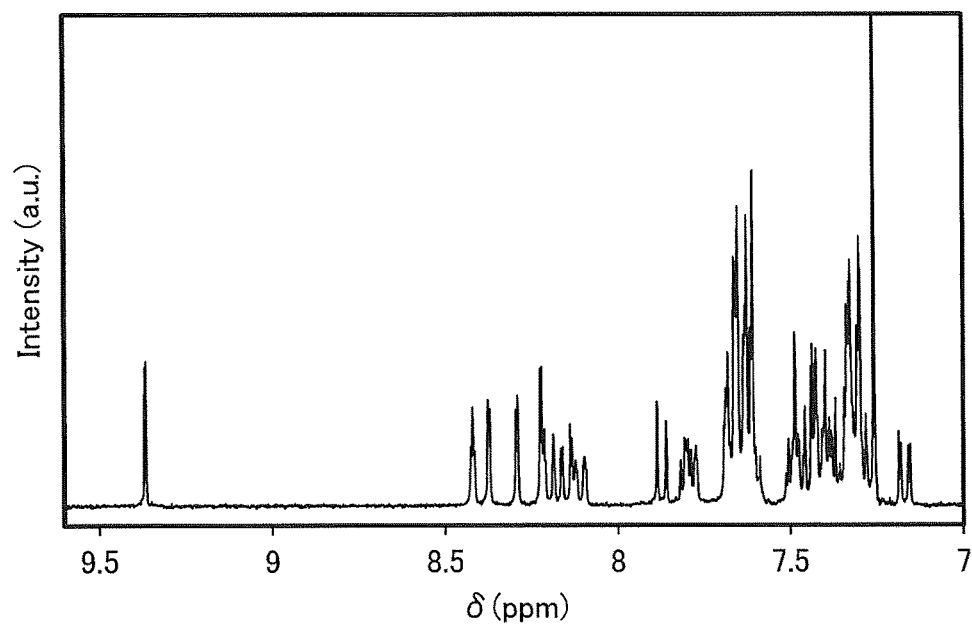

FIGS. 43A and 43B are $^1$H NMR charts of the obtained solid. Note that FIG. 43B is a chart showing an enlarged part in the range of 7.0 ppm to 9.5 ppm of FIG. 43A. The measurement results reveal that 6FL-4mpPCBFBPPm, which is the target substance, was obtained.

<Properties of 6FL-4mpPCBFBPPm>

Figure 44:
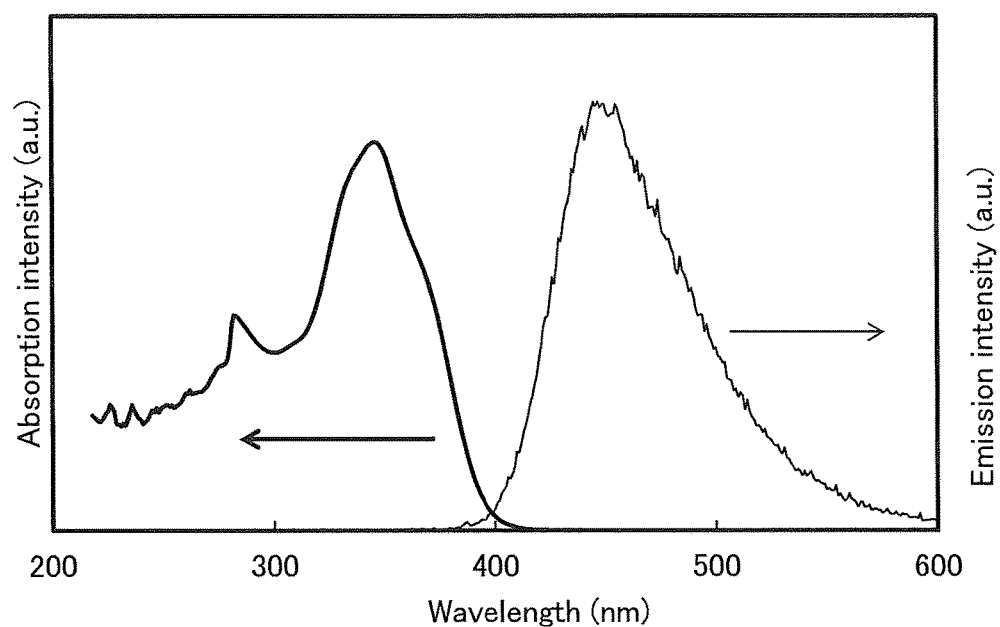
FIG. 44 shows absorption and emission spectra of a compound in Example.

FIG. 44 shows an absorption spectrum and an emission spectrum of 6FL-4mpPCBFBPPm in a toluene solution.

As shown in FIG. 44, 6FL-4mpPCBFBPPm in the toluene solution has absorption peaks at around 346 nm, and an emission wavelength peak at 448 nm (excitation wavelength: 346 nm). The compound of one embodiment of the present invention can be used as a host material for a light-emitting substance or a host material for a substance emitting fluorescence in the visible region.

Next, the HOMO level and the LUMO level of 6FL-4mpPCBFBPPm were obtained through a cyclic voltammetry (CV) measurement. A calculation method is similar to that described in Example 1.

As a result, in the measurement of an oxidation potential Ea [V] of 6FL-4mpPCBFBPPm, the HOMO level was −5.37 eV. In contrast, the LUMO level was found to be −2.81 eV.

Example 10

In this example, a method for synthesizing N-[4-(9-phenyl-9H-carbazol-3-yl)phenyl]-N-{4-[6-(9,9-dimethyl-9H-fluoren-2-yl)pyrimidin-4-yl]phenyl}-1,1′-biphenyl-4-amine (abbreviation: 6FL-4PCBBiPPm), which is the organic compound of one embodiment of the present invention represented by Structural Formula (108), and the physical properties of the compound are described.

Synthesis Example 10

Step 1: Synthesis of N-(4-chlorophenyl)-N-[4-(9-phenyl-9H-carbazol-3-yl)phenyl]-1,1′-biphenyl-4-amine Into a reaction container were put 2.92 g (6.0 mmol) of N-[4-(9-phenyl-9H-carbazol-3-yl)phenyl]-1,1′-biphenyl-4-amine, 1.73 g (18 mmol) of sodium tert-butoxide, 1.50 g (6.3 mmol) of 4-chloroiodobenzene, and 30 mL of toluene. The mixture was degassed by being stirred while the pressure was reduced, and the air in the reaction container was replaced with nitrogen. Then, 34.5 mg (0.06 mmol) of bis(dibenzylideneacetone)palladium(0) and 0.36 mL (0.12 mmol) of tri(tert-butyl)phosphine (a 10 wt % hexane solution) were added. The mixture was stirred under a nitrogen stream at 85° C. for 5 hours. Then, the mixture was cooled to room temperature, 350 mL of toluene was added to the mixture and the resulting mixture was stirred, and then a solid was separated by suction filteration. The obtained filtrate was concentrated to give approximately 100 mL of a brown liquid. The brown liquid was purified using Celite, alumina, and Florisil. After the obtained filtrate was concentrated, ethanol was added and recrystallization was performed to give 3.60 g of a pale yellow solid. The pale yellow solid was heated and stirred with ethanol and filtered to give 2.29 g of a pale yellow powder, which was the target substance, in a yield of 64%. The synthesis scheme of Step 1 is shown in (A-13) below.

[Chemical Formula 19]

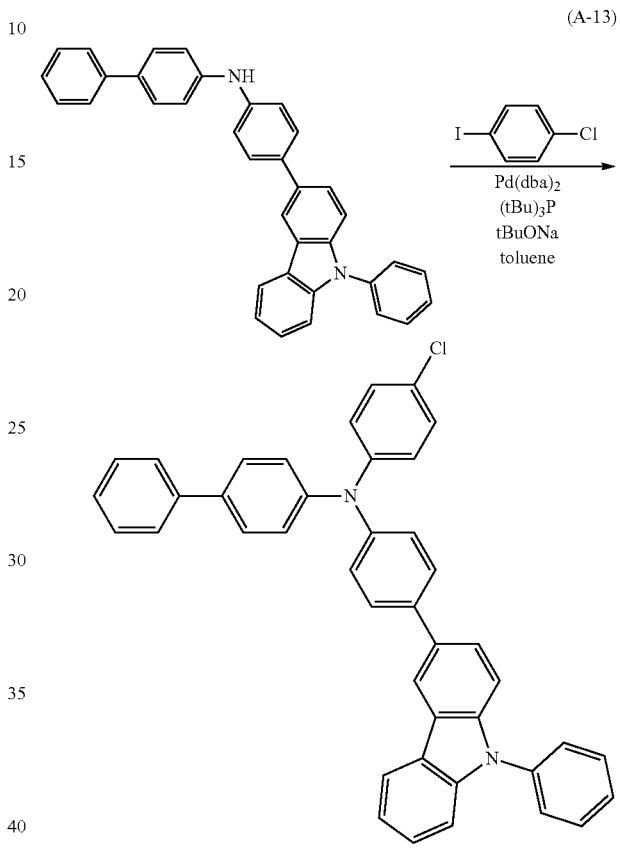

(A-13)

Step 2: Synthesis of N-[4-(4,4,5,5-tetramethyl-1,3,2-dioxaborolan-2-yl)phenyl]-N-[4-(9-phenyl-9H-carbazol-3-yl)phenyl]-1,1′-biphenyl-4-amine Into a reaction container were put 1.49 g (2.5 mmol) of N-(4-chlorophenyl)-N-[4-(9-phenyl-9H-carbazol-3-yl)phenyl]-1,1′-biphenyl-4-amine, 0.95 g (3.75 mmol) of bis(pinacolato)diboron, 0.74 g (7.5 mmol) of potassium acetate, and 30 mL of ethylene glycol dimethyl ether. The mixture was degassed by being stirred while the pressure was reduced, and the air in the reaction container was replaced with nitrogen. Then, after the mixture in the reaction container was heated and stirred to approximately 60° C., 20.4 mg (0.025 mmol) of [1,1′-bis(diphenylphosphino)ferrocene]palladium(II) dichloride dichloromethane adduct and 20.5 mg (0.050 mmol) of 2-dichlorohexylphosphino-2′,6′-dimethoxybiphenyl were added. The mixture was stirred under a nitrogen stream for 19 hours while being heated and refluxed. Then, the mixture was cooled to room temperature, toluene was added, and the obtained mixture was concentrated to give 50 mL of a brown liquid. The brown liquid was purified using Celite and silica gel. After the obtained filtrate was concentrated, ethanol was added and recrystallization was performed to give 1.34 g of a yellow powder, which was the target substance, in a yield of 78%. The synthesis scheme of Step 2 is shown in (A-14) below.

[Chemical Formula 20]

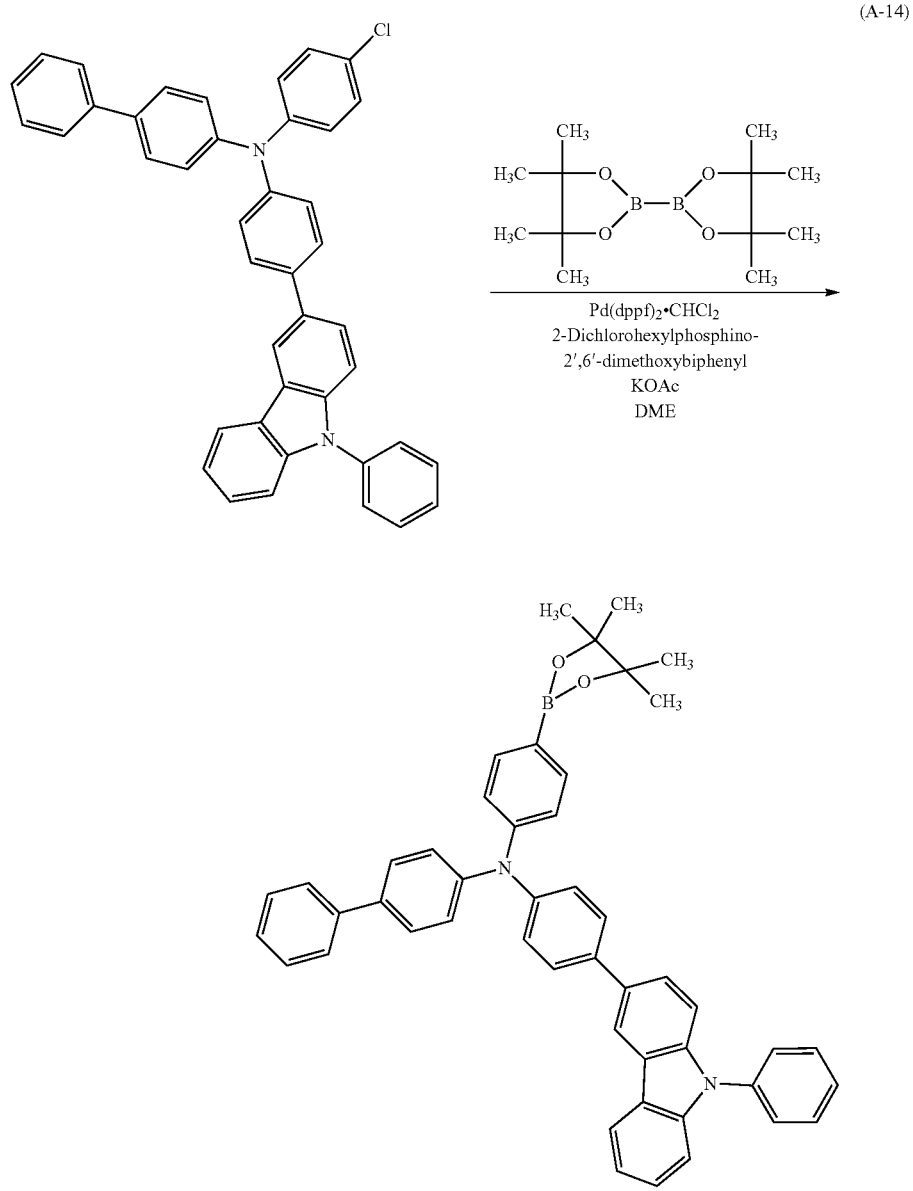

(A-14)

Step 3: Synthesis of N-[4-(9-phenyl-9H-carbazol-3-yl)phenyl]-N-{4-[6-(9,9-dimethyl-9H-fluoren-2-yl)pyrimidin-4-yl]phenyl}-1,1'-biphenyl-4-amine (abbreviation: 6FL-4PCBBiPPm)

Into a reaction container were put 1.38 g (2.0 mmol) of N-(4-chlorophenyl)-N-[4-(9-phenyl-9H-carbazol-3-yl)phenyl]-1,1'-biphenyl-4-amine, 0.61 g (2.0 mmol) of 4-chloro-6-(9,9-dimethyl-9H-fluoren-2-yl)pyrimidine, 1.27 g (6.0 mmol) of tripotassium phosphate, and 20 mL of diethylene glycol dimethyl ether (diglyme). The mixture was degassed by being stirred while the pressure was reduced, and the air in the reaction container was replaced with nitrogen. Then, after the mixture in the reaction container was heated and stirred to approximately 60° C., 4.5 mg (0.02 mmol) of palladium(II) acetate and 14.3 mg (0.04 mmol) of di(1-adamantyl)-n-butylphosphine were added. The mixture was stirred under a nitrogen stream for 24 hours while being heated at 120° C. After that, the mixture was cooled to room temperature, and then toluene and water were added and extraction and washing were performed to give a black solution. Magnesium sulfate was added to the solution and then separated to remove moisture and concentrate to give a black solution. The solution was subjected to column purification using silica gel and a 100:1 toluene-ethyl acetate mixed solvent as a developing solvent. After the obtained solution was concentrated, ethanol was added and recrystallization was performed to give 1.10 g of a yellow powder, which was the target substance, in a yield of 66%. The synthesis scheme of Step 3 is shown in (A-15) below.

[Chemical Formula 21]

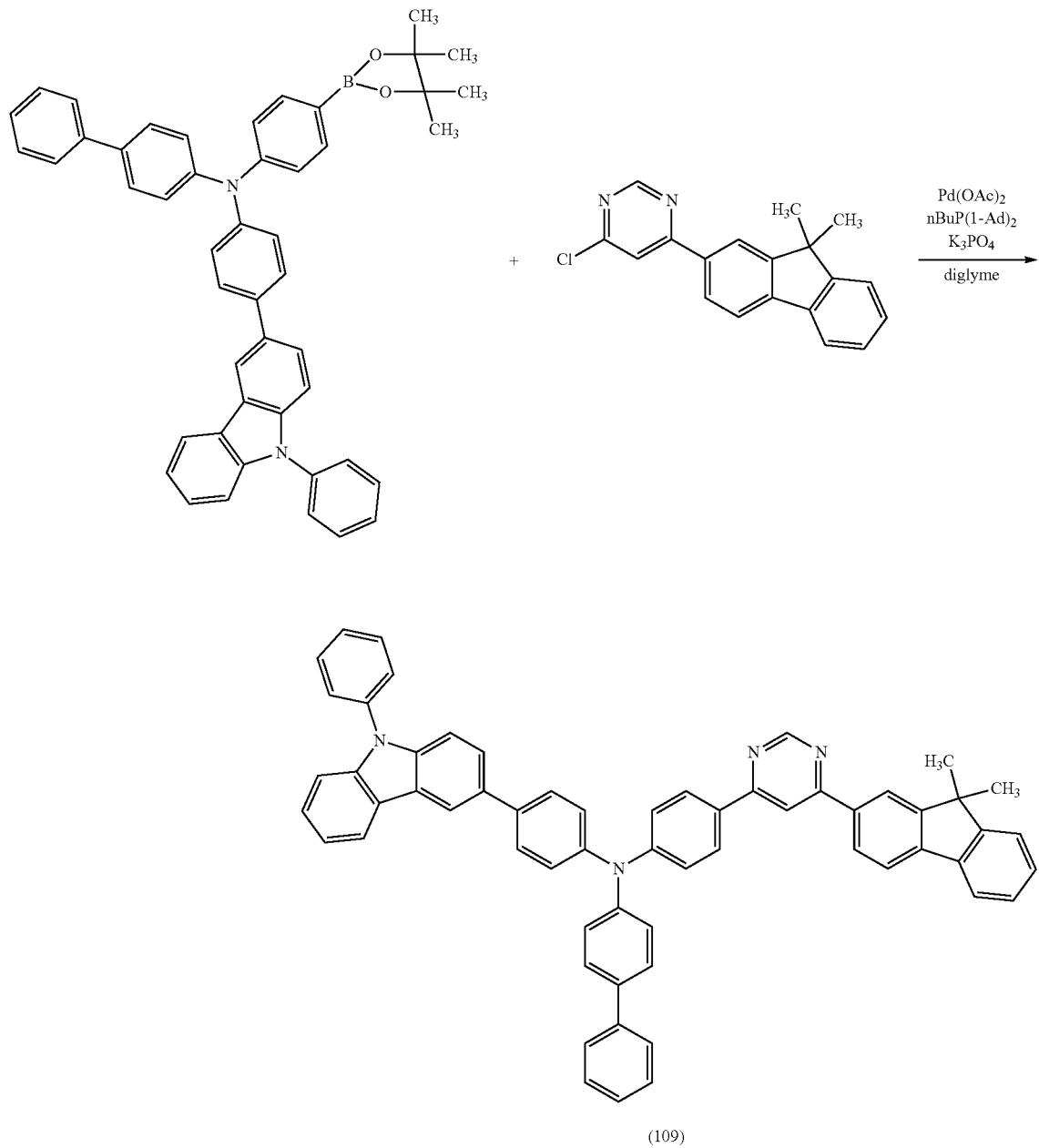

Then, 1.10 g of the obtained yellow powder was purified by a train sublimation method. The purification by sublimation was performed by heating the yellow powder at 370° C. under a pressure of 3.23 Pa with an argon flow rate of 15 mL/min to give 0.48 g of a pale yellow solid, which was the target substance, was obtained at a collection rate of 43%.

The obtained solid was subjected to analysis by nuclear magnetic resonance spectrometry ($^1$H NMR), and the results are shown below.

$^1$H NMR (CDCl$_3$, 500 MHz):δ=1.58 (s, 6H), 7.31-7.40 (m, 10H), 7.44-7.50 (m, 7H), 7.57-7.71 (m, 11H), 7.80 (dd, J$_1$=8.7 Hz, J$_2$=2.4 Hz, 1H), 7.87 (d, J=8.1 Hz, 1H), 8.10-8.13 (m, 4H), 8.20 (d, J=8.4 Hz, 1H), 8.26 (d, J=1.2 Hz, 1H), 8.37 (s, 1H), 9.29 (d, J=1.2 Hz, 1H).

Figure 45A:
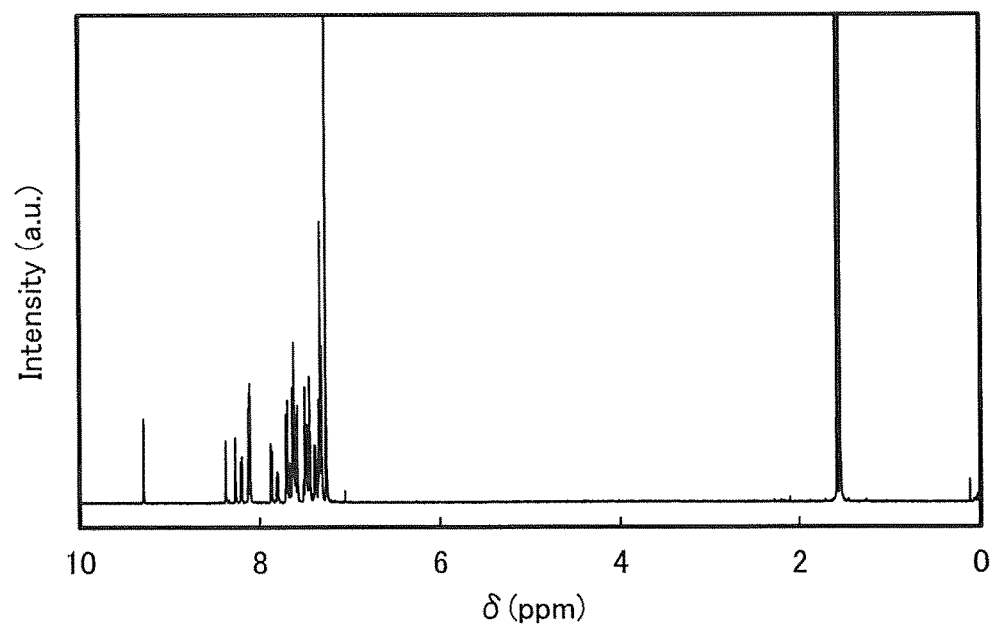
FIGS. 45A and 45B are NMR charts of Example.
Figure 45B:
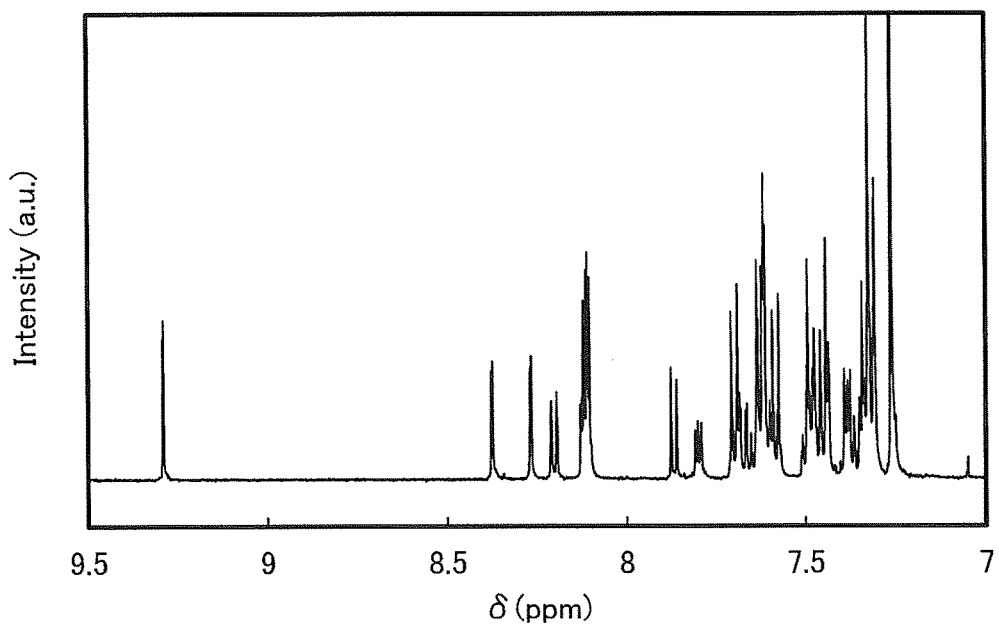

FIGS. 45A and 45B are $^1$H NMR charts of the obtained solid. Note that FIG. 45B is a chart showing an enlarged part in the range of 7.0 ppm to 9.5 ppm of FIG. 45A. The measurement results reveal that 6FL-4PCBBiPPm, which is the target substance, was obtained.

<Properties of 6FL-4PCBBiPPm>

Figure 46:
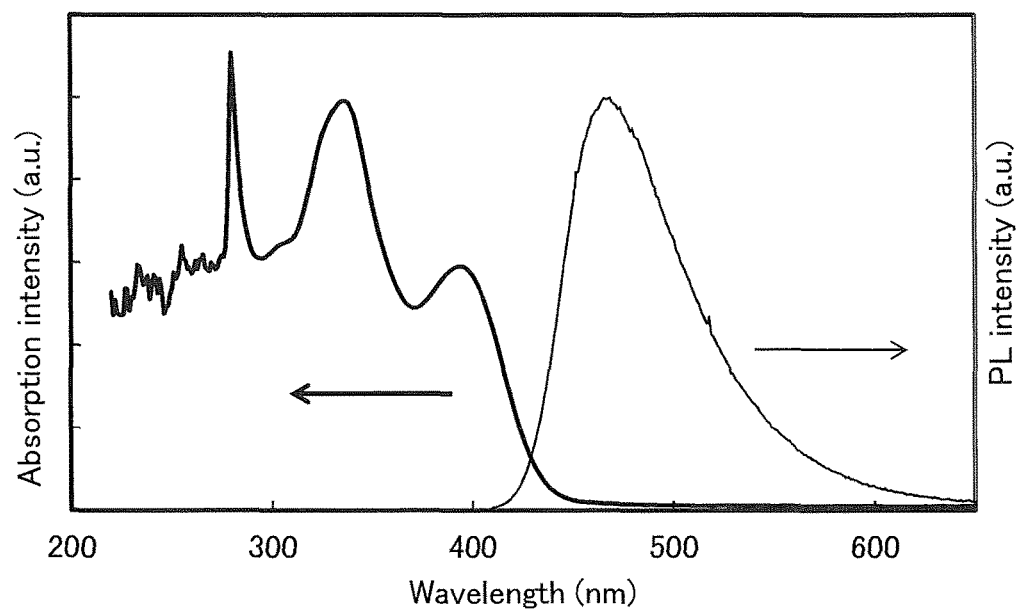
FIG. 46 shows absorption and emission spectra of a compound in Example.
Figure 47:
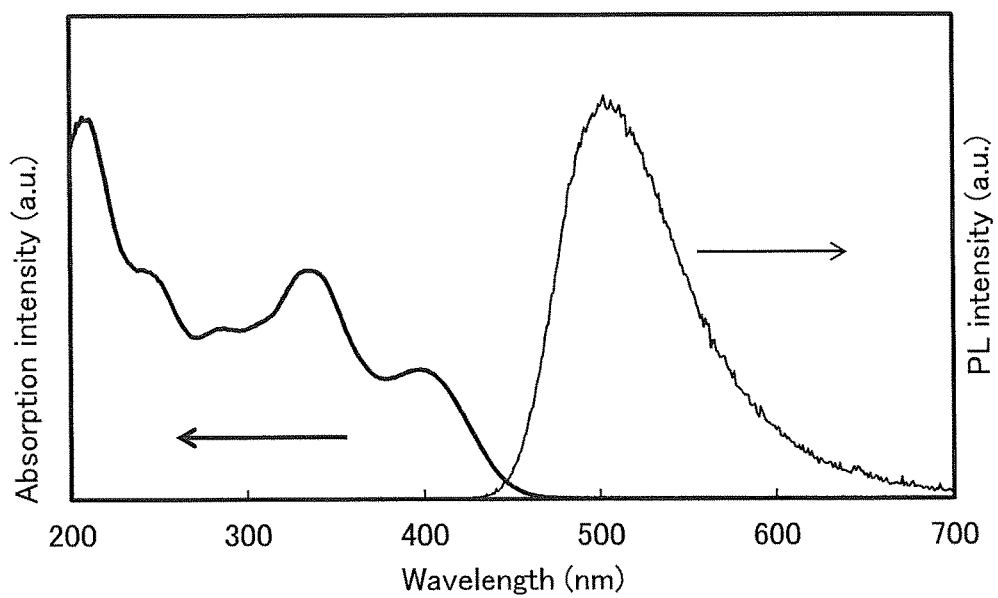
FIG. 47 shows absorption and emission spectra of a compound in Example.

FIG. 46 shows an absorption spectrum and an emission spectrum of 6FL-4PCBBiPPm in a toluene solution. FIG. 47 shows an absorption spectrum and an emission spectrum of a thin film of 6FL-4PCBBiPPm. The measurement was performed in a manner similar to that described in Example 1.

As shown in FIG. 46, 6FL-4PCBBiPPm in the toluene solution has absorption peaks at around 394 nm and 338 nm, and an emission wavelength peak at 467 nm (excitation wavelength: 394 nm). As shown in FIG. 47, the thin film of 6FL-4PCBBiPPm has absorption peaks at around 400 nm, 335 nm, 309 nm, 287 nm, 242 nm, and 207 nm, and an emission wavelength peak at around 505 nm (excitation wavelength: 410 nm). The compound of one embodiment of the present invention can be used as a host material for a light-emitting substance or a host material for a substance emitting fluorescence in the visible region.

It was found that aggregation of the thin film of 6FL-4PCBBiPPm is not easily caused even under the air and the thin film suffers only a small change in shape and has high film quality.

Next, the HOMO level and the LUMO level of 6FL-4PCBBiPPm were obtained through a cyclic voltammetry (CV) measurement. A calculation method is similar to that described in Example 1.

As a result, in the measurement of an oxidation potential Ea [V] of 6FL-4PCBBiPPm, the HOMO level was −5.48 eV. In contrast, the LUMO level was found to be −2.80 eV. When the oxidation-reduction wave was repeatedly measured, in the Ea measurement, the peak intensity of the oxidation-reduction wave after the hundredth cycle was maintained to be 81% of that of the oxidation-reduction wave at the first cycle, and in the Ec measurement, the peak intensity of the oxidation-reduction wave after the hundredth cycle was maintained to be 86% of that of the oxidation-reduction wave at the first cycle; thus, resistance to oxidation and reduction of 6FL-4PCBBiPPm was found to be extremely high.

Example 11

Figure 48:
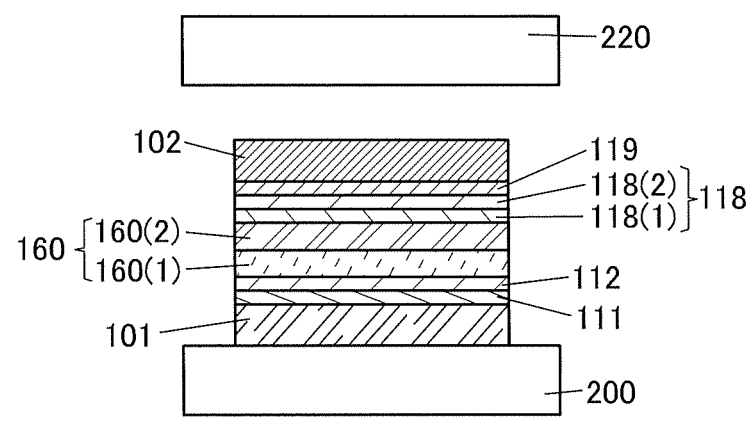
FIG. 48 is a schematic view of a light-emitting element in Example.
Figure 49:
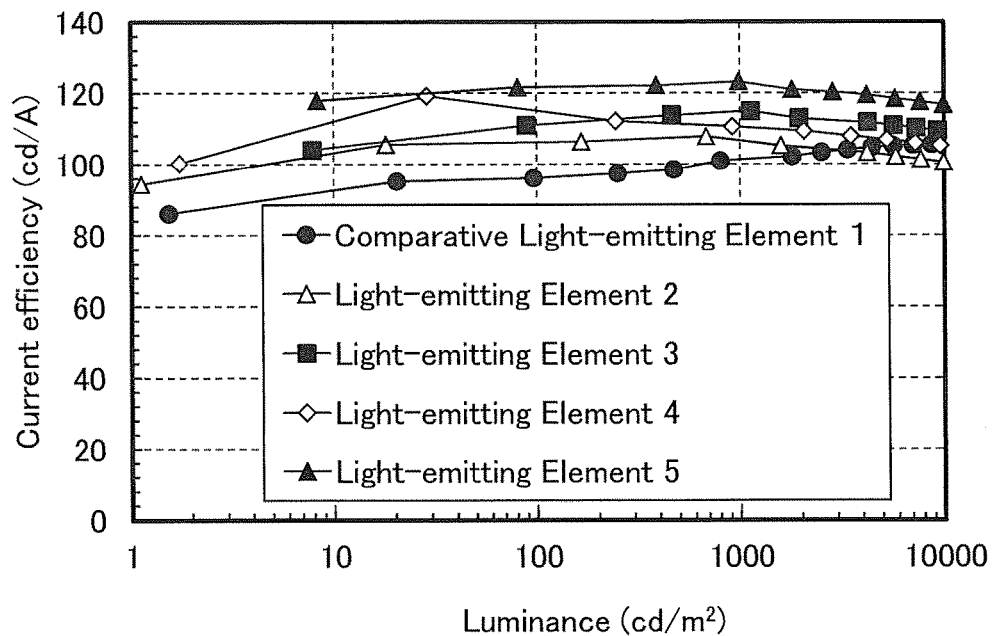
FIG. 49 shows current efficiency-luminance characteristics of light-emitting elements in Example.
Figure 50:
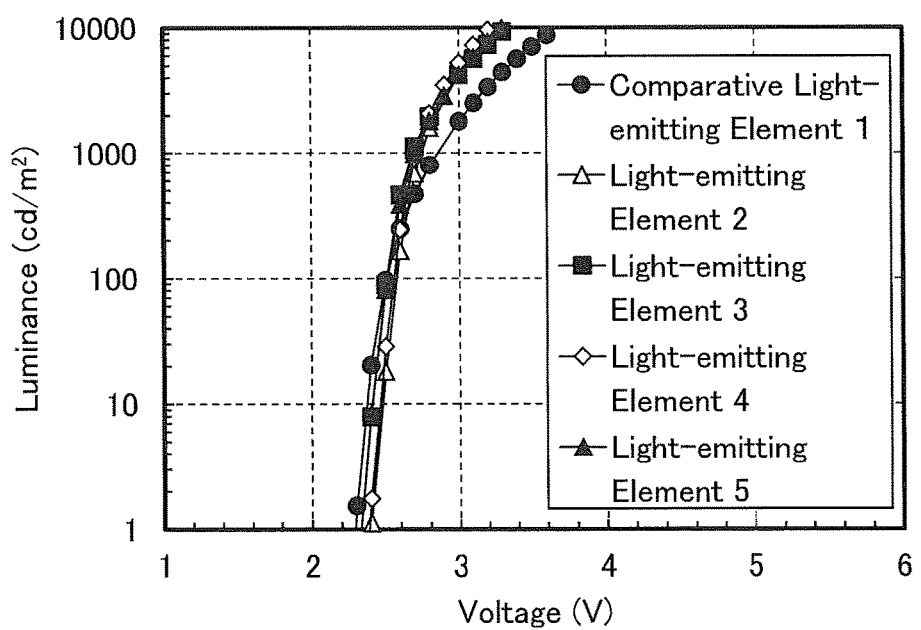
FIG. 50 shows luminance-voltage characteristics of light-emitting elements in Example.
Figure 51:
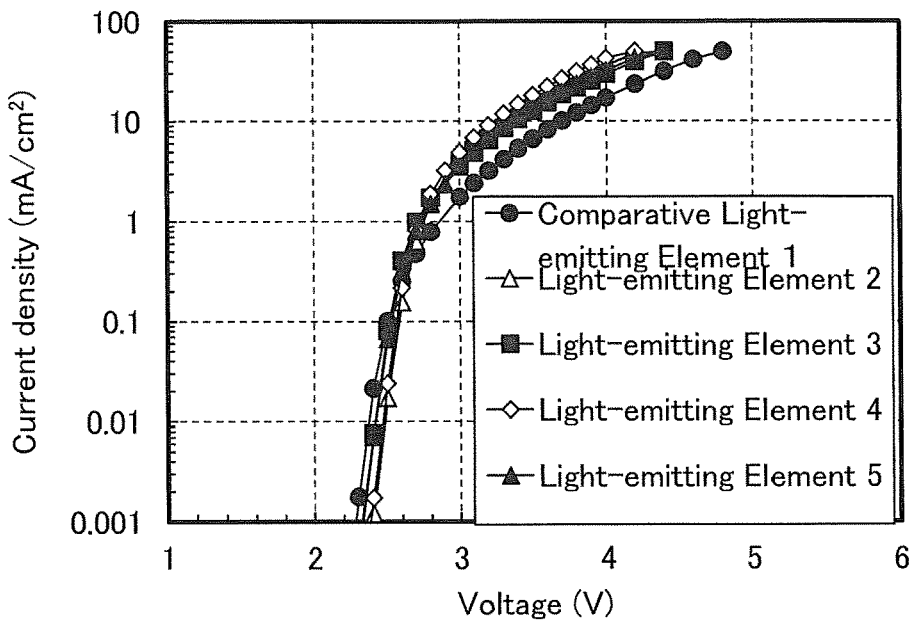
FIG. 51 shows current density-voltage characteristics of light-emitting elements in Example.

In this example, examples of fabricating light-emitting elements 2 to 5, each of which is a light-emitting element of one embodiment of the present invention, and a comparative light-emitting element 1 are described. The comparative light-emitting element 1 and the light-emitting elements 2 to 5 each include two kinds of host materials and one kind of guest material in a light-emitting layer. Two kinds of bipolar materials were used as the host materials. As a bipolar material which receives an electron (a material which has a lower LUMO level) in the light-emitting layer, 2-[3′-(dibenzothiophen-4-yl)biphenyl-3-yl]dibenzo[f,h]quinoxaline (abbreviation: 2mDBTBPDBq-II) was used and a bipolar material which receives a hole (a material which has a higher HOMO level) differed between elements, and the element characteristics were compared with each other. FIG. 48 is a schematic cross-sectional view of each of the light-emitting elements fabricated in this example, and Table 1 shows details of the element structures. In addition, Table 2 shows a difference between LUMO levels of the two kinds of bipolar materials used for the light-emitting layer of each element, which was estimated by CV. In addition, structures and abbreviations of compounds used here are given below. Note that Examples described above can be referred to for structures and abbreviations of other compounds.

[Chemical Formula 22]

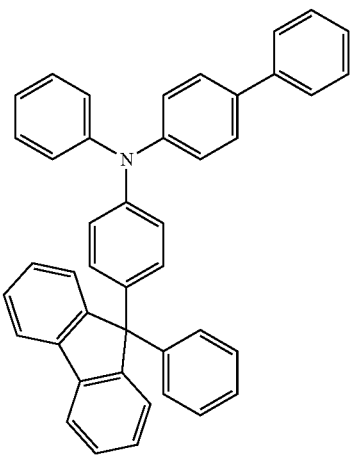

(BPAFLP)

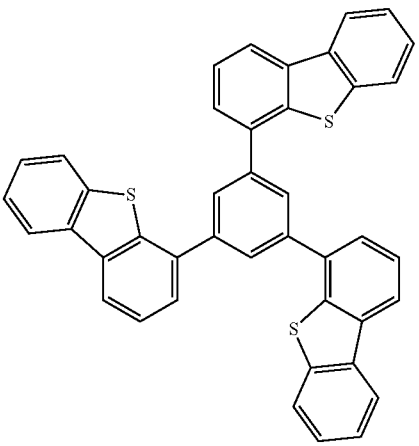

(DBT3P-II)

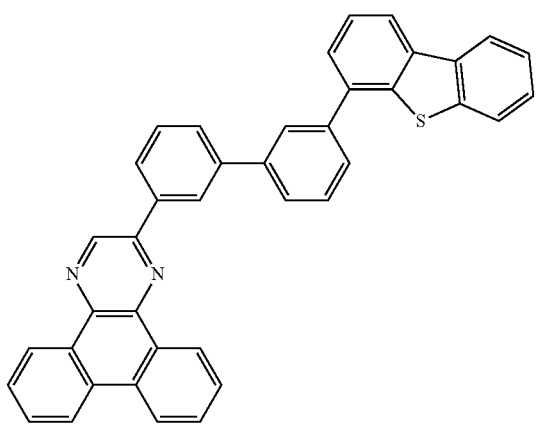

(2mDBTBPDBq-II)

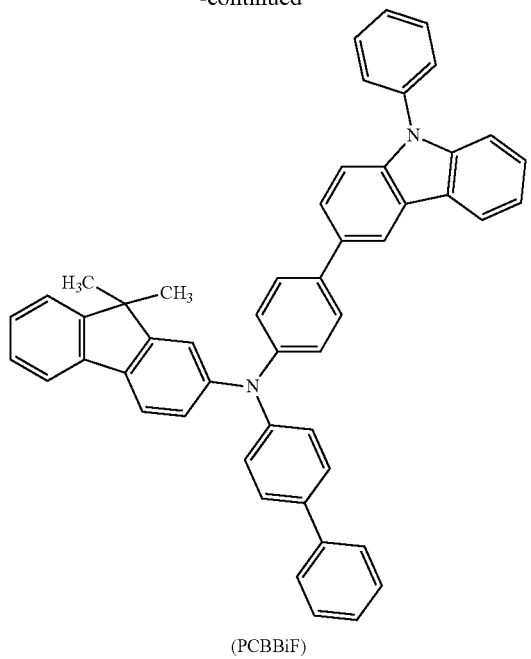

(PCBBiF)

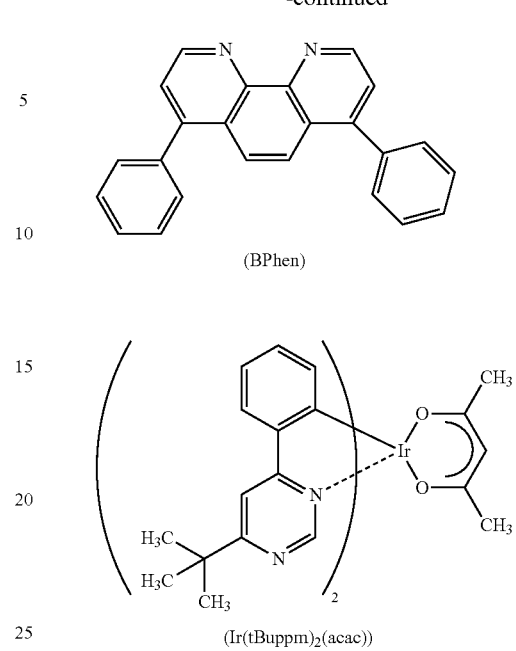

(BPhen)

(Ir(tBuppm)₂(acac))

TABLE 1

| Layer | | Reference numeral | Film thickness (nm) | Material | Weight ratio |
|---|---|---|---|---|---|
| Comparative light-emitting element 1 | Electrode | 102 | 200 | Al | — |
| | Electron-injection layer | 119 | 1 | LiF | — |
| | Electron-transport layer | 118(2) | 10 | BPhen | — |
| | | 118(1) | 20 | 2mDBTBPDBq-II | — |
| | Light-emitting layer | 160 | 40 | 2mDBTBPDBq-II:PCBBiF:Ir(tBuppm)₂(acac) | 0.6:0.4:0.05 |
| | Hole-transport layer | 112 | 20 | BPAFLP | — |
| | Hole-injection layer | 111 | 60 | DBT3P-II:MoO₃ | 1:0.5 |
| | Electrode | 101 | 70 | ITSO | — |
| Light-emitting element 2 | Electrode | 102 | 200 | Al | — |
| | Electron-injection layer | 119 | 1 | LiF | — |
| | Electron-transport layer | 118(2) | 10 | BPhen | — |
| | | 118(1) | 20 | 2mDBTBPDBq-II | — |
| | Light-emitting layer | 160 | 40 | 2mDBTBPDBq-II:6BP-4FBiPPm:Ir(tBuppm)₂(acac) | 0.8:0.2:0.05 |
| | Hole-transport layer | 112 | 20 | BPAFLP | — |
| | Hole-injection layer | 111 | 60 | DBT3P-II:MoO₃ | 1:0.5 |
| | Electrode | 101 | 70 | ITSO | — |
| Light-emitting element 3 | Electrode | 102 | 200 | Al | — |
| | Electron-injection layer | 119 | 1 | LiF | — |
| | Electron-transport layer | 118(2) | 10 | BPhen | — |
| | | 118(1) | 20 | 2mDBTBPDBq-II | — |
| | Light-emitting layer | 160 | 40 | 2mDBTBPDBq-II:6BP-4PCBBiPPm:Ir(tBuppm)₂(acac) | 0.8:0.2:0.05 |
| | Hole-transport layer | 112 | 20 | BPAFLP | — |
| | Hole-injection layer | 111 | 60 | DBT3P-II:MoO₃ | 1:0.5 |
| | Electrode | 101 | 70 | ITSO | — |
| Light-emitting element 4 | Electrode | 102 | 200 | Al | — |
| | Electron-injection layer | 119 | 1 | LiF | — |
| | Electron-transport layer | 118(2) | 10 | BPhen | — |
| | | 118(1) | 20 | 2mDBTBPDBq-II | — |

TABLE 1-continued

|  | Layer | Reference numeral | Film thickness (nm) | Material | Weight ratio |
|---|---|---|---|---|---|
| Light-emitting element 5 | Light-emitting layer | 160 | 40 | 2mDBTBPDBq-II:6BP-4mFBiPPm:Ir(tBuppm)$_2$(acac) | 0.8:0.2:0.05 |
|  | Hole-transport layer | 112 | 20 | BPAFLP | — |
|  | Hole-injection layer | 111 | 60 | DBT3P-II:MoO$_3$ | 1:0.5 |
|  | Electrode | 101 | 70 | ITSO | — |
|  | Electrode | 102 | 200 | Al | — |
|  | Electron-injection layer | 119 | 1 | LiF | — |
|  | Electron-transport layer | 118(2) | 10 | BPhen | — |
|  |  | 118(1) | 20 | 2mDBTBPDBq-II | — |
|  | Light-emitting layer | 160 | 40 | 2mDBTBPDBq-II:6BP-4mPCBBiPPm:Ir(tBuppm)$_2$(acac) | 0.8:0.2:0.05 |
|  | Hole-transport layer | 112 | 20 | BPAFLP | — |
|  | Hole-injection layer | 111 | 60 | DBT3P-II:MoO$_3$ | 1:0.5 |
|  | Electrode | 101 | 70 | ITSO | — |

TABLE 2

|  | LUMO level of bipolar material which receives electron (lower LUMO level) (eV) | LUMO level of bipolar material which receives hole (higher LUMO level) (eV) | Difference between LUMO levels (eV) |
|---|---|---|---|
| Comparative light-emitting element 1 | −2.94 (2mDBTBPDBq-II) | −2.00 (PCBBiF) | 0.94 |
| Light-emitting element 2 | −2.94 (2mDBTBPDBq-II) | −2.79 (6BP-4FBiPPm) | 0.15 |
| Light-emitting element 3 | −2.94 (2mDBTBPDBq-II) | −2.81 (6BP-4PCBBiPPm) | 0.13 |
| Light-emitting element 4 | −2.94 (2mDBTBPDBq-II) | −2.83 (6BP-4mFBiPPm) | 0.11 |
| Light-emitting element 5 | −2.94 (2mDBTBPDBq-II) | −2.84 (6BP-4PCBBiPPm) | 0.10 |

<Fabrication of Light-Emitting Elements>
<<Fabrication of Comparative Light-Emitting Element 1>>

As an electrode 101, an ITSO film was formed to a thickness of 70 nm over a substrate 200. The electrode area of the electrode 101 was set to 4 mm$^2$ (2 mm×2 mm).

As a hole-injection layer 111, 4,4',4"-(benzene-1,3,5-triyl)tri(dibenzothiophene) (abbreviation: DBT3P-II) and molybdenum oxide (MoO$_3$) were deposited over the electrode 101 by co-evaporation in a weight ratio of DBT3P-II:MoO$_3$=1:0.5 to a thickness of 60 nm.

As a hole-transport layer 112, 4-phenyl-4'-(9-phenylfluoren-9-yl)triphenylamine (abbreviation: BPAFLP) was deposited over the hole-injection layer 111 by evaporation to a thickness of 20 nm.

As a light-emitting layer 160, 2mDBTBPDBq-II, N-(1,1'-biphenyl-4-yl)-N-[4-(9-phenyl-9H-carbazol-3-yl)phenyl]-9,9-dimethyl-9H-fluor en-2-amine (abbreviation: PCBBiF), and bis[2-(6-tert-butyl-4-pyrimidinyl-κN$^3$)phenyl-κC](2,4-pentanedionato-κ$^2$O,O')iridium(III) (abbreviation: Ir(tBuppm)$_2$(acac)) were deposited by co-evaporation over the hole-transport layer 112 such that the deposited layer had a weight ratio of 2mDBTBPDBq-II:PCBBiF:Ir(tBuppm)$_2$(acac)=0.6:0.4:0.05 and a thickness of 40 nm. Note that in the light-emitting layer 160, 2mDBTBPDBq-II is a bipolar material which receives an electron, PCBBiF is a bipolar material which receives a hole, and Ir(tBuppm)$_2$(acac) is a guest material (phosphorescent material).

Next, over the light-emitting layer 160, 2mDBTBPDBq-II was deposited by evaporation to a thickness of 20 nm as an electron-transport layer 118(1), and then bathophenanthroline (abbreviation: BPhen) was deposited by evaporation to a thickness of 10 nm as an electron-transport layer 118(2). Then, as an electron-injection layer 119, lithium fluoride (LiF) was deposited over the electron-transport layer 118 by evaporation to a thickness of 1 nm.

As an electrode 102, aluminum (Al) was deposited over the electron-injection layer 119 to a thickness of 200 nm.

Next, in a glove box containing a nitrogen atmosphere, the comparative light-emitting element 1 was sealed by fixing the substrate 220 to the substrate 200 over which the organic material was deposited using a sealant for an organic EL device. Specifically, the sealant was applied on the substrate 220, and the substrate 220 was bonded to the substrate 200 over which the organic material was deposited. Then, irradiation with ultraviolet light having a wavelength of 365 nm at 6 J/cm$^2$ was performed, and then heat treatment at 80° C. for one hour was performed. Through the above steps, the comparative light-emitting element 1 was obtained.

<<Fabrication of Light-Emitting Element 2>>

The light-emitting element 2 is different from the above-described comparative light-emitting element 1 in only the material of the light-emitting layer 160, and steps for the other components are the same as those in a method for fabricating the comparative light-emitting element 1.

That is, as the light-emitting layer 160 of the light-emitting element 2, 2mDBTBPDBq-II, 6BP-4FBiPPm, and Ir(tBuppm)$_2$(acac) were deposited by co-evaporation such that the deposited layer had a weight ratio of 2mDBTBP-DBq-II:6BP-4FBiPPm:Ir(tBuppm)$_2$(acac)=0.6:0.4:0.05 and a thickness of 40 nm.

<<Fabrication of Light-Emitting Element 3>>

The light-emitting element 3 is different from the above-described comparative light-emitting element 1 in only the material of the light-emitting layer 160, and steps for the other components are the same as those in a method for fabricating the comparative light-emitting element 1.

That is, as the light-emitting layer 160 of the light-emitting element 3, 2mDBTBPDBq-II, 6BP-4PCBBiPPm, and Ir(tBuppm)$_2$(acac) were deposited by co-evaporation such that the deposited layer had a weight ratio of 2mDBT-BPDBq-II:6BP-4PCBBiPPm:Ir(tBuppm)$_2$(acac)=0.6:0.4:0.05 and a thickness of 40 nm.

<<Fabrication of Light-Emitting Element 4>>

As the light-emitting layer 160 of the light-emitting element 4, 2mDBTBPDBq-II, 6BP-4mFBiPPm, and Ir(tBuppm)$_2$(acac) were deposited by co-evaporation such that the deposited layer had a weight ratio of 2mDBTBP-DBq-II:6BP-4mFBiPPm:Ir(tBuppm)$_2$(acac)=0.6:0.4:0.05 and a thickness of 40 nm.

<<Fabrication of Light-Emitting Element 5>>

As the light-emitting layer 160 of the light-emitting element 5, 2mDBTBPDBq-II, 6BP-4mPCBBiPPm, and Ir(tBuppm)$_2$(acac) were deposited by co-evaporation such that the deposited layer had a weight ratio of 2mDBTBP-DBq-II:6BP-4mPCBBiPPm:Ir(tBuppm)$_2$(acac)=0.6:0.4:0.05 and a thickness of 40 nm.

<Characteristics of Light-Emitting Elements>

Next, the characteristics of the fabricated comparative light-emitting element 1 and light-emitting elements 2 to 5 were measured. For measuring the luminance and the CIE chromaticity, a luminance colorimeter (BM-5A produced by Topcon Technohouse Corporation) was used. For measuring the electroluminescence spectrum, a multi-channel spectrometer (PMA-11 produced by Hamamatsu Photonics K.K.) was used.

FIGS. 49, 50, 51, and 52 respectively show current efficiency-luminance characteristics, luminance-voltage characteristics, current density-voltage characteristics, and external quantum efficiency-luminance characteristics of the comparative light-emitting element 1 and the light-emitting elements 2 to 5. FIG. 53 shows emission spectra when a current at a current density of 2.5 mA/cm$^2$ was supplied to the comparative light-emitting element 1 and the light-emitting elements 2 to 5.

Table 3 shows the element characteristics of the comparative light-emitting element 1 and the light-emitting elements 2 to 5 at around 1000 cd/m$^2$.

TABLE 3

|  | Voltage (V) | Current density (mA/cm$^2$) | CIE chromaticity (x, y) | Luminance (cd/m$^2$) | Current efficiency (cd/A) | Power efficiency (lm/W) | External quantum efficiency (%) |
|---|---|---|---|---|---|---|---|
| Comparative light-emitting element 1 | 2.8 | 0.8 | (0.40, 0.59) | 800 | 101 | 113 | 26 |
| Light-emitting element 2 | 2.7 | 0.6 | (0.42, 0.57) | 682 | 108 | 125 | 28 |
| Light emitting element 3 | 2.7 | 1.0 | (0.41, 0.58) | 1131 | 115 | 134 | 30 |
| Light-emitting element 4 | 2.7 | 0.8 | (0.41, 0.58) | 919 | 111 | 129 | 29 |
| Light-emitting element 5 | 2.7 | 0.8 | (0.41, 0.58) | 989 | 123 | 143 | 32 |

As shown in FIG. 53, the electroluminescence spectra of green light from the comparative light-emitting element 1 and the light-emitting elements 2 to 5 have peak wavelengths at approximately 546 nm and full widths at half maximum of 57 nm to 65 nm.

Figure 52:
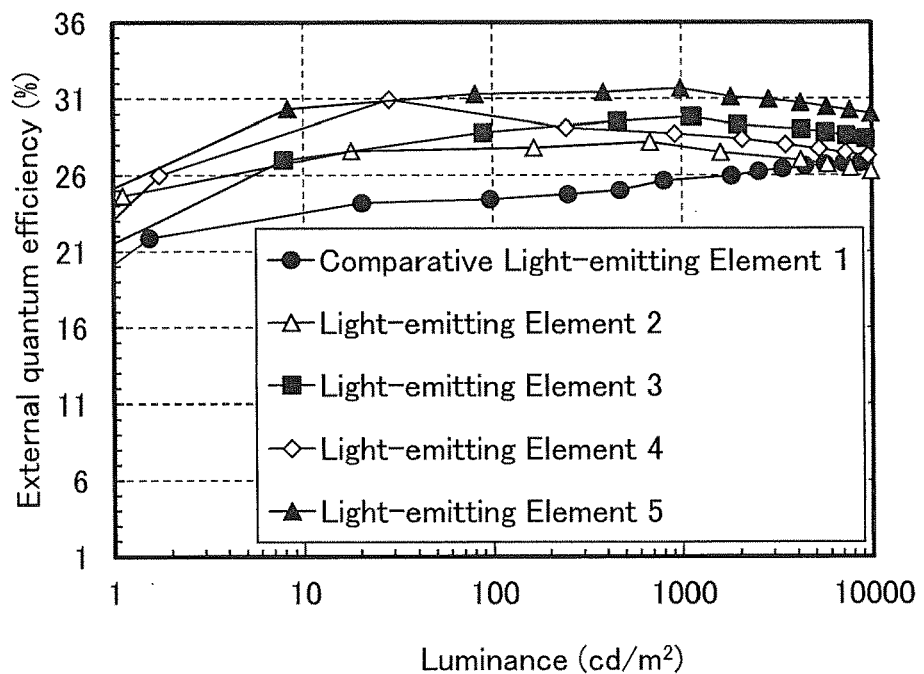
FIG. 52 shows external quantum efficiency-luminance characteristics of light-emitting elements in Example.
Figure 53:
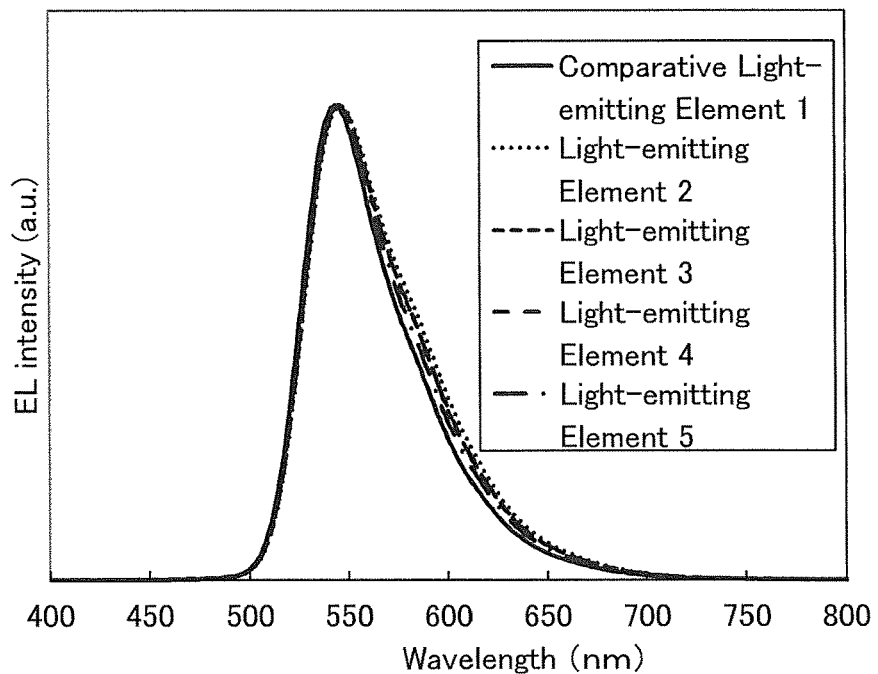
FIG. 53 shows emission spectra of light-emitting elements in Example.

As shown in FIG. 52 and Table 3, the maximum external quantum efficiency of the comparative light-emitting element 1 is 26%, whereas the maximum external quantum efficiencies of the light-emitting elements 2 to 5 are higher than or equal to 28%, which is extremely high.

Figure 54:
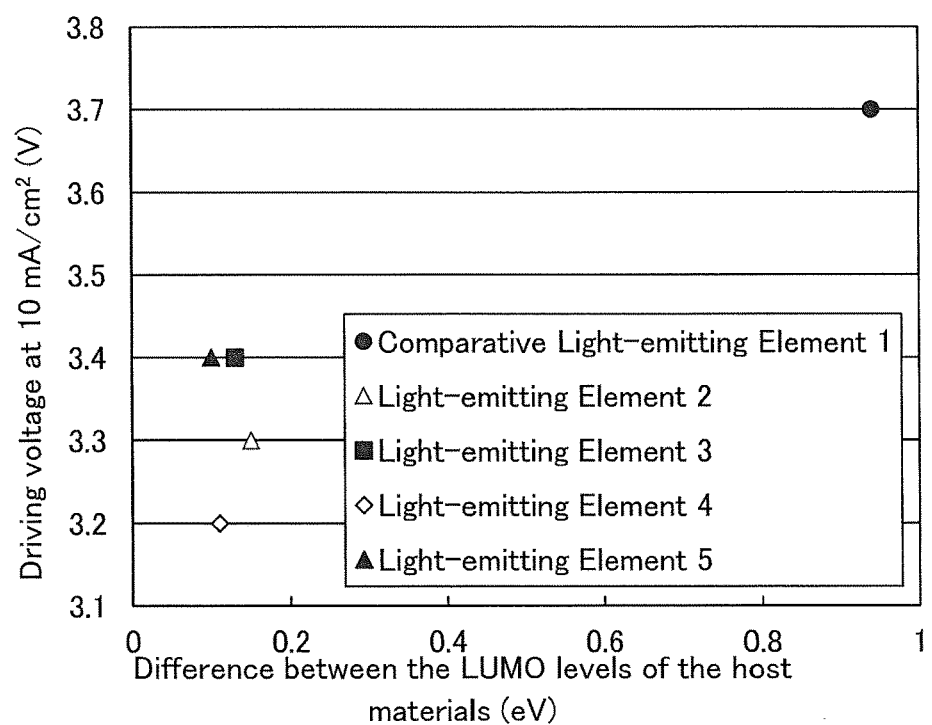
FIG. 54 shows a relationship between a driving voltage and a difference between LUMO levels of host materials.
Figure 55:
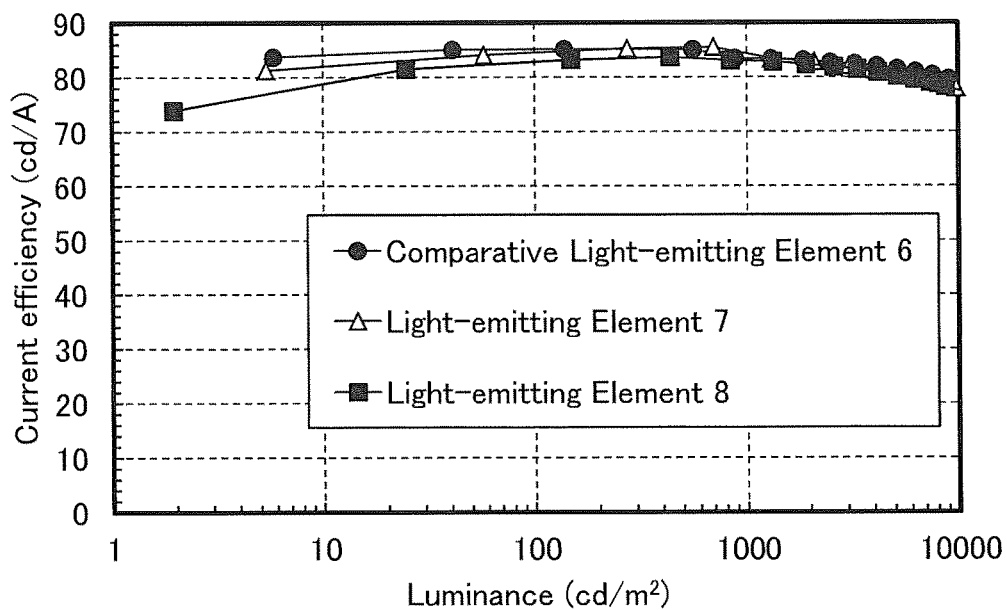
FIG. 55 shows current efficiency-luminance characteristics of light-emitting elements in Example.
Figure 56:
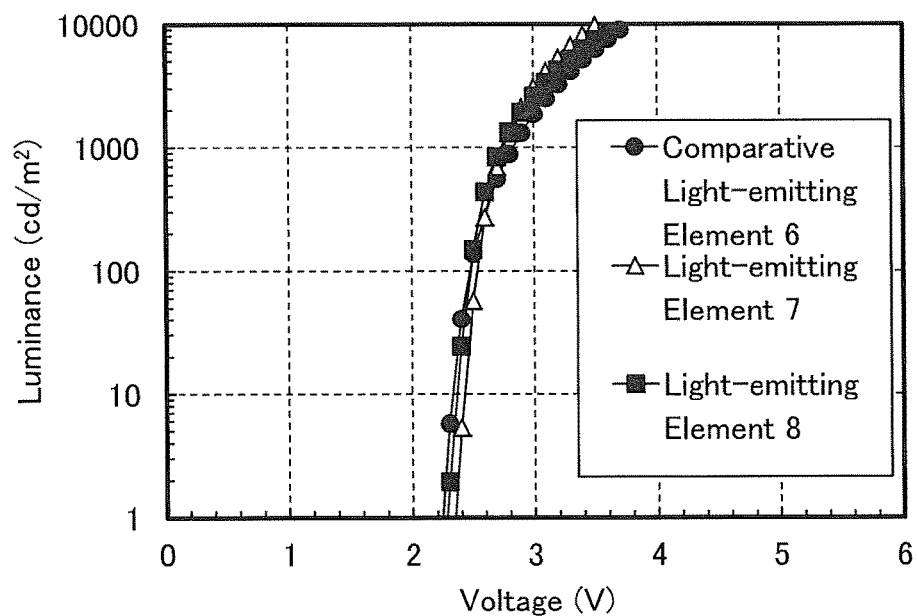
FIG. 56 shows luminance-voltage characteristics of light-emitting elements in Example.
Figure 57:
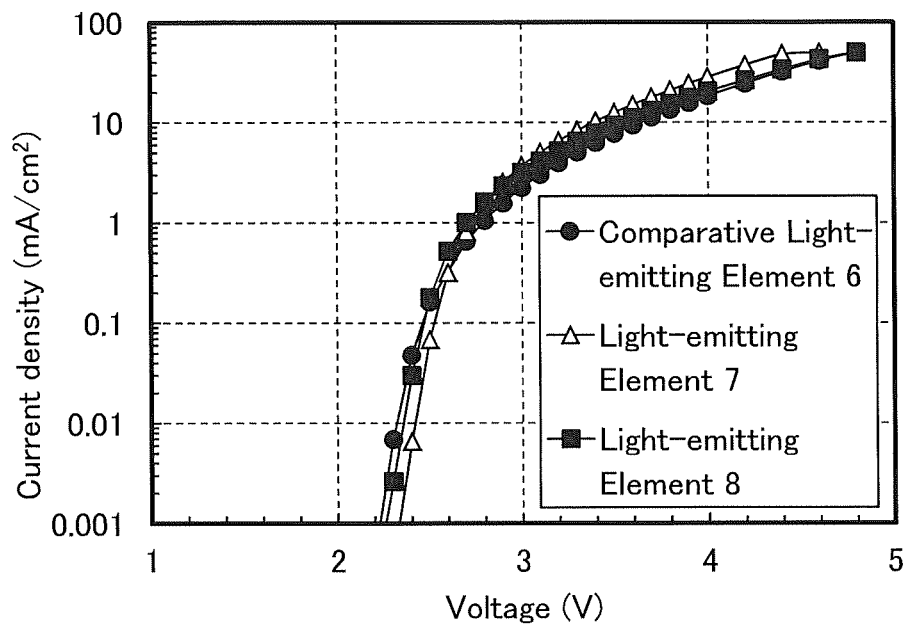
FIG. 57 shows current density-voltage characteristics of light-emitting elements in Example.

In addition, FIG. 54 shows a driving voltage at a current density of 10 mA/cm$^2$ as a function of a difference between the LUMO levels of the host materials in each element. As shown in FIG. 54, the driving voltages of the light-emitting elements 2 to 5 are lower than that of the comparative light-emitting element 1. This is because the difference between the LUMO levels of the two kinds of host materials in the light-emitting layer is smaller than 0.5 eV and a bipolar material is used for each of the two kinds of host materials.

Example 12

In this example, examples of fabricating light-emitting elements 7 and 8, each of which is a light-emitting element of one embodiment of the present invention, and a comparative light-emitting element 6 are described. The comparative light-emitting element 6 and the light-emitting elements 7 and 8 each include two kinds of host materials and one kind of guest material in a light-emitting layer. Two kinds of bipolar materials were used as the host materials. As a bipolar material which receives an electron (a material which has a lower LUMO level) in the light-emitting layer, 2mDBTBPDBq-II was used and a bipolar material which receives a hole (a material which has a higher HOMO level) differed between elements, and the element characteristics were compared with each other. FIG. 48 is a schematic cross-sectional view of each of the light-emitting elements fabricated in this example, and Table 4 shows details of the element structures. In addition, Table 5 shows a difference between LUMO levels of the two kinds of bipolar materials used for the light-emitting layer of each element, which was estimated by CV. In addition, structures and abbreviations of compounds used here are given below. Note that Examples described above can be referred to for structures and abbreviations of other compounds.

[Chemical Formula 23]

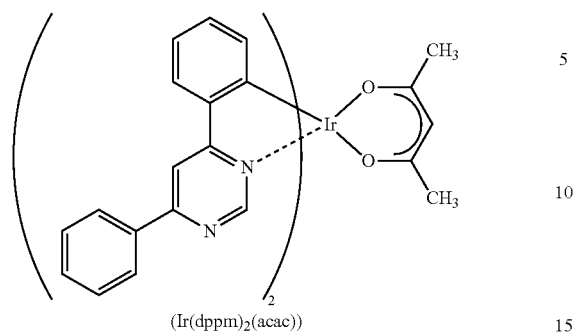

(Ir(dppm)₂(acac))

TABLE 4

| Layer | Reference numeral | Film thickness (nm) | Material | Weight ratio |
|---|---|---|---|---|
| Comparative light-emitting element 6 | | | | |
| Electrode | 102 | 200 | Al | — |
| Electron-injection layer | 119 | 1 | LiF | — |
| Electron-transport layer | 118(2) | 10 | BPhen | — |
|  | 118(1) | 20 | 2mDBTBPDBq-II | — |
| Light-emitting layer | 160 | 40 | 2mDBTBPDBq-II:PCBBiF:Ir(dppm)₂(acac) | 0.6:0.4:0.05 |
| Hole-transport layer | 112 | 20 | BPAFLP | — |
| Hole-injection layer | 111 | 60 | DBT3P-II:MoO₃ | 1:0.5 |
| Electrode | 101 | 70 | ITSO | — |
| Light-emitting element 7 | | | | |
| Electrode | 102 | 200 | Al | — |
| Electron-injection layer | 119 | 1 | LiF | — |
| Electron-transport layer | 118(2) | 10 | BPhen | — |
|  | 118(1) | 20 | 2mDBTBPDBq-II | — |
| Light-emitting layer | 160 | 40 | 2mDBTBPDBq-II:6BP-4FBiPPm:Ir(dppm)₂(acac) | 0.6:0.4:0.05 |
| Hole-transport layer | 112 | 20 | BPAFLP | — |
| Hole-injection layer | 111 | 60 | DBT3P-II:MoO₃ | 1:0.5 |
| Electrode | 101 | 70 | ITSO | — |
| Light-emitting element 8 | | | | |
| Electrode | 102 | 200 | Al | — |
| Electron-injection layer | 119 | 1 | LiF | — |
| Electron-transport layer | 118(2) | 10 | BPhen | — |
|  | 118(1) | 20 | 2mDBTBPDBq-II | — |
| Light-emitting layer | 160 | 40 | 2mDBTBPDBq-II:6BP-4PCBBiPPm:Ir(dppm)₂(acac) | 0.6:0.4:0.05 |
| Hole-transport layer | 112 | 20 | BPAFLP | — |
| Hole-injection layer | 111 | 60 | DBT3P-II:MoO₃ | 1:0.5 |
| Electrode | 101 | 70 | ITSO | — |

TABLE 5

| | LUMO level of bipolar material which receives electron (lower LUMO level) (eV) | LUMO level of bipolar material which receives hole (higher LUMO level) (eV) | Difference between LUMO levels (eV) |
|---|---|---|---|
| Comparative light-emitting element 6 | −2.94 (2mDBTBPDBq-II) | −2.00 (PCBBiF) | 0.94 |
| Light-emitting element 7 | −2.94 (2mDBTBPDBq-II) | −2.79 (6BP-4FBiPPm) | 0.15 |
| Light-emitting element 8 | −2.94 (2mDBTBPDBq-II) | −2.81 (6BP-4PCBBiPPm) | 0.13 |

<Fabrication of Light-Emitting Elements>
<<Fabrication of Comparative Light-Emitting Element 6>>

The comparative light-emitting element 6 is different from the above-described comparative light-emitting element 1 in only the material of the light-emitting layer 160, and steps for the other components are the same as those in a method for fabricating the comparative light-emitting element 1.

That is, as the light-emitting layer 160 of the comparative light-emitting element 6, 2mDBTBPDBq-II, PCBBiF, and bis[2-(6-phenyl-4-pyrimidinyl-κN3)phenyl-κC](2,4-pentanedionato-κ$^2$O,O')iridium(III) (abbreviation: Ir(dppm)$_2$(acac)) were deposited by co-evaporation such that the deposited layer had a weight ratio of 2mDBTBPDBq-II:PCBBiF:Ir(tBuppm)$_2$(acac)=0.6:0.4:0.05 and a thickness of 40 nm.

<<Fabrication of Light-Emitting Element 7>>

The light-emitting element 7 is different from the above-described comparative light-emitting element 1 in only the material of the light-emitting layer 160, and steps for the other components are the same as those in a method for fabricating the comparative light-emitting element 1.

That is, as the light-emitting layer 160 of the light-emitting element 7, 2mDBTBPDBq-II, 6BP-4FBiPPm, and Ir(dppm)$_2$(acac) were deposited by co-evaporation such that the deposited layer had a weight ratio of 2mDBTBPDBq-II:6BP-4FBiPPm:Ir(dppm)$_2$(acac)=0.6:0.4:0.05 and a thickness of 40 nm.

<<Fabrication of Light-Emitting Element 8>>

The light-emitting element 8 is different from the above-described comparative light-emitting element 1 in only the material of the light-emitting layer 160, and steps for the other components are the same as those in a method for fabricating the comparative light-emitting element 1.

That is, as the light-emitting layer 160 of the light-emitting element 8, 2mDBTBPDBq-II, 6BP-4PCBBiPPm, and Ir(dppm)$_2$(acac) were deposited by co-evaporation such that the deposited layer had a weight ratio of 2mDBTBP-DBq-II:6BP-4PCBBiPPm:Ir(dppm)$_2$(acac)=0.6:0.4:0.05 and a thickness of 40 nm.

<CHARACTERISTICS OF LIGHT-EMITTING ELEMENTS>

Next, the characteristics of the fabricated comparative light-emitting element 6 and light-emitting elements 7 and 8 were measured. The measurement method was similar to that used in Example 11.

FIGS. 55, 56, 57, and 58 respectively show current efficiency-luminance characteristics, luminance-voltage characteristics, current density-voltage characteristics, and external quantum efficiency-luminance characteristics of the comparative light-emitting element 6 and the light-emitting elements 7 and 8. FIG. 59 shows emission spectra when a current at a current density of 2.5 mA/cm$^2$ was supplied to the comparative light-emitting element 6 and the light-emitting elements 7 and 8.

Table 6 shows the element characteristics of the comparative light-emitting element 6 and the light-emitting elements 7 and 8 at around 1000 cd/m$^2$.

TABLE 6

|  | Voltage (V) | Current density (mA/cm$^2$) | CIE chromaticity (x, y) | Luminance (cd/m$^2$) | Current efficiency (cd/A) | Power efficiency (lm/W) | External quantum efficiency (%) |
|---|---|---|---|---|---|---|---|
| Comparative light-emitting element 6 | 2.8 | 1.1 | (0.55, 0.45) | 884 | 83 | 94 | 30 |
| Light-emitting element 7 | 2.7 | 0.8 | (0.56, 0.44) | 699 | 86 | 100 | 32 |
| Light-emitting element 8 | 2.7 | 1.0 | (0.56, 0.44) | 841 | 83 | 97 | 31 |

As shown in FIG. 59, the electroluminescence spectra of orange light from the comparative light-emitting element 6 and the light-emitting elements 7 and 8 have peak wavelengths at approximately 586 nm and full widths at half maximum of 69 nm to 73 nm.

Figure 58:
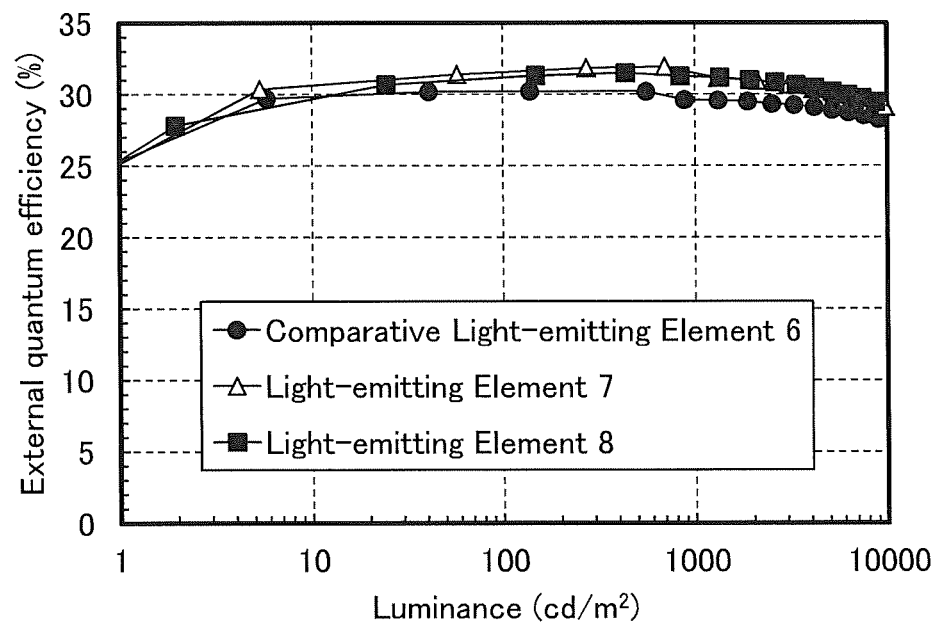
FIG. 58 shows external quantum efficiency-luminance characteristics of light-emitting elements in Example.
Figure 59:
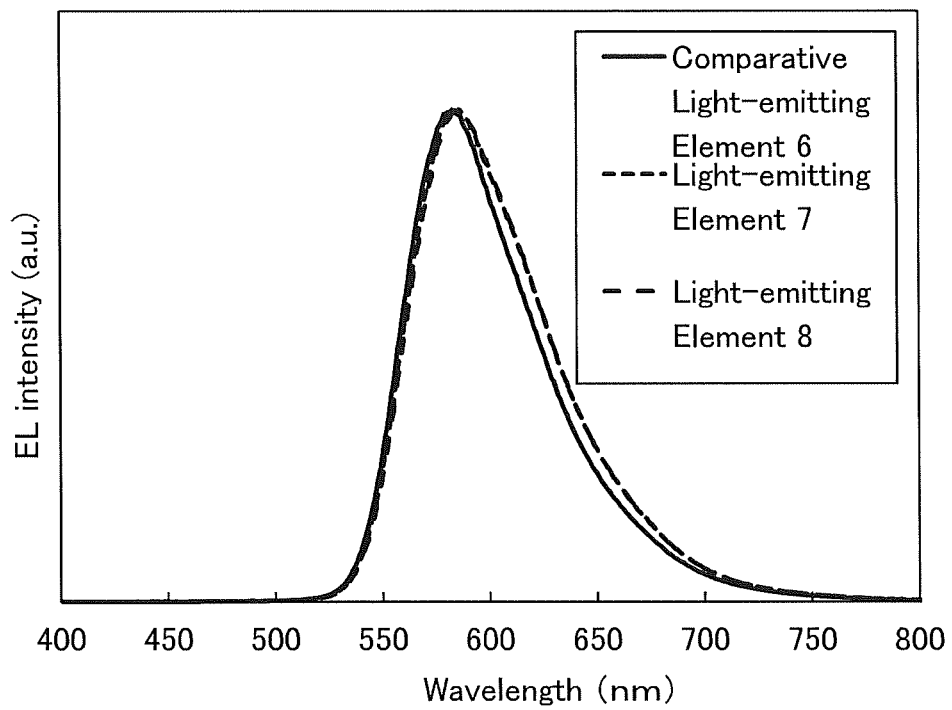
FIG. 59 shows emission spectra of light-emitting elements in Example.

As shown in FIG. 58 and Table 6, the maximum external quantum efficiency of the comparative light-emitting element 6 is 30%, and the maximum external quantum efficiencies of the light-emitting elements 7 and 8 are higher than or equal to 31%, which are extremely high. Furthermore, as shown in FIG. 58, the external quantum efficiencies of the light-emitting elements 7 and 8 are higher than that of the comparative light-emitting element 6. This is because the difference between the LUMO levels of the two kinds of host materials in the light-emitting layer of the light-emitting elements 7 and 8 is smaller than 0.5 eV and a bipolar material is used for each of the two kinds of host materials. This suggests that the carrier balance of the light-emitting elements 7 and 8 is excellent as compared with the comparative light-emitting element 6.

Figure 60:
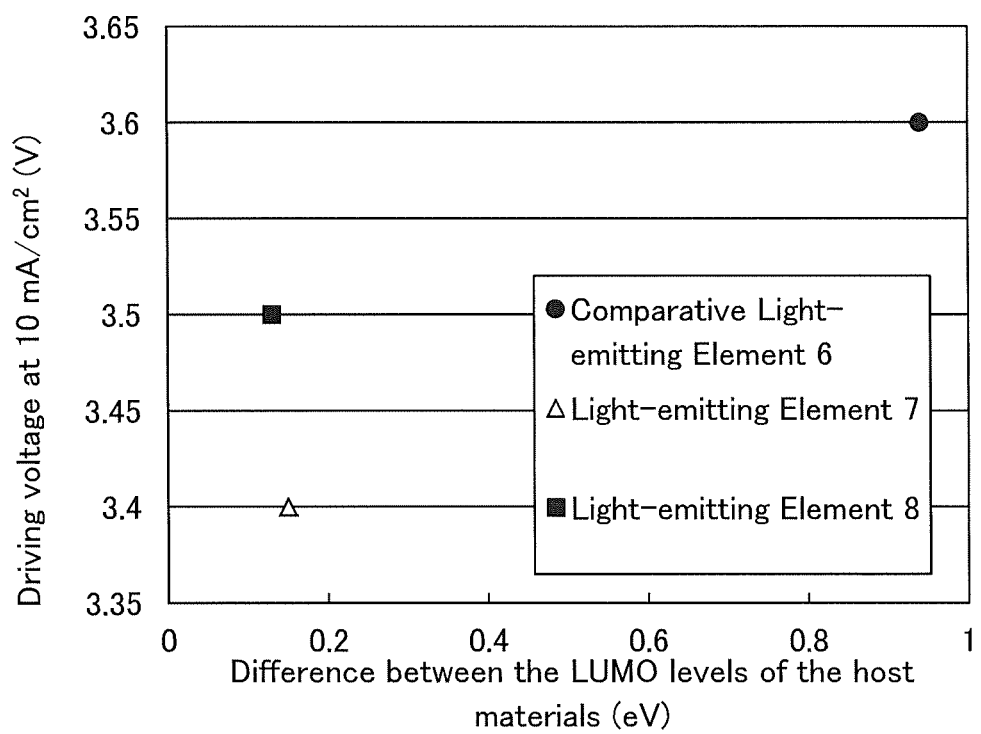
FIG. 60 shows a relationship between a driving voltage and a difference between LUMO levels of host materials.

In addition, FIG. 60 shows a driving voltage at a current density of 10 mA/cm$^2$ as a function of a difference between the LUMO levels of the host materials in each element. As shown in FIG. 60, the driving voltages of the light-emitting elements 7 and 8 are lower than that of the comparative light-emitting element 6. This is because the difference between the LUMO levels of the two kinds of host materials in the light-emitting layer is smaller than 0.5 eV and a bipolar material is used for each of the two kinds of host materials.

<Reliability of Light-Emitting Elements>

Figure 61:
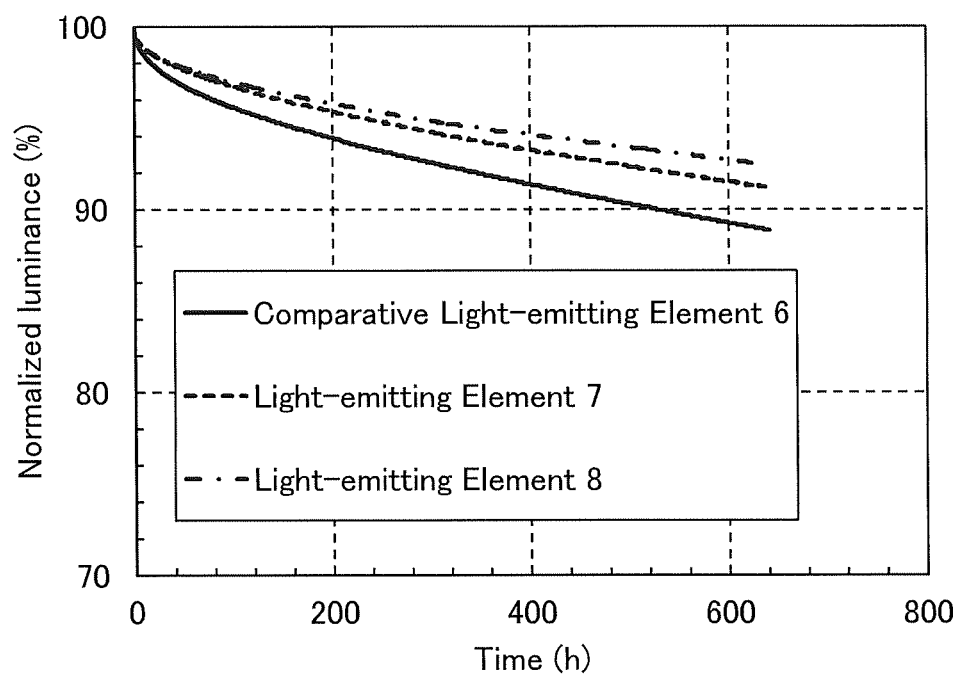
FIG. 61 shows reliability test results of light-emitting elements in Example.
Figure 62:
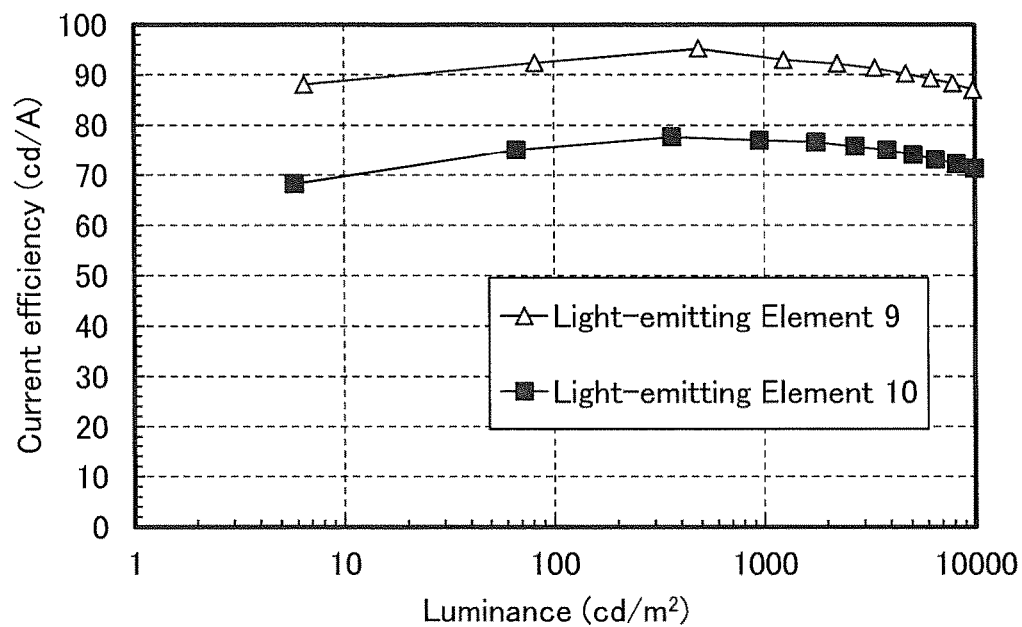
FIG. 62 shows current efficiency-luminance characteristics of light-emitting elements in Example.

Next, constant current driving tests were performed on the comparative light-emitting element 6 and the light-emitting elements 7 and 8, where the initial luminance was 5000 cd/m$^2$. FIG. 61 shows the results. As shown in FIG. 61, the light-emitting elements 7 and 8 each have higher reliability than the comparative light-emitting element 6. This is because, in each of the light-emitting elements 7 and 8, the difference between the LUMO levels of the two kinds of host materials used for the light-emitting layer is smaller and the electron-injection barrier is smaller than in the comparative light-emitting element 6.

Example 13

In this example, examples of fabricating light-emitting elements 9 and 10, each of which is a light-emitting element of one embodiment of the present invention, are described. The light-emitting elements 9 and 10 each include two kinds of host materials and one kind of guest material in a light-emitting layer. Two kinds of bipolar materials were used as the host materials. As a bipolar material which receives an electron (a material which has a lower LUMO level) in the light-emitting layer, 2mDBTBPDBq-II was used and a bipolar material which receives a hole (a material which has a higher HOMO level) differed between elements, and the element characteristics were compared with each other. FIG. 48 is a schematic cross-sectional view of each of the light-emitting elements fabricated in this example, and Table 7 shows details of the element structures. In addition, Table 8 shows a difference between LUMO levels of the two kinds of bipolar materials used for the light-emitting layer of each element, which was estimated by CV. Note that Examples described above can be referred to for structures and abbreviations of compounds used in Example 13.
<Fabrication of Light-Emitting Elements>
<<Fabrication of Light-Emitting Element 9>>

The light-emitting element 9 is different from the above-described comparative light-emitting element 1 in only the material of the light-emitting layer 160, and steps for the other components are the same as those in a method for fabricating the comparative light-emitting element 1.

That is, as the light-emitting layer 160 of the light-emitting element 9, 2mDBTBPDBq-II, 4,6mFBiP2Pm, and Ir(dppm)$_2$(acac) were deposited by co-evaporation such that the deposited layer had a weight ratio of 2mDBTBPDBq-II:4,6mFBiP2Pm:Ir(dppm)$_2$(acac)=0.6:0.4:0.05 and a thickness of 40 nm.

<<Fabrication of Light-Emitting Element 10>>

The light-emitting element 10 is different from the above-described comparative light-emitting element 1 in only the material of the light-emitting layer 160, and steps for the other components are the same as those in a method for fabricating the comparative light-emitting element 1.

That is, as the light-emitting layer 160 of the light-emitting element 10, 2mDBTBPDBq-II, 4,6FBiP2Pm, and Ir(dppm)$_2$(acac) were deposited by co-evaporation such that the deposited layer had a weight ratio of 2mDBTBPDBq-II:4,6FBiP2Pm:Ir(dppm)$_2$(acac)=0.6:0.4:0.05 and a thickness of 40 nm.

<Characteristics of Light-Emitting Elements>

Next, the characteristics of the fabricated light-emitting elements 9 and 10 were measured. The measurement method was similar to that used in Example 11.

FIGS. 62, 63, 64, and 65 respectively show current efficiency-luminance characteristics, luminance-voltage characteristics, current density-voltage characteristics, and external quantum efficiency-luminance characteristics of the light-emitting elements 9 and 10. FIG. 66 shows emission

TABLE 7

| | Layer | Reference numeral | Film thickness (nm) | Material | Weight ratio |
|---|---|---|---|---|---|
| Light-emitting element 9 | Electrode | 102 | 200 | Al | — |
| | Electron-injection layer | 119 | 1 | LiF | — |
| | Electron-transport layer | 118(2) | 10 | BPhen | — |
| | | 118(1) | 20 | 2mDBTBPDBq-II | — |
| | Light-emitting layer | 160 | 40 | 2mDBTBPDBq-II:4,6mFBiP2Pm:Ir(dppm)$_2$(acac) | 0.6:0.4:0.05 |
| | Hole-transport layer | 112 | 20 | BPAFLP | — |
| | Hole-injection layer | 111 | 60 | DBT3P-II:MoO$_3$ | 1:0.5 |
| | Electrode | 101 | 70 | ITSO | — |
| Light-emitting element 10 | Electrode | 102 | 200 | Al | — |
| | Electron-injection layer | 119 | 1 | LiF | — |
| | Electron-transport layer | 118(2) | 10 | BPhen | — |
| | | 118(1) | 20 | 2mDBTBPDBq-II | — |
| | Light-emitting layer | 160 | 40 | 2mDBTBPDBq-II:4,6FBiP2Pm:Ir(dppm)$_2$(acac) | 0.6:0.4:0.05 |
| | Hole-transport layer | 112 | 20 | BPAFLP | — |
| | Hole-injection layer | 111 | 60 | DBT3P-II:MoO$_3$ | 1:0.5 |
| | Electrode | 101 | 70 | ITSO | — |

TABLE 8

| | LUMO level of bipolar material which receives electron (lower LUMO level) (eV) | LUMO level of bipolar material which receives hole (higher LUMO level) (eV) | Difference between LUMO levels (eV) |
|---|---|---|---|
| Light-emitting element 9 | −2.94 (2mDBTBPDBq-II) | −2.80 (4,6mFBiP2Pm) | 0.14 |
| Light-emitting element 10 | −2.94 (2mDBTBPDBq-II) | −2.72 (4,6FBiP2Pm) | 0.22 |

That is, as the light-emitting layer 160 of the light-emitting element 9, 2mDBTBPDBq-II, 4,6mFBiP2Pm, and Ir(dppm)$_2$(acac) were deposited by co-evaporation such that the deposited layer had a weight ratio of 2mDBTBPDBqspectra when a current at a current density of 2.5 mA/cm$^2$ was supplied to the light-emitting elements 9 and 10.

Table 9 shows the element characteristics of the light-emitting elements 9 and 10 at around 1000 cd/m$^2$.

TABLE 9

|  | Voltage (V) | Current density (mA/cm$^2$) | CIE chromaticity (x, y) | Luminance (cd/m$^2$) | Current efficiency (cd/A) | Power efficiency (lm/W) | External quantum efficiency (%) |
|---|---|---|---|---|---|---|---|
| Light-emitting element 9 | 2.7 | 1.3 | (0.54, 0.45) | 1246 | 93 | 108 | 31 |
| Light-emitting element 10 | 2.7 | 1.2 | (0.54, 0.46) | 952 | 77 | 90 | 26 |

As shown in FIG. 66, the electroluminescence spectra of orange light from the light-emitting elements 9 and 10 have peak wavelengths at approximately 579 nm and full widths at half maximum of approximately 67 nm.

Figure 65:
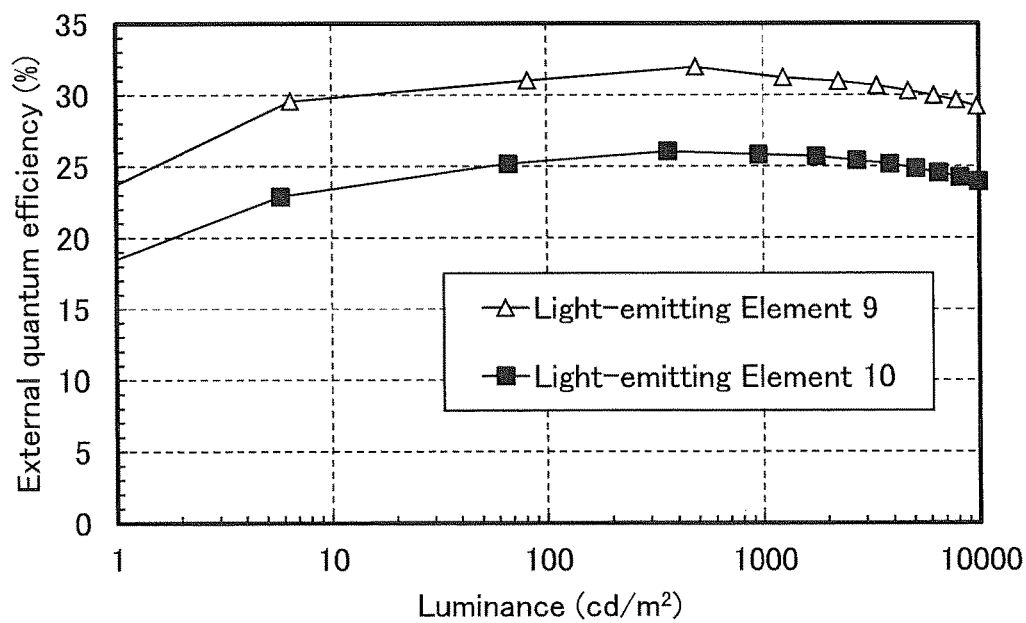
FIG. 65 shows external quantum efficiency-luminance characteristics of light-emitting elements in Example.
Figure 66:
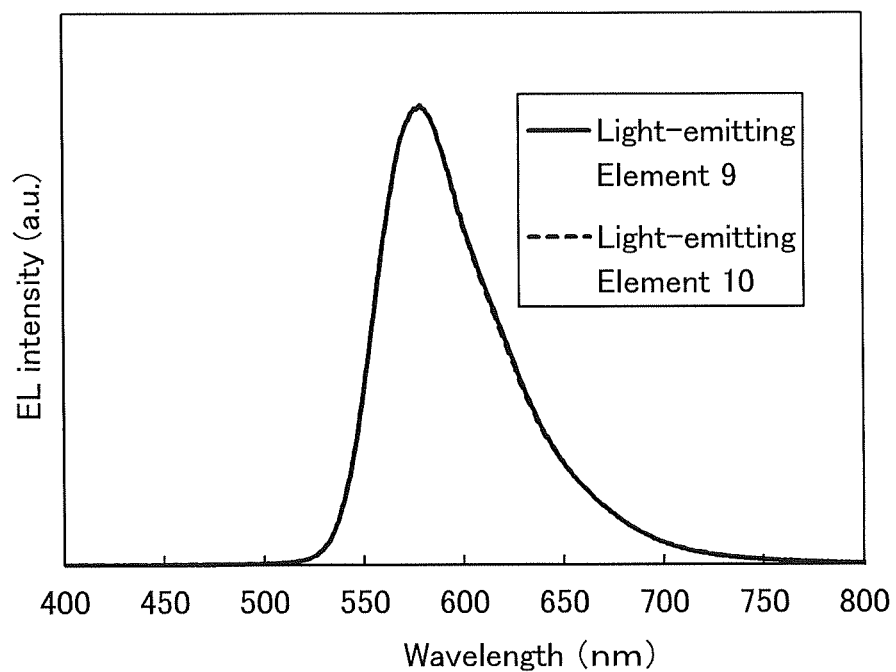
FIG. 66 shows emission spectra of light-emitting elements in Example.
Figure 67:
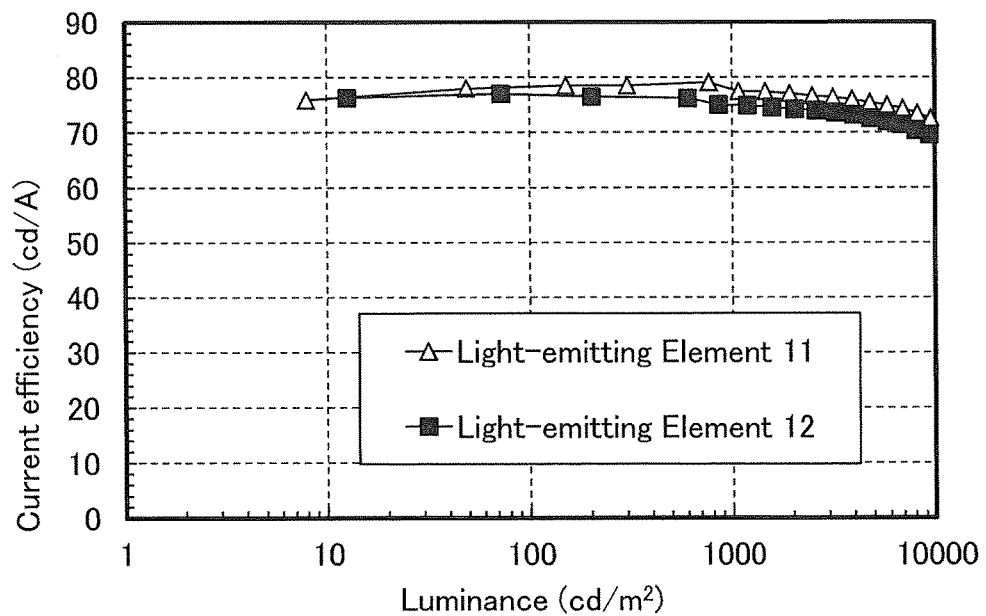
FIG. 67 shows current efficiency-luminance characteristics of light-emitting elements in Example.

As shown in FIG. 65 and Table 9, the maximum external quantum efficiencies of the light-emitting elements 9 and 10 are higher than or equal to 25%, which is extremely high.

Figure 63:
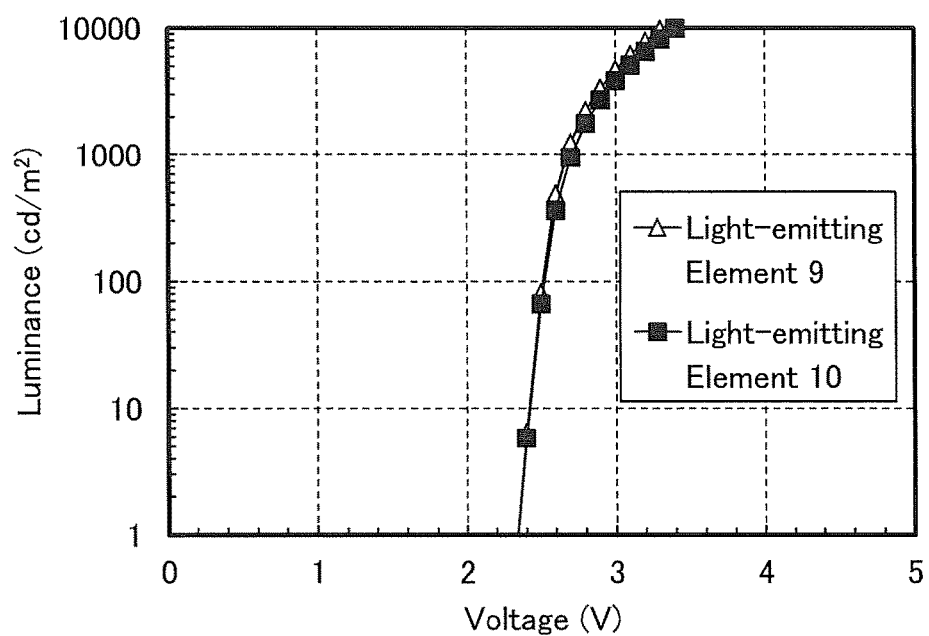
FIG. 63 shows luminance-voltage characteristics of light-emitting elements in Example.
Figure 64:
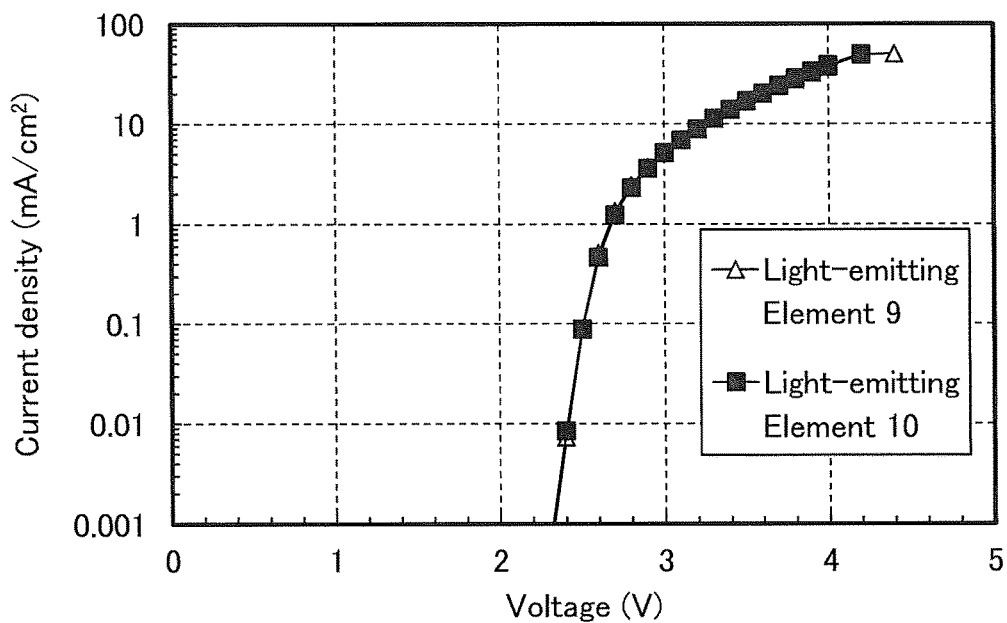
FIG. 64 shows current density-voltage characteristics of light-emitting elements in Example.

In addition, as shown in FIG. 63 and Table 9, the driving voltage of each of the light-emitting elements 9 and 10 at a luminance of approximately 1000 cd/m$^2$ is 2.7 V, which is an extremely low value. This is because the difference between the LUMO levels of the two kinds of host materials in the light-emitting layer is smaller than 0.5 eV and a bipolar material is used for each of the two kinds of host materials.

Example 14

In this example, examples of fabricating light-emitting elements 11 and 12, each of which is a light-emitting element of one embodiment of the present invention, are described. The light-emitting elements 11 and 12 each include two kinds of host materials and one kind of guest material in a light-emitting layer. Two kinds of bipolar materials were used as the host materials. As a bipolar material which receives an electron (a material which has a lower LUMO level) in the light-emitting layer, 2mDBTB-PDBq-II was used and a bipolar material which receives a hole (a material which has a higher HOMO level) differed between elements, and the element characteristics were compared with each other. FIG. 48 is a schematic cross-sectional view of each of the light-emitting elements fabricated in this example, and Table 10 shows details of the element structures. In addition, Table 11 shows a difference between LUMO levels of the two kinds of bipolar materials used for the light-emitting layer of each element, which was estimated by CV. Note that Examples described above can be referred to for structures and abbreviations of compounds used in Example 14.

TABLE 10

|  | Layer | Reference numeral | Film thickness (nm) | Material | Weight ratio |
|---|---|---|---|---|---|
| Light-emitting element 11 | Electrode | 102 | 200 | Al | — |
|  | Electron-injection layer | 119 | 1 | LiF | — |
|  | Electron-transport layer | 118(2) | 10 | BPhen | — |
|  |  | 118(1) | 20 | 2mDBTBPDBq-II | — |
|  | Light-emitting layer | 160(2) | 20 | 2mDBTBPDBq-II:2mpFBiBPDBq:Ir(dppm)$_2$(acac) | 0.8:0.2:0.05 |
|  |  | 160(1) | 20 | 2mDBTBPDBq-II:2mpFBiBPDBq:Ir(dppm)$_2$(acac) | 0.6:0.4:0.05 |
|  | Hole-transport layer | 112 | 20 | BPAFLP | — |
|  | Hole-injection layer | 111 | 60 | DBT3P-II:MoO$_3$ | 1:0.5 |
|  | Electrode | 101 | 70 | ITSO | — |
| Light-emitting element 12 | Electrode | 102 | 200 | Al | — |
|  | Electron-injection layer | 119 | 1 | LiF | — |
|  | Electron-transport layer | 118(2) | 10 | BPhen | — |
|  |  | 118(1) | 20 | 2mDBTBPDBq-II | — |
|  | Light-emitting layer | 160(2) | 20 | 2mDBTBPDBq-II:6FL-4mpFBiBPPm:Ir(dppm)$_2$(acac) | 0.8:0.2:0.05 |
|  |  | 160(1) | 20 | 2mDBTBPDBq-II:6FL-4mpFBiBPPm:Ir(dppm)$_2$(acac) | 0.6:0.4:0.05 |
|  | Hole-transport layer | 112 | 20 | BPAFLP | — |
|  | Hole-injection layer | 111 | 60 | DBT3P-II:MoO$_3$ | 1:0.5 |
|  | Electrode | 101 | 70 | ITSO | — |

TABLE 11

| | LUMO level of bipolar material which receives electron (lower LUMO level) (eV) | LUMO level of bipolar material which receives hole (higher LUMO level) (eV) | Difference between LUMO levels (eV) |
|---|---|---|---|
| Light-emitting element 11 | −2.94 (2mDBTBPDBq-II) | −2.93 (2mpFBiBPDBq) | 0.01 |
| Light-emitting element 12 | −2.94 (2mDBTBPDBq-II) | −2.8 (6FL-4mpFBiBPPm) | 0.14 |

<Fabrication of Light-Emitting Elements>
<<Fabrication of Light-Emitting Element 11>>

The light-emitting element 11 is different from the above-described comparative light-emitting element 1 in only the material of the light-emitting layer 160, and steps for the other components are the same as those in a method for fabricating the comparative light-emitting element 1.

That is, as the light-emitting layer 160 of the light-emitting element 11, 2mDBTBPDBq-II, 2mpFBiBPDBq, and Ir(dppm)$_2$(acac) were deposited by co-evaporation such that the deposited layer had a weight ratio of 2mDBTBPDBq-II:2mpFBiBPDBq:Ir(dppm)$_2$(acac)=0.6:0.4:0.05 and a thickness of 20 nm, and then 2mDBTBPDBq-II, 2mpFBiB-PDBq, and Ir(dppm)$_2$(acac) were deposited by co-evaporation such that the deposited layer had a weight ratio of 2mDBTBPDBq-II:2mpFBiBPDBq:Ir(dppm)$_2$(acac)=0.8:0.2:0.05 and a thickness of 20 nm.

<<Fabrication of Light-Emitting Element 12>>

The light-emitting element 12 is different from the above-described comparative light-emitting element 1 in only the material of the light-emitting layer 160, and steps for the other components are the same as those in a method for fabricating the comparative light-emitting element 1.

That is, as the light-emitting layer 160 of the light-emitting element 12, 2mDBTBPDBq-II, 6FL-4mpFBiB-PPm, and Ir(dppm)$_2$(acac) were deposited by co-evaporation such that the deposited layer had a weight ratio of 2mDBT-BPDBq-II:6FL-4mpFBiBPPm:Ir(dppm)$_2$(acac)=0.6:0.4:0.05 and a thickness of 20 nm, and then 2mDBTBPDBq-II, 6FL-4mpFBiBPPm, and Ir(dppm)$_2$(acac) were deposited by co-evaporation such that the deposited layer had a weight ratio of 2mDBTBPDBq-II:6FL-4mpFBiBPPm:Ir(dppm)$_2$(acac)=0.8:0.2:0.05 and a thickness of 20 nm.

Next, the characteristics of the fabricated light-emitting elements 11 and 12 were measured. The measurement method was similar to that used in Example 11.

FIGS. 67, 68, 69, and 70 respectively show current efficiency-luminance characteristics, luminance-voltage characteristics, current density-voltage characteristics, and external quantum efficiency-luminance characteristics of the light-emitting elements 11 and 12. FIG. 71 shows emission spectra when a current at a current density of 2.5 mA/cm$^2$ was supplied to the light-emitting elements 11 and 12.

Table 12 shows the element characteristics of the light-emitting elements 11 and 12 at around 1000 cd/m$^2$.

As shown in FIG. 71, the electroluminescence spectra of orange light from the light-emitting elements 11 and 12 have peak wavelengths at approximately 588 nm and full widths at half maximum of approximately 75 nm.

Figure 70:
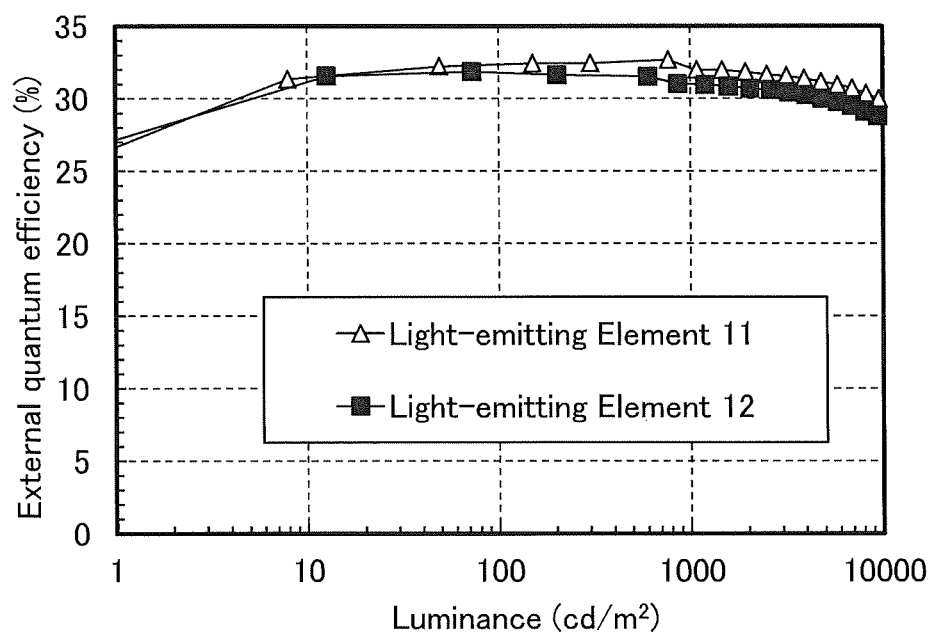
FIG. 70 shows external quantum efficiency-luminance characteristics of light-emitting elements in Example.
Figure 71:
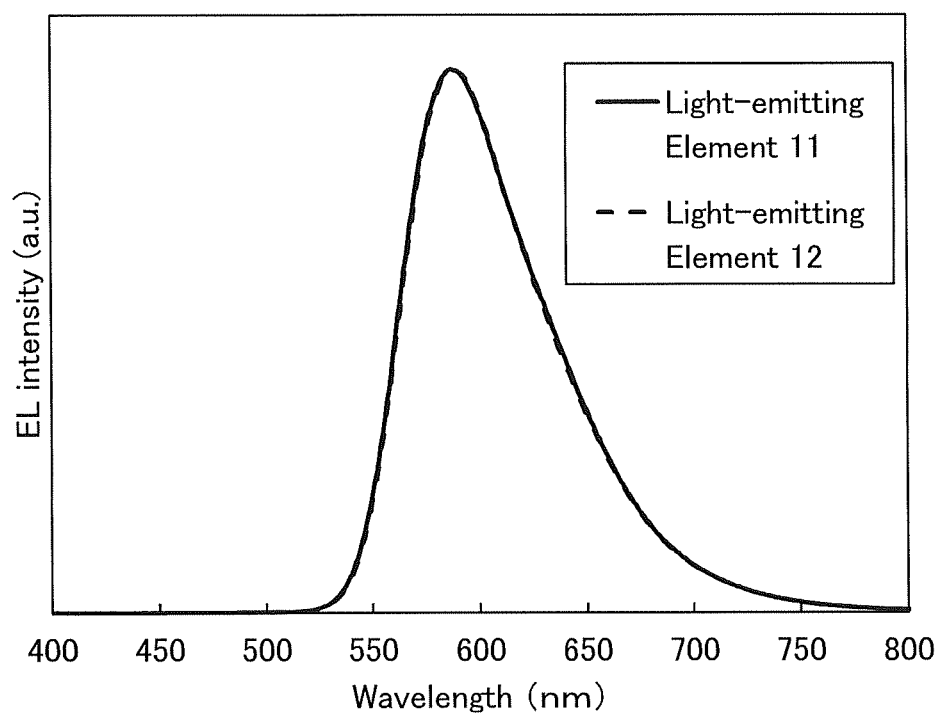
FIG. 71 shows emission spectra of light-emitting elements in Example.

As shown in FIG. 70 and Table 12, the maximum external quantum efficiencies of the light-emitting elements 11 and 12 are higher than or equal to 31%, which is extremely high.

Figure 68:
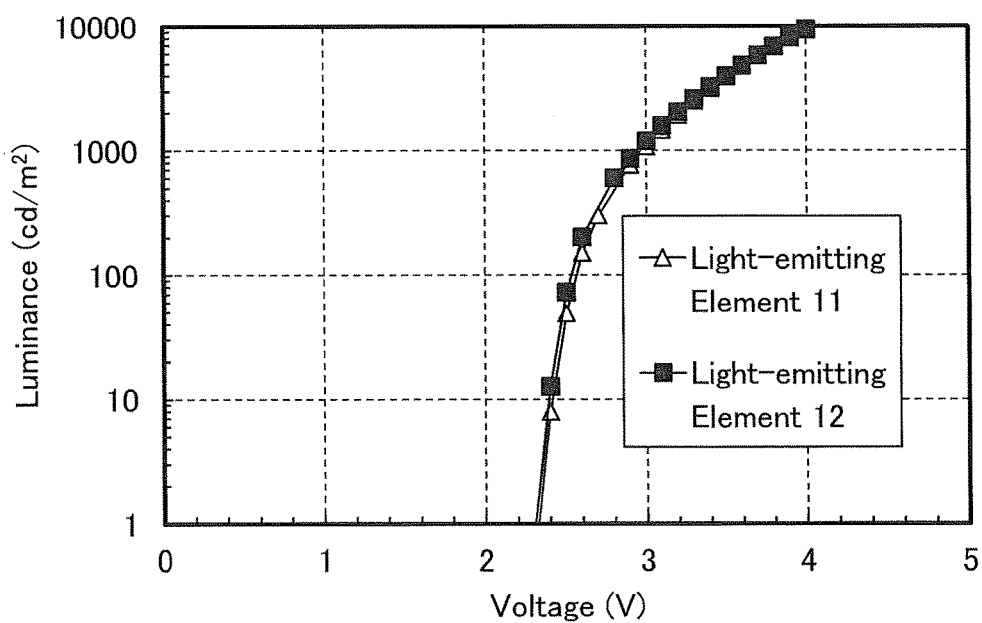
FIG. 68 shows luminance-voltage characteristics of light-emitting elements in Example.
Figure 69:
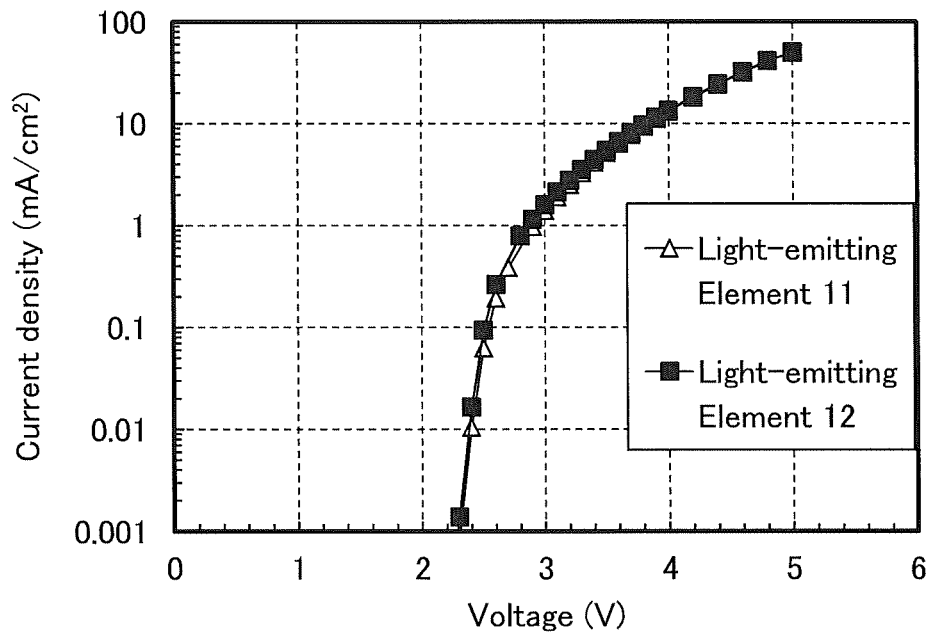
FIG. 69 shows current density-voltage characteristics of light-emitting elements in Example.

In addition, as shown in FIG. 68 and Table 12, the driving voltages of the light-emitting elements 11 and 12 at a luminance of approximately 1000 cd/m$^2$ are respectively 3.0 V and 2.9 V, which are extremely low values. This is because the difference between the LUMO levels of the two kinds of host materials in the light-emitting layer is smaller than 0.5 eV and a bipolar material is used for each of the two kinds of host materials.

<Reliability of Light-Emitting Elements>

Figure 72:
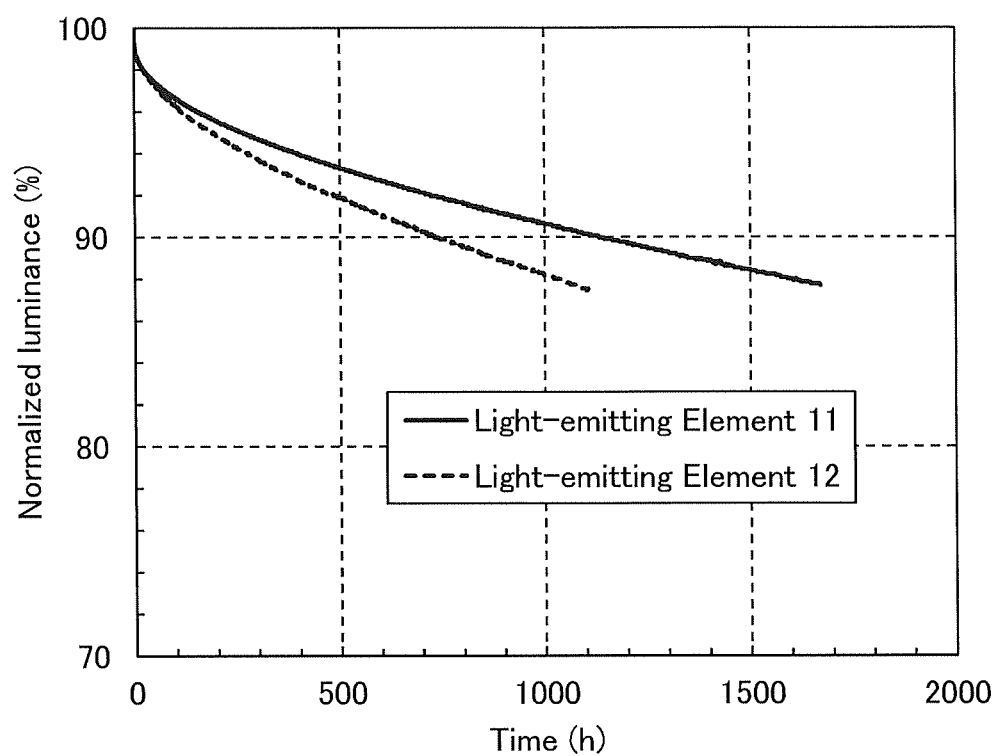
FIG. 72 shows reliability test results of light-emitting elements in Example.
Figure 73:
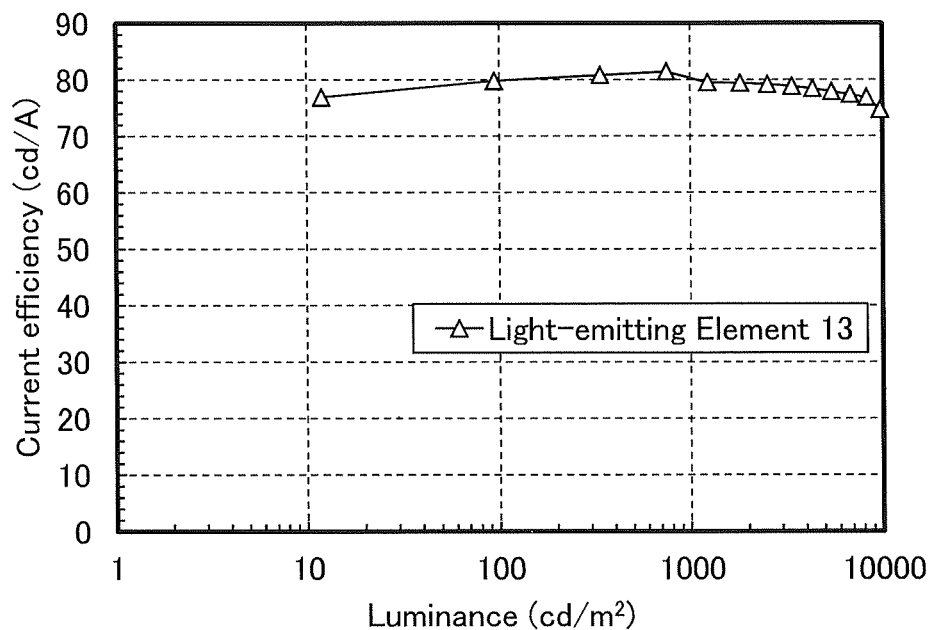
FIG. 73 shows current efficiency-luminance characteristics of a light-emitting element in Example.

Next, constant current driving tests were performed on the light-emitting elements 11 and 12 at an initial luminance of 5000 cd/m$^2$. FIG. 72 shows the results. As shown in FIG. 72, the light-emitting elements 11 and 12 each have LT$_{90}$ (time for which luminance is reduced by 10%) of 740 hours or longer, which indicates high reliability. In particular, the LT$_{90}$ of the light-emitting element 12 exceeds 1100 hours, which indicates extremely high reliability.

Example 15

In this example, an example of fabricating a light-emitting element 13, each of which is a light-emitting element of one embodiment of the present invention, are described. The light-emitting element 13 includes two kinds of host materials and one kind of guest material in a light-emitting layer. Two kinds of bipolar materials were used as the host materials. As a bipolar material which receives an electron (a material which has a lower LUMO level) in the light-emitting layer, 2mDBTBPDBq-II was used, and as a bipolar material which receives a hole (a material which has a higher HOMO level), 6FL-4PCBBiPPm was used. FIG. 48 is a schematic cross-sectional view of the light-emitting element fabricated in this example, and Table 13 shows details of the element structure. In addition, Table 14 shows a difference between LUMO levels of the two kinds of bipolar materials used for the light-emitting layer of the element, which was

TABLE 12

| | Voltage (V) | Current density (mA/cm$^2$) | CIE chromaticity (x, y) | Luminance (cd/m$^2$) | Current efficiency (cd/A) | Power efficiency (lm/W) | External quantum efficiency (%) |
|---|---|---|---|---|---|---|---|
| Light-emitting element 11 | 3.0 | 1.4 | (0.56, 0.44) | 1080 | 77 | 81 | 32 |
| Light-emitting element 12 | 2.9 | 1.1 | (0.56, 0.43) | 861 | 75 | 81 | 31 | estimated by CV. Note that Examples described above can be referred to for structures and abbreviations of compounds used in Example 15.

TABLE 13

| Layer | | Reference numeral | Film thickness (nm) | Material | Weight ratio |
|---|---|---|---|---|---|
| Light-emitting element 13 | Electrode | 102 | 200 | Al | — |
| | Electron-injection layer | 119 | 1 | LiF | — |
| | Electron-transport layer | 118(2) | 10 | BPhen | — |
| | | 118(1) | 20 | 2mDBTBPDBq-II | — |
| | Light-emitting layer | 160(2) | 20 | 2mDBTBPDBq-II:6FL-4PCBBiPPm:Ir(dppm)$_2$(acac) | 0.8:0.2:0.05 |
| | | 160(1) | 20 | 2mDBTBPDBq-II:6FL-4PCBBiPPm:Ir(dppm)$_2$(acac) | 0.7:0.3:0.05 |
| | Hole-transport layer | 112 | 20 | BPAFLP | — |
| | Hole-injection layer | 111 | 60 | DBT3P-II:MoO$_3$ | 1:0.5 |
| | Electrode | 101 | 70 | ITSO | — |

TABLE 14

| | LUMO level of bipolar material which receives electron (lower LUMO level) (eV) | LUMO level of bipolar material which receives hole (higher LUMO level) (eV) | Difference between LUMO levels (eV) |
|---|---|---|---|
| Light-emitting element 13 | −2.94 (2mDBTBPDBq-II) | −2.78 (6FL-4PCBBiPPm) | 0.16 |

<Fabrication of Light-Emitting Element>
<<Fabrication of Light-Emitting Element 13>>

The light-emitting element 13 is different from the above-described comparative light-emitting element 1 in only the material of the light-emitting layer 160, and steps for the other components are the same as those in a method for fabricating the comparative light-emitting element 1.

That is, as the light-emitting layer 160 of the light-emitting element 13, 2mDBTBPDBq-II, 6FL-4PCBBiPPm, and Ir(dppm)$_2$(acac) were deposited by co-evaporation such that the deposited layer had a weight ratio of 2mDBTBPDBq-II:6FL-4PCBBiPPm:Ir(dppm)$_2$(acac)=0.7:0.3:0.05 and a thickness of 20 nm, and then 2mDBTBPDBq-II, 6FL-4PCBBiPPm, and Ir(dppm)$_2$(acac) were deposited by co-evaporation such that the deposited layer had a weight ratio of 2mDBTBPDBq-II:6FL-4PCBBiPPm:Ir(dppm)$_2$(acac)=0.8:0.2:0.05 and a thickness of 20 nm.

Next, the characteristics of the fabricated light-emitting element 13 were measured. The measurement method was similar to that used in Example 11.

FIGS. 73, 74, 75, and 76 respectively show current efficiency-luminance characteristics, luminance-voltage characteristics, current density-voltage characteristics, and external quantum efficiency-luminance characteristics of the light-emitting element 13. FIG. 77 shows emission spectra when a current at a current density of 2.5 mA/cm$^2$ was supplied to the light-emitting element 13.

Table 15 shows the element characteristics of the light-emitting element 13 at around 1000 cd/m$^2$.

TABLE 15

| | Voltage (V) | Current density (mA/cm$^2$) | CIE chromaticity (x, y) | Luminance (cd/m$^2$) | Current efficiency (cd/A) | Power efficiency (lm/W) | External quantum efficiency (%) |
|---|---|---|---|---|---|---|---|
| Light-emitting element 13 | 2.8 | 1.5 | (0.55, 0.45) | 1232 | 80 | 89 | 29 |

As shown in FIG. 77, the electroluminescence spectrum of orange light from the light-emitting element 13 have a peak wavelength at 581 nm and a full width at half maximum of 69 nm.

Figure 76:
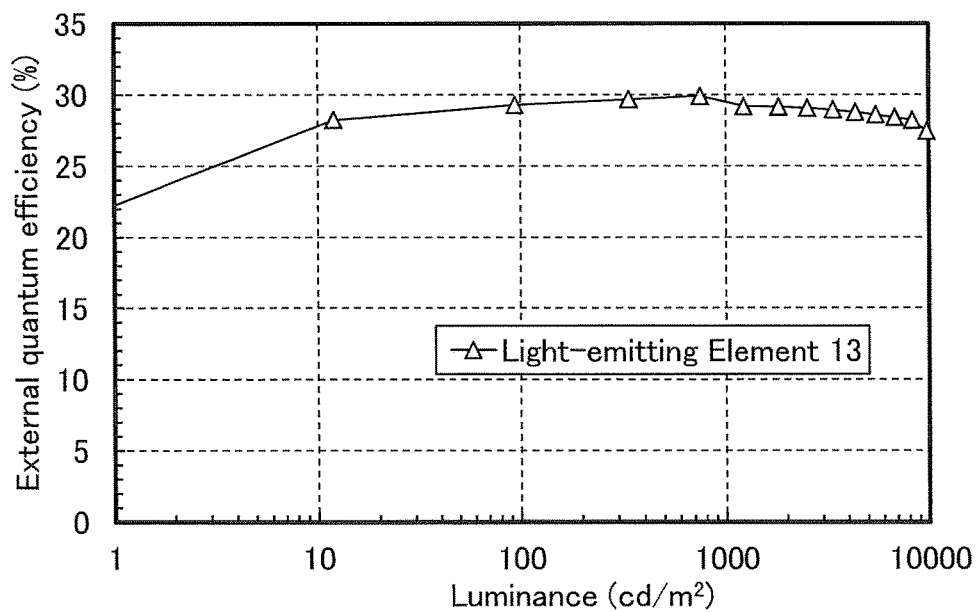
FIG. 76 shows external quantum efficiency-luminance characteristics of a light-emitting element in Example.
Figure 77:
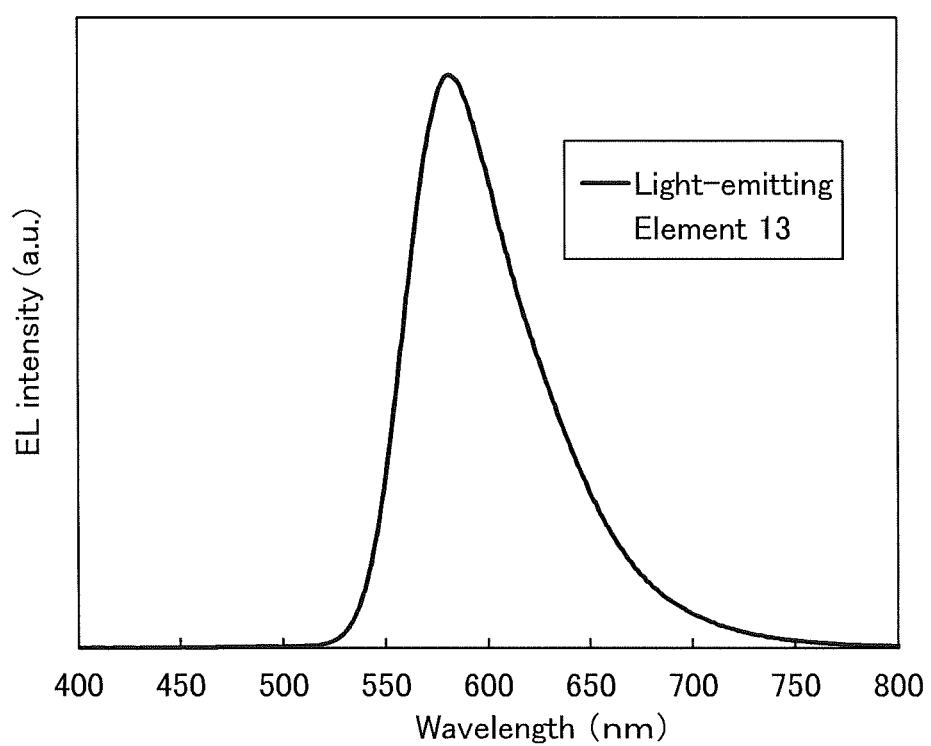
FIG. 77 shows an emission spectrum of a light-emitting element in Example.

As shown in FIG. 76 and Table 15, the maximum external quantum efficiency of the light-emitting element 13 is higher than or equal to 29%, which is extremely high.

Figure 74:
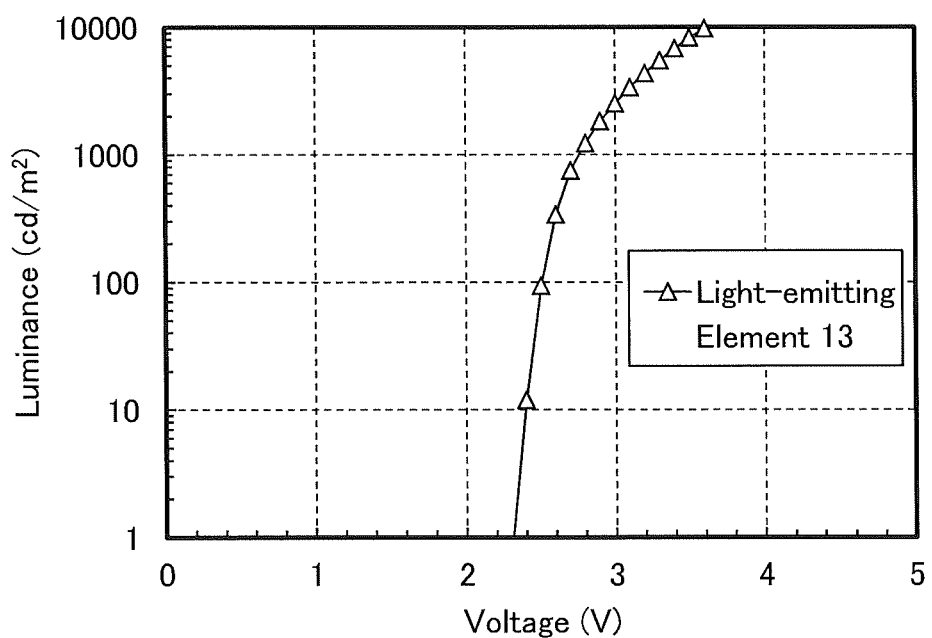
FIG. 74 shows luminance-voltage characteristics of a light-emitting element in Example.
Figure 75:
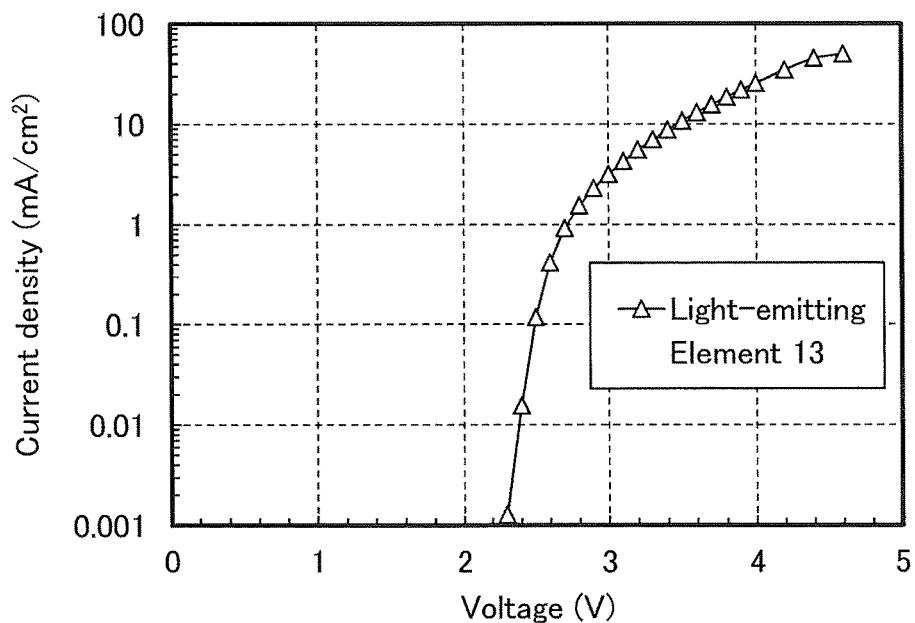
FIG. 75 shows current density-voltage characteristics of a light-emitting element in Example.

In addition, as shown in FIG. 74 and Table 15, the driving voltage of the light-emitting element 13 at a luminance of approximately 1000 cd/m$^2$ is 2.8 V, which is an extremely low value. This is because the difference between the LUMO levels of the two kinds of host materials in the light-emitting layer is smaller than 0.5 eV and a bipolar material is used for each of the two kinds of host materials.

Thus, it is shown that the difference between the LUMO levels of the two kinds of host materials used for the light-emitting layer is preferably smaller than 0.5 eV and a bipolar material is preferably used as each of the two kinds of host materials, in which case the driving voltage is reduced, the emission efficiency is improved, and the reliability is increased.

This application is based on Japanese Patent Application Serial No. 2016-223771 filed with Japan Patent Office on Nov. 17, 2016, and Japanese Patent Application Serial No. 2016-225013 filed with Japan Patent Office on Nov. 18, 2016, the entire contents of which are hereby incorporated by reference.

What is claimed is:

1. A light-emitting element comprising a light-emitting layer between a pair of electrodes,
wherein the light-emitting layer comprises a first organic compound, a second organic compound, and a guest material,
wherein a LUMO level of the first organic compound is lower than a LUMO level of the second organic compound,
wherein a difference between the LUMO level of the first organic compound and the LUMO level of the second organic compound is larger than 0 eV and smaller than or equal to 0.5 eV,
wherein a HOMO level of the first organic compound is lower than a HOMO level of the second organic compound,
wherein the guest material is capable of converting triplet excitation energy into light emission,
wherein the first organic compound and the second organic compound form an exciplex,
wherein the first organic compound comprises a first electron-transport skeleton and a first hole-transport skeleton, and
wherein the second organic compound comprises a second electron-transport skeleton and a second hole-transport skeleton.

2. The light-emitting element according to claim 1,
wherein the difference between the LUMO level of the first organic compound and the LUMO level of the second organic compound is larger than 0 eV and smaller than or equal to 0.3 eV.

3. The light-emitting element according to claim 1,
wherein the first electron-transport skeleton and the second electron-transport skeleton each comprise one or more of a π-electron deficient heteroaromatic ring, an arylborane skeleton, and a phosphine oxide skeleton, and
wherein the first hole-transport skeleton and the second hole-transport skeleton each comprise one of or both a π-electron rich heteroaromatic ring and an aromatic amine skeleton.

4. The light-emitting element according to claim 1,
wherein the first electron-transport skeleton is a nitrogen-containing heteroaromatic ring having 8 to 18 carbon atoms, and
wherein the second electron-transport skeleton is a nitrogen-containing heteroaromatic ring having 3 to 8 carbon atoms.

5. The light-emitting element according to claim 1,
wherein the first hole-transport skeleton is a π-electron rich heteroaromatic ring, and
wherein the second hole-transport skeleton is an amine skeleton.

6. The light-emitting element according to claim 1,
wherein the first electron-transport skeleton comprises any one of a quinoline skeleton and a quinoxaline skeleton, and
wherein the second electron-transport skeleton comprises any one of a triazine skeleton, a pyrimidine skeleton, a pyridine skeleton, and a pyrazine skeleton.

7. The light-emitting element according to claim 1,
wherein the second organic compound is any one of organic compounds represented by Structural Formulae (100) to (109).

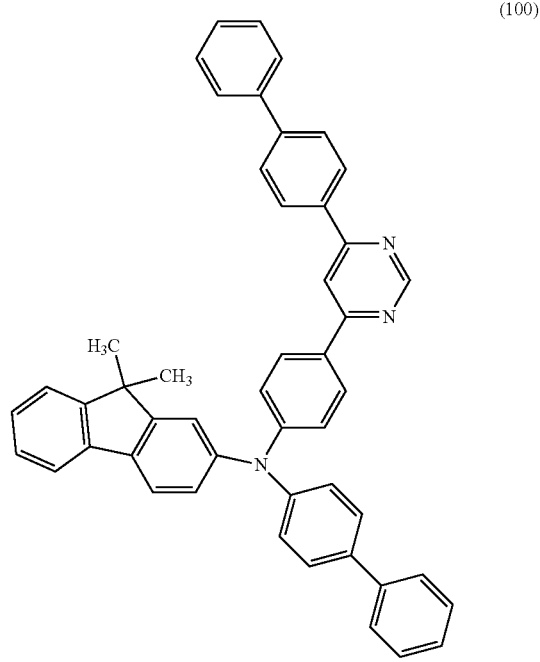

(100)

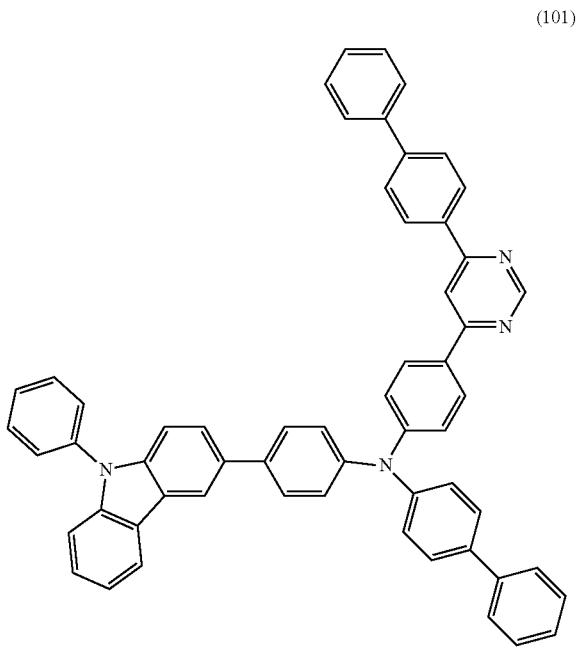

(101)

-continued
(102)
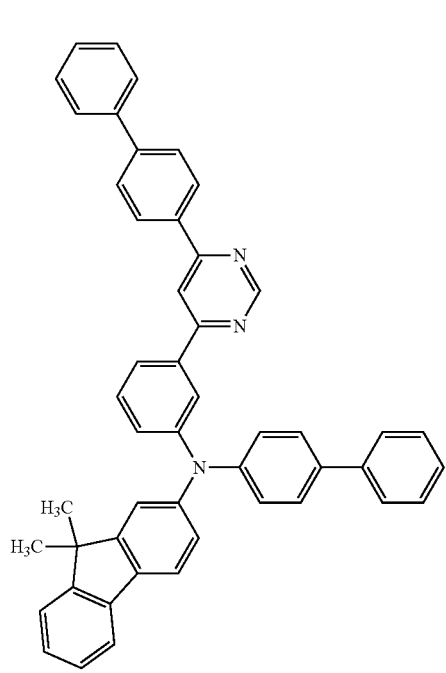
(103)
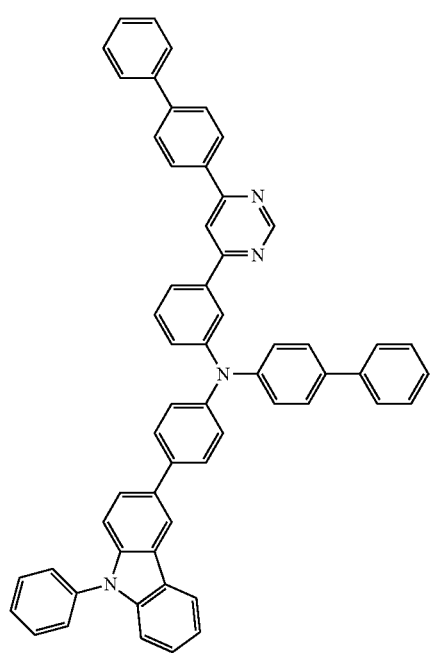
-continued
(104)
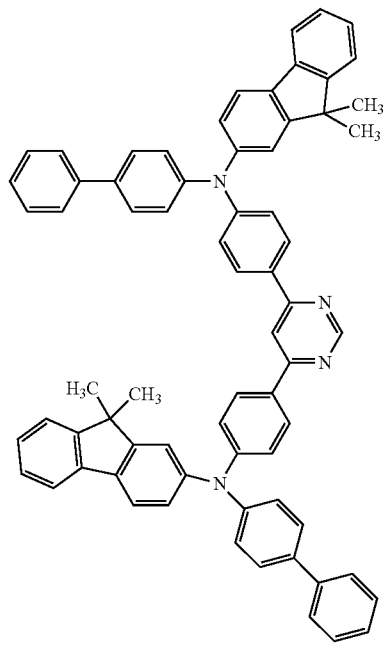
(105)
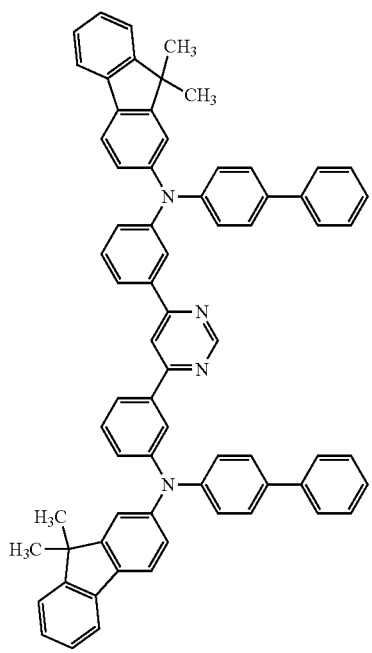

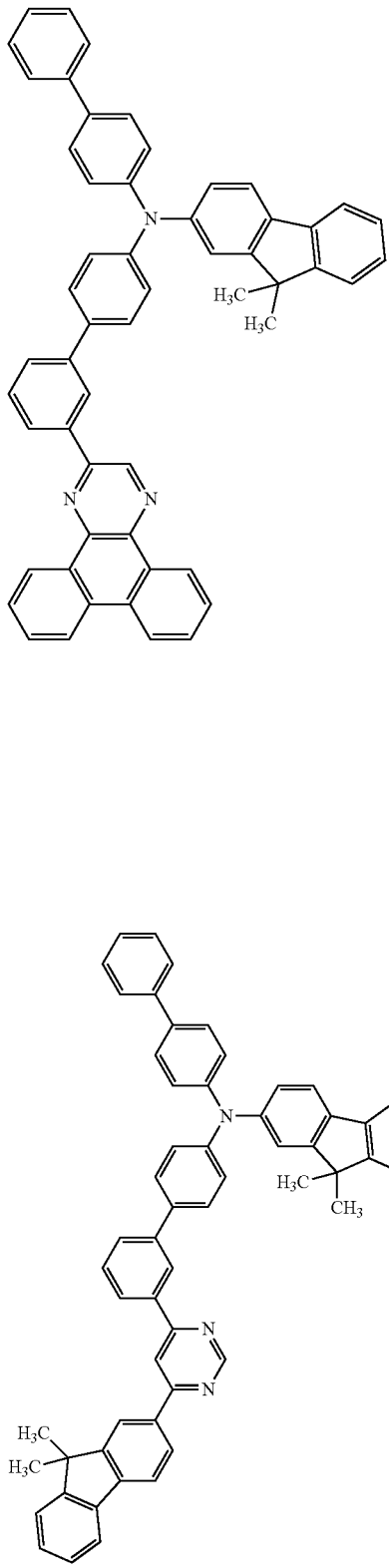

(106)

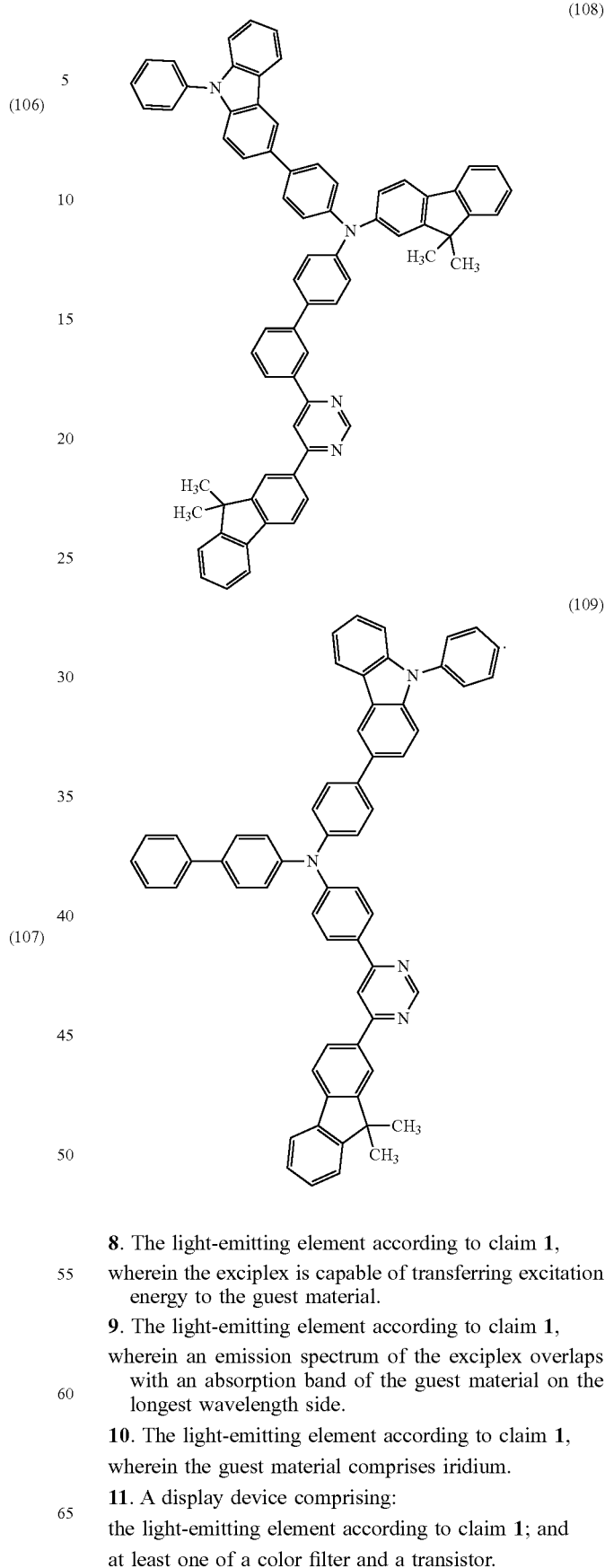

(108)

(109)

(107)

8. The light-emitting element according to claim 1, wherein the exciplex is capable of transferring excitation energy to the guest material.

9. The light-emitting element according to claim 1, wherein an emission spectrum of the exciplex overlaps with an absorption band of the guest material on the longest wavelength side.

10. The light-emitting element according to claim 1, wherein the guest material comprises iridium.

11. A display device comprising:
the light-emitting element according to claim 1; and
at least one of a color filter and a transistor.

12. An electronic device comprising:
the display device according to claim 11; and
at least one of a housing and a touch sensor.
13. A lighting device comprising:
the light-emitting element according to claim 1; and
at least one of a housing and a touch sensor.
14. An organic compound represented by any one of Structural Formulae (100) to (109)
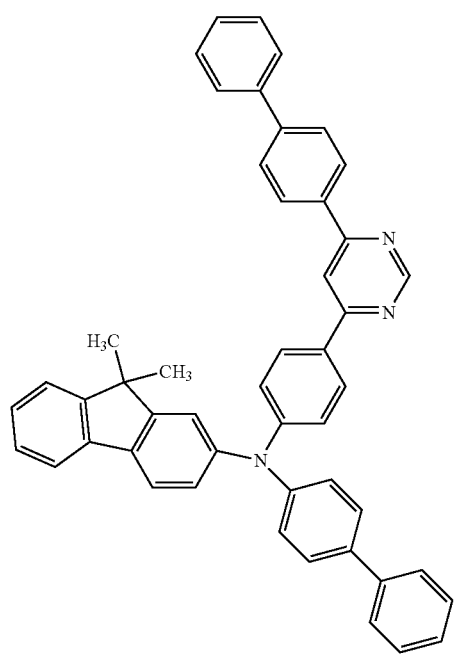
(100)
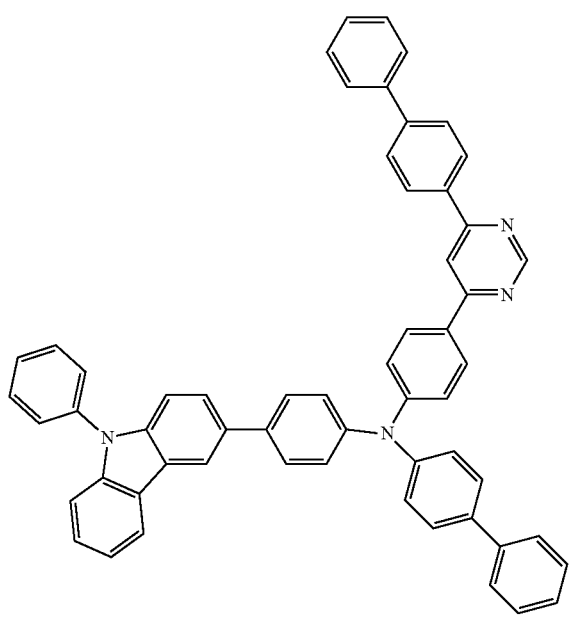
(101)
-continued
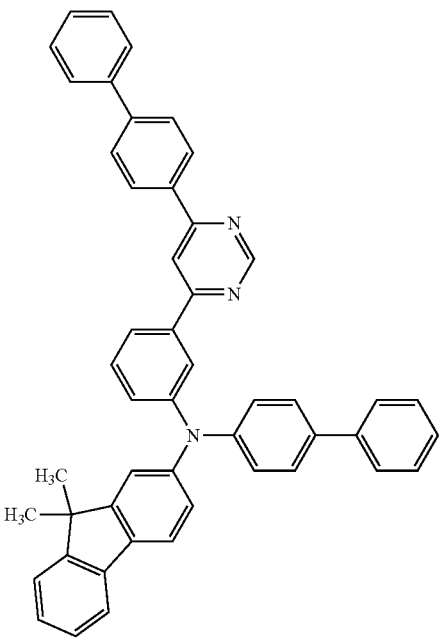
(102)
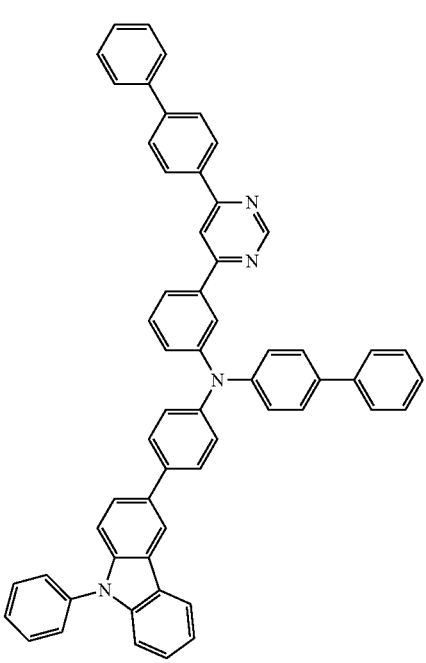
(103)

121
-continued
122
-continued
(104)
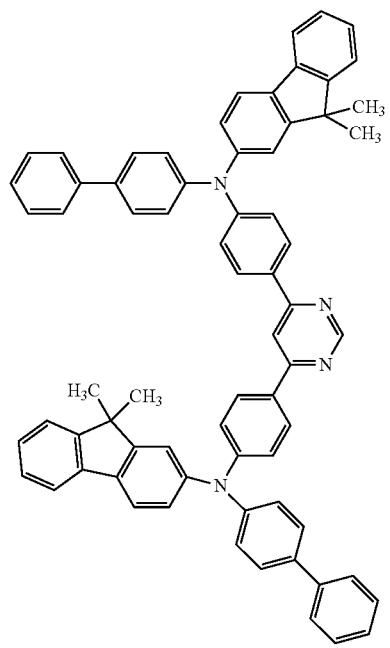
(106)
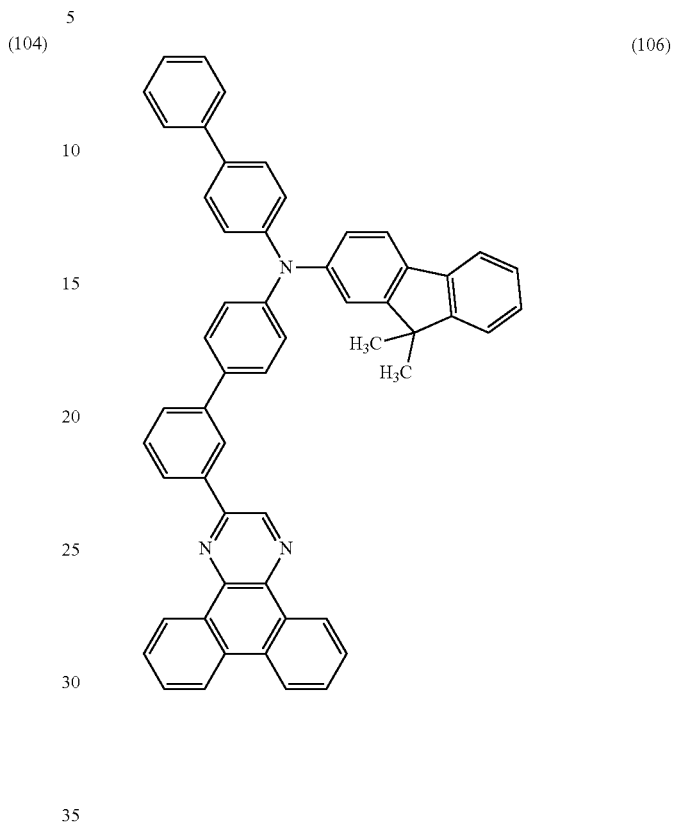
(105)
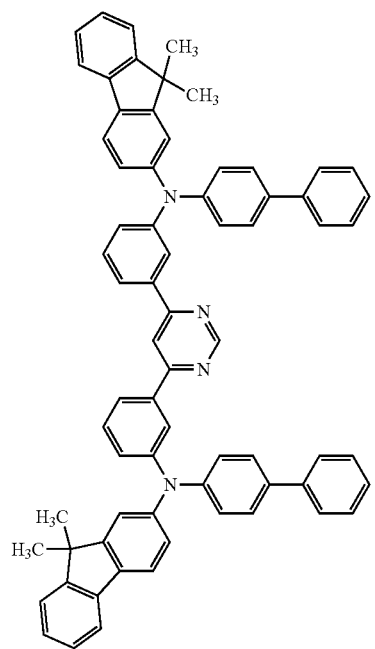
(107)
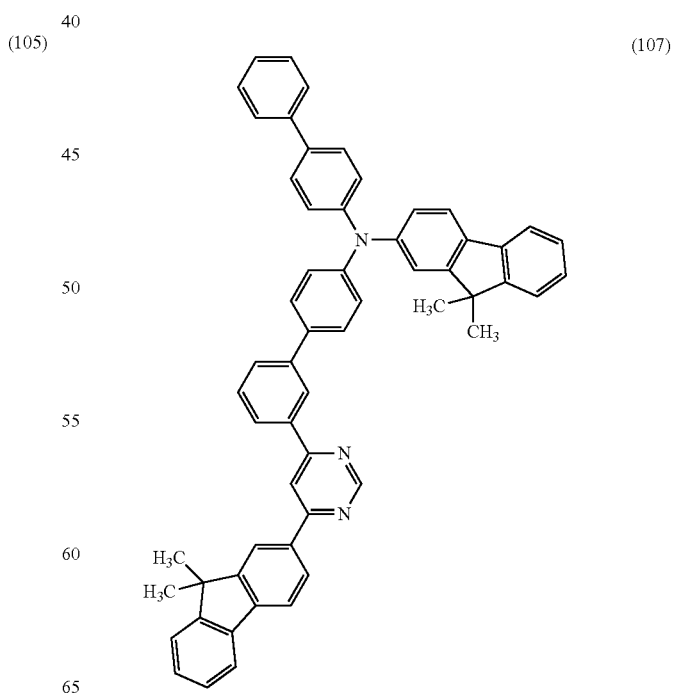

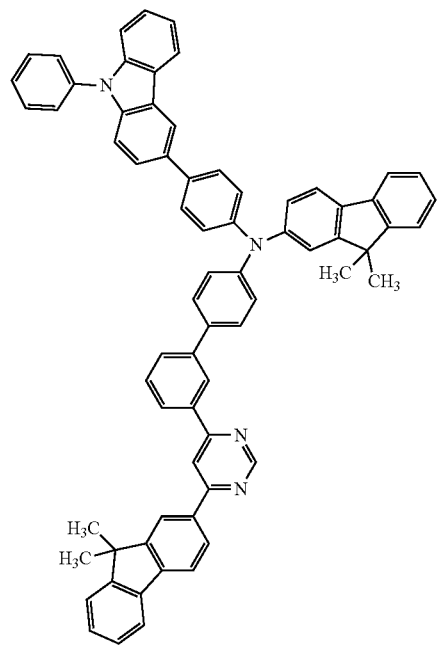
(108)
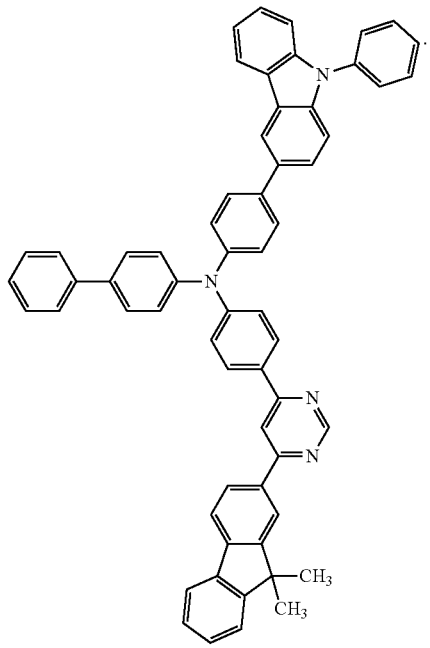
(109)
15. A light-emitting element comprising the organic compound according to claim 14.
* * * * *